US007163947B2

(12) United States Patent
Griesgraber et al.

(10) Patent No.: US 7,163,947 B2
(45) Date of Patent: Jan. 16, 2007

(54) 1-AMINO 1H-IMIDAZOQUINOLINES

(75) Inventors: George W. Griesgraber, Eagan, MN (US); Karl J. Manske, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 96 days.

(21) Appl. No.: 10/933,658

(22) Filed: Sep. 3, 2004

(65) Prior Publication Data
US 2005/0054640 A1 Mar. 10, 2005

Related U.S. Application Data

(63) Continuation-in-part of application No. 10/794,099, filed on Mar. 5, 2004, now abandoned.

(60) Provisional application No. 60/532,191, filed on Dec. 23, 2003, provisional application No. 60/453,128, filed on Mar. 7, 2003.

(51) Int. Cl.
*A01N 43/42* (2006.01)
*A61K 31/44* (2006.01)
*C07D 491/00* (2006.01)
*C07D 498/00* (2006.01)
*C07D 513/00* (2006.01)

(52) U.S. Cl. ........................................ 514/293; 546/82

(58) Field of Classification Search ............. 514/227.8, 514/234.2, 291, 293; 544/60, 361; 546/82
See application file for complete search history.

(56) References Cited

U.S. PATENT DOCUMENTS

| | | | |
|---|---|---|---|
| 3,314,941 A | 4/1967 | Littell et al. | |
| 4,689,338 A | 8/1987 | Gerster | |
| 4,698,348 A | 10/1987 | Gerster | |
| 4,929,624 A | 5/1990 | Gerster et al. | |
| 4,988,815 A | 1/1991 | Andre et al. | |
| 5,037,986 A | 8/1991 | Gerster | |
| 5,175,296 A | 12/1992 | Gerster | |
| 5,238,944 A | 8/1993 | Wick et al. | |
| 5,266,575 A * | 11/1993 | Gerster et al. | 514/293 |
| 5,268,376 A | 12/1993 | Gester | |
| 5,346,905 A | 9/1994 | Gerster | |
| 5,352,784 A | 10/1994 | Nikolaides et al. | |
| 5,367,076 A | 11/1994 | Gerster | |
| 5,389,640 A | 2/1995 | Gerster et al. | |
| 5,395,937 A | 3/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,693,811 A | 12/1997 | Lindstrom | |
| 5,741,908 A | 4/1998 | Gerster et al. | |
| 5,756,747 A | 5/1998 | Gerster | |
| 5,939,090 A | 8/1999 | Beaurline et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,194,425 B1 | 2/2001 | Gerster et al. | |
| 6,245,776 B1 | 6/2001 | Skwierczynski et al. | |
| 6,331,539 B1 | 12/2001 | Crooks et al. | |
| 6,376,669 B1 | 4/2002 | Rice et al. | |
| 6,451,810 B1 | 9/2002 | Coleman et al. | |
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,656,938 B1 | 12/2003 | Crooks et al. | |
| 6,660,735 B1 | 12/2003 | Crooks et al. | |
| 6,660,747 B1 | 12/2003 | Crooks et al. | |
| 6,664,260 B1 | 12/2003 | Charles et al. | |
| 6,664,264 B1 | 12/2003 | Dellaria et al. | |
| 6,664,265 B1 | 12/2003 | Crooks et al. | |
| 6,667,312 B1 | 12/2003 | Bonk et al. | |
| 6,670,372 B1 | 12/2003 | Charles et al. | |
| 6,677,347 B1 | 1/2004 | Crooks et al. | |
| 6,677,348 B1 | 1/2004 | Heppner et al. | |
| 6,677,349 B1 | 1/2004 | Griesgraber | |
| 6,683,088 B1 | 1/2004 | Crooks et al. | |

(Continued)

FOREIGN PATENT DOCUMENTS

| | | |
|---|---|---|
| EP | 0 394 026 | 10/1990 |
| EP | 1 104 764 | 6/2001 |
| HU | 34479 * | 3/1985 |
| JP | 9-208584 | 8/1997 |
| JP | 9-255926 | 3/1999 |
| JP | 11-222432 | 8/1999 |
| JP | 2000-247884 | 9/2000 |
| WO | WO 01/58900 A1 | 8/2001 |
| WO | WO 02/36592 | 5/2002 |

OTHER PUBLICATIONS

Liu et al., "Sle lab Mediates the Aberrant Activation of STAT3 and Ras-ERK Signaling Pathways in B Lymphocytes", The journal of Immunization, pp. 1630-1637.*
Strandtman et al., "Reaction of Cyclic B-Diketones with 3,4-Dihydroisoquinolines and Related Compounds. Preparation and Anticancer Activity of 2-Substituted 1,3-Cyclohexanediones", J. Med. Chem., pp. 1063-1065.*

(Continued)

*Primary Examiner*—Thomas McKenzie
*Assistant Examiner*—Niloofar Rahmani
(74) *Attorney, Agent, or Firm*—Dean A. Ersfeld

(57) ABSTRACT

1-Amino 1H-imidazoquinoline compounds, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

60 Claims, No Drawings

U.S. PATENT DOCUMENTS

| | | |
|---|---|---|
| 6,797,718 B1 | 9/2004 | Dellaria et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0162390 A1 | 8/2004 | Gorden et al. |
| 2004/0167367 A1 | 8/2004 | Griesgraber et al. |
| 2004/0176367 A1* | 9/2004 | Griesgraber et al. ..... 514/227.8 |

OTHER PUBLICATIONS

Sofina et al., "Experimental Evaluation of Antitumor Drugs in the USA and USSR and Clinical Correlations", NIH publication No. 80-1933, p. 76-78.*

Wozniak, et al, "The Amination of 3-nitro-1, 5-naphthyridines by Liquid Ammonia/Potassium Permanganate[1,2]. A New Convenient Amination Method.", *Journal of the Royal Netherlands Chemical Society,* 102, pp. 511-513, Dec. 12, 1983.

Brennan, et al, "Automated Bioassay of Interferons in Micro-test Plates", *Biotechniques,* Jun./Jul. 78, 1983.

Testerman, et al., "Cytokine Induction by the Immunomodulators Imiquimod and S-27609", *Journal of Leukocyte Biology,* vol. 58, pp. 365-372, Sep. 1995.

Bachman, et al, "Synthesis of Substituted Quinolylamines. Derivatives of 4-Amino-7-Chloroquinoline", *J. Org. Chem,* 15, pp. 1278-1284 (1950).

Jain, et al, "Chemical and Pharmacological Investigations of Some ω-Substituted Alkylamino-3-aminopyridines", *J. Med Chem.,* 11, pp. 87-92 (1968).

Baranov, et al., *Chem. Abs.* 85, 94362, (1976).

Berényi, et al, "Ring Transformation of Condensed Dihydro-astriazines", *J. Heterocyclic Chem.,* 18, pp. 1537-1540 (1981).

Chollet, et al, "Development of a Topically Active Imiquimod Formulation", *Pharmaceutical Development and Technology,* 4(1), pp. 35-43 (1999).

Izumi, et al., "1*H*-Imidazo[4,5-*c*]quinoline Derivatives as Novel Potent TNF- α Suppressors: Synthesis and Structure-Activity Relationship of 1-, 2- and 4-Substituted 1*H*-imidazo[4,5-*c*]pyridines", *Bioorganic & Medicinal Chemistry,* 11, pp. 2541-2550 (2003).

* cited by examiner

1-AMINO 1H-IMIDAZOQUINOLINES

CROSS-REFERENCE TO RELATED APPLICATIONS

The present application is a continuation-in-part of U.S. application Ser. No. 10/794,099, filed Mar. 5, 2004, now abandoned, which claims priority to U.S. Provisional Application No. 60/453,128, filed Mar. 7, 2003, and to U.S. Provisional Application No. 60/532,191, filed Dec. 23, 2003, each of which is incorporated herein by reference in it entirety.

FIELD OF THE INVENTION

This invention relates to 1-amino 1H-imidazoquinoline compounds, pharmaceutical compositions containing such compounds, intermediates used in their preparation, and the use of these compounds as immunomodulators.

BACKGROUND OF THE INVENTION

There has been a major effort in recent years to find compounds that modulate the immune system. Examples of such compounds, which have demonstrated cytokine inducing and immunomodulating activity, are disclosed by U.S. Pat. Nos. 4,689,338; 4,929,624; 5,266,575; 5,268,376; 5,352,784; 5,389,640; 5,446,153; 5,482,936; 5,494,916; 5,756,747; 6,110,929; 6,194,425; 6,331,539; 6,376,669; 6,451,810; 6,525,064; 6,541,485; 6,545,016; 6,545,017; 6,656,938; 6,660,735; 6,660,747; 6,664,260; 6,664,264; 6,664,265; 6,667,312; 6,670,372; 6,677,347; 6,677,348; and 6,683,088.

But despite important progress in the effort to find immunomodulating compounds, there is still a critical scientific and medical need for additional compounds that have an ability to modulate aspects of the immune response, by induction of cytokine biosynthesis or other mechanisms.

SUMMARY OF THE INVENTION

It has now been found that certain 1-amino 1H-imidazoquinoline compounds modulate cytokine biosynthesis. In one aspect, the present invention provides compounds of the Formulas I and II:

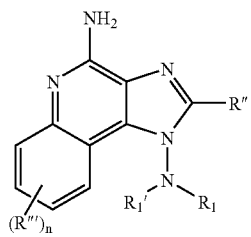

I

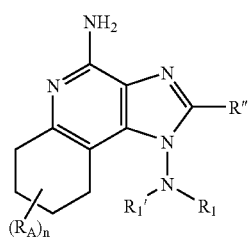

II and more specifically the following compounds of the Formulas I-1, I-2, I-3, and II-1:

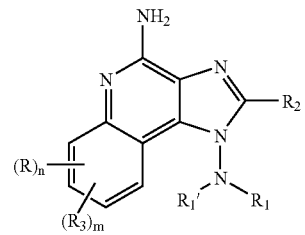

I-1

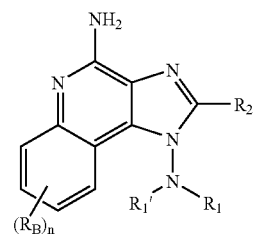

I-2

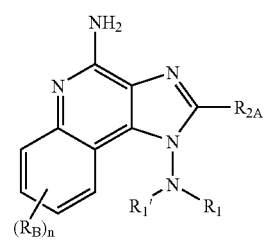

I-3

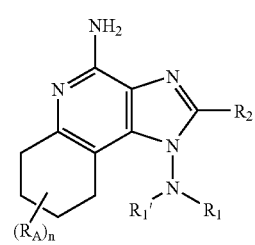

II-1 wherein $R_1'$, $R_1$, $R_2$, $R_{2A}$, $R_3$, R", R'", R, $R_A$, $R_B$, n and m are as defined below; and pharmaceutically acceptable salts thereof.

The compounds of Formulas I, I-1, I-2, I-3, II, and II-1 are useful as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human PBMC in a culture with the compound(s) at a concentration range of 30 to 0.014 µM and analyzing for interferon (a) or tumor necrosis factor (a) in the culture supernatant. Compounds can be tested for inhibition of cytokine biosynthesis by incubating mouse macrophage cell line Raw 264.7 in a culture with the compound(s) at a single concentration of, for example, 5 µM and analyzing for tumor necrosis factor (a) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing cytokine biosynthesis in animal cells, treating a viral disease in an animal, and/or treating a neoplastic disease in an animal by administering to the animal one or more compounds of the Formulas I, I-1, I-2, I-3, II, and/or II-1, and/or pharmaceutically acceptable salts thereof.

In another aspect, the invention provides methods of synthesizing the compounds of Formulas I, I-1, I-2, I-3, II, and II-1 and intermediates useful in the synthesis of these compounds.

As used herein, "a," an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

In one aspect, the present invention provides compounds of the Formulas I and II:

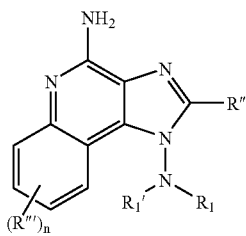

I

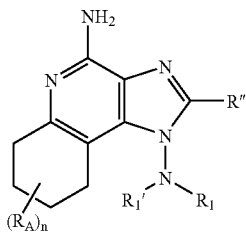

II and more specifically the following compounds of the Formulas I-1, I-2, I-3, and II-1:

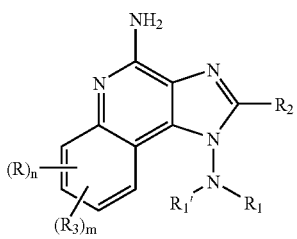

I-1

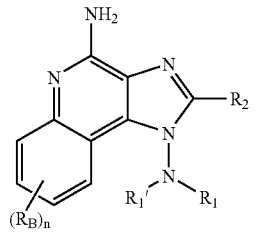

I-2

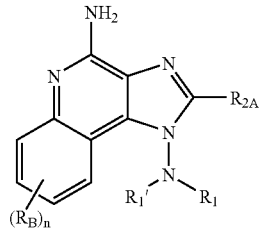

I-3

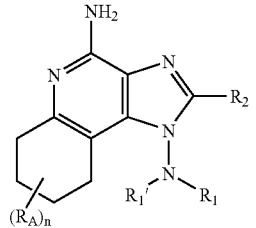

II-1 wherein $R_1'$, $R_1$, $R_2$, $R_{2A}$, $R_3$, R", R''', R, $R_A$, $R_B$, n, and m are as defined below; and pharmaceutically acceptable salts thereof.

In one embodiment, the present invention provides 1-amino 1H-imidazoquinoline compounds of the following Formula I:

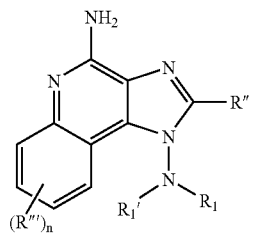

I wherein:
$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;
$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—O—C($R_7$)—N($R_6$)—$R_4$,
—X—S(O)$_2$—N($R_6$)—$R_4$, and
—X—O—$R_4$;

or $R_1'$ and $R_1$ together with the nitrogen atom to which they are bonded can join to form a group selected from the group consisting of:

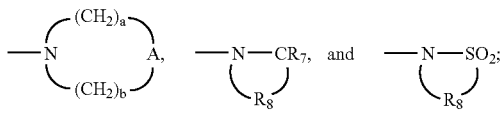

$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of:

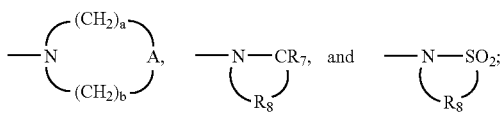

each $R_6$ is independently selected from the group consisting of hydrogen, alkyl, and arylalkylenyl;

$R_7$ is selected from the group consisting of =O and =S;

$R_8$ is $C_{2-7}$ alkylene;

A is selected from the group consisting of —CH($R_6$)—, —O—, —N($R_6$)—, —N(Y—$R_4$)—, and —N(X—N($R_6$)—Y—$R_4$)—;

X is $C_{2-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

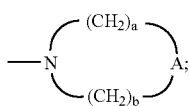

a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

each R'' is independently hydrogen or a non-interfering substituent;

each R''' is independently a non-interfering substituent; and n is an integer from 0 to 4;

or a pharmaceutically acceptable salt thereof

In some embodiments of Formula I, R'' is selected from the group consisting of:
 hydrogen,
 alkyl,
 alkenyl,
 aryl,
 heteroaryl,
 heterocyclyl,
 -alkylene-Z-alkyl,
 -alkylene-Z-aryl,
 -alkylene-Z-alkenyl, and
 alkyl or alkenyl substituted by one or more substituents
  selected from the group consisting of:
   —OH,
   halogen,
   —N($R_6$)$_2$,
   —C($R_7$)—N($R_6$)$_2$,
   —S(O)$_2$—N($R_6$)$_2$,
   —N($R_6$)—C($R_7$)—$C_{1-10}$ alkyl,
   —N($R_6$)—C($R_7$)-aryl,
   —N($R_6$)—S(O)$_2$—$C_{1-10}$ alkyl,
   —N($R_6$)—S(O)$_2$-aryl,
   —C(O)—$C_{1-10}$ alkyl,
   —O—C($R_7$)—$C_{1-10}$ alkyl,
   —O—C($R_7$)-aryl,
   —O—C($R_7$)—N($R_6$)—$C_{1-10}$ alkyl,
   —O—C($R_7$)—N($R_6$)-aryl;
   —C(O)—O—$C_{1-10}$ alkyl,
   —N$_3$,
   aryl,
   heteroaryl,
   heterocyclyl,
   —C(O)-aryl, and
   —C(O)-heteroaryl;
 each $R_6$ is independently selected from the group consisting of hydrogen, alkyl, and arylalkylenyl;
 each $R_7$ is independently selected from the group consisting of =O and =S; and
 Z is selected from the group consisting of —O— and —S(O)$_{0-2}$—.

In some embodiments of Formula I, R''' is R or $R_3$ when n is 1, R or one R and one $R_3$ when n is 2, R or two R's and one $R_3$ when n is 3, or R when n is 4; wherein:

R is selected from the group consisting of alkyl, alkenyl, alkoxy, halogen, fluoroalkyl, hydroxy, amino, alkylamino, and dialkylamino;

$R_3$ is selected from the group consisting of:
 -Z'-$R_4'$,
 -Z'-X'—$R_4'$,
 -Z'-X'—Y'—$R_4'$, and
 -Z'-X'—$R_5'$;

Z' is a bond or —O—;

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:
 —S(O)$_{0-2}$—,
 —S(O)$_2$—N($R_{11}$)—,
 —C($R_7$)—,
 —C($R_7$)—O—,
 —O—C($R_7$)—,
 —O—C(O)—O—,
 —N($R_{11}$)—Q—,
 —C($R_7$)—N($R_{11}$)—,

—O—C(R$_7$)—N(R$_{11}$)—,
—C(R$_7$)—N(OR$_{12}$)—,

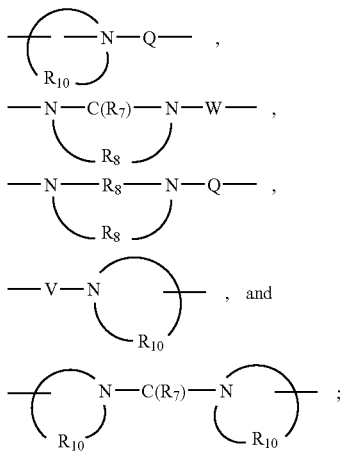

R$_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$' is selected from the group consisting of:

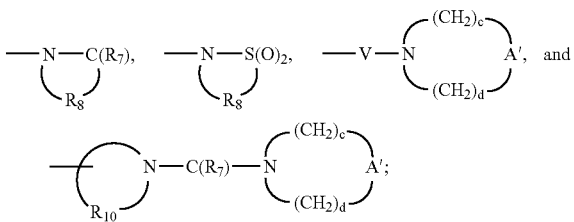

each R$_7$ is independently selected from the group consisting of =O and =S;
each R$_8$ is independently C$_{2-7}$ alkylene;
R$_{10}$ is C$_{3-8}$ alkylene;
each R$_{11}$ is independently selected from the group consisting of hydrogen, C$_{1-10}$ alkyl, C$_{2-10}$ alkenyl, C$_{1-10}$ alkoxyC$_{2-10}$ alkylenyl, and arylC$_{1-10}$ alkylenyl;
R$_{12}$ is selected from the group consisting of hydrogen and alkyl;
A' is selected from the group consisting of —CH$_2$—, —O—, —C(O)—, —S(O)$_{0-2}$—, and —N(R$_4$')—;
Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;

V is selected from the group consisting of —C(R$_7$)—, —O—C(R$_7$)—, —N(R$_{11}$)—C(R$_7$)—, and —S(O)$_2$—;
W is selected from the group consisting of a bond, —C(O)—, and —S(O)$_2$—; and
c and d are independently integers from 1 to 6 with the proviso that c+d is ≦7, and when A' is —O— or —N(R$_4$')— then c and d are independently integers from 2 to 4.

In one embodiment, the present invention provides 1-amino 6,7,8,9-tetrahydro 1H-imidazoquinoline compounds of the following Formula II:

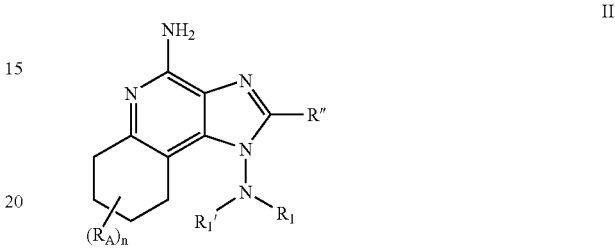

II wherein:
each R$_A$ is independently selected from the group consisting of:
halogen,
hydroxy,
alkyl,
alkenyl,
haloalkyl,
alkoxy,
alkylthio,
—NH$_2$,
—NH(alkyl), and
—N(alkyl)$_2$;
n is an integer from 0 to 4;
R$_1$' is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which R$_1$' is bonded;
R$_1$ is selected from the group consisting of:
—R$_4$,
—Y—R$_4$,
—X—R$_5$,
—X—N(R$_6$)—Y—R$_4$,
—X—C(R$_7$)—N(R$_6$)—R$_4$,
—X—O—C(R$_7$)—N(R$_6$)—R$_4$,
—X—S(O)$_2$—N(R$_6$)—R$_4$, and
—X—O—R$_4$;
or R$_1$' and R$_1$ together with the nitrogen atom to which they are bonded can join to form a group selected from the group consisting of:

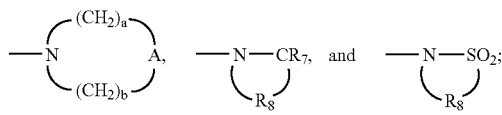

R$_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of:

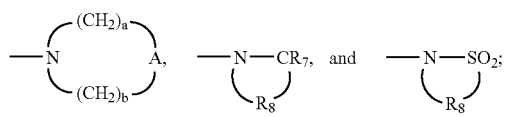

each $R_6$ is independently selected from the group consisting of hydrogen, alkyl, and arylalkylenyl;

$R_7$ is selected from the group consisting of =O and =S;

$R_8$ is $C_{2-7}$ alkylene;

A is selected from the group consisting of —CH($R_6$)—, —O—, —N($R_6$)—, —N(Y—$R_4$)—, and —N(X—N($R_6$)—Y—$R_4$)—;

X is $C_{2-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

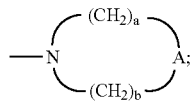

a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4; and R" is hydrogen or a non-interfering substituent;

or a pharmaceutically acceptable salt thereof.

The present invention also provides compounds of the following Formula I-1:

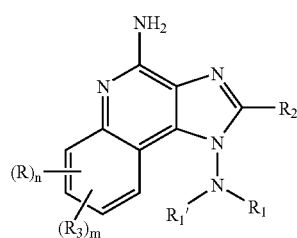

wherein:

$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;

$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—O—C($R_7$)—N($R_6$)—$R_4$,
—X—S(O)$_2$—N($R_6$)—$R_4$, and
—X—O—$R_4$;

or $R_1'$ and $R_1$ together with the nitrogen atom to which they are bonded can join to form a group selected from the group consisting of:

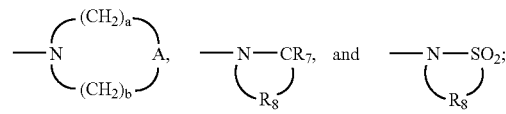

$R_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—C($R_7$)-aryl,
—N($R_6$)—S(O)$_2$—$C_{1-10}$ alkyl,
—N($R_6$)—S(O)$_2$-aryl,
—C(O)—$C_{1-10}$ alkyl,
—O—C($R_7$)—$C_{1-10}$ alkyl,
—O—C($R_7$)-aryl,
—O—C($R_7$)—N($R_6$)—$C_{1-10}$ alkyl,
—O—C($R_7$)—N($R_6$)-aryl;
—C(O)—O—$C_{1-10}$ alkyl,
—N$_3$,
aryl,
heteroaryl,
heterocyclyl,
—C(O)-aryl, and
—C(O)-heteroaryl;

$R_3$ is selected from the group consisting of:
-Z'-X'—$R_4'$,
-Z'-X'—Y'—$R_4'$, and
-Z'-X'—$R_5'$;

each R is independently selected from the group consisting of alkyl, alkenyl, alkoxy, halogen, fluoroalkyl, hydroxy, amino, alkylamino, and dialkylamino;

n is an integer from 0 to 4;

m is 0 or 1; with the proviso that when m is 1, then n is 0, 1, or 2;

R$_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the nitrogen atom to which R$_1$ is bonded;

R$_5$ is selected from the group consisting of:

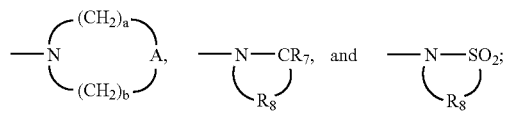

X is C$_{2-20}$ alkylene;

Y is selected from the group consisting of —C(R$_7$)—, —C(R$_7$)—O—, —S(O)$_2$—, —S(O)$_2$—N(R$_6$)—, and —C(R$_7$)—N(R$_9$)—; wherein R$_9$ is selected from the group consisting of hydrogen, alkyl, and arylalkylenyl; or R$_9$ and R$_4$ together with the nitrogen atom to which R$_9$ is bonded can join to form the group

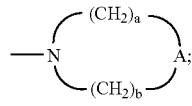

Z is selected from the group consisting of —O— and —S(O)$_{0-2}$—;

A is selected from the group consisting of —CH(R$_6$)—, —O—, —N(R$_6$)—, —N(Y—R$_4$)—, and —N(X—N(R$_6$)—Y—R$_4$)—;

a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;

R$_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$' is selected from the group consisting of:

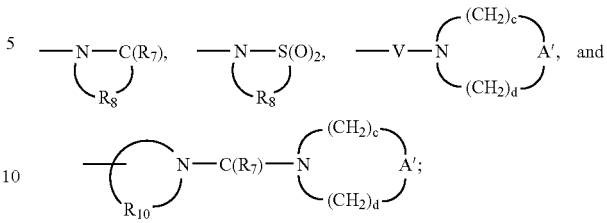

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:
—S(O)$_{0-2}$—,
—S(O)$_2$—N(R$_{11}$)—,
—C(R$_7$)—,
—C(R$_7$)—O—,
—O—C(R$_7$)—,
—O—C(O)—O—,
—N(R$_{11}$)—Q—,
—C(R$_7$)—N(R$_{11}$)—,
—O—C(R$_7$)—N(R$_{11}$)—,
—C(R$_7$)—N(OR$_{12}$)—,

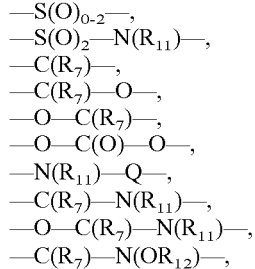

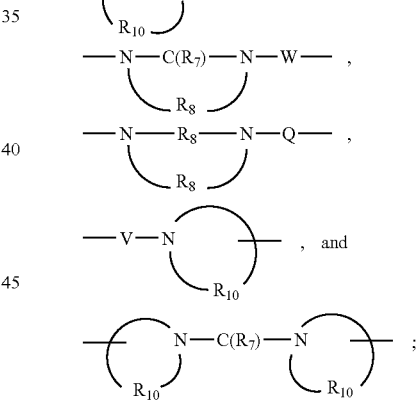

Z' is a bond or —O—;

A' is selected from the group consisting of —CH$_2$—, —O—, —C(O)—, —S(O)$_{0-2}$—, and —N(R$_4$')—;

Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;

V is selected from the group consisting of —C(R$_7$)—, —O—C(R$_7$)—, —N(R$_{11}$)—C(R$_7$)—, and —S(O)$_2$—;

W is selected from the group consisting of a bond, —C(O)—, and —S(O)$_2$—;

c and d are independently integers from 1 to 6 with the proviso that c+d is ≦7, and when A' is —O— or —N(R$_4$')— then c and d are independently integers from 2 to 4;

each R$_6$ is independently selected from the group consisting of hydrogen, alkyl, and arylalkylenyl;

each $R_7$ is independently selected from the group consisting of =O and =S;

each $R_8$ is independently $C_{2-7}$ alkylene;

$R_{10}$ is $C_{3-8}$ alkylene;

each $R_{11}$ is independently selected from the group consisting of hydrogen, $C_{1-10}$ alkyl, $C_{2-10}$ alkenyl, $C_{1-10}$ alkoxy$C_{2-10}$ alkylenyl, and aryl$C_{1-10}$ alkylenyl; and $R_{12}$ is selected from the group consisting of hydrogen and alkyl;

or a pharmaceutically acceptable salt thereof.

In some embodiments of Formula I-1, $R_1$ is selected from the group consisting of —$R_4$, —Y—$R_4$, and —X—N($R_6$)—Y—$R_4$ wherein Y is —C($R_7$)—, —S(O)$_2$—, or —C($R_7$)—N($R_9$)—.

In certain embodiments of Formula I-1, $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylcarbonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, arylaminocarbonylaminoalkylenyl, heteroarylcarbonylaminoalkylenyl, and heteroarylaminocarbonylaminoalkylenyl.

In certain embodiments of Formula I-1, $R_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein $R_{13}$ is selected from the group consisting of methylcarbonyl, isopropylcarbonyl, cyclopentylcarbonyl, tetrahydropyran-4-ylcarbonyl, methanesulfonyl, phenylsulfonyl, benzyl, ethylaminocarbonyl, isopropylaminocarbonyl, morpholine-4-carbonyl, phenylaminocarbonyl, pyridin-3-ylcarbonyl, and pyridin-3-ylaminocarbonyl.

In some embodiments of Formula I-1, $R_1'$ is hydrogen.

In some embodiments of Formula I-1, $R_1$ and $R_1'$ are each independently alkyl.

In some embodiments of Formula I-1, $R_1$ and $R_1'$ join to form the group:

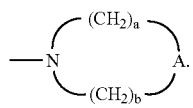

In some embodiments of Formula I-1, $R_2$ is selected from the group consisting of hydrogen, alkyl, alkoxyalkylenyl, and hydroxyalkylenyl. In certain embodiments, $R_2$ is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

In some embodiments of Formula I-1, n is 0.

In some embodiments of Formula I-1, n is 0, and $R_3$ is selected from the group consisting of -Z'-$R_4'$, -Z-X'—$R_4'$, and -Z'-X'—Y'—$R_4'$. In certain embodiments, $R_3$ is selected from the group consisting of 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy.

In one embodiment, the present invention provides compounds of the following Formula I-2:

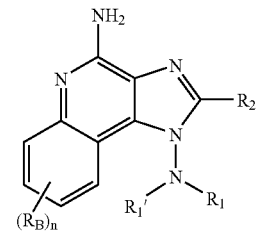

wherein:

$R_B$ is selected from the group consisting of alkyl, alkoxy, halogen, hydroxy, and trifluoromethyl;

n is an integer from 0 to 4;

$R_1'$ is selected from the group consisting of hydrogen and alkyl;

$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$, and
—X—O—$R_4$;

or $R_1'$ and $R_1$ together with the nitrogen atom to which they are bonded can join to form a group selected from the group consisting of:

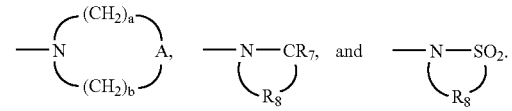

$R_2$ is selected from the group consisting of:
-hydrogen,
-alkyl,
-alkenyl,
-aryl,
-heteroaryl,
-heterocyclyl,
-alkylene-Z-alkyl,
-alkylene-Z-aryl,
-alkylene-Z-alkenyl, and
-alkyl or alkenyl substituted by one or more substituents selected from the group consisting of:
—OH,
-halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—N$_3$,
-aryl,
-heteroaryl,
-heterocyclyl,
—C(O)-aryl, and
—C(O)-heteroaryl;

R₄ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R₄ is a substituted alkyl group and the substituent contains a hetero atom which bonds directly to the alkyl group then the alkyl group contains at least two carbons between the substituent and the nitrogen atom to which R₁ is bonded;

R₅ is selected from the group consisting of:

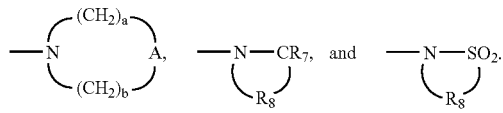

each R₆ is independently selected from the group consisting of hydrogen, alkyl, and arylalkylenyl;

each R₇ is independently selected from the group consisting of =O and =S;

R₈ is C₂₋₇ alkylene;

A is selected from the group consisting of —CH(R₆)—, —O—, —N(R₆)—, —N(Y—R₄)—, and —N(X—N(R₆)—Y—R₄)—;

X is C₂₋₂₀ alkylene;

Y is selected from the group consisting of —C(R₇)—, —C(R₇)—O—, —S(O)₂—, —S(O)₂—N(R₆)—, and —C(R₇)—N(R₉)—; wherein R₉ is selected from the group consisting of hydrogen, alkyl, and arylalkylenyl; or R₉ and R₄ together with the nitrogen atom to which R₉ is bonded can join to form the group

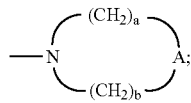

Z is selected from the group consisting of —O— and —S(O)₀₋₂—; and a and b are independently integers from 1 to 4 with the proviso that when A is —O—, —N(R₆)—, —N(Y—R₄)—, or —N(X—N(R₆)—Y—R₄)— then a and b are independently integers from 2 to 4;

or a pharmaceutically acceptable salt thereof.

In some embodiments of Formula I-2, R₁ is selected from the group consisting of —R₄, —Y—R₄, and —X—N(R₆)—Y—R₄ wherein Y is —C(R₇)—, —S(O)₂—, or —C(R₇)—N(R₉)—.

In certain embodiments of Formula I-2, R₁ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl) aminoalkylenyl, and arylaminocarbonylaminoalkylenyl.

In certain embodiments of Formula I-2, R₁ is selected from the group consisting of hydrogen, methyl, isopropyl, butyl, 2-methylpropyl, 1-ethylpropyl, 3-methylbutyl, cyclohexyl, benzyl, cinnamyl, furan-2-ylmethyl, and —CH₂CH₂CH₂—NHR₁₃, wherein R₁₃ is selected from the group consisting of methanesulfonyl, phenylsulfonyl, benzyl, and phenylaminocarbonyl.

In some embodiments of Formula I-2, R₁' is hydrogen.

In some embodiments of Formula I-2, R₁ and R₁' are each independently alkyl.

In some embodiments of Formula I-2, R₁ and R₁' join to form the group:

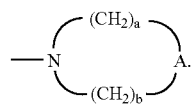

In some embodiments of Formula I-2, R₂ is selected from the group consisting of hydrogen, alkyl, and alkoxyalkylenyl, and in certain embodiments R₂ is selected from the group consisting of hydrogen, butyl, 2-methoxyethyl, and ethoxymethyl.

In some embodiments of Formula I-2, n is 0.

In some embodiments of Formula I-2, n is 1, and R_B is halogen or hydroxy.

In one embodiment, the present invention provides compounds of the following Formula I-3:

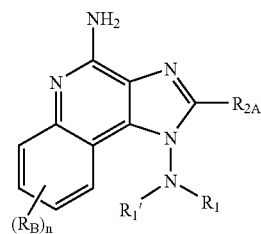

wherein:

R_B is selected from alkyl, alkoxy, halogen, hydroxy, and trifluoromethyl;

n is an integer from 0 to 4;

R₁' is selected from hydrogen and alkyl;

R₁ is selected from:
—R₄,
—Y—R₄,
—X—R₅,
—X—N(R₆)—Y—R₄,
—X—CR₇—N(R₆)—R₄, and
—X—O—R₄;

or R₁' and R₁ together with the nitrogen atom to which they are bonded can join to form a group selected from:

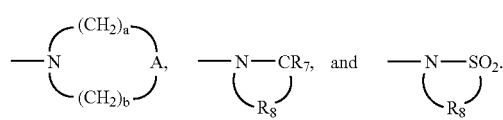

$R_{2A}$ is selected from:
- hydrogen,
- alkyl,
- alkenyl,
- aryl,
- heteroaryl,
- alkylene-Z-alkyl,
- alkylene-Z-aryl,
- alkylene-Z-alkenyl, and
- alkyl or alkenyl substituted by one or more substituents selected from:
  —OH,
  - halogen,
  —N($R_6$)$_2$,
  —$CR_7$—N($R_6$)$_2$,
  —$SO_2$—N($R_6$)$_2$,
  —N($R_6$)—$CR_7$—$C_{1-10}$ alkyl,
  —N($R_6$)—$SO_2$—$C_{1-10}$ alkyl,
  —C(O)—$C_{1-10}$ alkyl,
  —C(O)—O—$C_{1-10}$ alkyl,
  —$N_3$,
  - aryl,
  - heteroaryl,
  - heterocyclyl,
  —C(O)-aryl, and
  —C(O)-heteroaryl;

$R_4$ is selected from hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from:

—N(—(CH$_2$)$_a$—A—(CH$_2$)$_b$—),   —N(—$CR_7$—$R_8$—),   and   —N(—$SO_2$—$R_8$—).

$R_6$ is selected from hydrogen, alkyl, and arylalkylenyl;
$R_7$ is selected from =O and =S;
$R_8$ is $C_{2-7}$ alkylene;
$R_9$ is selected from hydrogen, alkyl, and arylalkylenyl, or $R_9$ and $R_4$ together with the nitrogen atom to which $R_9$ is bonded can join to form the group —N(—(CH$_2$)$_a$—A—(CH$_2$)$_b$—);

A is selected from —$CHR_6$—, —O—, —N($R_6$)—, —N(Y—$R_4$)—, and —N(X—N($R_6$)—Y—$R_4$)—;
X is $C_{2-20}$ alkylene;
Y is selected from —$CR_7$—, —$SO_2$—, —$SO_2$—N($R_6$)—, and —$CR_7$—N($R_9$)—;
Z is selected from —O— and —S(O)$_{0-2}$—;
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

and pharmaceutically acceptable salts thereof.

In some embodiments of Formula I-3, $R_1$ is selected from —$R_4$, —Y—$R_4$, and —X—N(R)—Y—$R_4$ wherein Y is —$CR_7$—, —$SO_2$—, or —$CR_7$—N($R_9$)—.

In certain embodiments of Formula I-3, $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl)aminoalkylenyl, and arylaminocarbonylaminoalkylenyl.

In certain embodiments of Formula I-3, $R_1$ is selected from hydrogen, isopropyl, butyl, cyclohexyl, benzyl, cinnamyl, and —$CH_2CH_2CH_2$—$NHR_{13}$, wherein $R_{13}$ is selected from methanesulfonyl, phenylsulfonyl, benzyl, and phenylaminocarbonyl.

In some embodiments of Formula I-3, $R_1'$ is hydrogen.

In some embodiments of Formula I-3, $R_{2A}$ is selected from hydrogen, alkyl, and alkoxyalkylenyl, and in certain embodiments $R_{2A}$ is selected from hydrogen, butyl, methoxyethyl (e.g., 2-methoxyethyl), and ethoxymethyl.

In some embodiments of Formula I-3, n is 0.

In one embodiment, the present invention provides compounds of the following Formula II-1:

II-1

[Structure: tricyclic imidazoquinoline with NH$_2$, $R_2$, $R_1'$, $R_1$, and $(R_A)_n$ substituents]

wherein:
each $R_A$ is independently selected from the group consisting of:
  halogen,
  hydroxy,
  alkyl,
  alkenyl,
  haloalkyl,
  alkoxy,
  alkylthio,
  —$NH_2$,
  —NH(alkyl), and
  —N(alkyl)$_2$;
n is an integer from 0 to 4;
$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;

$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—O—C($R_7$)—N($R_6$)—$R_4$,
—X—S(O)$_2$—N($R_6$)—$R_4$, and
—X——$R_4$;

or $R_1'$ and $R_1$ together with the nitrogen atom to which they are bonded can join to form a group selected from the group consisting of:

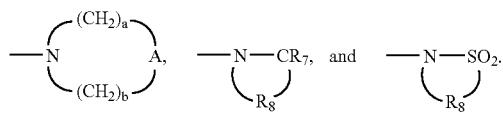

$R_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—C($R_7$)-aryl,
—N($R_6$)—S(O)$_2$—$C_{1-10}$ alkyl,
—N($R_6$)—S(O)$_2$-aryl,
—C(O)—$C_{1-10}$ alkyl,
—O—C($R_7$)—$C_{1-10}$ alkyl,
—O—C($R_7$)-aryl,
—O—C($R_7$)—N($R_6$)—$C_{1-10}$ alkyl,
—O—C($R_7$)—N($R_6$)-aryl;
—C(O)—O—$C_{1-10}$ alkyl,
—$N_3$,
aryl,
heteroaryl,
heterocyclyl,
—C(O)-aryl, and
—C(O)-heteroaryl;

$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of:

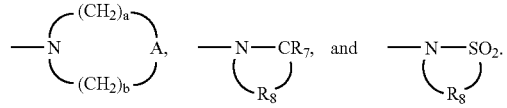

each $R_6$ is independently selected from the group consisting of hydrogen, alkyl, and arylalkylenyl;

each $R_7$ is independently selected from the group consisting of =O and =S;

$R_8$ is $C_{2-7}$ alkylene;

A is selected from the group consisting of —CH($R_6$)—, —O—, —N($R_6$)—, —N(Y—$R_4$)—, and —N(X—N($R_6$)—Y—$R_4$)—;

X is $C_{2-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

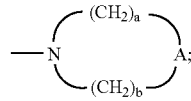

Z is selected from the group consisting of —O— and —S(O)$_{0-2}$—; and a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

or a pharmaceutically acceptable salt thereof.

In some embodiments of Formula II-1, $R_1$ is selected from the group consisting of —$R_4$, —Y—$R_4$, and —X—N($R_6$)—Y—$R_4$ wherein Y is —C($R_7$)—, —S(O)$_2$—, or —C($R_7$)—N($R_9$)—.

In certain embodiments of Formula II-1, $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl) aminoalkylenyl, and arylaminocarbonylaminoalkylenyl.

In certain embodiments of Formula II-1, $R_1$ is selected from the group consisting of hydrogen, methyl, isopropyl, butyl, 2-methylpropyl, 1-ethylpropyl, 3-methylbutyl, cyclohexyl, benzyl, cinnamyl, furan-2-ylmethyl, and —CH$_2$CH$_2$CH$_2$—NHR$_{13}$, wherein $R_{13}$ is selected from the group consisting of methanesulfonyl, phenylsulfonyl, benzyl, and phenylaminocarbonyl.

In certain embodiments of Formula II-1, $R_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein $R_{13}$ is selected from the group consisting of methanesulfonyl, phenylsulfonyl, benzyl, isopropylaminocarbonyl, and phenylaminocarbonyl.

In certain embodiments of Formula II-1, $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylcarbonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, arylaminocarbonylaminoalkylenyl, heteroarylcarbonylaminoalkylenyl, and heteroarylaminocarbonylaminoalkylenyl.

For certain embodiments of Formula II-1, $R_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —$CH_2CH_2CH_2$—$NHR_{13}$, wherein $R_{13}$ is selected from the group consisting of methylcarbonyl, isopropylcarbonyl, cyclopentylcarbonyl, tetrahydropyran-4-ylcarbonyl, methanesulfonyl, phenylsulfonyl, benzyl, ethylaminocarbonyl, isopropylaminocarbonyl, morpholine-4-carbonyl, phenylaminocarbonyl, pyridin-3-ylcarbonyl, and pyridin-3-ylaminocarbonyl.

In some embodiments of Formula II-1, $R_1'$ is hydrogen.

In some embodiments of Formula II-1, $R_1$ and $R_1'$ are each independently alkyl.

In some embodiments of Formula II-1, $R_1$ and $R_1'$ join to form the group:

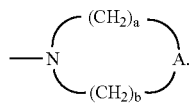

In some embodiments of Formula II-1, $R_2$ is selected from the group consisting of hydrogen, alkyl, and alkoxyalkylenyl, in certain embodiments $R_2$ is selected from the group consisting of hydrogen, butyl, 2-methoxyethyl, and ethoxymethyl, and in certain embodiments $R_2$ is selected from the group consisting of hydrogen, methyl, propyl, butyl, 2-methoxyethyl, and ethoxymethyl.

In some embodiments of Formula II-1, $R_2$ is selected from the group consisting of hydrogen, alkyl, alkoxyalkylenyl, and hydroxyalkylenyl.

In some embodiments of Formula II-1, $R_2$ is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

In some embodiments of Formula II-1, n is 0.

The present invention also provides compounds that are useful as intermediates in the synthesis of compounds of Formula I, I-1, I-2, I-3, II, and/or II-1. These intermediate compounds have the structural Formulas VII, IX, X, XLII, and XLIII described below.

In one embodiment, the present invention provides compounds of the following Formula VII:

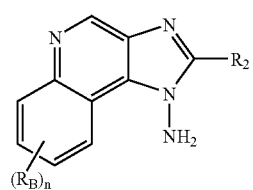

VII wherein:
each $R_B$ is independently selected from the group consisting of alkyl, alkoxy, halogen, hydroxy, and trifluoromethyl;
n is an integer from 0 to 4;
$R_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—$N(R_6)_2$,
—$C(R_7)$—$N(R_6)_2$,
—$S(O)_2$—$N(R_6)_2$,
—$N(R_6)$—$C(R_7)$—$C_{1-10}$ alkyl,
—$N(R_6)$—$C(R_7)$-aryl,
—$N(R_6)$—$S(O)_2$—$C_{1-10}$ alkyl,
—$N(R_6)$—$S(O)_2$-aryl,
—$C(O)$—$C_{1-10}$ alkyl,
—O—$C(R_7)$—$C_{1-10}$ alkyl,
—O—$C(R_7)$-aryl,
—O—$C(R_7)$—$N(R_6)$—$C_{1-10}$ alkyl,
—O—$C(R_7)$—$N(R_6)$-aryl;
—$C(O)$—O—$C_{1-10}$ alkyl,
—$N_3$,
aryl,
heteroaryl,
heterocyclyl,
—C(O)-aryl, and
—C(O)-heteroaryl;
each $R_6$ is independently selected from the group consisting of hydrogen, alkyl, and arylalkylenyl;
$R_7$ is selected from the group consisting of =O and =S; and
Z is selected from the group consisting of —O— and —$S(O)_{0-2}$—;

or a pharmaceutically acceptable salt thereof.

The present invention also provides intermediate compounds of the following Formula IX:

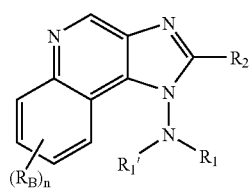

IX wherein:
each $R_B$ is independently selected from the group consisting of alkyl, alkoxy, halogen, hydroxy, and trifluoromethyl;
n is an integer from 0 to 4;
$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;

$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—O—C($R_7$)—N($R_6$)—$R_4$,
—X—S(O)$_2$—N($R_6$)—$R_4$, and
—X—O—$R_4$;

or $R_1'$ and $R_1$ together with the nitrogen atom to which they are bonded can join to form a group selected from the group consisting of:

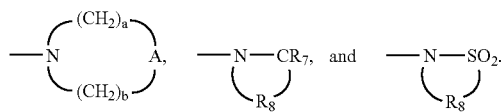

$R_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—C($R_7$)-aryl,
—N($R_6$)—S(O)$_2$—$C_{1-10}$ alkyl,
—N($R_6$)—S(O)$_2$-aryl,
—C(O)—$C_{1-10}$ alkyl,
—O—C($R_7$)—$C_{1-10}$ alkyl,
—O—C($R_7$)-aryl,
—O—C($R_7$)—N($R_6$)—$C_{1-10}$ alkyl,
—O—C($R_7$)—N($R_6$)-aryl;
—C(O)—O—$C_{1-10}$ alkyl,
—$N_3$,
aryl,
heteroaryl,
heterocyclyl,
—C(O)-aryl, and
—C(O)-heteroaryl;

$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of

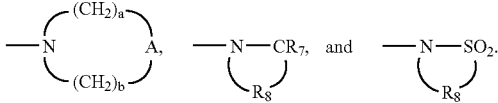

each $R_6$ is independently selected from the group consisting of hydrogen, alkyl, and arylalkylenyl;

each $R_7$ is independently selected from the group consisting of =O and =S;

$R_8$ is $C_{2-7}$ alkylene;

A is selected from the group consisting of —CH($R_7$)—, —O—, —N($R_6$)—, —N(Y—$R_4$)—, and —N(X—N($R_6$)—Y—$R_4$)—;

X is $C_{2-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

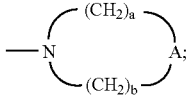

Z is selected from the group consisting of —O— and —S(O)$_{0-2}$—; and a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

or a pharmaceutically acceptable salt thereof.

The present invention also provides intermediate compounds of the following Formula X:

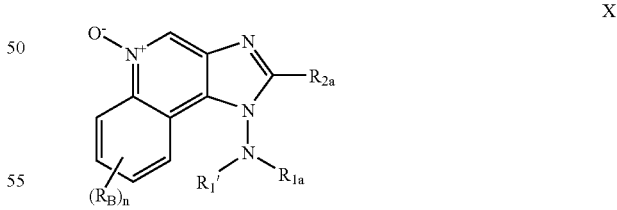

X wherein:

each $R_B$ is independently selected from the group consisting of alkyl, alkoxy, halogen, hydroxy, and trifluoromethyl;

n is an integer from 0 to 4;

$R_1'$ is hydrogen or alkyl;

$R_{1a}$ is selected from the group consisting of:
—$R_{4a}$,
—Y—$R_{4a}$,

—X—R$_5$,
—X—N(R$_6$)Y-R$_{4a}$,
—X—C(R$_7$)—N(R$_6$)—R$_{4a}$, and
—X—O—R$_{4a}$;
or R$_1$' and R$_{1a}$ together with the nitrogen atom to which they are bonded can join to form a group selected from the group consisting of:

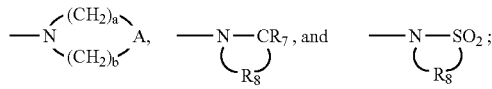

R$_{2a}$ is selected from the group consisting of:
-hydrogen,
-alkyl,
-alkenyl,
-aryl,
-alkylene-Z"-alkyl,
-alkylene-Z"-aryl,
-alkylene-Z"-alkenyl, and
-alkyl or alkenyl substituted by one or more substituents selected from the group consisting of:
—OH,
-halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—S(O)$_2$—C$_{1-10}$ alkyl,
—C(O)—C$_{1-10}$ alkyl,
—C(O)—O—C$_{1-10}$ alkyl,
—N$_3$,
-aryl,
-heterocyclyl, and
—C(O)-aryl;

R$_{4a}$ is selected from the group consisting of hydrogen, alkyl, alkenyl, alkynyl, aryl, and heterocyclyl wherein the alkyl, alkenyl, alkynyl, aryl, and heterocyclyl groups can be unsubstituted or substituted by one or more substituents independently selected from the group consisting of alkyl, alkoxy, haloalkyl, haloalkoxy, halogen, nitro, hydroxy, cyano, carboxy, formyl, aryl, aryloxy, arylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_{4a}$ is a substituted alkyl group and the substituent contains a hetero atom which bonds directly to the alkyl group then the alkyl group contains at least two carbons between the substituent and the nitrogen atom to which R$_1$ is bonded;

R$_5$ is selected from the group consisting of

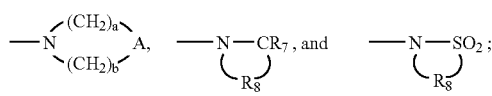

each R$_6$ is independently selected from the group consisting of hydrogen, alkyl, and arylalkylenyl;
each R$_7$ is independently selected from the group consisting of =O and =S;
R$_8$ is C$_{2-7}$ alkylene;

A is selected from the group consisting of —CH(R$_6$)—, —O—, —N(R$_6$)—, —N(Y—R$_4$)—, and —N(X—N(R$_6$)—Y—R$_4$)—;
X is C$_{2-20}$ alkylene;
Y is selected from the group consisting of —C(R$_7$)—, —C(R$_7$)—O—, —S(O)$_2$—, —S(O)$_2$—N(R$_6$)—, and —C(R$_7$)—N(R$_9$)—; wherein R$_9$ is selected from the group consisting of hydrogen, alkyl and arylalkylenyl, or R$_9$ and R$_4$ together with the nitrogen atom to which R$_9$ is bonded can join to form the group

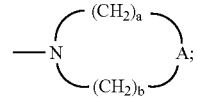

Z" is selected from the group consisting of —O— and —S(O)$_2$—; and
a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;
or a pharmaceutically acceptable salt thereof.

The present invention also provides intermediate compounds of the following Formula XLII:

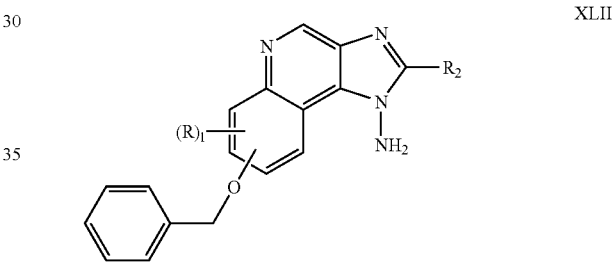

XLII wherein:
R is selected from the group consisting of alkyl, alkenyl, alkoxy, halogen, fluoroalkyl, hydroxy, amino, alkylamino, and dialkylamino;
l is 0, 1, or 2;
R$_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—C(R$_7$)-aryl,
—N(R$_6$)—S(O)$_2$—C$_{1-10}$ alkyl,
—N(R$_6$)—S(O)$_2$-aryl, —C(O)—C$_{1-10}$ alkyl,
—O—C(R$_7$)—C$_{1-10}$ alkyl,
—O—C(R$_7$)-aryl,
—O—C(R$_7$)—N(R$_6$)—C$_{1-10}$ alkyl,
—O—C(R$_7$)—N(R$_6$)-aryl;
—C(O)—O—C$_{1-10}$ alkyl,
—N$_3$,
aryl,
heteroaryl,
heterocyclyl,
—C(O)-aryl, and
—C(O)-heteroaryl;

each R$_6$ is independently selected from the group consisting of hydrogen, alkyl, and arylalkylenyl;

R$_7$ is selected from the group consisting of =O and =S; and

Z is selected from the group consisting of —O— and —S(O)$_{0-2}$—;

or a pharmaceutically acceptable salt thereof.

The present invention also provides intermediate compounds of the following Formula XLIII:

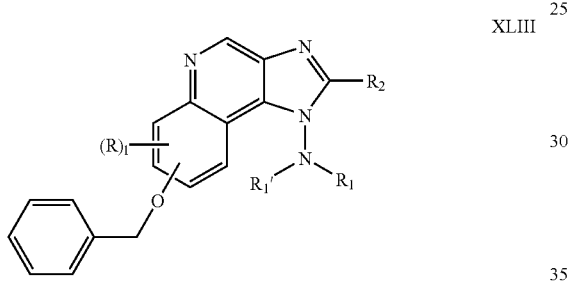

XLIII wherein:

R is selected from the group consisting of alkyl, alkenyl, alkoxy, halogen, fluoroalkyl, hydroxy, amino, alkylamino, and dialkylamino;

l is 0, 1 or 2;

R$_1$' is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which R$_1$' is bonded;

R$_1$ is selected from the group consisting of:
—R$_4$,
—Y—R$_4$,
—X—R$_5$,
—X—N(R$_6$)—Y—R$_4$,
—X—C(R$_7$)—N(R$_6$)—R$_4$,
—X—O—C(R$_7$)—N(R$_6$)—R$_4$,
—X—S(O)$_2$—N(R$_6$)—R$_4$, and
—X—O—R$_4$;

or R$_1$' and R$_1$ together with the nitrogen atom to which they are bonded can join to form a group selected from the group consisting of:

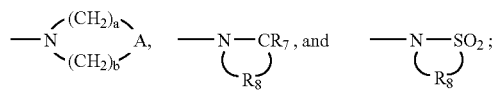

R$_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—C(R$_7$)-aryl,
—N(R$_6$)—S(O)$_2$—C$_{1-10}$ alkyl,
—N(R$_6$)—S(O)$_2$-aryl,
—C(O)—C$_{1-10}$ alkyl,
—O—C(R$_7$)—C$_{1-10}$ alkyl,
—O—C(R$_7$)-aryl,
—O—C(R$_7$)—N(R$_6$)—C$_{1-10}$ alkyl,
—O—C(R$_7$)—N(R$_6$)-aryl;
—C(O)—O—C$_{1-10}$ alkyl,
—N$_3$,
aryl,
heteroaryl,
heterocyclyl,
—C(O)-aryl, and
—C(O)-heteroaryl;

R$_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the nitrogen atom to which R$_1$ is bonded;

R$_5$ is selected from the group consisting of

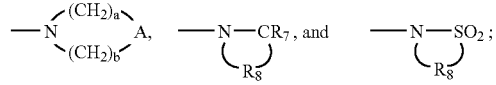

each R$_6$ is independently selected from the group consisting of hydrogen, alkyl, and arylalkylenyl;

each R$_7$ is independently selected from the group consisting of =O and =S;

R$_8$ is C$_{2-7}$ alkylene;

A is selected from the group consisting of —CH(R$_6$)—, —O—, —N(R$_6$)—, —N(Y—R$_4$)—, and —N(X—N(R$_6$)—Y—R$_4$)—;

X is $C_{2-20}$ alkylene;

Y is selected from the group consisting of —C(R$_7$)—, —C(R$_7$)—O—, —S(O)$_2$—, —S(O)$_2$—N(R$_6$)—, and —C(R$_7$)—N(R$_9$)—; wherein R$_9$ is selected from the group consisting of hydrogen, alkyl, and arylalkylenyl; or R$_9$ and R$_4$ together with the nitrogen atom to which R$_9$ is bonded can join to form the group

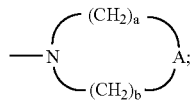

Z is selected from the group consisting of —O— and —S(O)$_{0-2}$—; and a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;

or a pharmaceutically acceptable salt thereof.

For any of the compounds presented herein, each one of the following variables (e.g., R, R'', R''', R$_1$', R$_1$, R$_2$, R$_{2A}$, R$_3$, R$_4$, R$_B$, m, n, A, X, X', Y, Y', and so on) in any of its embodiments can be combined with any one or more of the other variables in any of their embodiments as would be understood by one of skill in the art. Each of the resulting combinations of variables is an embodiment of the present invention.

For certain embodiments, each of R'' and R''' is independently a non-interfering substituent. For certain embodiments, R'' is selected from the group consisting of hydrogen and non-interfering substituents. Herein, "non-interfering" means that the ability of the compound or salt to modulate (e.g., induce or inhibit) the biosynthesis of one or more cytokines is not destroyed by the non-interfering substitutent. Illustrative non-interfering Rat groups include those described above for R$_2$ in Formulas I-1, I-2, and II-1, and for R$_{2A}$ in Formula I-3. Illustrative non-interfering R''' groups include those described above for R and R$_3$ in Formula I-1, and for R$_B$ in Formulas I-2 and I-3.

For certain embodiments, R is selected from the group consisting of alkyl, alkenyl, alkoxy, halogen, fluoroalkyl, hydroxy, amino, alkylamino, and dialkylamino. For certain embodiments, R is halogen or hydroxy.

For certain embodiments, R$_4$ is selected from the group consisting of halogen, hydroxy, alkyl, alkenyl, haloalkyl, alkoxy, alkylthio, —NH$_2$, —NH(alkyl), and —N(alkyl)$_2$.

For certain embodiments, R$_B$ is selected from the group consisting of alkyl, alkoxy, halogen, hydroxyl, and trifluoromethyl. For certain embodiments, R$_B$ is halogen or hydroxy.

For certain embodiments, R$_1$' is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which R$_1$' is bonded. For certain embodiments, R$_1$' is selected from the group consisting of: hydrogen and alkyl. For certain embodiments, R$_1$' is hydrogen.

For certain embodiments, R$_1$ and R$_1$' are each independently alkyl.

For certain embodiments, R$_1$' and R$_1$ together with the nitrogen atom to which they are bonded can join to form a group selected from the group consisting of:

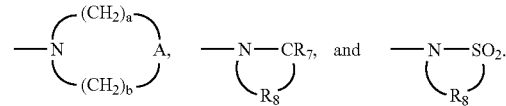

For certain embodiments, R$_1$ and R$_1$' join to form the group:

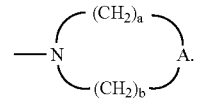

For certain embodiments, R$_1$ is selected from the group consisting of —R$_4$, —Y—R$_4$, —X—R$_5$, —X—N(R$_6$)—Y—R$_4$, —X—C(R$_7$)—N(R$_6$)—R$_4$, —X—O—C(R$_7$)—N(R$_6$)—R$_4$, —X—S(O)$_2$—N(R$_6$)—R$_4$, and —X—O—R$_4$.

For certain embodiments, R$_1$ is selected from the group consisting of —R$_4$, —Y—R$_4$, —X—R$_5$, —X—N(R$_6$)—Y—R$_4$, —X—C(R$_7$)—N(R$_6$)—R$_4$, and —X—O—R$_4$; and R$_1$' is selected from the group consisting of hydrogen and alkyl.

For certain embodiments, R$_1$ is selected from the group consisting of —R$_4$, —Y—R$_4$, —X—R$_5$, —X—N(R$_6$)—Y—R$_4$, —X—C(R$_7$)—N(R$_6$)—R$_4$, and —X—O—R$_4$.

For certain embodiments, R$_1$ is selected from the group consisting of —R$_4$, —Y—R$_4$, and —X—N(R$_6$)—Y—R$_4$ wherein Y is —C(R$_7$)—, —S(O)$_2$—, or —C(R$_7$)—N(R$_9$)—.

For certain embodiments, R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl)aminoalkylenyl, and arylaminocarbonylaminoalkylenyl.

For certain embodiments, R$_1$ is selected from the group consisting of hydrogen, methyl, isopropyl, butyl, 2-methylpropyl, 1-ethylpropyl, 3-methylbutyl, cyclohexyl, benzyl, cinnamyl, furan-2-ylmethyl, and —CH$_2$CH$_2$CH$_2$—NHR$_{13}$, wherein R$_{13}$ is selected from the group consisting of methanesulfonyl, phenylsulfonyl, benzyl, and phenylaminocarbonyl.

For certain embodiments, R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, and arylaminocarbonylaminoalkylenyl.

For certain embodiments, R$_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein R$_{13}$ is selected from the group consisting of methanesulfonyl, phenylsulfonyl, benzyl, isopropylaminocarbonyl, morpholine-4-carbonyl, and phenylaminocarbonyl.

For certain embodiments, R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylcarbonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, arylaminocarbonylaminoalkylenyl, heteroarylcarbonylaminoalkylenyl, and heteroarylaminocarbonylaminoalkylenyl.

For certain embodiments, $R_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —$CH_2CH_2CH_2$—$NHR_{13}$, wherein $R_{13}$ is selected from the group consisting of methylcarbonyl, isopropylcarbonyl, cyclopentylcarbonyl, tetrahydropyran-4-ylcarbonyl, methanesulfonyl, phenylsulfonyl, benzyl, ethylaminocarbonyl, isopropylaminocarbonyl, morpholine-4-carbonyl, phenylaminocarbonyl, pyridin-3-ylcarbonyl, and pyridin-3-ylaminocarbonyl.

For certain embodiments, $R_1$ is selected from the group consisting of —$R_4$, —Y—$R_4$, —X'—$R_5$, —X—N($R_6$)—Y—$R_4$, —X—C($R_7$)—N($R_6$)—$R_4$, and —X—O—$R_4$; $R_1{}'$ is selected from the group consisting of hydrogen and alkyl; and $R_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and -alkyl or alkenyl substituted by one or more substituents selected from the group consisting of —OH, halogen, —N($R_6$)$_2$, —C($R_7$)—N($R_6$)$_2$, —S(O)$_2$—N($R_6$)$_2$, —N($R_6$)—C($R_7$)—$C_{1-10}$ alkyl, —N($R_6$)—S(O)$_2$—$C_{1-10}$ alkyl, —C(O)—$C_{1-10}$ alkyl, —C(O)—O—$C_{1-10}$ alkyl, —$N_3$, aryl, heteroaryl, heterocyclyl, —C(O)-aryl, and —C(O)-heteroaryl.

For certain embodiments, R" is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of —OH, halogen, —N($R_6$)$_2$, —C($R_7$)—N($R_6$)$_2$, —S(O)$_2$—N($R_6$)$_2$, —N($R_6$)—C($R_7$)—$C_{1-10}$ alkyl, —N($R_6$)—C($R_7$)-aryl, —N($R_6$)—S(O)$_2$—$C_{1-10}$ alkyl, —N($R_6$)—S(O)$_2$-aryl, —C(O)-$C_{1-10}$ alkyl, —O—C($R_7$)—$C_{1-10}$ alkyl, —O—C($R_7$)-aryl, —O—C($R_7$)—N($R_6$)—$C_{1-10}$ alkyl, —O—C($R_7$)—N($R_6$)-aryl; —C(O)—O—$C_{1-10}$ alkyl, —$N_3$, aryl, heteroaryl, heterocyclyl, —C(O)-aryl, and —C(O)-heteroaryl.

For certain embodiments, R" is selected from the group consisting of hydrogen, alkyl, alkoxyalkylenyl, and hydroxyalkylenyl. For certain embodiments, R" is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

For certain embodiments, $R_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of —OH, halogen, —N($R_6$)$_2$, —C($R_7$)—N($R_6$)$_2$, —S(O)$_2$—N($R_6$)$_2$, —N(R)—C($R_7$)—$C_{1-10}$ alkyl, —N($R_6$)—C($R_7$)-aryl, —N($R_6$)—S(O)$_2$—$C_{1-10}$ alkyl, —N($R_6$)—S(O)$_2$-aryl, —C(O)—$C_{1-10}$ alkyl, —O—C($R_7$)—$C_{1-10}$ alkyl, —O—C($R_7$)-aryl, —O—C($R_7$)—N($R_6$)—$C_{1-10}$ alkyl, —O—C($R_7$)—N($R_6$)-aryl; —C(O)—O—$C_{1-10}$ alkyl, —$N_3$, aryl, heteroaryl, heterocyclyl, —C(O)-aryl, and —C(O)-heteroaryl.

For certain embodiments, $R_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and -alkyl or alkenyl substituted by one or more substituents selected from the group consisting of —OH, halogen, —N($R_6$)$_2$, —C($R_7$)—N($R_6$)$_2$, —S(O)$_2$—N($R_6$)$_2$, —N($R_6$)—C($R_7$)—$C_{1-10}$ alkyl, —N($R_6$)—S(O)$_2$—$C_{1-10}$ alkyl, —C(O)—$C_{1-10}$ alkyl, —C(O)—O—$C_{1-10}$ alkyl, —$N_3$, aryl, heteroaryl, heterocyclyl, —C(O)-aryl, and —C(O)-heteroaryl.

For certain embodiments, $R_2$ is selected from the group consisting of hydrogen, alkyl, and alkoxyalkylenyl. For certain embodiments, $R_2$ is selected from the group consisting of hydrogen, butyl, 2-methoxyethyl, and ethoxymethyl. For certain embodiments, $R_2$ is selected from the group consisting of hydrogen, methyl, propyl, butyl, 2-methoxyethyl, and ethoxymethyl.

For certain embodiments, $R_2$ is selected from the group consisting of hydrogen, alkyl, alkoxyalkylenyl, and hydroxyalkylenyl. For certain embodiments, $R_2$ is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

For certain embodiments, $R_{2A}$ is selected from hydrogen, alkyl, alkenyl, aryl, heteroaryl, -alkylene-Z-alkyl, -alkylene-Z-aryl, -alkylene-Z-alkenyl, and alkyl or alkenyl substituted by one or more substituents selected from —OH, halogen, —N($R_6$)$_2$, —$CR_7$—N($R_6$)$_2$, —SO$_2$—N($R_6$)$_2$, —N($R_6$)—$CR_7$—$C_{1-10}$ alkyl, —N($R_6$)—SO$_2$—$C_{1-10}$ alkyl, —C(O)—$C_{1-10}$ alkyl, —C(O)—O—$C_{1-10}$ alkyl, —$N_3$, aryl, heteroaryl, heterocyclyl, —C(O)-aryl, and —C(O)-heteroaryl. For certain embodiments, $R_{2A}$ is selected from hydrogen, alkyl, and alkoxyalkylenyl. For certain embodiments, $R_{2A}$ is selected from hydrogen, butyl, methoxyethyl, and ethoxymethyl.

For certain embodiments, $R_3$ is selected from the group consisting of -Z'-$R_4$', -Z'-X'—$R_4$', -Z'-X'—Y'—$R_4$', and -Z'-X'—$R_5$'. For certain embodiments, $R_3$ is selected from the group consisting of -Z'-$R_4$', -Z'-X'—$R_4$', and -Z'-X'—Y'—$R_4$'.

For certain embodiments, $R_3$ is selected from the group consisting of hydroxyl, 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy. For certain embodiments, $R_3$ is selected from the group consisting of 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy. For certain embodiments, $R_3$ is selected from the group consisting of 2-(pyridin-3-yl)ethyl,pyridinyl, (hydroxymethyl)pyridinyl, ethoxyphenyl, (morpholine4-carbonyl)phenyl, 2-(methanesulfonylamino)ethoxy, and benzyloxy.

For certain embodiments, R''' is R or $R_3$ when n is 1, R or one R and one $R_3$ when n is 2, R or two R's and one $R_3$ when n is 3, or R when n is 4. For certain embodiments, R''' is R or $R_3$ when n is 1, R or one R and one $R_3$ when n is 2, or R when n is 3 or 4.

For certain embodiments, R''' is $R_3$. For certain of these embodiments, $R_3$ is selected from the group consisting of -Z'-$R_4$', -Z'-X'—$R_4$', and -Z'-X'—Y'—R'.

For certain embodiments, R''' is selected from the group consisting of 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, and benzyloxy.

For certain embodiments, R''' is selected from the group consisting of hydroxyl, 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy. For certain embodiments, R''' is selected from the group consisting of 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy. For certain embodiments, R''' is selected from the group consisting of 2-(pyridin-3-yl)ethyl, pyridinyl, (hydroxymethyl)pyridinyl, ethoxyphenyl, (morpholine-4-carbonyl)phenyl, 2-(methanesulfonylamino)ethoxy, and benzyloxy.

For certain embodiments, $R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl) amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded.

For certain embodiments, $R_4$ is selected from the group consisting of $C_{1-6}$ alkyl, arylalkylenyl, and heterocyclyl. For certain embodiments, $R_4$ is $C_{2-6}$ alkyl.

For certain embodiments, $R_4'$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. For certain embodiments, $R_4'$ is hydrogen, alkyl, aryl, arylalkylenyl, heteroaryl, or heteroarylalkylenyl wherein the aryl and heteroaryl groups are unsubstituted or substituted by one or more of hydroxyalkyl or alkoxy.

For certain embodiments, $R_5$ is selected from the group consisting of:

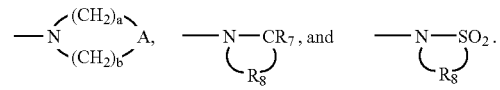

For certain embodiments, $R_5'$ is selected from the group consisting of:

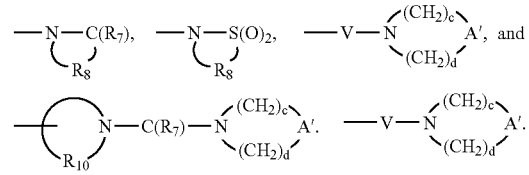

For certain embodiments, $R_5'$ is

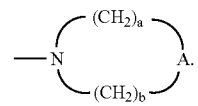

In certain of these embodiments, V is —C(O)—. In certain of these embodiments, A' is —O— and c and d are each the integer 2.

For certain embodiments, $R_6$ is selected from the group consisting of hydrogen, alkyl, and arylalkylenyl. For certain embodiments, $R_6$ is hydrogen.

For certain embodiments, $R_7$ is selected from the group consisting of =O and =S.

For certain embodiments, $R_7$ is =O.

For certain embodiments, $R_8$ is $C_{2-7}$ alkylene.

For certain embodiments, $R_9$ is selected from the group consisting of hydrogen, alkyl, and arylalkylenyl; or $R_9$ and $R_4$ together with the nitrogen atom to which $R_9$ is bonded can join to form the group

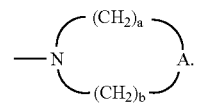

For certain embodiments, $R_9$ is hydrogen.

For certain embodiments, $R_9$ and $R_4$ together with the nitrogen atom to which $R_9$ is bonded join to form the group

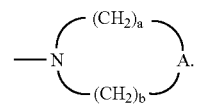

For certain of these embodiments, A is —O—. For certain of these embodiments, a and b are each the integer 2.

For certain embodiments, $R_{10}$ is $C_{3-8}$ alkylene.

For certain embodiments, $R_{11}$ is selected from the group consisting of hydrogen, $C_{1-10}$ alkyl, $C_{2-10}$ alkenyl, $C_{1-10}$ alkoxy$C_{2-10}$ alkylenyl, and aryl$C_{1-10}$ alkylenyl. For certain embodiments, $R_{11}$ is hydrogen.

For certain embodiments, $R_{12}$ is selected from the group consisting of hydrogen and alkyl.

For certain embodiments, A is selected from the group consisting of —CH($R_6$)—, —O—, —N($R_6$)—, —N(Y—$R_4$)—, and —N(X—N($R_6$)—Y—$R_4$)—.

For certain embodiments, A' is selected from the group consisting of —CH$_2$—, —O—, —C(O)—, —S(O)$_{0-2}$—, and —N($R_4$')'. For certain embodiments, A' is —O—.

For certain embodiments, Q is selected from the group consisting of a bond, —C($R_7$)—, —C($R_7$)—C($R_7$)—, —S(O)$_2$—, —C($R_7$)—N($_{11}$)—W—, —S(O)$_2$—N($R_{11}$)—, —C($R_7$)—O—, and —C($R_7$)—N(O$R_{12}$)—. For certain embodiments, Q is —S(O)$_2$—.

For certain embodiments, V is selected from the group consisting of —C($R_7$)—, —O—C($R_7$)—, —N($R_{11}$)—C($R_7$)—, and —S(O)$_2$—. For certain embodiments, V is —C($R_7$)—.

For certain embodiments, W is selected from the group consisting of a bond, —C(O)—, and —S(O)$_2$—.

For certain embodiments, X is $C_{2-20}$ alkylene. For certain embodiments, X is $C_{2-4}$ alkylene.

For certain embodiments, X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups. For certain embodiments, X' is $C_{14}$ alkylene.

For certain embodiments, Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

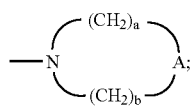

wherein a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4. For certain embodiments, Y is selected from —C($R_7$)—, —S(O)$_2$—, —S(O)$_2$—N($R_6$)—, and —C($R_7$)—N($R_9$)—. For certain embodiments, Y is —C($R_7$)—, —S(O)$_2$—, and —C($R_7$)—N($R_9$)—.

For certain embodiments, Y' is selected from the group consisting of —S(O)$_{0-2}$—, —S(O)$_2$—N($R_{11}$)—, —C($R_7$)—, —C($R_7$)—O—, —O—C($R_7$)—, —O—C(O)—O—, —N($R_{11}$)—Q—, —C($R_7$)—N($R_{11}$)—, —O—C($R_7$)—N($R_{11}$)—, —C($R_7$)—N(O$R_{12}$)—,

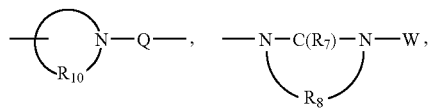

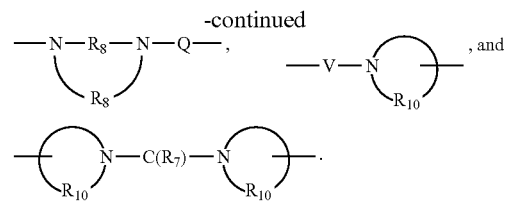

For certain embodiments, Y' is —S(O)$_2$—N($R_{11}$)— or —C($R_7$)—. For certain of these embodiments, $R_{11}$ is hydrogen, and $R_7$ is =O.

For certain embodiments, Z is selected from the group consisting of —O— and —S(O)$_{0-2}$—. For certain embodiments, Z is —O—.

For certain embodiments, Z' is a bond or —O—. For certain embodiments, Z' is a bond. For certain embodiments, Z' is —O—.

For certain embodiments, a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4. For certain embodiments, a and b are each the integer 2.

For certain embodiments, c and d are independently integers from 1 to 6 with the proviso that c+d is ≦7, and when A' is —O— or —N($R_4$')— then c and d are independently integers from 2 to 4. For certain embodiments, c and d are each the integer 2.

For certain embodiments, n is an integer from 0 to 4. For certain embodiments, n is 0. For certain embodiments, n is 1.

For certain embodiments, n is 1, and $R_B$ is halogen or hydroxy.

For certain embodiments, m is 0 or 1; with the proviso that when m is 1, then n is 0, 1, or 2. For certain embodiments, m is 0 or 1, and n is 0 or 1. For certain m is 1 and n is 0. For certain embodiments, m is 0, and n is 0.

For certain embodiments, m is 0 and n is 1. For certain of these embodiments, R is halogen or hydroxy.

For certain embodiments, 1 is 0, 1, or 2. For some embodiments, 1 is 0 or 1.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene", "heteroarylene", and "heterocyclylene" are the divalent forms of the "aryl", "heteroaryl", and "heterocyclyl" groups defined above. The terms "arylenyl," "heteroarylenyl," and "heterocyclylenyl" are used when "arylene", "heteroarylene", and "heterocyclylene", respectively, are substituted. For example, an alkylarylenyl group comprises an arylene moiety to which an alkyl group is attached.

The term "acyl" includes alkylcarbonyl and arylcarbonyl groups. In certain embodiments, "acyl" is alkanoyl or benzoyl.

When a group (or substituent or variable) is present more than once in any Formula described herein, each group (or substituent or variable) is independently selected, whether explicitly stated or not. For example, for the formula —N($R_6$)$_2$ each $R_6$ group is independently selected. In another example, when an $R_1$ and an $R_2$ group both contain an $R_7$ group, each $R_7$ group is independently selected. In a further example, when more than one

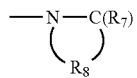

group is present (i.e., $R_5$ and $R_5$' both contain a

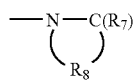

group) each $R_8$ group is independently selected and each $R_7$ group is independently selected.

The invention is inclusive of the compounds described herein and salts thereof in any of their pharmaceutically acceptable forms, including isomers such as diastereomers and enantiomers, solvates, polymorphs, and the like. In particular, if a compound is optically active, the invention specifically includes each of the compound's enantiomers as well as racemic mixtures of the enantiomers.

Preparation of the Compounds

Compounds of the invention can be prepared according to Reaction Scheme I wherein R, $R_{1a}$, $R_{2a}$, and n are as defined above.

In step (1) of Reaction Scheme I, a 4-chloro-3-nitroquinoline of Formula III is reacted with tert-butyl carbazate or an alternate carbazate to provide a carbazate compound of Formula IV. The reaction can be carried out by adding tert-butyl carbazate to a solution of a compound of Formula III in a suitable solvent such as anhydrous dichloromethane in the presence of a base such as triethylamine. The reaction can be run at ambient temperature. The product or a pharmaceutically acceptable salt thereof can be isolated by conventional methods. Many compounds of Formula III are known or can be prepared using known synthetic methods, see for example, U.S. Pat. Nos. 4,689,338; 5,175,296; 5,367,076; and 5,389,640; and the documents cited therein. Tertiary-butyl carbazate is commercially available (for example, from Aldrich, Milwaukee, Wis.). Many alternate carbazate reagents (for example, benzyl carbazate) may be prepared using known synthetic methods.

In step (2) of Reaction Scheme I a carbazate compound of Formula IV is reduced to provide a compound of Formula V. The reduction can be carried out using a conventional heterogeneous hydrogenation catalyst such as platinum on carbon or palladium on carbon. For some compounds of Formula IV, for example, compounds in which R is halogen, a platinum catalyst is preferred. The reaction can be conveniently carried out on a Parr apparatus in a suitable solvent such as toluene and/or isopropanol. The product or a pharmaceutically acceptable salt thereof can be isolated by conventional methods.

Other reduction processes may be used for the reduction in step (2). For example, an aqueous solution of sodium dithionite can be added to a solution or suspension of the compound of Formula IV in a suitable solvent such as ethanol or isopropanol. The reaction can be carried out at an elevated temperature, for example at reflux, or at ambient temperature.

In step (3) of Reaction Scheme I a compound of Formula V is (i) reacted with an acyl halide of Formula $R_{2a}$C(O)Cl or $R_{2a}$C(O)Br and then (ii) cyclized to provide a 1H-imidazo compound of Formula VI. In part (i) the acyl halide is added to a solution of a compound of Formula V in a suitable solvent such as anhydrous dichloromethane in the presence of a base such as triethylamine. The reaction can be run at a reduced temperature, for example, 0° C., or at ambient temperature. In part (ii) the product of part (i) is heated in an alcoholic solvent in the presence of a base. For example, the product of part (i) is refluxed in ethanol in the presence of excess triethylamine or is heated with methanolic ammonia.

Alternatively, step (3) can be carried out by reacting a compound of Formula V with a carboxylic acid or an equivalent thereof. Suitable equivalents to carboxylic acid include orthoesters and 1,1-dialkoxyalkyl alkanoates. The carboxylic acid or equivalent is selected such that it will provide the desired $R_{2a}$ substituent in a compound of Formula VI. For example, triethyl orthoformate will provide a compound where $R_{2a}$ is hydrogen, and triethyl orthovalerate will provide a compound where $R_{2a}$ is butyl. The reaction can be run in the absence of solvent or in an inert solvent such as anhydrous toluene. The reaction is run with sufficient heating to drive off any alcohol or water formed as a byproduct of the reaction. Optionally a catalyst such as pyridine hydrochloride can be included. The product or a pharmaceutically acceptable salt thereof can be isolated by conventional methods.

In step (4) of Reaction Scheme I, the tert-butoxycarbonyl or alternate oxycarbonyl group is removed from a 1H-imidazo compound of Formula VI by hydrolysis under acidic conditions to provide a 1H-imidazo[4,5-c]quinolin-1-amine of Formula VIIa or a salt (for example, hydrochloride salt) thereof. For example, a compound of Formula VI is dissolved in 1.5M HCl in ethanol and heated to reflux. The product or a pharmaceutically acceptable salt thereof can be isolated by conventional methods.

In step (5a) of Reaction Scheme I, a 1H-imidazo[4,5-c]quinolin-1-amine of Formula VIIa or a salt thereof is treated with a ketone, aldehyde, or corresponding ketal or acetal thereof, under acidic conditions to provide a compound of Formula VIII. For example, a ketone is added to a solution of the hydrochloride salt of a compound of Formula VIIa in a suitable solvent such as isopropanol in the presence of an acid or acid resin, for example, DOWEX W50-X1 acid resin. The ketone, aldehyde, or corresponding ketal or acetal thereof, is selected with $R_i$ and $R_{ii}$ groups that will provide the desired $R_{1a}$ substituent in a 1H-imidazo[4,5-c]quinolin-1-amine compound of Formula IXa. For example, acetone will provide a compound where $R_{1a}$ is isopropyl, and benzaldehyde will provide a compound where $R_{1a}$ is benzyl. The reaction is run with sufficient heating to drive off the water formed as a byproduct of the reaction. The product or a pharmaceutically acceptable salt thereof can be isolated by conventional methods.

In step (6) of Reaction Scheme I, a compound of Formula VIII is reduced to provide a 1H-imidazo[4,5-c]quinolin-1-amine compound of Formula IXa. The reaction can be carried out by adding sodium borohydride to a solution of a compound of Formula VIII in a suitable solvent, for example, methanol. The reaction can be run at ambient temperature. The product or a pharmaceutically acceptable salt thereof can be isolated by conventional methods.

Alternatively, in step (5b) of Reaction Scheme I, a 1H-imidazo[4,5-c]quinolin-1-amine of Formula VIIa can be treated with a ketone and a borohydride under acidic conditions to provide a 1H-imidazo[4,5-c]quinolin-1-amine compound of Formula IXa. For example, the hydrochloride salt of a 1H-imidazo[4,5-c]quinolin-1-amine of Formula VIIa, dissolved in a suitable solvent such as 1,2-dichloroethane, can be treated with a ketone and sodium triacetoxyborohydride at room temperature. The product or a pharmaceutically acceptable salt thereof can be isolated by conventional methods.

In step (7) of Reaction Scheme I, a 1H-imidazo[4,5-c]quinolin-1-amine compound of Formula IXa is oxidized to provide an N-oxide of Formula Xa using a conventional oxidizing agent that is capable of forming N-oxides. The reaction is carried out by treating a solution of a compound of Formula IXa in a suitable solvent such as chloroform or dichloromethane with 3-chloroperoxybenzoic acid at ambient temperature. The product or a pharmaceutically acceptable salt thereof can be isolated by conventional methods.

In step (8) of Reaction Scheme I, an N-oxide of Formula Xa is aminated to provide a 1H-imidazo[4,5-c]quinoline-1,4-diamine of the Formula Ia, which is a subgenus of compounds of the Formulas I, I-1, I-2, and I-3. The reaction is carried out in two parts. In part (i) a compound of Formula Xa is reacted with an acylating agent. Suitable acylating agents include alkyl- or arylsulfonyl chorides (e.g., benzenesulfonyl choride, methanesulfonyl choride, and p-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula Xa in a suitable solvent such as dichloromethane, adding ammonium hydroxide to the solution, and then adding p-toluenesulfonyl chloride. The product or a pharmaceutically acceptable salt thereof can be isolated using conventional methods.

Alternatively, the oxidation of step (7) and the amination of step (8) can be carried out sequentially without isolating the product of the oxidation to provide a 1H-imidazo[4,5-c]quinoline-1,4-diamine of the Formula Ia. In step (7), after the 1H-imidazo[4,5-c]quinolin-1-amine compound of Formula IXa is consumed by reaction with 3-chloroperoxybenzoic acid as described in step (7), the aminating and acylating agents are added to the reaction mixture as in step (8). The product or a pharmaceutically acceptable salt thereof can be isolated using conventional methods.

Reaction Scheme I

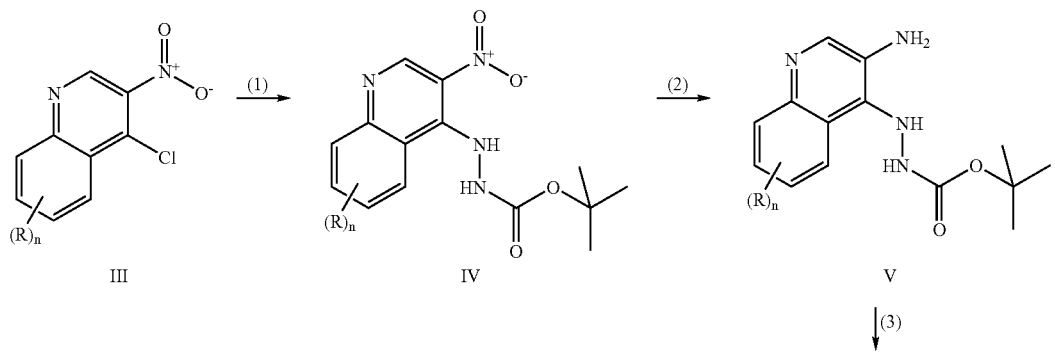

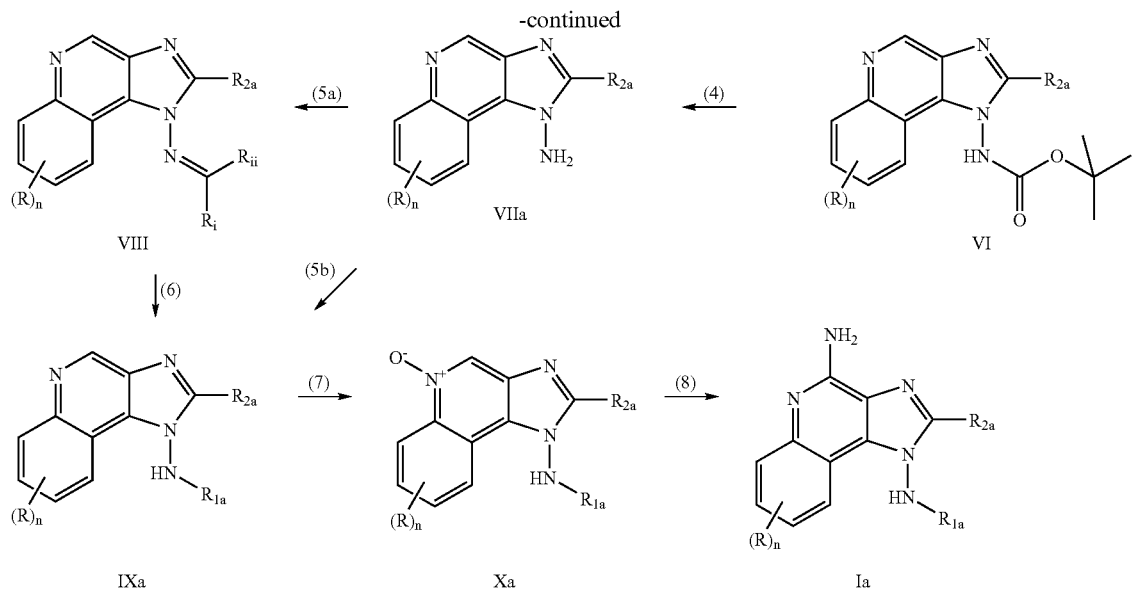

Compounds of the invention can be prepared according to Reaction Scheme II wherein R, $R_1$, $R_{2a}$ and n are as defined above.

In step (1) of Reaction Scheme II, a 1H-imidazo compound of Formula VI is oxidized to provide an N-oxide of Formula XI using the method of step (7) in Reaction Scheme I. The product or a pharmaceutically acceptable salt thereof can be isolated by conventional methods.

In step (2) of Reaction Scheme II, an N-oxide of Formula XI is aminated using the method of step (8) in Reaction Scheme I to provide a 4-amino compound of the Formula XIIa. The product or a pharmaceutically acceptable salt thereof can be isolated using conventional methods.

In step (3) of Reaction Scheme II, the tert-butoxycarbonyl or alternate oxycarbonyl group is removed from a 4-amino compound of the Formula XIIa using the method of step (4) in Reaction Scheme I to provide a 1H-imidazo[4,5-c]quinoline-1,4-diamine of Formula XIIIa or a salt (for example, hydrochloride salt) thereof. The product or a pharmaceutically acceptable salt thereof can be isolated by conventional methods.

In step (4a) of Reaction Scheme II, a 1H-imidazo[4,5-c]quinoline-1,4-diamine of Formula XIIIa is treated with a ketone, aldehyde, or corresponding ketal or acetal thereof, using the method of step (5a) in Reaction Scheme I to provide a compound of Formula XIVa. The ketone, aldehyde, or corresponding ketal or acetal thereof, is selected with $R_i$ and $R_{ii}$ groups that will provide the desired $R_1$ substituent in a 1H-imidazo[4,5-c]quinoline-1,4-diamine compound of Formula Ib. The product or a pharmaceutically acceptable salt thereof can be isolated by conventional methods.

In step (5) of Reaction Scheme II, a compound of Formula XIVa is reduced to provide a 1H-imidazo[4,5-c]quinolin-1-amine compound of Formula Ib using the method of step (6) in Reaction Scheme I. The product or a pharmaceutically acceptable salt thereof can be isolated by conventional methods.

Alternatively, in step (4b) of Reaction Scheme II, a 1H-imidazo[4,5-c]quinoline-1,4-diamine of Formula XIIIa can be treated with a ketone and a borohydride using the method of step (5b) of Reaction Scheme I to provide a 1H-imidazo[4,5-c]quinolin-1-amine compound of Formula Ib, which is a subgenus of compounds of the Formulas I, I-1, I-2, and I-3. The product or a pharmaceutically acceptable salt thereof can be isolated by conventional methods.

Reaction Scheme II

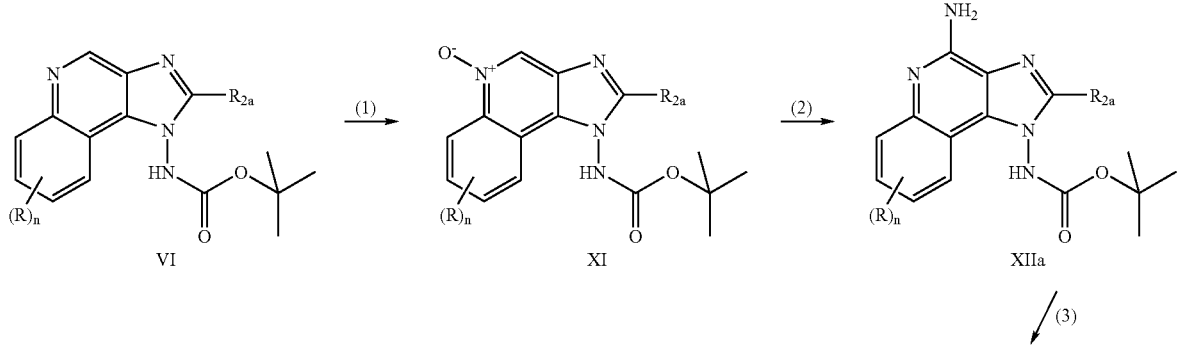

-continued

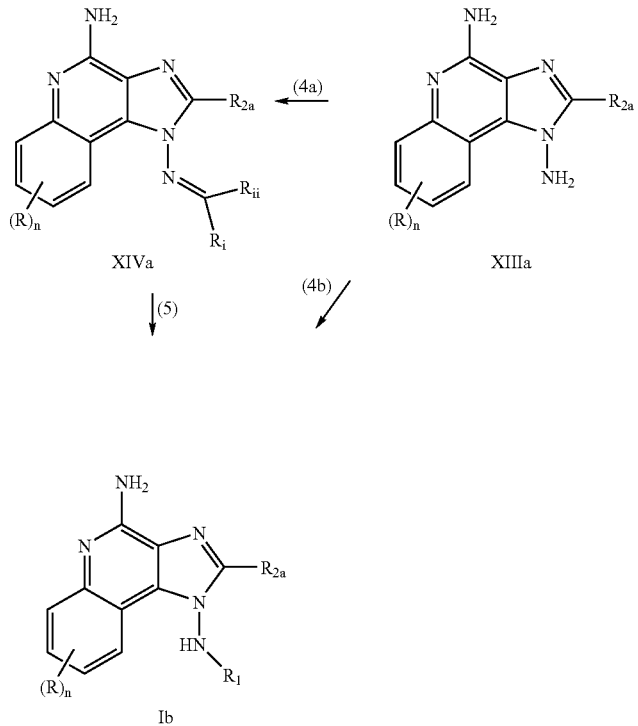

Compounds of the invention can be prepared according to Reaction Scheme III wherein R, $R_1'$, $R_{1a}$, $R_{2a}$, and n are as defined above.

In step (1) of Reaction Scheme III, a 4-chloro-3-nitroquinoline of Formula III is reacted with a hydrazino compound of Formula XVa to provide a compound of Formula XVI. The reaction can be carried out by adding the hydrazino compound of Formula XVa to a solution of a compound of Formula III in a suitable solvent such as anhydrous dichloromethane in the presence of a base such as triethylamine. The reaction can be run at ambient temperature. The product or a pharmaceutically acceptable salt thereof can be isolated by conventional methods. Many hydrazino compounds of Formula XVa are commercially available; others can be readily prepared using known synthetic methods.

In step (2) of Reaction Scheme III, a compound of Formula XVI is reduced to provide a compound of Formula XVII using the methods of step (2) in Reaction Scheme I. The product or a pharmaceutically acceptable salt thereof can be isolated by conventional methods.

In step (3) of Reaction Scheme III, a compound of formula XVII is cyclized using the methods of step (3) in Reaction Scheme I to provide a 1H-imidazo[4,5-c]quinolin-1-amine compound of Formula IXb. The product of step (i) (described in step (3) of Reaction Scheme I) can be isolated to provide a compound of the following formula:

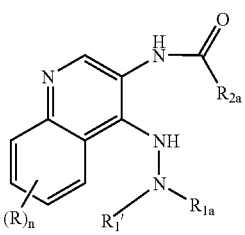

In part (ii) the product of part (i) can be refluxed in suitable solvent such as toluene in the presence of pyridine hydrochloride. The product or a pharmaceutically acceptable salt thereof can be isolated by conventional methods.

In step (4) of Reaction Scheme III, a 1H-imidazo[4,5-c]quinolin-1-amine compound of Formula IXb is oxidized to provide an N-oxide of Formula X using the method of step (7) in Reaction Scheme I. The product or a pharmaceutically acceptable salt thereof can be isolated by conventional methods.

In step (5) of Reaction Scheme III, an N-oxide of Formula X is aminated using the method of step (8) in Reaction Scheme I to provide a 1H-imidazo[4,5-c]quinoline-1,4-diamine of the Formula Ic, which is a subgenus of compounds of the Formulas I, I-1, I-2, and I-3. The product or a pharmaceutically acceptable salt thereof can be isolated using conventional methods.

Alternatively, the oxidation of step (4) and the amination of step (5) can be carried out sequentially without isolating the product of the oxidation to provide a 1H-imidazo[4,5-c]quinoline-1,4-diamine of the Formula Ic. In step (4), after the 1H-imidazo[4,5-c]quinolin-1-amine compound of Formula IXb is consumed by reaction with 3-chloroperoxybenzoic acid as described in step (4), the aminating and acylating agents are added to the reaction mixture as in step (5). The product or a pharmaceutically acceptable salt thereof can be isolated using conventional methods.

selected such that it provides the desired $R_2$ substituent in compounds of Formula XXI. The product or a pharmaceutically acceptable salt thereof can be isolated by conventional methods.

In step (4) of Reaction Scheme IV, the tert-butoxycarbonyl or alternate oxycarbonyl group is removed from a 4-chloro-1H-imidazo[4,5-c]quinoline of Formula XXI using the method of step (4) of Reaction Scheme I to provide a

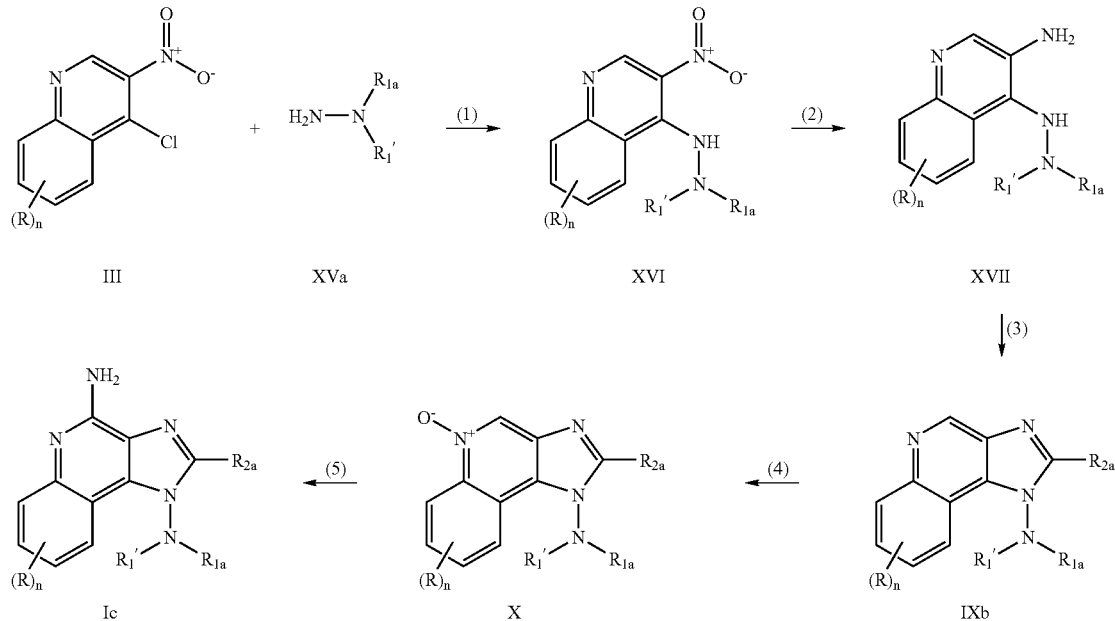

Reaction Scheme III

Compounds of the invention can be prepared according to Reaction Scheme IV wherein R, $R_1$, $R_2$ and n are as defined above.

In step (1) of Reaction Scheme IV, a 2,4-dichloro-3-nitroquinoline of Formula XVIII is reacted with tert-butyl carbazate or an alternate carbazate to provide a carbazate compound of Formula XIX. The reaction can be carried out by adding tert-butyl carbazate or an alternate carbazate to a solution of a 2,4-dichloro-3-nitroquinoline of Formula XVIII in a suitable solvent such as anhydrous dichloromethane in the presence of a base such as triethylamine. The reaction can be run at ambient temperature. The product or a pharmaceutically acceptable salt thereof can be isolated by conventional methods. Many quinolines of Formula XVIII are known or can be prepared using known synthetic methods (see for example, Andre et al., U.S. Pat. No. 4,988,815 and references cited therein).

In step (2) of Reaction Scheme IV, a carbazate compound of Formula XIX is reduced to provide a 2-chloroquinolin-3-amine of Formula XX using the method of step (2) in Reaction Scheme I. The product or a pharmaceutically acceptable salt thereof can be isolated by conventional methods.

In step (3) of Reaction Scheme IV, a 2-chloroquinolin-3-amine of Formula XX is reacted with an acyl halide of formula $R_2C(O)Cl$ or $R_2C(O)Br$, or a carboxylic acid or equivalent thereof, using the methods of step (3) in Reaction Scheme I to provide a 4-chloro-1H-imidazo[4,5-c]quinoline of Formula XXI. The carboxylic acid or equivalent is 4-chloro-1H-imidazo[4,5-c]quinolin-1-amine of Formula XXII or a salt thereof. The product or a pharmaceutically acceptable salt thereof can be isolated by conventional methods.

In step (5a) of Reaction Scheme IV, a 4-chloro-1H-imidazo[4,5-c]quinolin-1-amine of Formula XXII or a salt thereof is treated with a ketone, aldehyde, or corresponding ketal or acetal using the method of step (5a) of Reaction Scheme I to provide a compound of Formula XXIII. The ketone, aldehyde, or corresponding ketal or acetal thereof, is selected with $R_i$ and $R_{ij}$ groups that will provide the desired $R_1$ substituent in a 4-chloro-1H-imidazo[4,5-c]quinolin-1-amine compound of Formula XXIVa. The product or a pharmaceutically acceptable salt thereof can be isolated by conventional methods.

In step (6) of Reaction Scheme IV, a compound of Formula XXIII is reduced using the method of step (6) in Reaction Scheme I to provide a 4-chloro-1H-imidazo[4,5-c]quinolin-1-amine compound of Formula XXIVa. The product or a pharmaceutically acceptable salt thereof can be isolated by conventional methods.

Alternatively, in step (5b) of Reaction Scheme IV, a 4-chloro-1H-imidazo[4,5-c]quinolin-1-amine of Formula XXII can be treated with a ketone and a borohydride using the method of step (5b) in Reaction Scheme I to provide a 4-chloro-1H-imidazo[4,5-c]quinolin-1-amine compound of Formula XXIVa. The product or a pharmaceutically acceptable salt thereof can be isolated by conventional methods.

In step (7) of Reaction Scheme IV, a 4-chloro-1H-imidazo[4,5-c]quinolin-1-amine of Formula XXIVa is aminated to provide a 1H-imidazo[4,5-c]quinoline-1,4-diamine of Formula Id, which is a subgenus of compounds of the Formulas I, I-1, I-2, and I-3. The reaction is carried out by heating (e.g., 125–175° C.) a compound of Formula XXIVa under pressure in a sealed reactor in the presence of a solution of ammonia in an alkanol. The product or a pharmaceutically acceptable salt thereof can be isolated using conventional methods.

product or a pharmaceutically acceptable salt thereof can be isolated by conventional methods.

In step (3a) of Reaction Scheme V, a 1H-imidazo[4,5-c]quinoline-1,4-diamine of Formula XIII or a salt thereof is treated with a ketone, aldehyde, or corresponding ketal or acetal using the method of step (5a) of Reaction Scheme I to provide a compound of Formula XIV. The ketone, aldehyde, or corresponding ketal or acetal thereof, is selected with $R_i$ and $R_{ii}$ groups that will provide the desired $R_1$ substituent in a 1H-imidazo[4,5-c]quinoline-1,4-diamine compound of

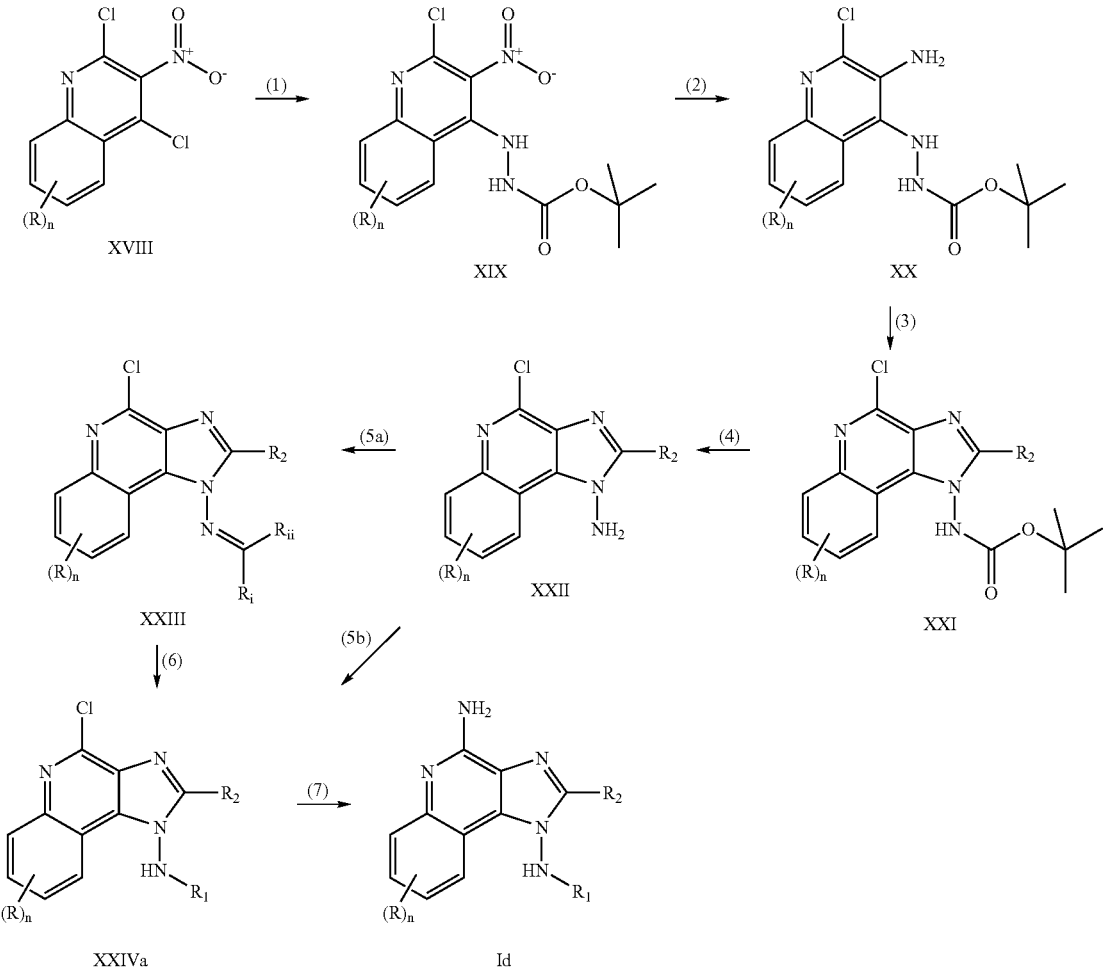

Reaction Scheme IV

Compounds of the invention can be prepared according to Reaction Scheme V wherein R, $R_1$, $R_2$ and n are as defined above.

In step (1) of Reaction Scheme V, a 4-chloro-1H-imidazo[4,5-c]quinoline of Formula XXI is aminated, using the method of step (7) in Reaction Scheme IV, to provide a 4-amino compound of the Formula XII. The product or a pharmaceutically acceptable salt thereof can be isolated by conventional methods.

In step (2) of Reaction Scheme V, the tert-butoxycarbonyl or alternate oxycarbonyl group is removed from a 4-amino compound of the Formula XII using the method of step (4) of Reaction Scheme I to provide a 1H-imidazo[4,5-c]quinoline-1,4-diamine of Formula XIII or a salt thereof. The Formula Id. The product or a pharmaceutically acceptable salt thereof can be isolated by conventional methods.

In step (4) of Reaction Scheme V, a compound of Formula XIV is reduced using the method of step (6) in Reaction Scheme I to provide a 1H-imidazo[4,5-c]quinoline-1,4-diamine compound of Formula Id, which is a subgenus of compounds of the Formulas I, I-1, I-2, and I-3. The product or a pharmaceutically acceptable salt thereof can be isolated by conventional methods.

Alternatively, in step (3b) of Reaction Scheme V, a 1H-imidazo[4,5-c]quinoline-1,4-diamine of Formula XIII or a salt thereof can be treated with a ketone and a borohydride using the method of step (5b) in Reaction Scheme I to provide a 1H-imidazo[4,5-c]quinoline-1,4-diamine compound of Formula Id. The product or a pharmaceutically acceptable salt thereof can be isolated by conventional methods.

Reaction Scheme V

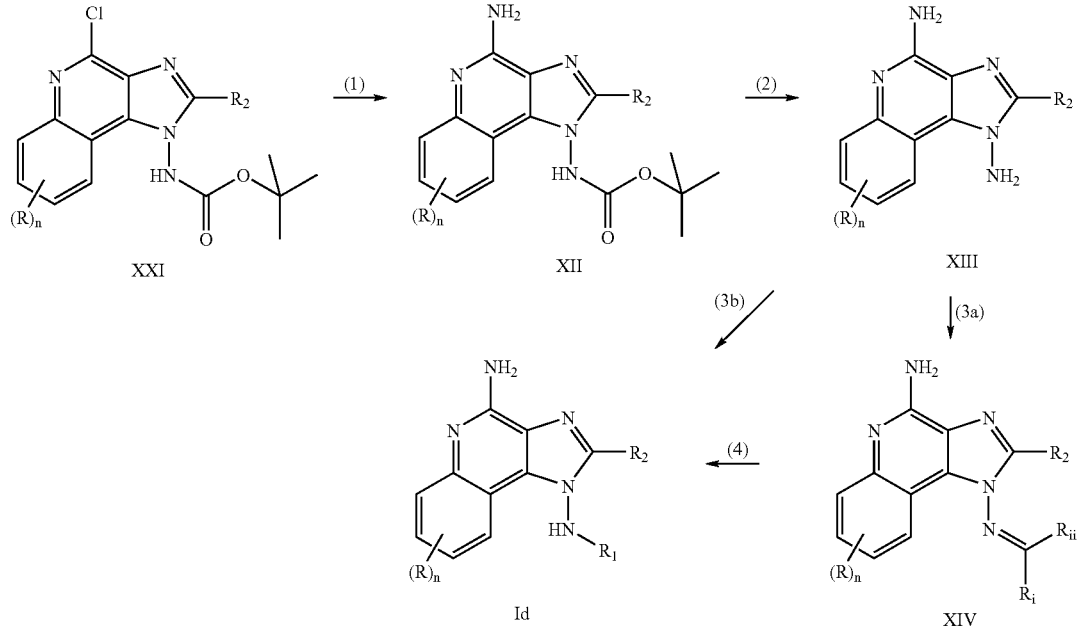

Compounds of the invention can also be prepared according to Reaction Scheme VI wherein R, $R_1'$, $R_1$, $R_2$ and n are as defined above.

In step (1) of Reaction Scheme VI, a 2,4-dichloro-3-nitroquinoline of Formula XVIII is reacted with a hydrazino compound of Formula XV, using the method of step (1) in Reaction Scheme III, to provide a compound of Formula XXV. The product or a pharmaceutically acceptable salt thereof can be isolated by conventional methods.

In step (2) of Reaction Scheme VI, a compound of Formula XXV is reduced using the method of step (2) in Reaction Scheme I to provide a compound of Formula XXVI. The product or a pharmaceutically acceptable salt thereof can be isolated by conventional methods.

In step (3) of Reaction Scheme VI, a compound of Formula XXVI is reacted with an acyl halide of formula $R_2C(O)Cl$ or $R_2C(O)Br$, or a carboxylic acid or equivalent thereof using the methods of step (3) in Reaction Scheme I to provide a 4-chloro-1H-imidazo[4,5-c]quinolin-1-amine compound of Formula XXIV. The carboxylic acid or equivalent is selected such that it provides the desired $R_2$ substituent in a compound of Formula XXIV. The product or a pharmaceutically acceptable salt thereof can be isolated by conventional methods.

In step (4) of Reaction Scheme VI, a 4-chloro-1H-imidazo[4,5-c]quinolin-1-amine compound of Formula XXIV is aminated using the method of step (7) in Reaction Scheme IV to provide a 1H-imidazo[4,5-c]quinoline-1,4-diamine of Formula Ie, which is a subgenus of compounds of the Formulas I, I-1, I-2, and I-3. The product or a pharmaceutically acceptable salt thereof can be isolated by conventional methods.

Reaction Scheme VI

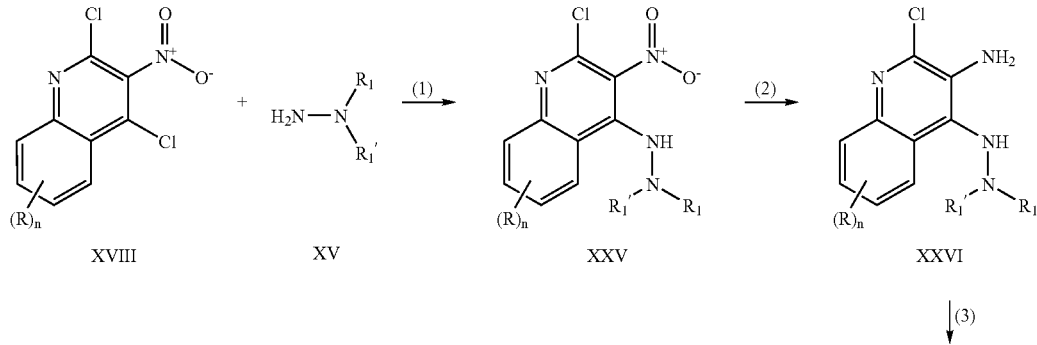

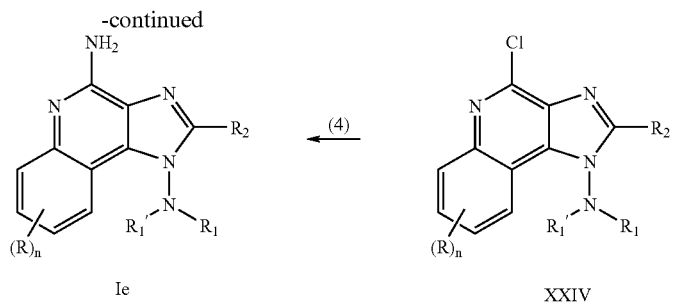

Compounds of the invention can be prepared according to Reaction Scheme VII wherein R $R_1$', $R_{2a}$, $R_4$, n, and Y are as defined above, and $X_a$ is $C_{1-20}$ alkylene.

In step (1) of Reaction Scheme VII, a 1H-imidazo[4,5-c] quinolin-1-amine of Formula VIIa or a salt thereof is treated with a ketal or acetal, containing a protected amino group, using the method of step (5a) of Reaction Scheme I to provide a compound of Formula XXVII. The product or a pharmaceutically acceptable salt thereof can be isolated by conventional methods.

The amino ketal or acetal is selected with $R_1$' and X groups that will provide the desired $R_1$' and X groups in a 1H-imidazo[4,5-c]quinolin-1,4-diamine of Formula XXX, XXXI, or XXXII, which are subgenera of compounds of the Formulas I, I-1, I-2, and I-3. For example, tert-butyl (3,3-diethoxypropyl)carbamate will provide a compound where $R_1$' is hydrogen and X is ethylene. The amino group of an amino ketal or acetal can be protected with a tert-butoxycarbonyl or an alternate oxycarbonyl group. For example, 1-amino-3,3-diethoxypropane can be reacted with di-tert-butyl dicarbonate in a suitable solvent such as tetrahydrofuran (THF) in the presence of triethylamine to provide tert-butyl (3,3-diethoxypropyl)carbamate.

In step (2) of Reaction Scheme VII, a compound of Formula XXVII is reduced using the method of step (6) in Reaction Scheme I to provide a compound of Formula XXVIII, which is a subgenus of compounds of the Formula IX. The product or a pharmaceutically acceptable salt thereof can be isolated by conventional methods.

In step (3) of Reaction Scheme VII, a compound of Formula XXVIII is oxidized to provide an N-oxide of Formula XXIX using the method of step (7) in Reaction Scheme I. The product or a pharmaceutically acceptable salt thereof can be isolated by conventional methods.

In step (4) of Reaction Scheme VII, an N-oxide of Formula XXIX is aminated using the method of step (8) in Reaction Scheme I to provide a 1H-imidazo[4,5-c]quinoline-1,4-diamine of the Formula XXX, which is a subgenus of compounds of the Formulas I, I-1, I-2, and I-3. The product or a pharmaceutically acceptable salt thereof can be isolated using conventional methods.

In step (5) of Reaction Scheme VII, a the tert-butoxycarbonyl or alternate oxycarbonyl group is removed from a 1H-imidazo[4,5-c]quinoline-1,4-diamine of the Formula XXX using the method of step (4) of Reaction Scheme I to provide a 1H-imidazo[4,5-c]quinoline-1,4-diamine of the Formula XXXI, which is a subgenus of compounds of the Formulas I, I-1, I-2, and I-3. The product or a pharmaceutically acceptable salt thereof can be isolated by conventional methods.

In step (6) of Reaction Scheme VII, a 1H-imidazo[4,5-c] quinoline-1,4-diamine of the Formula XXXI is converted to a 1H-imidazo[4,5-c]quinoline-1,4-diamine of Formula XXXII using conventional methods. For example, a 1H-imidazo[4,5-c]quinoline-1,4-diamine of the Formula XXXI can react with an acid chloride of Formula $R_4C(O)Cl$ to provide a compound of Formula XXXII in which Y is —C(O)—. In addition, a 1H-imidazo[4,5-c]quinoline-1,4-diamine of the Formula XXXI can react with sulfonyl chloride of Formula $R_4S(O)_2Cl$ or a sulfonic anhydride of Formula $(R_4S(O)_2)_2O$ to provide a compound of Formula XXXII in which Y is —$S(O)_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction can be conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a cooled solution of a 1H-imidazo [4,5-c]quinoline-1,4-diamine of the Formula XXXI and a base such as triethylamine in a suitable solvent such as chloroform, dichloromethane, or acetonitrile. The reaction can be carried out at ambient temperature or at a sub-ambient temperature such as 0° C. The product or pharmaceutically acceptable salt thereof can be isolated using conventional methods.

Ureas of Formula XXXII, where Y is —$C(R_7)$—$N(R_9)$—, in which $R_7$ is =O, and $R_9$ is as defined above, can be prepared by reacting a 1H-imidazo[4,5-c]quinoline-1,4-diamine of the Formula XXXI with isocyanates of Formula $R_4N$=C=O. Numerous isocyanates of Formula $R_4N$=C=O are commercially available; others can be readily prepared using known synthetic methods. The reaction can be conveniently carried out by adding the isocyanate of Formula $R_4N$=C=O to a cooled solution of a 1H-imidazo[4,5-c]quinoline-1,4-diamine of the Formula XXXI in a suitable solvent such as dichloromethane or chloroform. The reaction can be carried out at ambient temperature or at a sub-ambient temperature such as 0° C. Alternatively, a compound of Formula XXXI can be treated with a thioisocyanate of Formula $R_4N$=C=S, or a carbamoyl chloride of Formula $R_4N(R_9)$—$C(O)Cl$ to provide a compound of Formula XXXII, where Y is —C(S)—N ($R_9$)—, in which $R_9$, is as defined above. The product or pharmaceutically acceptable salt thereof can be isolated using conventional methods.

Reaction Scheme VII

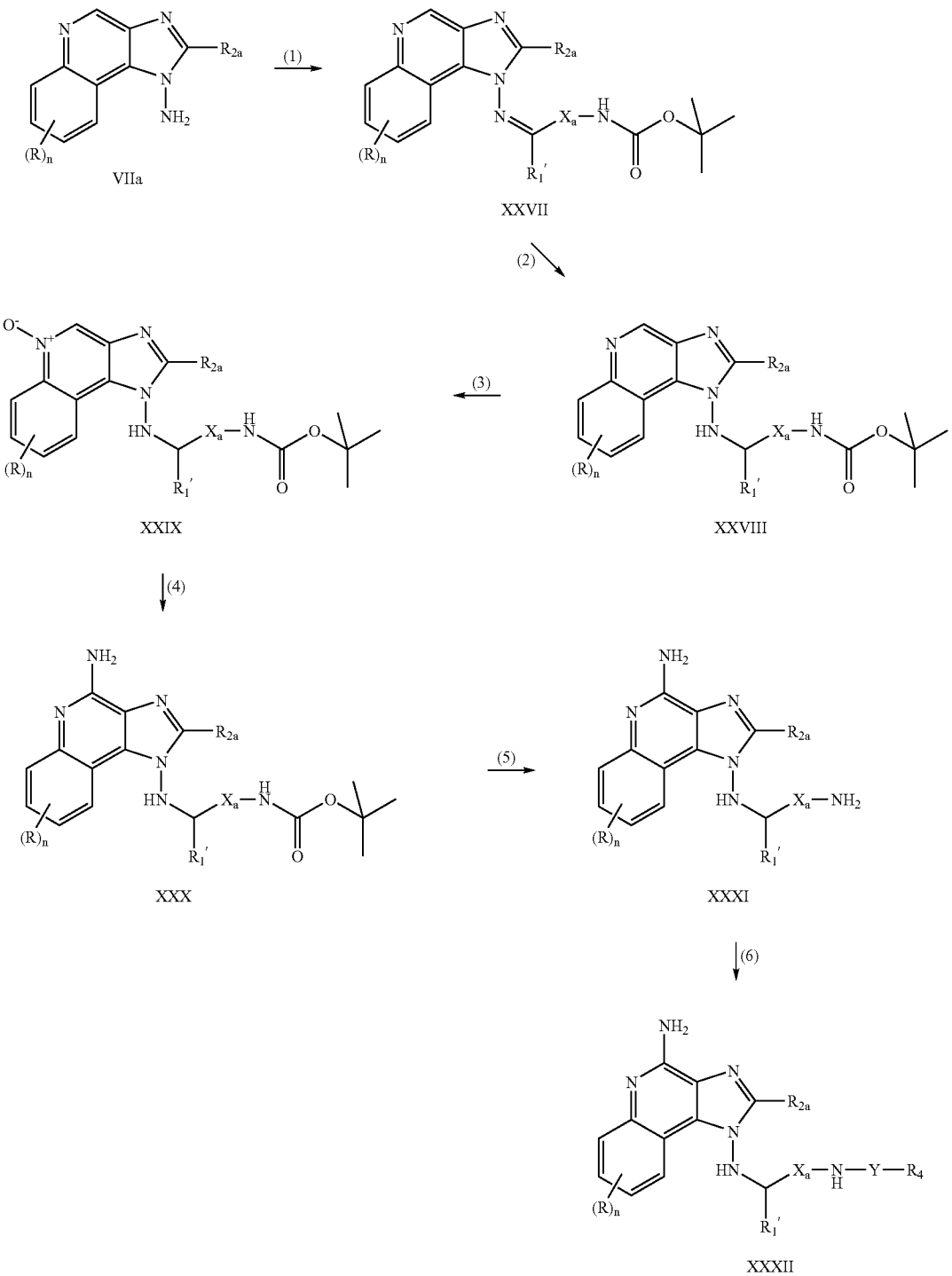

Compounds of the invention can be prepared according to Reaction Scheme VIII where n is as defined above; each $R_c$ is independently selected from the group consisting of hydroxy, alkyl, and alkoxy; and $R_{1b}$ and $R_{2b}$ are a subset of $R_1$ and $R_2$, respectively, as defined above, which do not include those groups that one skilled in the art would recognize as being susceptible to reduction under the acidic hydrogenation conditions in step (1). These susceptible groups include, for example, alkenyl, alkynyl, and aryl groups, and groups bearing nitro substituents.

In step (1) of Reaction Scheme VIII, a 1H-imidazo[4,5-c]quinolin-4-amine of Formula If is reduced to provide a 6,7,8,9-tetrahydro-1H-imidazo[4,5-c]quinolin-4-amine of Formula IIa, which is a subgenus of compounds of the Formulas II and II-1. The reaction can be conveniently carried out by suspending or dissolving a compound of Formula If in trifluoroacetic acid, adding platinum(IV) oxide, and hydrogenating under an atmosphere of hydrogen. The reaction can be carried out in a Parr apparatus. The product or a pharmaceutically acceptable salt thereof can be isolated using conventional methods.

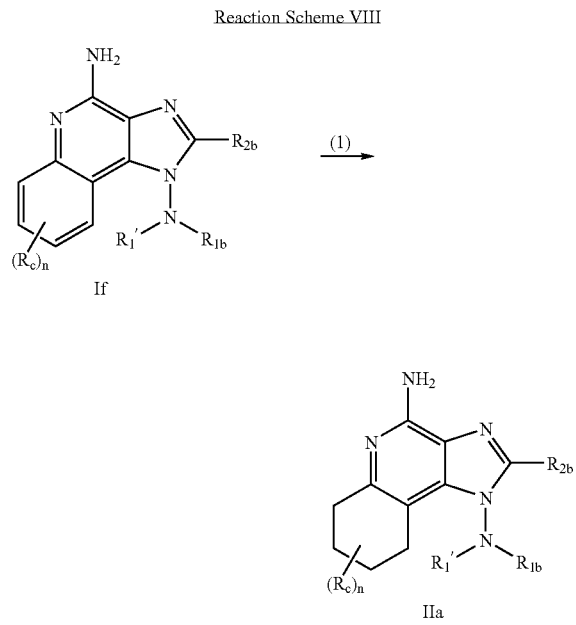

Reaction Scheme VIII

Compounds of the invention may be prepared according to Reaction Scheme IX where $R_4$, $R_1$, $R_1'$, $R_2$, and n is as defined above; and each $R_a$ is independently alkyl. Steps (1) through (4) may be carried out as described in U.S. Pat. No. 5,352,784 and documents cited therein. In step (1) the amino group of a compound of Formula XXXIII may be acylated to provide a compound of Formula XXXIV. The reaction may be conveniently carried out by reacting a compound of Formula XXXIII with an alkyl malonyl chloride in the presence of a base such as triethylamine in a suitable solvent such as methylene chloride. The product or a pharmaceutically acceptable salt thereof may be isolated using conventional methods. Certain compounds of Formula XXXIII are commercially available and others can be prepared as described in U.S. Pat. No. 5,352,784 and documents cited therein. Alkyl malonyl chlorides are known, some of which are commercially available, and others can be made my known methods.

In step (2) of Reaction Scheme IX, a compound of Formula XXXIV may be cyclized to provide a compound of Formula XXXV. The reaction may be conveniently carried out by adding a solution of a compound of Formula XXXIV in a suitable solvent such as THF to a suspension of sodium hydride (or other base capable of removing a malonyl methylene proton) in a suitable solvent such as THF. The reaction may be run at an elevated temperature, for example the reflux temperature. The product or a pharmaceutically acceptable salt thereof may be isolated using conventional methods.

In step (3) of Reaction Scheme IX, a compound of Formula XXXV may be hydrolyzed and decarboxylated to provide a compound of Formula XXXVI. The reaction may be carried out by conventional methods, for example, by combining a compound of Formula XXXV with an acid, such as hydrochloric acid, with heating. The product may be isolated using conventional methods.

In step (4) of Reaction Scheme IX, a compound of Formula XXXVI may be nitrated to provide a compound of Formula XXXVII. The reaction may be carried out under conventional nitration conditions, such as by heating a compound of Formula XXXVI in the presence of nitric acid, preferably in a solvent such acetic acid. The product or a pharmaceutically acceptable salt thereof may be isolated using conventional methods.

In step (5) of Reaction Scheme IX, a compound of Formula XXXVII may be chlorinated to provide a 2,4-dichloro-3-nitro-5,6,7,8-tetrahydroquinoline of Formula XXXVIII. The reaction may be carried out by combining a compound of Formula XXXVII with a conventional chlorinating agent (e.g., phosphorus oxychloride, thionyl chloride, phosgene, oxalyl chloride, or phosphorus pentachloride), optionally in solvent such as N,N-dimethylformamide (DMF) or methylene chloride, with heating (e.g., at the reflux temperature). The product or a pharmaceutically acceptable salt thereof may be isolated from the reaction mixture using conventional methods.

In step (6) of Reaction Scheme IX, a 2,4-dichloro-3-nitro-5,6,7,8-tetrahydroquinoline of Formula XXXVIII may be reacted with a hydrazino compound of Formula XV ($H_2N$—$N(R_1')(R_1)$), using the method of step (1) in Reaction Scheme III, to provide a compound of Formula XXXIX. The product or a pharmaceutically acceptable salt thereof may be isolated by conventional methods.

In step (7) of Reaction Scheme IX, a compound of Formula XXXIX may be reduced using the method of step (2) in Reaction Scheme I to provide a compound of Formula XL. The product or a pharmaceutically acceptable salt thereof may be isolated by conventional methods.

In step (8) of Reaction Scheme IX, a compound of Formula XL may be reacted with an acyl halide of formula $R_2C(O)Cl$ or $R_2C(O)Br$, or a carboxylic acid or equivalent thereof using the methods of step (3) in Reaction Scheme I to provide a 4-chloro-1H-imidazo[4,5-c]quinolin-1-amine compound of Formula XLI. The carboxylic acid or equivalent may be selected such that it provides the desired $R_2$ substituent in a compound of Formula II-1. The product or a pharmaceutically acceptable salt thereof may be isolated by conventional methods.

In step (9) of Reaction Scheme IX, a 4-chloro-1H-imidazo[4,5-c]quinolin-1-amine compound of Formula XLI may be aminated using the method of step (7) in Reaction Scheme IV to provide a 1H-imidazo[4,5-c]quinoline-1,4-diamine of Formula II-1. The product or a pharmaceutically acceptable salt thereof may be isolated by conventional methods.

Reaction Scheme IX

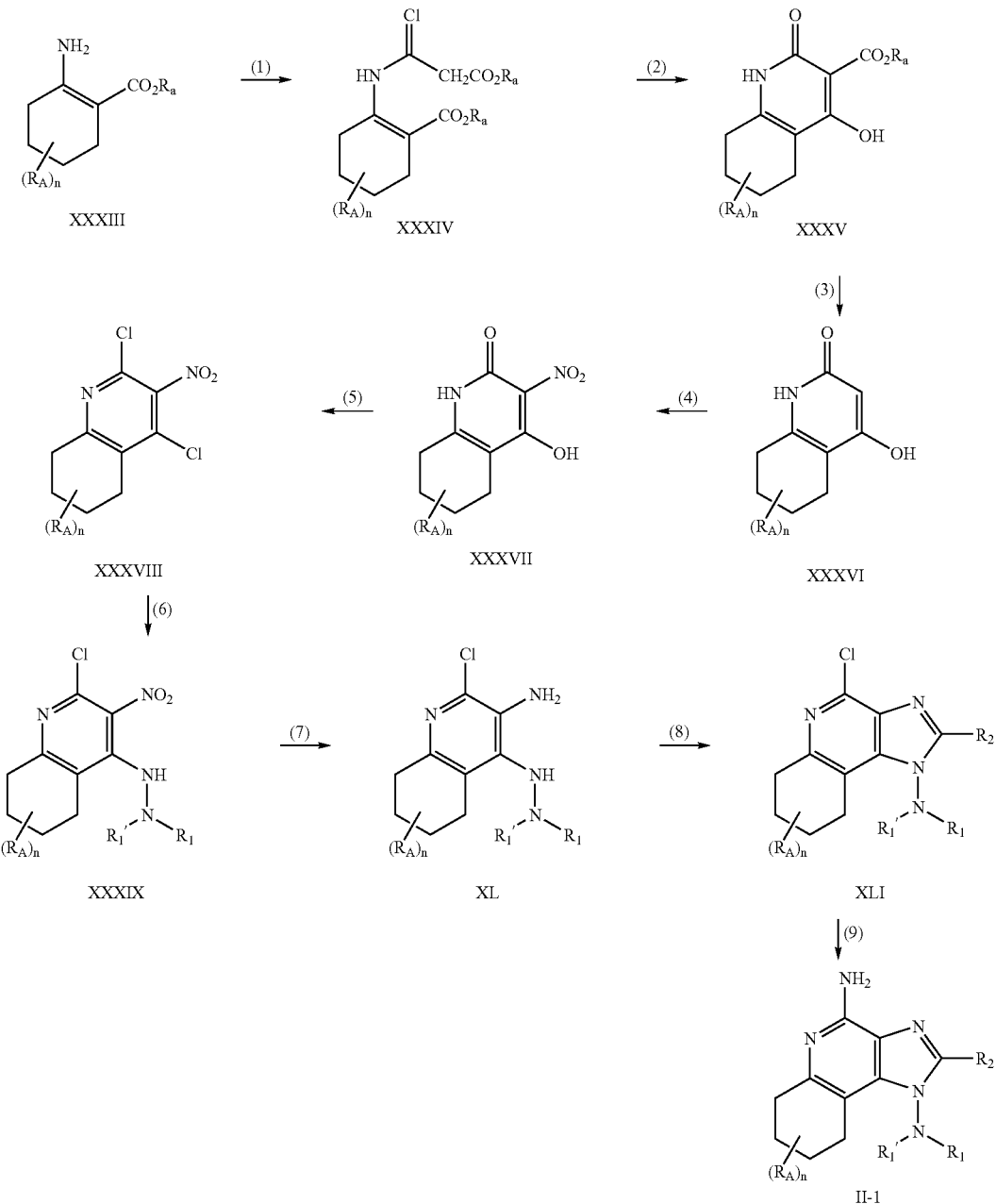

For some embodiments, compounds of the invention are prepared according to Reaction Scheme X, wherein R, $R_{1a}$, $R_{2a}$, and l are as defined above; Hal is chloro, bromo, or iodo; $R_{3a}$ is -Z'-$R_4$', -Z'-X'—$R_4$', -Z'-X'—Y'—$R_4$', or -Z'-X'—$R_5$'; wherein $R_4$', Y', X', and $R_5$' are as defined above; and Z' is a bond.

In step (1) of Reaction Scheme X, a 4-chloro-3-nitro-quinoline of Formula XLIV is converted to a carbazate of Formula XLV according to the method described in step (1) of Reaction Scheme I. Compounds of Formula XLIV can be readily prepared using known synthetic routes; see for example, U.S. Pat. Nos. 4,689,338 (Gerster), 5,367,076 (Gerster), 6,331,539 (Crooks et al.), 6,451,810 (Coleman et al.), 6,541,485 (Crooks et al.) and the documents cited therein.

In steps (2) and (3) of Reaction Scheme X, a nitro-substituted quinoline of Formula XLV is first reduced to an amino-substituted quinoline of Formula XLVI, which is then cyclized to a 1H-imidazoquinoline of Formula XLVII. Steps (2) and (3) of Reaction Scheme X can be carried out as described for steps (2) and (3) of Reaction Scheme I.

In step (4) of Reaction Scheme X, the tert-butoxycarbonyl group of a 1H-imidazoquinoline of Formula XLVII is hydrolyzed under acidic conditions to provide a 1H-imidazo[4,5-c]quinolin-1-amine of Formula VIIb or a pharmaceutically acceptable salt thereof. The reaction is conveniently carried out as described in step (4) of Reaction Scheme I.

The 1H-imidazo[4,5-c]quinolin-1-amine of Formula VIIb is then converted to a 1H-imidazo[4,5-c]quinolin-1-amine of Formula IXc using either a two-step procedure as shown in steps (5a) and (6) of Reaction Scheme X or a one-step procedure as shown in step (5b). The two-step procedure, in which a compound of Formula VIIIb is isolated, can be carried out as described in steps (5a) and (6) of Reaction Scheme I. In step (5a), the ketone, aldehyde, or corresponding ketal or acetal thereof, is selected with $R_i$ and $R_{ii}$ groups that will provide the desired $R_{1a}$ substituent in a 1H-imidazo[4,5-c]quinolin-1-amine compound of Formula IXc. Step (5b) of Reaction Scheme X can be carried out as described for step (5b) of Reaction Scheme I.

In steps (7) and (8) of Reaction Scheme X, a 1H-imidazo[4,5-c]quinolin-1-amine of Formula IXc is first oxidized to an N-oxide of Formula Xb, which is then aminated to provide a 1H-imidazo[4,5-c]quinoline-1,4-diamine of Formula Ig, which is a subgenus of the compounds of the Formulas I, I-1, I-2, and I-3. Steps (7) and (8) of Reaction Scheme X can be carried out according to the procedures described in steps (7) and (8) of Reaction Scheme I.

Step (9) of Reaction Scheme X can be carried out using known palladium-catalyzed coupling reactions such as Suzuki coupling, Stille coupling, Sonogashira coupling, and the Heck reaction. For example, a 1H-imidazo[4,5-c]quinoline-1,4-diamine of Formula Ig undergoes Suzuki coupling with a boronic acid of Formula $R_{3a}$—B(OH)$_2$, an anhydride thereof, or a boronic acid ester of Formula $R_{3a}$—B(O-alkyl)$_2$ to provide an 1H-imidazo[4,5-c]quinoline-1,4-diamine of Formula I-1b, a subgenus of Formulas I and I-1, wherein $R_{3a}$ is -Z'-R$_4$', -Z'-X'—R$_4$', -Z'-X'—Y'—R$_4$', or -Z'-X'—R$_5$'; -Z' is a bond; —X'— is alkenylene, arylene, heteroarylene, or the alkenylene optionally terminated by arylene or heteroarylene; and R$_4$', Y', and R$_5$' are as defined above. The coupling is carried out by combining a compound of Formula Ig with a boronic acid or an ester or anhydride thereof in the presence of palladium (II) acetate, triphenylphosphine, and a base such as sodium carbonate in a suitable solvent such as n-propanol. The reaction can be carried out at an elevated temperature (e.g., 80–100° C.). Numerous boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods. See, for example, Li, W. et al, *J Org. Chem.*, 67, 5394–5397 (2002). The product of Formula I-1b or a pharmaceutically acceptable salt thereof can be isolated by conventional methods.

The Heck reaction can also be used in step (9) of Reaction Scheme X to provide compounds of Formula I-1b, wherein $R_{3a}$ is -Z'-X'—R$_4$' or -Z'-X'—Y'—R$_4$'; -Z' is a bond; —X'— is alkenylene optionally terminated by arylene or heteroarylene; and R$_4$' and Y' are as defined above. The Heck reaction is carried out by coupling a 1H-imidazo[4,5-c]quinoline-1,4-diamine of Formula Ig with a vinyl-substituted arylene or heteroarylene compound. Several vinyl-substituted arylene or heteroarylene compounds, such as 2-vinylpyridine, 3-vinylpyridine, and 4-vinylpyridine, are commercially available; others can be prepared by known methods. The reaction is conveniently carried out by combining the 1H-imidazo[4,5-c]quinoline-1,4-diamine of Formula Ig and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100–120° C. under an inert atmosphere. The compound or pharmaceutically acceptable salt thereof can be isolated using conventional methods.

Compounds of Formula I-1b, wherein $R_{3a}$ is -Z'-X'—R$_4$' or -Z'-X'—Y'—R$_4$', -Z' is a bond and —X'— is alkenylene optionally terminated by arylene or heteroarylene, may be reduced to provide compounds wherein —X'— is alkylene optionally terminated by arylene or heteroarylene. For example, compounds wherein $R_{3a}$ is a 2-(pyridin-3-yl)ethyl group may be prepared in this manner. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The compound or pharmaceutically acceptable salt thereof can be isolated using conventional methods.

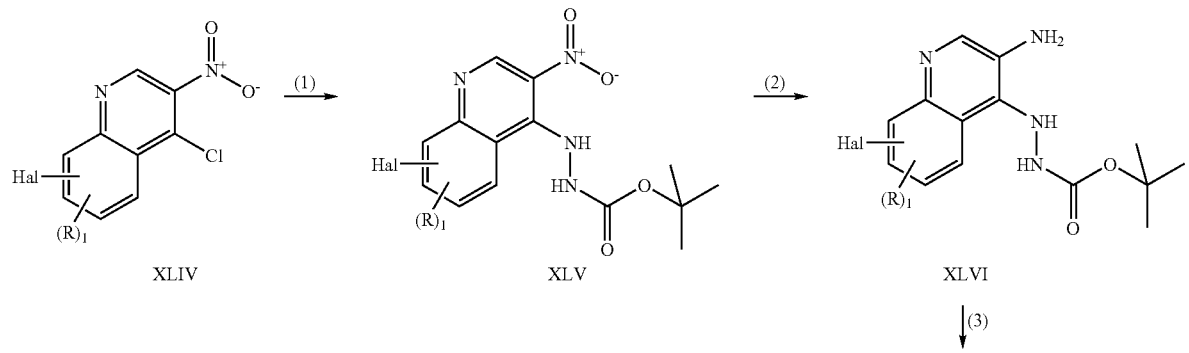

Reaction Scheme X

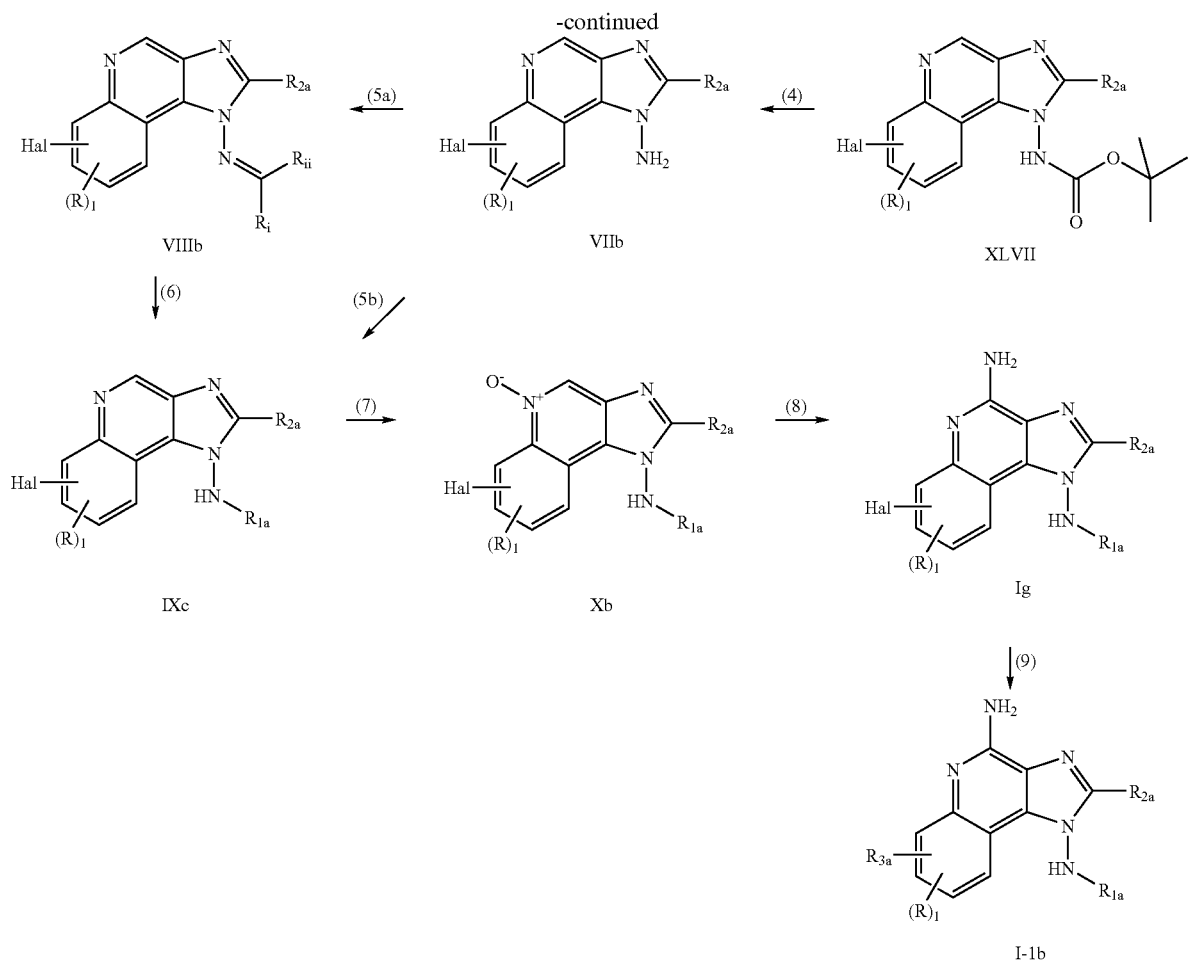

For some embodiments, compounds of the invention can be prepared according to Reaction Scheme XI where R, $R_{1a}$, $R_{2a}$, and 1 are as defined above; Boc is tert-butoxycarbonyl; $R_{3b}$ is $-Z'-R_4'$, $-Z'-X'-R_4'$, $-Z'-X'-Y'-R_4'$, or $-Z'-X'-R_5'$; $X'$, $Y'$, and $R_4'$ are as defined above; and $Z'$ is —O—.

In step (1) of Reaction Scheme XI, a benzyloxyaniline of Formula XLVIII is treated with the condensation product generated from 2,2-dimethyl-1,3-dioxane4,6-dione (Meldrum's acid) and triethyl orthoformate to provide an imine of Formula XLIX. The reaction is conveniently carried out by adding a solution of a benzyloxyaniline of Formula XLVIII to a heated mixture of Meldrum's acid and triethyl orthoformate and heating the reaction at an elevated temperature such as 45° C. The product can be isolated using conventional methods.

In step (2) of Reaction Scheme XI, an imine of Formula XLIX undergoes thermolysis and cyclization to provide a benzyloxyquinolin-4-ol of Formula L. The reaction is conveniently carried out in a heat transfer fluid such as DOWTHERM A heat transfer fluid at a temperature between 200 and 250° C. The product can be isolated using conventional methods.

In step (3) of Reaction Scheme XI, a benzyloxyquinolin-4-ol of Formula L is nitrated under conventional nitration conditions to provide a benzyloxy-3-nitroquinolin-4-ol of Formula LI. The reaction is conveniently carried out by adding nitric acid to the benzyloxyquinolin4-ol of Formula L in a suitable solvent such as propionic acid and heating the mixture at an elevated temperature such as 125° C. The product can be isolated using conventional methods.

In step (4) of Reaction Scheme XI, a benzyloxy-3-nitroquinolin-4-ol of Formula LI is chlorinated using conventional chlorination chemistry to provide a benzyloxy4-chloro-3-nitroquinoline of Formula LII. The reaction is conveniently carried out by treating the benzyloxy-3-nitroquinolin-4-ol of Formula LI with phosphorous oxychloride in a suitable solvent such as DMF. The reaction can be carried out at ambient temperature or at an elevated temperature such as 100° C., and the product can be isolated using conventional methods.

In step (5) of Reaction Scheme XI, a benzyloxy-4-chloro-3-nitroquinoline of Formula LII is converted to a carbazate of Formula LIII. The reaction is conveniently carried out as described in step (1) of Reaction Scheme I.

In steps (6) and (7) of Reaction Scheme XI, a nitro-substituted quinoline of Formula LIII is first reduced to an amino-substituted quinoline of Formula LIV, which is then cyclized to a benzyloxy-1H-imidazo[4,5-c]quinoline of Formula LV. Steps (6) and (7) of Reaction Scheme XI can be carried out as described for steps (2) and (3) of Reaction Scheme I.

In step (8) of Reaction Scheme XI, the Boc group of a benzyloxy-1H-imidazo[4,5-c]quinoline of Formula LV is hydrolyzed under acidic conditions to provide a benzyloxy- 1H-imidazo[4,5-c]quinolin-1-amine of Formula XLIIa or a pharmaceutically acceptable salt thereof. The reaction is conveniently carried out as described in step (4) of Reaction Scheme I.

The benzyloxy-1H-imidazo[4,5-c]quinolin-1-amine of Formula XLIIa is then converted to a benzyloxy-1H-imidazo[4,5-c]quinolin-1-amine of Formula XLIIIa using either a two-step procedure as shown in steps (9a) and (10) of Reaction Scheme XI or a one-step procedure as shown in step (9b). The two-step procedure, in which a compound of Formula LVI is isolated, can be carried out as described in steps (5a) and (6) of Reaction Scheme I. In step (9a), the ketone, aldehyde, or corresponding ketal or acetal thereof, is selected with $R_i$ and $R_{ii}$ groups that will provide the desired $R_{1a}$ substituent in a benzyloxy-1H-imidazo[4,5-c]quinolin-1-amine compound of Formula XLIIIa. Step (9b) of Reaction Scheme XI can be carried out as described for step (5b) of Reaction Scheme I.

In steps (11) and (12) of Reaction Scheme XI, a benzyloxy-1H-imidazo[4,5-c]quinolin-1-amine of Formula XLIIIa is first oxidized to an N-oxide of Formula LVII, which is then aminated to provide a benzyloxy-1H-imidazo[4,5-c]quinoline-1,4-diamine of Formula LVIII, which is a subgenus of the compounds of the Formulas I and I-1. Steps (11) and (12) of Reaction Scheme XI can be carried out according to the procedures described in steps (7) and (8) of Reaction Scheme I.

In step (13) of Reaction Scheme XI, the benzyl group of a benzyloxy-1H-imidazo[4,5-c]quinoline-1,4-diamine of Formula LVIII is cleaved to provide a hydroxy-1H-imidazo[4,5-c]quinoline-1,4-diamine of Formula Ih. The cleavage is conveniently carried out on a Parr apparatus under hydrogenolysis conditions using a suitable heterogeneous catalyst such as palladium on carbon in a solvent such as ethanol. The product or pharmaceutically acceptable salt thereof can be isolated using conventional methods.

In step (14) of Reaction Scheme XI a hydroxy-1H-imidazo[4,5-c]quinoline-1,4-diamine of Formula Ih is converted to an ether-substituted 1H-imidazo[4,5-c]quinoline-1,4-diamine of Formula I-1c (a subgenus of compounds of Formulas I and I-1) using a Williamson-type ether synthesis. The reaction is effected by treating a compound of Formula Ih with an alkyl halide of Formula Halide-$R_4'$, Halide-$X'$—$Y'$—$R_4'$, Halide-$X'$—$R_4'$, or Halide-$X'$—$R_5'$ in the presence of a base. The reaction is conveniently carried out by combining the alkyl halide with a compound of Formula Ih in a solvent such as DMF in the presence of a suitable base such as cesium carbonate. The reaction can be carried out at ambient temperature or at an elevated temperature, for example 65° C. or 85° C. Alternatively, the reaction can be carried out by treating a solution of a compound of Formula Ih in a solvent such as DMF with sodium hydride and then adding the alkyl halide. The product or pharmaceutically acceptable salt thereof can be isolated using conventional methods.

Numerous reagents of Formulas Halide-$R_4'$, Halide-$X'$—$R_4'$, and Halide-$X'$—$Y'$—$R_4'$ are commercially available, for example, bromo-substituted ketones, esters, and heterocycles. Other reagents of Formulas Halide-$R_4'$, Halide-$X'$—$Y'$—$R_4'$, or Halide-$X'$—$R_5'$ can be prepared using conventional synthetic methods; for example, a bromo-substituted acid halide of Formula ClC(O)—$X'$—Br can be treated with a secondary amine in a suitable solvent such as dichloromethane to provide a variety of bromo-substituted amides of

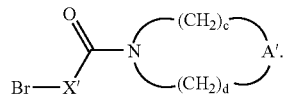

The reaction can be run at a sub-ambient temperature such as −25° C., and the product or pharmaceutically acceptable salt thereof can be isolated using conventional methods.

Reagents of Formula I—$X'$—NH—C(O)—O—C(CH$_3$)$_3$ can be prepared in two steps from amino alcohols of Formula HO—$X'$—NH$_2$, many of which are commercially available or readily prepared by known synthetic methods. An amino alcohol of Formula HO—$X'$—NH$_2$ is first protected with a tert-butoxy carbonyl group by treating the amino alcohol with di-tert-butyl dicarbonate in the presence of a base such as aqueous sodium hydroxide in a suitable solvent such as tetrahydrofuran. The resulting hydroxyalkylcarbamate of Formula HO—$X'$—NH—C(O)—O—C(CH$_3$)$_3$ is then treated with a solution of iodine, triphenylphosphine, and imidazole at ambient temperature in a suitable solvent such as dichloromethane. The product of Formula I—$X'$—NH—C(O)—O—C(CH$_3$)$_3$ can be isolated using conventional methods.

Step (14) of Reaction Scheme XI can alternatively be carried out by treating a hydroxy-1H-imidazo[4,5-c]quinoline-1,4-diamine of Formula Ih with an alcohol of Formula HO—$X'$—$Y'$—$R_4'$, HO—$X'$—$R_5'$, HO—$X'$—$R_4'$, or HO—$R_4'$ under Mitsunobu reaction conditions. Numerous alcohols of these formulas are commercially available, and others can be prepared using conventional synthetic methods. The reaction is conveniently carried out by out by adding triphenylphosphine and an alcohol of Formula HO—$X'$—$Y'$—$R_4'$, HO—$X'$—$R_5'$, HO—$X'$—$R_4'$, or HO—$R_4'$ to a solution of a compound of Formula Ih in a suitable solvent such as tetrahydrofuran and then slowly adding diisopropyl azodicarboxylate or diethyl azodicarboxylate. The reaction can be carried out at ambient temperature or at a sub-ambient temperature, such as 0° C. The product or pharmaceutically acceptable salt thereof can be isolated using conventional methods.

Compounds of Formula I-1c, wherein $R_{3b}$ is —O—$X'$—NH—C(O)—O—C(CH$_3$)$_3$, can be prepared by treating compounds of Formula Ih with alcohols such as tert-butyl N-(4-hydroxybutyl)carbamate and tert-butyl N-(5-hydroxypentyl)carbamate under Mitsunobu conditions or with alkyl halides of Formula I—$X'$—NH—C(O)—O—C(CH$_3$)$_3$ in a Williamson-type ether synthesis. These compounds of Formula I-1c, wherein $R_{3b}$ is —O—$X'$—NH—C(O)—O—C(CH$_3$)$_3$, are then readily converted to other compounds of Formula I-1 c using conventional synthetic methods. For example, compounds in which $R_{3b}$ is —O—$X'$—NH—C(O)—O—C(CH$_3$)$_3$ can be deprotected and treated according to the methods described in steps (5) and (6) of Reaction Scheme VII, Parts F and G of Example 14, and Examples 15 and 23 to provide compounds of Formula I-1c wherein $R_{3b}$ is -$Z'$-$X'$—$Y'$—$R_4'$; $Z'$ is —O—; $Y'$ is —NH—Q—; Q is —C($R_7$)—, —S(O)$_2$—, or —C($R_7$)—N($R_{11}$)—; and $X'$, $R_4'$, $R_7$, and $R_{11}$ are as defined above. Compounds in which $R_{3b}$ is a 2-methanesulfonylaminoethoxy group or a 3-methanesulfonylaminopropoxy group are available using these methods.

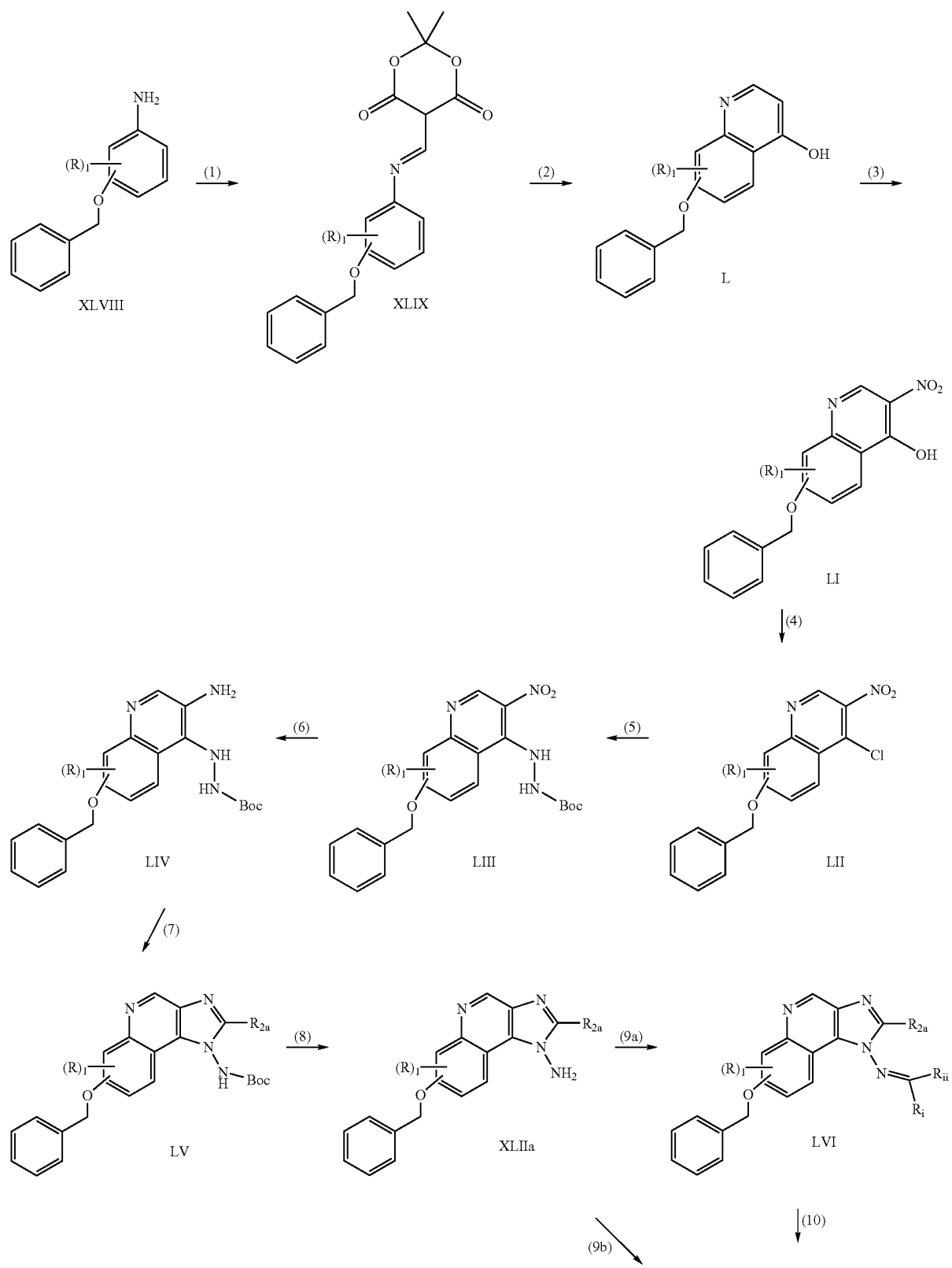

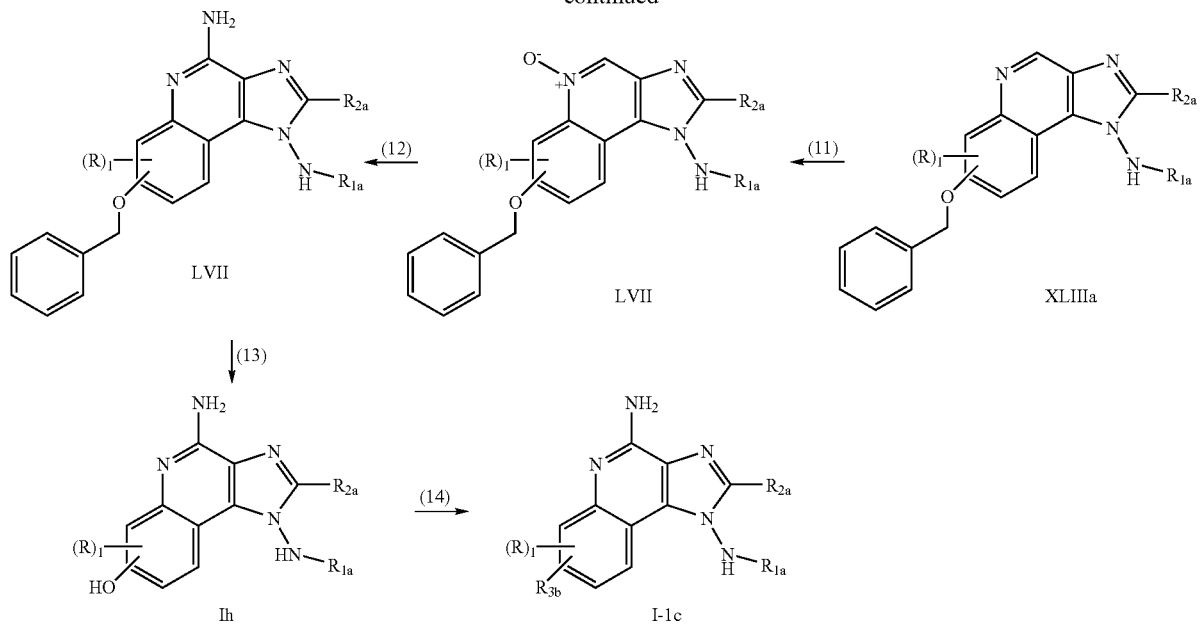

For some embodiments, compounds of Formula I-1c can be prepared according to Reaction Scheme XII, in which R, $R_{1a}$, $R_{2a}$, $R_{3b}$, and 1 are as defined above. In step (1) of Reaction Scheme XII, the benzyl group of a benzyloxy-1H-imidazo[4,5-c]quinolin-1-amine of Formula XLIIa is cleaved to provide a hydroxy-1H-imidazo[4,5-c]quinolin-1-amine of Formula IXd. In step (2) of Reaction Scheme XII a hydroxy-1H-imidazo[4,5-c]quinolin-1-amine of Formula IXd is converted to an ether-substituted 1H-imidazo[4,5-c]quinolin-1-amine of Formula LIX. In steps (3) and (4) of Reaction Scheme XII, an ether-substituted 1H-imidazo[4,5-c]quinolin-1-amine of Formula LIX is first oxidized to an N-oxide of Formula LX, which is then aminated to provide an ether-substituted 1H-imidazo[4,5-c]quinoline-1,4-diamine of Formula I-1c, which is a subgenus of the compounds of Formula I-1. Steps (1), (2), (3), and (4) of Reaction Scheme XII can be carried out as described in steps (13), (14), (11), and (12), respectively, of Reaction Scheme XI.

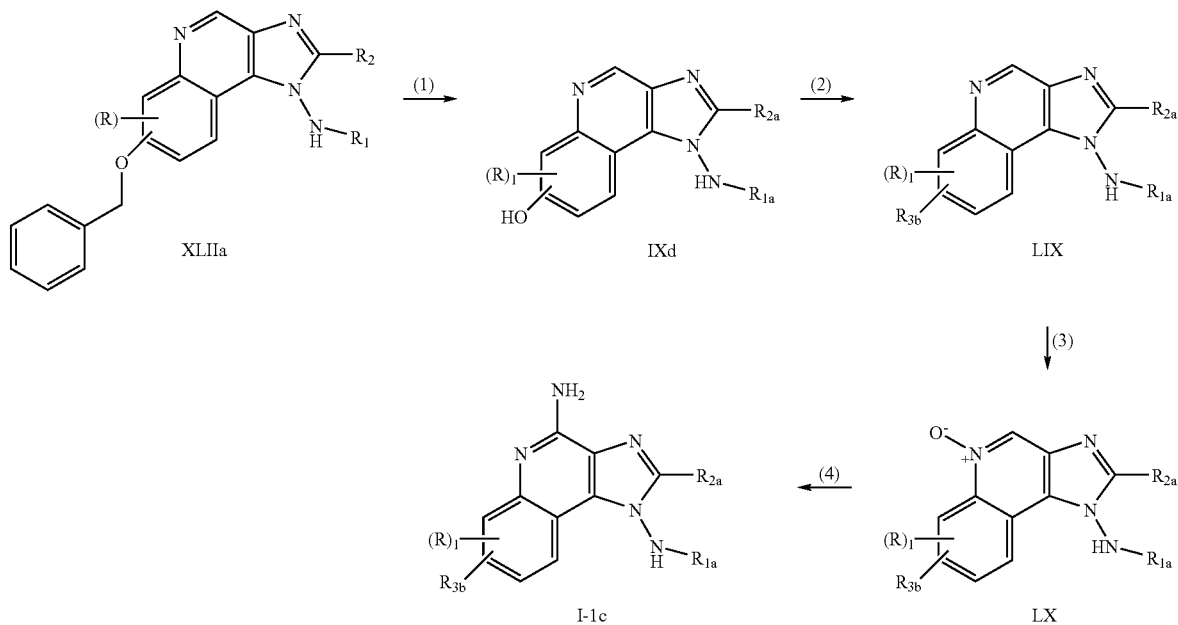

Reaction Scheme XII

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" or "effective amount" means an amount of the compound sufficient to induce a therapeutic or prophylactic effect, such as cytokine induction, cytokine inhibition, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

Compounds of the invention have been shown to induce, and certain compounds of the invention may inhibit, the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, compounds of the invention may affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds.

Other cytokines whose production may be inhibited by the administration of certain compounds according to the invention include tumor necrosis factor-α (TNF-α). Among other effects, inhibition of TNF-α production can provide prophylaxis or therapeutic treatment of diseases in animals in which TNF is mediated, making the compounds useful in the treatment of, for example, autoimmune diseases. Accordingly, the invention provides a method of inhibiting TNF-α biosynthesis in an animal comprising administering an effective amount of a compound or composition of the invention to the animal. The animal to which the compound or composition is administered for inhibition of TNF-α biosynthesis may have a disease as described infra, for example an autoimmune disease, and administration of the compound may provide therapeutic treatment. Alternatively, the compound may be administered to the animal prior to the animal aquiring the disease so that administration of the compound may provide a prophylactic treatment.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV), a coronavirus (e.g., SARS), a papovavirus, (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases, such as, for example, diseases resulting from infection by bacteria of, for example, the genus *Escherichia, Enterobacter, Salmonella, Staphylococci, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such as chlamydia, fungal diseases, such as, for example, candidiasis, aspergillosis, histoplasmonsis, cryptococcal meningitis, or parasitic diseases, such as, for example, malaria, *pneumocystis carnii* pneomonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, aenal cell leukemia, Karposi's sarcoma, melanoma, renal cell carcinoma, leukemias, such as, for example, myelogeous leukemia, chronic lymphocytic leukemia, and multiple myeloma, non-Hodgkin's lymphoma, cutaneous T-cell lymphoma, B-cell lymphoma, hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing wound healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; and the like, for use in connection with, for example, BCG, cholera, plague, typhoid, hepatitis A, hepatitis B, and hepatitis C, influenza A and influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs identified herein may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of Formula I, I-1, I-2, I-3, II, II-1, any of the embodiments described herein, or a combination thereof to the animal. An animal may also be vaccinated by administering an effecive amount of a compound or salt of Formula I, I-1, I-2, I-3, II, II-1, any of the embodiments described herein, or a combination thereof to the animal as a vaccine adjuvant.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal.

An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

In certain embodiments, there is provided a method of inducing cytokine biosynthesis in an animal comprising administering an effective amount of a compound or salt described herein to the animal. In another embodiment, there is provided a method of treating a viral disease in an animal comprising administering a therapeutically effective amount of a compound or salt described herein to the animal. In another embodiment, there is provided a method of treating a neoplastic disease in an animal comprising administering a therapeutically effective amount of a compound or salt described herein to the animal. In another embodiment, there is provided a method of vaccinating an animal comprising administering an effective amount of a compound or salt described herein to the animal as a vaccine adjuvant.

EXAMPLES

Objects and advantages of this invention are further illustrated by the following examples, but the particular materials and amounts thereof recited in these examples, as well as other conditions and details, should not be construed to unduly limit this invention.

Example 1

2-Butyl-N¹-isopropyl-1H-imidazo[4,5-c]quinoline-1,4-diamine

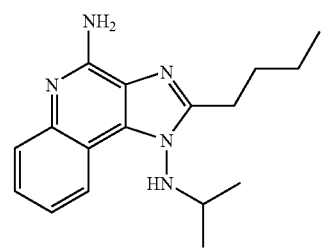

Part A

A solution of 4-chloro-3-nitroquinoline (5.00 g, 24.0 mmol) in 120 mL of anhydrous $CH_2Cl_2$ was treated with triethylamine (6.7 mL, 48.2 mmol) and tert-butyl carbazate (3.20 g, 24.2 mmol). After stirring under nitrogen for 2.5 hour (h), an additional portion of tert-butyl carbazate (3.2 g, 24.2 mmol) was added. After stirring overnight, the deep red solution was washed with $H_2O$ (2×) and brine. The organic portion was dried over $Na_2SO_4$ and concentrated to give a red foam. The material was passed through a $SiO_2$ column eluting with 2.5% methanol/$CH_2Cl_2$. The resulting red powder was treated with 5:1 hexanes/$CH_2Cl_2$ and filtered. The solid was washed several times with hexanes and was dried under vacuum to give tert-butyl N'-(3-nitroquinolin-4-yl) hydrazinecarboxylate (4.97 g) as an orange powder.

Part B

A suspension of tert-butyl N'-(3-nitroquinolin-4-yl)hydrazinecarboxylate (2.50 g, 8.22 mmol) in 150 mL of isopropanol was treated with 1.0 g of 10% palladium on carbon and the mixture was shaken under an atmosphere of hydrogen (3.8×10⁵ Pa) for 2 h. The reaction mixture was then filtered through a pad of CELITE filter agent and rinsed with isopropanol, and the filtrate was concentrated under reduced pressure to give tert-butyl N'-(3-aminoquinolin-4-yl)hydrazinecarboxylate (2.18 g) as a yellow solid.

Part C

A solution of tert-butyl N'-(3-aminoquinolin-4-yl)hydrazinecarboxylate (2.18 g, 7.96 mmol) in 80 mL of anhydrous $CH_2Cl_2$ was cooled to 0° C. and treated with triethylamine (1.12 mL, 8.00 mmol) and valeryl chloride (0.95 mL, 8.00 mmol) under an atmosphere of nitrogen. After stirring for 3 h, the reaction mixture was concentrated under reduced pressure and the residue was treated with $Et_2O$ and filtered. The filtrate was concentrated and the resulting black tar was dissolved in 80 mL of ethanol and treated with 3 mL of triethylamine and the mixture was refluxed overnight. The reaction mixture was concentrated under reduced pressure. Chromatography ($SiO_2$, 1–5% methanol (MeOH)/$CHCl_3$) gave tert-butyl N-(2-butyl-1H-imidazo[4,5-c]quinolin-1-yl)carbamate (1.41 g) as a mauve foam.

Part D tert-Butyl N-(2-butyl-1H-imidazo[4,5-c]quinolin-1-yl)carbamate (830 mg, 2.44 mmol) was dissolved in 20 mL of 1.5 M HCl in ethanol (EtOH) and the reaction mixture was heated to reflux for 1.5 h. The reaction mixture was cooled and concentrated under reduced pressure to give a brown solid. The material was dissolved in 50 mL of hot isopropanol and the solution was allowed to cool overnight. The resulting crystals were isolated by filtration. A second crop was obtained from the filtrate by crystallization from isopropanol/$Et_2O$. The total yield of 2-butyl-1H-imidazo[4,5-c]quinolin-1-amine hydrochloride was 570 mg. mp>250° C. ¹H NMR (300 MHz, DMSO-d₆) δ 9.68 (s, 1H), 9.35 (d, J=8.3 Hz, 1H), 8.47 (d, J=8.0 Hz, 1H), 8.03 (t, J=7.1 Hz, 1H), 7.98 (t, J=7.1 Hz, 1H), 6.85 (s, 2H), 3.13 (t, J=7.6 Hz, 2H), 1.89, (m, 2H), 1.49 (m, 2H), 0.98 (t, J=7.3 Hz, 3H); ¹³C NMR (75 MHz, DMSO-d₆) δ 163.5, 139.4, 136.1, 134.0, 131.8, 130.4, 128.9, 122.6, 120.2, 115.6, 28.2, 25.7, 22.1, 13.3; Anal. Calcd for $C_{14}H_{16}N_4$·HCl: C, 60.76; H, 6.19; N, 20.24; Cl, 12.81. Found: C, 60.78; H, 6.19; N, 20.21; Cl, 12.78.

Part E

A solution of 2-butyl-1H-imidazo[4,5-c]quinolin-1-amine hydrochloride (520 mg, 2.17 mmol) in 10 mL of isopropanol was treated with 2 mL of acetone and 200 mg of DOWEX W50-X1 acid resin. The reaction mixture was heated to 55° C. overnight. The reaction mixture was treated with an additional 10 mL of isopropanol and 5 mL of acetone and heated to 70° C. for 2 h. The reaction mixture was filtered and the filtrate was treated with 0.5 mL of triethylamine and concentrated under reduced pressure. Chromatography ($SiO_2$, 3% MeOH/$CHCl_3$) gave N-(2-butyl-1H-imidazo[4,5-c]quinolin-1-yl)isopropylideneamine (421 mg) as a brown oil.

Part F

A solution of N-(2-butyl-1H-imidazo[4,5-c]quinolin-1-yl)isopropylideneamine (406 mg, 1.45 mmol) in 15 mL of MeOH was treated with $NaBH_4$ (500 mg, 13.2 mmol). After stirring for 2 days (d), the reaction was quenched with saturated $NaHCO_3$ solution and extracted into ethyl acetate (EtOAc). The organic portion was washed with $H_2O$ and brine and dried over $Na_2SO_4$. Chromatography ($SiO_2$, EtOAc) gave N-(2-butyl-1H-imidazo[4,5-c]quinolin-1-yl)isopropylamine (372 mg) as a mauve solid.

Part G

A solution of N-(2-butyl-1H-imidazo[4,5-c]quinolin-1-yl)isopropylamine (334 mg, 1.18 mmol) in 10 mL of $CH_2Cl_2$ was treated with 3-chloroperoxybenzoic acid (MCPBA) (77% max., 334 mg, 1.45 mmol). After stirring for 3 h, the reaction was quenched with saturated $NaHCO_3$ solution and extracted into $CH_2Cl_2$. The organic portion was washed with saturated $NaHCO_3$ solution, $H_2O$ and brine. The organic portion was dried over $Na_2SO_4$, filtered and concentrated to give N-(2-butyl-5-oxido-1H-imidazo[4,5-c]quinolin-1-yl)isopropylamine (338 mg) as a light brown solid.

Part H

A solution of N-(2-butyl-5-oxido-1H-imidazo[4,5-c]quinolin-1-yl)isopropylamine (332 mg, 1.11 mmol) in 15 mL of 1,2-dichloroethane was placed in a pressure vessel and heated to 70° C. The rapidly stirred solution was then treated with 3 mL of concentrated $NH_4OH$ solution and p-toluenesulfonyl chloride (233 mg, 1.22 mmol), the reaction vessel was capped, and heating was continued for 2 h. The reaction mixture was then cooled to ambient temperature and treated with 50 mL of $CH_2Cl_2$. The reaction mixture was washed with $H_2O$, 1% $Na_2CO_3$ solution (3×), $H_2O$ and brine. The organic portion was dried over $Na_2SO_4$, filtered and concentrated. Chromatography ($SiO_2$, 5–10% MeOH/$CHCl_3$) gave 320 mg of a light brown solid. Crystallization from $CH_2Cl_2$/hexanes gave 2-butyl-$N^1$-isopropyl-1H-imidazo[4,5-c]quinoline-1,4-diamine (230 mg) as colorless crystals. mp 157.1–158.7° C. ¹H NMR (300 MHz, DMSO-d6) δ 8.40 (m, 1H), 7.80 (m, 1H), 7.50 (m, 1H), 7.31 (m, 1H), 5.41 (s, 2H), 4.95 (s, 1H), 3.68 (m, 1H), 2.96 (t, J=7.6 Hz, 2H), 1.93–1.82 (m, 2H), 1.48 (m, 2H), 1.16 d, J=6.4 Hz, 6H), 1.00 (t, J=7.3 Hz, 3H); ¹³C NMR (75 MHz, DMSO-d₆) δ 155.1, 151.8, 144.7, 133.1, 127.3, 126.6, 124.7, 122.0, 120.4, 115.3, 52.1, 30.3, 26.8, 23.0, 20.8, 14.2; MS m/z 298 (M+H)⁺; Anal. Calcd for $C_{17}H_{23}N_5$: C, 68.66; H, 7.80; N, 23.55. Found: C, 68.30; H, 7.68; N, 23.33.

Example 2

$N^1$-Benzyl-2-butyl-1H-imidazo[4,5-c]quinoline-1,4-diamine

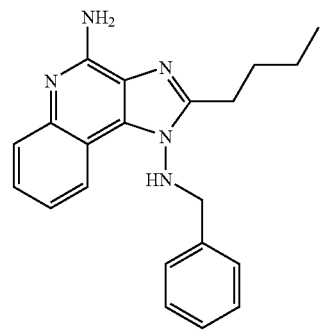

Part A

A solution of 2-butyl-1H-imidazo[4,5-c]quinolin-1-amine hydrochloride (503 mg, 1.82 mmol) in 10 mL of isopropanol was treated with benzaldehyde (220 μL, 2.17 mmol) and 200 mg of DOWEX W50-X1 acid resin. The reaction mixture was heated to reflux overnight. The reaction mixture was filtered, and the filtrate was treated with 0.5 mL of triethylamine and concentrated under reduced pressure. The resulting oil was dissolved in 75 mL of CH₂Cl₂ and washed with saturated NaHCO₃ solution, H₂O and brine. The organic was dried over Na₂SO₄, filtered and concentrated to give N-benzylidene(2-butyl-1H-imidazo[4,5-c]quinolin-1-yl)amine (575 mg) as a light yellow solid.

Part B

A solution of N-benzylidene(2-butyl-1H-imidazo[4,5-c]quinolin-1-yl)amine (575 mg, 1.75 mmol) in 40 mL of MeOH was treated with NaBH₄ (250 mg, 6.58 mmol). After stirring for 4 h, the reaction was quenched with saturated NaHCO₃ solution and extracted into CHCl₃. The organic portion was washed with H₂O and brine and dried over Na₂SO₄. Chromatography (SiO₂, 50–67% EtOAc/hexanes) gave N-benzyl(2-butyl-1H-imidazo[4,5-c]quinolin-1-yl)amine (427 mg) as a yellow solid.

Part C

A solution of N-benzyl(2-butyl-1H-imidazo[4,5-c]quinolin-1-yl)amine (427 mg, 1.29 mmol) in 20 mL of CH₂Cl₂ was treated with MCPBA (77% max., 325 mg, 1.41 mmol). After stirring for 3 h, the reaction was quenched with saturated NaHCO₃ solution and extracted into CH₂Cl₂. The organic portion was washed with saturated NaHCO₃ solution, H₂O and brine. The organic was dried over Na₂SO₄, filtered and concentrated to give N-benzyl(2-butyl-5-oxido-1H-imidazo[4,5-c]quinolin-1-yl)amine (393 mg) as a light brown foam.

Part D

A solution of N-benzyl(2-butyl-5-oxido-1H-imidazo[4,5-c]quinolin-1-yl)amine (393 mg, 1.14 mmol) in 20 mL of 1,2-dichloroethane was placed in a pressure vessel and heated to 70° C. The rapidly stirred solution was then treated with 5 mL of concentrated NH₄OH solution and p-toluenesulfonyl chloride (239 mg, 1.25 mmol), the reaction vessel was capped, and heating was continued for 2 h. The reaction mixture was then cooled to ambient temperature and treated with 50 mL of CH₂Cl₂. The reaction mixture was washed with H₂O, 1% Na₂CO₃ solution (3×), H₂O and brine. The organic portion was dried over Na₂SO₄, filtered and concentrated. Chromatography (SiO₂, 5% MeOH/CHCl₃) followed by crystallization from propyl acetate/hexanes gave N-benzyl-2-butyl-1H-imidazo[4,5-c]quinoline-1,4-diamine (237 mg) as light-yellow crystals. mp 159.3–160.5° C. ¹H NMR (300 MHz, DMSO-d₆) δ 8.31 (d, J=8.2 Hz, 1H), 7.83 (d, J=8.4 Hz, 1H), 7.54 (m, 1H), 7.42–7.31 (m, 6H), 5.44 (s, 2H), 5.26 (t, J=5.6 Hz, 1H), 4.37 (d, J=5.6 Hz, 2H), 2.71 (t, J=8.4 Hz, 2H), 1.74 (m, 2H), 1.42 (m, 2H), 0.95 (t, J=7.3 Hz, 3H); MS m/z 346 (M+H)⁺; Anal. Calcd for C₂₁H₂₃N₅: C, 73.02; H, 6.71; N, 20.27. Found: C, 72.75; H, 6.55; N, 20.46.

Example 3

N¹-Isopropyl-2-methyl-1H-imidazo[4,5-c]quinoline-1,4-diamine

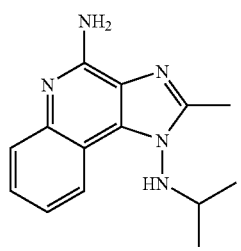

Part A

A solution of tert-butyl N'-(3-aminoquinolin-4-yl)hydrazinecarboxylate (11.67 g, 42.5 mmol) in 400 mL of anhydrous toluene was treated with trimethyl orthoacetate (5.96 mL, 46.8 mmol) and pyridine hydrochloride (100 mg) under an atmosphere of N₂ and heated to reflux. After stirring for 3 h, the reaction mixture was concentrated under reduced pressure to give a red solid. Chromatography (SiO₂, 0–10% MeOH/EtOAc) gave tert-butyl N-(2-methyl-1H-imidazo[4,5-c]quinolin-1-yl)carbamate (10.7 g) as a yellow foam.

Part B tert-Butyl N-(2-methyl-1H-imidazo[4,5-c]quinolin-1-yl)carbamate (5.00 g, 16.8 mmol) was dissolved in 40 mL of 1.65 M HCl in EtOH, and the reaction mixture was heated to reflux for 2 h. The reaction mixture was cooled and concentrated under reduced pressure to give a brown solid. The brown solid was crystallized from ethanol/H₂O to give 3.13 g of 2-methyl-1H-imidazo[4,5-c]quinolin-1-amine hydrochloride.

Part C

A suspension of 2-methyl-1H-imidazo[4,5-c]quinolin-1-amine hydrochloride (1.79 g, 7.62 mmol) in 30 mL of 2,2-dimethoxypropane was treated with 90 mg of p-toluenesulfonic acid. The reaction mixture was heated to 100° C. overnight. The reaction mixture was then treated with 10 mL of H₂O and 10 mL of MeOH, and heating was continued for 24 h. The reaction mixture was cooled and concentrated under reduced pressure. The resulting oil was dissolved in 50 mL of CHCl₃ and washed with 2% Na₂CO₃ solution, H₂O and brine. The organic portion was dried over Na₂SO₄, filtered and concentrated to give N-isopropylidene(2-methyl-1H-imidazo[4,5-c]quinolin-1-yl)amine (1.82 g) as a yellow solid.

Part D

A solution of N-isopropylidene(2-methyl-1H-imidazo[4,5-c]quinolin-1-yl)amine (1.82 g, 7.64 mmol) dissolved in 40 mL of MeOH was treated with NaBH₄ (1.16 g, 30.6 mmol). After stirring for 18 h, the reaction was quenched with saturated NH₄Cl solution and partitioned between CH₂Cl₂ and 2% Na₂CO₃ solution. The organic portion was washed with 2% Na₂CO₃ solution, H₂O and brine and dried over Na₂SO₄. The resulting organic portion was filtered and concentrated under reduced pressure to give N-isopropyl(2-methyl-1H-imidazo[4,5-c]quinolin-1-yl)amine (1.84 g) as a yellow foam.

Part E

A solution of N-isopropyl(2-methyl-1H-imidazo[4,5-c]quinolin-1-yl)amine (1.84 g, 7.66 mmol) dissolved in 50 mL of 1,2-dichloroethane was treated with MCPBA (77% max., 2.36 g, 9.58 mmol). After stirring for 3 h, the reaction mixture was treated with 2% Na₂CO₃ solution and extracted into CH₂Cl₂. The organic portion was washed with saturated 2% Na₂CO₃ solution, H₂O and brine. The organic portion was dried over Na₂SO₄, filtered and concentrated to give N-isopropyl(2-methyl-5-oxido-1H-imidazo[4,5-c]quinolin-1-yl)amine (1.95 g) as a light orange solid.

Part F

A solution of N-isopropyl(2-methyl-5-oxido-1H-imidazo[4,5-c]quinolin-1-yl)amine (1.95 g, 7.61 mmol) in 75 mL of CH₂Cl₂ was treated with 35 mL of concentrated NH₄OH solution. To the rapidly stirred solution was added p-toluenesulfonyl chloride (1.52 g, 7.99 mmol). After stirring for 30 min, the reaction mixture was treated with CHCl₃ (25 mL) and H₂O (35 mL). The layers were separated and the organic portion was washed with 2% Na₂CO₃ solution (2×), H₂O and brine. The organic portion was dried over Na₂SO₄, filtered and concentrated to give a light-yellow solid. Crystallization from propyl acetate gave $N^1$-isopropyl-2-methyl-1H-imidazo[4,5-c]quinoline-1,4-diamine (747 mg) as off-white crystals. mp 227–229° C.; $^1$H NMR (300 MHz, CDCl$_3$) δ 8.19 (dd, J=8.2, 1.1 Hz, 1H), 7.79 (dd, J=8.4, 0.7 Hz, 1H), 7.53–7.45 (m, 1H), 7.33–7.26 (m, 1H), 5.42 (s, 2H), 4.91 (d, J=1.4 Hz, 1H), 3.73–3.62 (m, 1H), 2.64 (s, 3H), 1.15 (d, J=6.2 Hz, 6H); $^{13}$C NMR (75 MHz, CDCl$_3$) δ 151.4, 151.3, 144.9, 133.3, 127.6, 127.3, 124.6, 122.4, 120.2, 115.4, 52.3, 20.9, 13.8; MS m/z 256 (M+H)$^+$; Anal. Calcd for $C_{14}H_{17}N_5$: C, 65.86; H, 6.71; N, 27.43; Found: C, 65.59; H, 6.56; N, 27.09.

Example 4

$N^1$-Benzyl-2-ethoxymethyl-1H-imidazo[4,5-c]quinoline-1,4-diamine

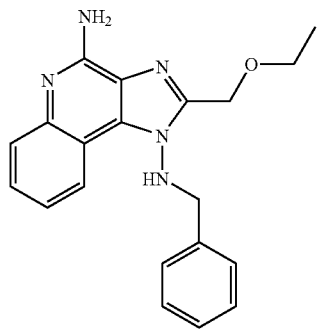

Part A

A solution of tert-butyl N'-(3-aminoquinolin-4-yl)hydrazinecarboxylate (12.15 g, 44.3 mmol) in 200 mL of anhydrous CH$_2$Cl$_2$ was cooled to 0° C. and treated with triethylamine (7.72 mL, 55.4 mmol) and 2-ethoxyacetyl chloride (5.70 g, 46.5 mmol) under an atmosphere of N$_2$. After 3 h, an additional 1 mL of 2-ethoxyacetyl chloride was added. After stirring for 2 h, the reaction mixture was concentrated under reduced pressure to give a brown solid. This was dissolved in 150 mL of EtOH and treated with 18.5 mL of triethylamine, and the mixture was refluxed overnight. The reaction mixture was concentrated under reduced pressure to give a dark-red oil. The red oil was dissolved in 200 mL of CH$_2$Cl$_2$ and washed with H$_2$O (2×75 mL) and brine (75 mL). The organic portion was dried over Na$_2$SO$_4$, filtered, and concentrated under reduced pressure to give a red solid. The solid was treated with a minimum amount of hot Et$_2$O and filtered to remove insoluble material. The filtrate was concentrated to give tert-butyl N-(2-ethoxymethyl-1H-imidazo[4,5-c]quinolin-1-yl)carbamate (14.3 g) as a tan solid.

Part B tert-Butyl N-(2-ethoxymethyl-1H-imidazo[4,5-c]quinolin-1-yl)carbamate (14.3 g, 41.8 mmol) was dissolved in 150 mL of 2 M HCl in EtOH, and the reaction mixture was heated to reflux for 3 h. The reaction mixture was cooled and concentrated under reduced pressure to give a brown solid. The brown solid was dissolved in 100 mL of H$_2$O and treated with 100 mL of concentrated NH$_4$OH solution. The basic, aqueous solution was then extracted with CH$_2$Cl$_2$ (4×). The combined organic layers were then washed with brine and dried over Na$_2$SO$_4$. The solution was filtered and concentrated under reduced pressure to give a brown foam. The foam was triturated with Et$_2$O (150 mL) and filtered. The filtrate was concentrated to give 2-ethoxymethy-1H-imidazo[4,5-c]quinolin-1-amine (5.77 g) as a tan solid.

Part C

A solution of 2-ethoxymethy-1H-imidazo[4,5-c]quinolin-1-amine (1.50 g, 6.19 mmol) in 50 mL of isopropanol was treated with benzaldehyde (0.66 mL, 6.50 mmol) and 10 mg of p-toluenesulfonic acid. The reaction mixture was heated to 120° C. for 3 d. The reaction mixture was cooled, and a precipitate started to form. The reaction mixture was treated with Et$_2$O and then filtered to give N-benzylidene-(2-ethoxymethy-1H-imidazo[4,5-c]quinolin-1-yl)amine (1.21 g) as a gray solid.

Part D

A solution of N-benzylidene-(2-ethoxymethy-1H-imidazo[4,5-c]quinolin-1-yl)amine (1.00 g, 3.03 mmol) in 50 mL of MeOH was treated with NaBH$_4$ (458 mg, 12.1 mmol). After stirring for 1.5 h, the reaction mixture was concentrated, then treated with saturated NaHCO$_3$ solution, and extracted into CHCl$_3$. The organic portion was washed with H$_2$O and brine and dried over Na$_2$SO$_4$. The resulting solution was filtered and concentrated to give N-benzyl-(2-ethoxymethy-1H-imidazo[4,5-c]quinolin-1-yl)amine (1.01 g) as a tan solid.

Part E

A solution of N-benzyl-(2-ethoxymethy-1H-imidazo[4,5-c]quinolin-1-yl)amine (1.01 g, 3.04 mmol) in 50 mL of CH$_2$Cl$_2$ was treated with MCPBA (77% max., 1.02 g, 4.56 mmol). After stirring for 3 h, the reaction mixture was quenched with 2% Na$_2$CO$_3$ solution and extracted into CH$_2$Cl$_2$. The organic portion was washed with H$_2$O and brine. The organic portion was dried over Na$_2$SO$_4$, filtered and concentrated to give N-benzyl-(2-ethoxymethy-5-oxido-1H-imidazo[4,5-c]quinolin-1-yl)amine (0.99 g) as a light-yellow solid.

Part F

A solution of N-benzyl-(2-ethoxymethy-5-oxido-1H-imidazo[4,5-c]quinolin-1-yl)amine (0.99 g, 2.84 mmol) in 50 mL of CH$_2$Cl$_2$ was treated with 25 mL of concentrated NH$_4$OH solution. To the rapidly stirred solution was added p-toluenesulfonyl chloride (569 mg, 2.98 mmol). After stirring for 30 min, the reaction was treated with CH$_2$Cl$_2$ (50 mL) and H$_2$O (25 mL). The layers were separated and the organic portion was washed 2% Na$_2$CO$_3$ solution, H$_2$O and brine. The organic portion was dried over Na$_2$SO$_4$, filtered and concentrated to give a tan solid. Chromatography (SiO$_2$, 2% MeOH/CHCl$_3$ containing 0.5% concentrated NH$_4$OH) followed by crystallization from propyl acetate gave $N^1$-benzyl-2-ethoxymethyl-1H-imidazo[4,5-c]quinoline-1,4-diamine (148 mg) as white needles. mp 152–155° C.; $^1$H NMR (300 MHz, DMSO-d$_6$) δ 8.61 (dd, J=8.2, 1.2 Hz, 1H), 7.85–7.77 (m, 1H), 7.59–7.52 (m, 1H), 7.42–7.34 (m, 4H), 7.33–7.24 (m, 2H), 6.02 (t, J=6.6 Hz, 1H), 5.39 (s, 2H), 4.43 (s, 2H), 4.40 (d, J=6.7 Hz, 2H), 3.55 (q, J=7.0 Hz, 2H), 1.22 (t, J=7.0 Hz, 3H); 13C NMR (75 MHz, CDCl$_3$) δ 151.1, 147.9, 144.9, 135.7, 129.2, 129.1, 128.6, 127.8, 126.7, 122.4, 120.7, 66.7, 65.3, 56.7, 15.0; MS m/z 348 (M+H)$^+$; Anal. Calcd for C$_2$OH$_{21}$N$_5$O.0.36H$_2$O: C, 68.90; H, 6.11; N, 20.09; Found: C, 68.50; H, 6.07; N, 20.11.

Example 5

2-Ethoxymethyl-N$^1$-isopropyl-1H-imidazo[4,5-c]quinoline-1,4-diamine

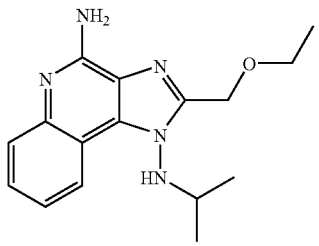

Part A

A solution of 2-ethoxymethy-1H-imidazo[4,5-c]quinolin-1-amine (2.50 g, 10.3 mmol) in 250 mL of 1,2-dichloroethane was treated with acetone (0.83 mL, 11.3 mmol), acetic acid (0.65 mL, 11.3 mmol) and sodium triacetoxyborohydride (2.39 g, 11.3 mL). After stirring overnight, additional acetone (5 mL), acetic acid (0.65 mL, 11.3 mmol) and sodium triacetoxyborohydride (2.39 g, 11.3 mL) were added. After 2 d, the reaction was carefully quenched by addition of saturated NaHCO$_3$ solution. The layers were separated and the aqueous portion was extracted with additional CH$_2$Cl$_2$. The combined organic layers were washed with H$_2$O and brine, dried over Na$_2$SO$_4$, and concentrated under reduced pressure to give a brown oil. Some isopropylidene intermediate was still present, so the material was dissolved in 50 mL of MeOH and treated with NaBH$_4$ (1.0 g). After 2 h, the reaction was quenched by the addition of H$_2$O and the reaction mixture was concentrated under reduced pressure. The residue was partitioned between saturated NaHCO$_3$ solution and CH$_2$Cl$_2$. The layers were separated and the organic portion was washed with saturated NaHCO$_3$, H$_2$O and brine. The organic portion was dried over Na$_2$SO$_4$, filtered, and concentrated under reduced pressure. Chromatography (SiO$_2$, 4% MeOH/CHCl$_3$) gave N-(2-ethoxymethy-1H-imidazo[4,5-c]quinolin-1-yl)isopropylamine (0.98 g) as a brown oil.

Part B

A solution of N-(2-ethoxymethy-1H-imidazo[4,5-c]quinolin-1-yl)isopropylamine (0.98 g, 3.45 mmol) in 35 mL of CH$_2$Cl$_2$ was treated with MCPBA (77% max., 1.10 g, 4.48 mmol). After stirring for 3 h, the reaction was quenched with 2% Na$_2$CO$_3$ solution and extracted into CH$_2$Cl$_2$. The organic portion was washed with H$_2$O and brine. The organic portion was dried over Na$_2$SO$_4$, filtered and concentrated to give N-(2-ethoxymethy-5-oxido-1H-imidazo[4,5-c]quinolin-1-yl)isopropylamine (0.93 g) as a light-orange solid.

Part C

A solution of N-(2-ethoxymethy-5-oxido-1H-imidazo[4,5-c]quinolin-1-yl)isopropylamine (0.93 g, 3.10 mmol) in 25 mL of CH$_2$Cl$_2$ was treated with 15 mL of concentrated NH$_4$OH solution. To the rapidly stirred solution was added p-toluenesulfonyl chloride (620 mg, 3.25 mmol). After stirring for 30 min, the reaction was treated with CH$_2$Cl$_2$ (20 mL) and H$_2$O (15 mL). The layers were separated and the organic portion was washed with 2% Na$_2$CO$_3$ solution, H$_2$O and brine. The organic portion was dried over Na$_2$SO$_4$, filtered and concentrated to give a tan solid. Chromatography (SiO$_2$, 5% MeOH/CHCl$_3$) gave 2-ethoxymethyl-N$^1$-isopropyl-1H-imidazo[4,5-c]quinoline-1,4-diamine (368 mg) as a tan solid. mp 162–164° C.; $^1$H NMR (300 MHz, CDCl$_3$) δ 8.60 (dd, J=8.2, 1.1 Hz, 1H), 7.77 (dd, J=8.4, 0.7 Hz, 1H), 7.54–7.47 (m, 1H), 7.33–7.54 (m, 1H), 5.55 (d, J=3.2 Hz, 1H), 5.41 (s, 2H), 4.89 (s, 2H), 3.73–3.60 (m, 3H), 1.26 (t, J=7.0 Hz, 3H); 1.15 (d, J=6.2 Hz, 6H); $^{13}$C NMR (75 MHz, CDCl$_3$) δ 151.1, 148.7, 145.0, 127.7, 126.6, 123.9, 121.9, 121.3, 115.4, 66.8, 65.7, 52.5, 20.6, 15.1; MS m/z 300 (M+H)$^+$; Anal. Calcd for C$_{16}$H$_{21}$N$_5$O.0.48 H$_2$O: C, 62.39; H, 7.19; N, 22.74; Found: C, 62.38, H, 6.90; N, 22.79.

Example 6

N$^1$-Cyclohexyl-2-(ethoxymethyl)-1H-imidazo[4,5-c]quinoline-1,4-diamine

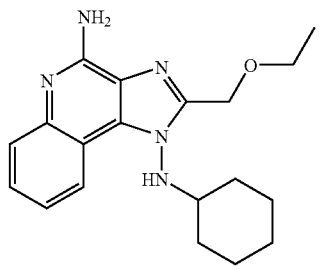

Part A 2-(Ethoxymethyl)-1H-imidazo[4,5-c]quinolin-1-amine (0.900 g, 3.71 mmol) was placed in a 50 mL round bottom flask, dissolved in 1,2-dichloromethane, and placed under N$_2$. Cyclohexanone (1.19 mL, 11.5 mmol), acetic acid (0.45 mL, 7.79 mmol) and sodium triacetoxyborohydride (1.65 g, 7.79 mmol) were added and the reaction was stirred under N$_2$ at room temperature for 5 days. The reaction was quenched by slow addition of saturated NaHCO$_3$ solution (25 mL) and dichloromethane (25 mL). The mixture was transferred to a separatory funnel and the phases separated. The aqueous portion was extracted with dichloromethane (25 mL). The combined organic portions were washed sequentially with water (25 mL) and brine (25 mL), dried (Na$_2$SO$_4$), filtered and then concentrated to yield a thick brown oil. Analysis by liquid chromatography/mass spectroscopy (LC/MS) of the crude product showed it to be a mixture of the hydrazone and hydrazine. The oil was dissolved in methanol (25 mL), chilled in an ice water bath and then treated with sodium borohydride (1.25 g). The reaction was quenched with water (25 mL) and the mixture concentrated. The residue was partitioned between dichloromethane 50 mL) and water (15 mL), transferred to a separatory funnel, and the phases were separated. The organic portion was washed sequentially with saturated NaHCO$_3$ solution (20 mL), water (20 mL) and brine (20 mL), dried (Na$_2$SO$_4$), filtered and then concentrated to yield a thick brown oil. The material was purified by column chromatography (35 g SiO$_2$, 97:3 chloroform:methanol) to yield 0.51 g of N-cyclohexyl-2-(ethoxymethyl)-1H-imidazo[4,5-c]quinolin-1-amine as a light brown oil/solid.

Part B

N-Cyclohexyl-2-(ethoxymethyl)-1H-imidazo[4,5-c]quinolin-1-amine (0.51 g, 1.57 mmol) was placed in a 200 mL round bottom flask, purged with N$_2$ and dissolved in dichloromethane (25 mL). MCPBA (0.484 g, 1.96 mmol, 77% max) was added over a 5 min period. The reaction was stirred at room temperature under N$_2$. After 2 h, analysis by thin layer chromatography (TLC) (SiO$_2$, 95:5 chloroform:methanol) showed complete conversion. The solution was diluted with dichloromethane (15 mL) and 2% sodium carbonate solution (15 mL). The mixture was transferred to a separatory funnel, and the phases were separated. The organic portion was washed sequentially with 2% sodium carbonate solution (15 mL), water (15 mL) and brine (15 mL), dried (Na$_2$SO$_4$), filtered and then concentrated to yield 0.431 g of N-cyclohexyl-2-(ethoxymethyl)-5-oxido-1H-imidazo[4,5-c]quinolin-1-amine as a tan foam.

Part C

N-Cyclohexyl-2-(ethoxymethyl)-5-oxido-1H-imidazo[4,5-c]quinolin-1-amine (0.425 g, 1.25 mmol) was placed in a 100 mL round bottom flask and dissolved in dichloromethane (20 mL). Ammonium hydroxide solution (10 mL) was added and the mixture was stirred vigorously. The stirred mixture was chilled in an ice water bath. Para-toluenesulfonyl chloride (0.250 g, 1.31 mmol) was added over 5 min. After 30 min of stirring at 0° C. TLC (SiO$_2$, 95:5 chloroform:methanol) showed complete conversion. The mixture was warmed to room temperature and then diluted with dichloromethane (25 mL) and water (10 mL). The mixture was transferred to a separatory funnel and the phases separated. The organic portion was washed sequentially with 2% sodium carbonate solution (15 mL), water (15 mL) and brine (15 mL), dried over Na$_2$SO$_4$, filtered and then concentrated to yield an orange/tan foamy solid. The material was purified by column chromatography (40 g SiO$_2$, 95:5 chloroform:methanol) to yield the product as an off white solid. The off-white solid was dissolved in 3 mL of a 9:1 chloroform:methanol mixture. A small spatula tip full of activated carbon (DARCO G 60–100 mesh) was added and the mixture was stirred at room temperature for 3 h. The mixture was filtered through a short column of SiO$_2$ (5 g) eluting with 9:1 chloroform:methanol. The filtrate was concentrated to yield a glassy solid. The glassy solid was triturated in 15 mL diethyl ether for 2 h to provide a white solid. The solid was collected by vacuum filtration and rinsed with diethyl ether. The solid was dried in a vacuum oven (70° C.) to yield 0.062 g of N$^1$-cyclohexyl-2-(ethoxymethyl)-1H-imidazo[4,5-c]quinoline-1,4-diamine. mp 143–145° C.; $^1$H NMR (300 MHz, DMSO-d$_6$) δ 8.61 (dd, J=8.1, 1.1 Hz, 1H), 7.58 (dd, J=8.3, 0.9 Hz, 1H), 7.46–7.38 (m, 1H), 7.28–7.21 (m, 1H), 6.99 (d, J=1.9 Hz, 1H), 6.69 (s, 2H), 4.77 (s, 2H), 3.63 (q, J=7.0 Hz, 2H), 3.32–3.23 (m, 1H), 1.71–1.52 (m, 5H), 1.30–1.05 (m, 8H); $^{13}$C NMR (75 MHz, DMSO-d$_6$) δ; MS m/z 152.1, 150.3, 145.0, 133.4, 127.4, 125.8, 123.9, 121.6, 121.1, 115.0, 65.8, 63.1, 59.8, 30.9, 25.8, 24.3, 15.4; MS m/z 340 (M+H)$^+$; Anal. Calcd for C$_{19}$H$_{25}$N$_5$O: C, 67.23; H, 7.42; N, 20.63; Found: C, 67.32; H, 7.37; N, 20.55.

Example 7

N$^1$,N$^1$-Dimethyl-2-ethoxymethyl-1H-imidazo[4,5-c]quinoline-1,4-diamine

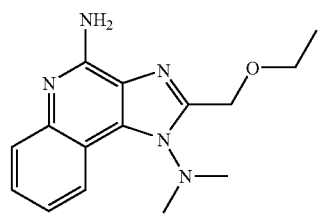

Part A

A solution of 4-chloro-3-nitroquinoline (5.00 g, 24.0 mmol) in 100 mL CH$_2$Cl$_2$ was cooled to 0° C. and treated with triethylamine (8.40 mL, 60.0 mmol) and N,N-dimethylhydrazine (5.65 mL, 74.4 mmol) under an atmosphere of nitrogen. After 18 h, the mixture was diluted with 2% Na$_2$CO$_3$ solution and CHCl$_3$ and separated. The organic portion was washed with water and brine, dried over Na$_2$SO$_4$, filtered and concentrated under reduced pressure to yield 4-(2,2-dimethylhydrazino)-3-nitroquinoline (5.33 g) as a yellow/orange crystalline solid.

Part B

A suspension of 4-(2,2-dimethylhydrazino)-3-nitroquinoline (5.33 g, 23.0 mmol) in 125 mL of acetonitrile was treated with 5% platinum on carbon (0.45 g, 0.11 mmol) and the mixture was shaken under an atmosphere of hydrogen (3.8×10$^5$ Pa). After 5 h, the reaction mixture was filtered through a pad of CELITE filter agent and rinsed with 80:20 acetonitrile:MeOH. The filtrate was concentrated under reduced pressure. The resulting oil was dissolved in CH$_2$Cl$_2$, dried over Na$_2$SO$_4$, filtered and concentrated under reduced pressure to give 4-(2,2-dimethylhydrazino)quinolin-3-amine (4.64 g) as a red foam.

Part C

A solution of 4-(2,2-dimethylhydrazino)quinolin-3-amine (4.64 g, 23.0 mmol) in 75 mL of CH$_2$Cl$_2$ was cooled to 0° C. under an atmosphere of nitrogen. The reaction mixture was treated with triethylamine (6.72 mL, 48.2 mmol) followed by dropwise addition of ethoxyacetyl chloride (2.95 g, 24.1 mmol). After 1.5 h, the reaction mixture was concentrated under reduced pressure. The resulting oil was dissolved in 75 mL of ethanol, treated with triethylamine (9.60 mL, 68.9 mmol) and heated to reflux. After 5 d, the reaction mixture was concentrated under reduced pressure. The resulting oil was dissolved in CH$_2$Cl$_2$, washed with 2% Na$_2$CO$_3$ solution, water and brine, dried over Na$_2$SO$_4$, filtered and concentrated under reduced pressure to yield a brown oil. Chromatography (SiO$_2$, 5–10% MeOH/CHCl$_3$) gave N,N-dimethyl-2-(ethoxymethyl)-1H-imidazo[4,5-c]quinolin-1-amine (0.89 g) as a brown oil.

Part D

A solution of N,N-dimethyl-2-(ethoxymethyl)-H-imidazo[4,5-c]quinolin-1-amine (0.89 g, 3.3 mmol) in 25 mL of CH$_2$Cl$_2$ was treated with MCPBA (1.01 g, 4.10 mmol, 77% max). After 1.5 h, the reaction mixture was treated with 7 mL of concentrated NH₄OH solution and p-toluenesulfonyl chloride (0.69 g, 3.6 mmol). After 30 min, the reaction was diluted with CH₂Cl₂ and water and the phases were separated. The organic portion was washed with 2% Na₂CO₃ solution (2×), water and brine, dried over Na₂SO₄, filtered and concentrated under reduced pressure to yield an orange solid. Recrystallization twice from acetonitrile gave N¹,N¹-dimethyl-2-ethoxymethyl-1H-imidazo[4,5-c]quinoline-1,4-diamine (0.208 g) as gold, needle-like crystals. mp 213–215° C.; ¹H NMR (300 MHz, CDCl₃) δ 8.57 (dd, J=8.3, 1.4 Hz, 1H), 7.79 (dd, J=8.4, 0.7 Hz, 1H), 7.56–7.48 (m, 1H), 7.38–7.29 (m, 1H), 5.45 (s, 2H), 4.48 (s, 2H), 3.69 (a, J=7.0 Hz, 2H), 3.20 (s, 6H), 1.29 (t, J=7.0 Hz, 3H); 13C NMR (75 MHz, CDCl₃) δ 151.2, 149.3, 145.1, 133.5, 127.7, 126.7, 123.8, 122.1, 115.3, 66.4, 65.6, 45.3, 15.1; MS (APCI) m/z 286 (M+H)⁺; Anal. Calcd for C₁₅H₁₉N₅O: C, 63.14; H, 6.71; N, 24.54; Found: C, 63.02; H, 6.91; N, 24.57.

Example 8

2-Ethoxymethyl-N¹-(furan-2-ylmethyl)-1H-imidazo[4,5-c]quinoline-1,4-diamine

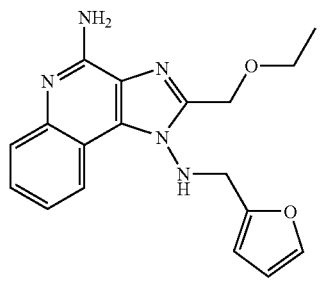

Part A

A solution of 2-ethoxymethyl-1H-imidazo[4,5-c]quinolin-1-amine (1.50 g, 6.19 mmol) in 20 mL of isopropanol was treated with 2-furaldehyde (1.08 mL, 13.0 mmol) and 2 drops of concentrated HCl and heated to reflux under an atmosphere of nitrogen. After 48 h, the reaction was concentrated under reduced pressure to yield a brown oil. The oil was dissolved in 30 mL of CHCl₃ and washed with 5% Na₂CO₃ solution, water and brine, dried over Na₂SO₄, filtered and concentrated under reduced pressure to yield N-(2-ethoxymethyl-1H-imidazo[4,5-c]quinolin-1-yl)(furan-2-ylmethylene)amine (1.86 g) as a light brown solid.

Part B

A solution of N-(2-ethoxymethyl-1H-imidazo[4,5-c]quinolin-1-yl)(furan-2-ylmethylene)amine (1.86 g, 5.81 mmol) in 20 mL of methanol was treated with NaBH₄ (0.659 g, 17.4 mmol) and stirred under an atmosphere of nitrogen. After 18 h the reaction was quenched by addition of 20 mL of water. The reaction mixture was concentrated under reduced pressure and dissolved in CHCl₃. The organic portion was washed with 2% Na₂CO₃ solution, water and brine, dried over Na₂SO₄, filtered and concentrated under reduced pressure to yield N-(2-ethoxymethyl-1H-imidazo[4,5-c]quinolin-1-yl)(furan-2-ylmethyl)amine (1.70 g) as a thick orange syrup.

Part C

A solution of N-(2-ethoxymethyl-1H-imidazo[4,5-c]quinolin-1-yl)(furan-2-ylmethyl)amine (1.70 g, 5.27 mmol) in 45 mL of CH₂Cl₂ was treated with MCPBA (1.48 g, 6.59 mmol, 77% max). After 1.5 h the reaction mixture was treated with 15 mL of concentrated NH₄OH solution and p-toluenesulfonyl chloride (1.06 g, 5.54 mmol). After 45 min the reaction mixture was diluted with water and CHCl₃ and separated. The organic portion was washed with 3% Na₂CO₃ solution, water and brine, dried over Na₂SO₄, and concentrated under reduced pressure to yield a yellow foam. Chromatography (SiO₂, 95:5 CHCl₃:MeOH) gave an off white foam. The foam was triturated with diethyl ether and filtered to give 2-ethoxymethyl—NM-(furan-2-ylmethyl)-1H-imidazo[4,5-c]quinoline-1,4-diamine (1.03 g) as an off white powder. mp dec.>200° C.; ¹H NMR (300 MHz, CDCl₃) δ 8.57 (dd, J=8.1, 1.1 Hz, 1H), 7.80 (dd, J=8.4, 0.8 Hz, 1H), 7.57–7.51 (m, 1H), 7.45 (d, J=1.8 Hz, 1H), 7.39–7.33 (m, 1H), 6.34–6.32 (m, 1H), 6.24 (t, J=5.3 Hz, 1H), 6.07 (d, J=3.1 Hz, 1H), 5.43 (s, 2H), 4.40–4.38 (m, 4H), 3.57 (q, J=7.0 Hz, 2H), 1.25 (t, J=7.0 Hz, 3H); ¹³C NMR (75 MHz, CDCl₃) δ 151.1, 149.5, 147.8, 144.8, 143.0, 132.6, 127.8, 126.6, 124.1, 122.5, 120.7, 115.1, 111.1, 110.1, 66.8, 64.9, 48.5, 15.0; MS (APCI) m/z 338 (M+H)⁺; Anal. Calcd for C₁₈H₁₉N₅O₂: C, 64.08; H, 5.68; N, 20.76; Found: C, 63.89; H, 5.75; N, 20.48.

Example 9

2-Ethoxymethyl-N¹-(1-ethylpropyl)-1H-imidazo[4,5-c]quinoline-1,4-diamine

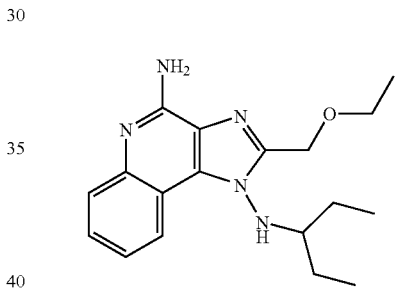

Part A

A solution of 2-ethoxymethyl-1H-imidazo[4,5-c]quinolin-1-amine (1.50 g, 6.19 mmol) in 20 mL of toluene and 5 mL of isopropanol was treated with 3-pentanone (5.00 mL, 47.2 mmol) and pyridinium p-toluenesulfonate (0.015 g, 0.062 mmol) and the reaction mixture was heated to reflux under an atmosphere of nitrogen. After 7 d, the reaction mixture was concentrated under reduced pressure, dissolved in CHCl₃, washed with water (2×) and brine, dried over Na₂SO₄, filtered and concentrated under reduced pressure to yield a light brown oil. Chromatography (SiO₂, 95:5 CHCl₃:MeOH) gave N-(2-ethoxymethyl-1H-imidazo[4,5-c]quinolin-1-yl)(1-ethylpropylidene)amine (1.78 g) as a yellow/green syrup.

Part B

A solution of N-(2-ethoxymethyl-1H-imidazo[4,5-c]quinolin-1-yl)(1-ethylpropylidene)amine (1.78 g, 5.73 mmol) in 20 mL of methanol was treated with NaBH₄ (0.867 g, 22.9 mmol) and CeCl₃.7H₂O (15 mg, catalytic) and stirred under an atmosphere of nitrogen. After 24 h, the reaction was concentrated under reduced pressure, dissolved CHCl₃, washed with water (2×) and brine, dried over Na₂SO₄, filtered and concentrated under reduced pressure to yield a yellow/green syrup. Chromatography (SiO₂, 93:7

CHCl$_3$:MeOH) gave N-(2-ethoxymethyl-1H-imidazo[4,5-c]quinolin-1-yl)(1-ethylpropyl)amine (1.01 g) as a yellow/green oil.

Part C

A solution of N-(2-ethoxymethyl-1H-imidazo[4,5-c]quinolin-1-yl)(1-ethylpropyl)amine (1.01 g, 3.23 mmol) in 30 mL of CH$_2$Cl$_2$ was treated with MCPBA (1.04 g, 4.20 mmol, 77% max). After 1.5 h the reaction mixture was treated with 15 mL of concentrated NH$_4$OH solution and p-toluenesulfonyl chloride (0.65 g, 3.39 mmol). After 30 min, the reaction mixture was diluted with CH$_2$Cl$_2$ and water and the phases were separated. The organic portion was washed with 2% Na$_2$CO$_3$ solution and water. The combined aqueous washes were back extracted with CHCl$_3$ (2×). The combined organic portions were washed with brine, dried over Na$_2$SO$_4$, filtered and concentrated under reduced pressure to yield a light yellow foam. Chromatography (SiO$_2$, 97:3 CHCl$_3$:MeOH) gave a white foam. The foam was triturated with CH$_2$Cl$_2$/hexanes and filtered to give 2-ethoxymethyl-N$^1$-(1-ethylpropyl)-1H-imidazo[4,5-c]quinoline-1,4-diamine (0.652 g) as a white solid. mp 125–128° C.; $^1$H NMR (300 MHz, CDCl$_3$) δ 8.66 (dd, J=8.3, 1.1 Hz, 1H), 7.77 (dd, J=7.6, 0.8 Hz, 1H), 7.55–7.48 (m, 1H), 7.33–7.26 (m, 1H), 5.66, (d, J=3.0 Hz, 1H), 5.41 (s, 2H), 4.87 (s, 2H), 3.64 (q, J=7.0 Hz, 2H), 3.32–3.23 (m, 1H), 1.70–1.56 (m, 2H), 1.55–1.41 (m, 2H), 1.27 (t, J=7.1 Hz, 3H), 0.94 (t, J=7.5 Hz, 6H); $^{13}$C NMR (75 MHz, CDCl$_3$) δ 151.5, 149.1, 145.4, 135.0, 132.4, 128.1, 126.9, 124.1, 122.2, 122.0, 115.9, 67.2, 66.2, 64.0, 24.5, 15.5, 10.2; MS (APCI) m/z 328 (M+H)$^+$; Anal. Calcd for C$_{18}$H$_{25}$N$_5$O: C, 66.03; H, 7.70; N, 21.39; Found: C, 65.64; H, 7.89; N, 21.02.

Example 10

2-Ethoxymethyl-N$^1$-isobutyl-1H-imidazo[4,5-c]quinoline-1,4-diamine

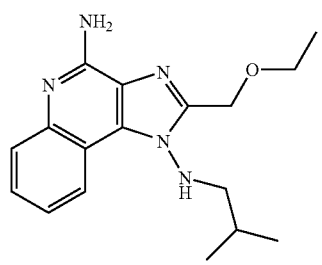

Part A

A solution of 2-ethoxymethyl-1H-imidazo[4,5-c]quinolin-1-amine (0.940 g, 3.88 mmol) in 20 mL of toluene and 5 mL of isopropanol was treated with isobutyraldehyde (0.800 mL, 8.81 mmol) and pyridinium p-toluenesulfonate (0.098 g, 0.39 mmol) and the reaction mixture was heated to reflux under an atmosphere of nitrogen. After 48 h, the reaction mixture was concentrated under reduced pressure and dissolved in CHCl$_3$. The organic portion was washed with water (2×) and brine, dried over Na$_2$SO$_4$, filtered and concentrated under reduced pressure to yield a light brown oil which solidified under vacuum to yield N-(2-ethoxymethyl-1H-imidazo[4,5-c]quinolin-1-yl)isobutylideneamine (1.15 g) as a tan solid.

Part B

A solution of N-(2-ethoxymethyl-1H-imidazo[4,5-c]quinolin-1-yl)isobutylideneamine (1.15 g, 3.88 mmol) in 15 mL of methanol was treated with NaBH$_4$ (0.44 g, 11.6 mmol) and stirred under an atmosphere of nitrogen. After 18 h, the reaction was concentrated under reduced pressure. The residue was partitioned between CHCl$_3$ and water, and the phases were separated. The organic portion was washed with water and brine, dried over Na$_2$SO$_4$, filtered and concentrated under reduced pressure to yield an orange oil. Chromatography (SiO$_2$, 97:3 CHCl$_3$:MeOH), gave N-(2-ethoxymethyl-1H-imidazo[4,5-c]quinolin-1-yl)isobutylamine (0.69 g) as clear, colorless crystals.

Part C

A solution of N-(2-ethoxymethyl-1H-imidazo[4,5-c]quinolin-1-yl)isobutylamine (1.16 g, 3.89 mmol) in 30 mL of CH$_2$Cl$_2$ was treated with MCPBA (1.25 g, 5.05 mmol, 77% max). After 1.5 h, the reaction mixture was treated with 15 mL of concentrated NH$_4$OH solution and p-toluenesulfonyl chloride (0.78 g, 4.08 mmol). After 30 min the reaction mixture was diluted with CH$_2$Cl$_2$ and water, and the phases were separated. The organic portion was washed with 2% Na$_2$CO$_3$ solution and water. The combined aqueous washes were back extracted with CHCl$_3$ (2×). The combined organic portions were washed with brine, dried over Na$_2$SO$_4$, filtered and concentrated under reduced pressure to yield a brown foam. Chromatography (SiO$_2$, 97:3 CHCl$_3$:MeOH) yielded 2-ethoxymethyl-N$^1$-isobutyl-1H-imidazo[4,5-c]quinoline-1,4-diamine (0.049 g) as an off white solid. mp 137–140° C.; $^1$H NMR (300 MHz, DMSO-d$_6$, 350 K) δ 8.47 (dd, J=8.1, 0.9 Hz, 1H), 7.60 (d, J=8.3 Hz, 1H), 7.45–7.36 (m, 1H), 7.28–7.19 (m, 1H), 6.67 (t, J=6.2 Hz, 1H), 6.22 (s, 2H), 4.76 (s, 2H), 3.64 (q, J=7.0 Hz, 2H), 3.02 (t, J=6.4 Hz, 2H), 1.97 (s, J=6.7 Hz, 1H), 1.19 (t, J=7.0 Hz, 3H), 1.05 (d J=6.7 Hz, 6H); $^{13}$C NMR (75 MHz, DMSO-d$_6$) δ 151.9, 148.9, 144.8, 131.9, 126.9, 125.7, 123.8, 120.8, 114.2, 65.4, 62.8, 59.6, 26.7, 20.5, 14.9; MS (APCI) m/z 314 (M+H)$^+$; Anal. Calcd for C$_{17}$H$_{23}$N$_5$O: C, 65.15; H, 7.40; N, 22.35; Found: C, 64.88; H, 7.39; N, 22.38.

Example 11

2-Ethoxymethyl-N$^1$-isopropyl-6,7,8,9-tetrahydro-1H-imidazo[4,5-c]quinoline-1,4-diamine

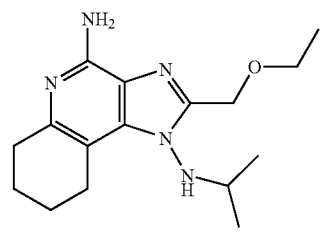

Part A

A solution of 2-ethoxymethyl-N$^1$-isopropyl-1H-imidazo[4,5-c]quinoline-1,4-diamine (0.700 g, 2.34 mmol) in 25 mL of trifluroacetic acid was treated with platinum(IV) oxide (0.27 g, 1.2 mmol) and the mixture was shaken under an atmosphere of hydrogen (3.8×10$^5$ Pa). After 15 h, the reaction mixture was filtered through a pad of CELITE filter agent, rinsed with 9:1:0.5 CHCl$_3$:MeOH:trifluoroacetic acid (TFA) and concentrated under reduced pressure to yield a creamy white solid. The solid was triturated with concentrated NH$_4$OH solution for 2 h and then extracted with CHCl$_3$ (3×). The organic portion was washed with brine, dried over Na$_2$SO$_4$, filtered and concentrated under reduced pressure to yield a white foam. The foam was triturated with diethyl ether, filtered and dried under reduced pressure to yield 2-ethoxymethyl-N$^1$-isopropyl-6,7,8,9-tetrahydro-1H-imidazo[4,5-c]quinoline-1,4-diamine (0.376 g) as a fine white solid. mp 144–146° C.; $^1$H NMR (300 MHz, CDCl$_3$) δ 5.08 (d, J=2.7 Hz, 1H), 4.92 (s, 2H), 4.78 (s, 2H), 3.61 (q, J=7.0 Hz, 2H), 3.53–3.43 (m, 1H), 3.07–3.03 (m, 2H), 2.85–2.81 (m, 2H), 1.92–1.79 (m, 4H), 1.25 (t, J=7.0 Hz, 3H), 1.08 (d, J=6.3 Hz, 6H); $^{13}$C NMR (75 MHz, CDCl$_3$) δ 149.4, 148.9, 148.1, 138.8, 122.9, 107.4, 66.6, 65.4, 53.0, 32.5, 23.7, 23.2, 22.8, 20.5, 15.1; MS (APCI) m/z 304 (M+H)$^+$; Anal. Calcd for C$_{16}$H$_{25}$N$_5$O: C, 63.34; H, 8.31; N, 23.08; Found: C, 63.32; H, 8.31; N, 22.97.

Example 12

2-Ethoxymethyl-N$^1$-(3-methylbutyl)-1H-imidazo[4,5-c]quinoline-1,4-diamine

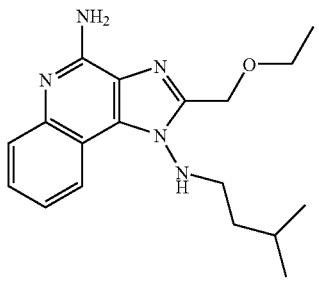

Part A

A solution of 2-ethoxymethyl-1H-imidazo[4,5-c]quinolin-1-amine (1.00 g, 4.13 mmol) in 20 mL of toluene and 5 mL of isopropanol was treated with isovaleraldehyde (0.94 mL, 8.76 mmol) and pyridinium p-toluenesulfonate (0.052 g, 0.21 mmol) and the reaction mixture was heated to reflux under an atmosphere of nitrogen. After 15 h, the reaction mixture was concentrated under reduced pressure to yield a brown oil. The oil was dissolved in CHCl$_3$ and washed with water (2×) and brine, dried over Na$_2$SO$_4$, filtered and concentrated under reduced pressure to yield N-(2-ethoxymethyl-1H-imidazo[4,5-c]quinolin-1-yl)(3-methylbutylidene)amine (1.28 g) as a dark orange oil.

Part B

A solution of N-(2-ethoxymethyl-1H-imidazo[4,5-c]quinolin-1-yl)(3-methylbutylidene)amine (1.28 g, 4.13 mmol) in 25 mL of methanol was treated with NaBH$_4$ (0.47 g, 12.39 mmol). After 1 h, the reaction was quenched with saturated NH$_4$Cl solution and the mixture was concentrated under reduced pressure. The residue was partitioned between CHCl$_3$ and saturated NaHCO$_3$ solution and the phases were separated The organic portion was washed with water and brine, dried over Na$_2$SO$_4$, filtered and concentrated under reduced pressure to yield N-(2-ethoxymethyl-1H-imidazo[4,5-c]quinolin-1-yl)(3-methylbutyl)amine (1.24 g) as a dark orange oil.

Part C

A solution of N-(2-ethoxymethyl-1H-imidazo[4,5-c]quinolin-1-yl)(3-methylbutyl)amine (1.24 g, 3.97 mmol) in 45 mL of CH$_2$Cl$_2$ was treated with MCPBA (1.87 g, 7.04 mmol, 77% max). After 1.5 h, the reaction mixture was treated with 15 mL of concentrated NH$_4$OH solution and p-toluenesulfonyl chloride (0.795 g, 4.17 mmol). After 30 min, the reaction mixture was diluted with CHCl$_3$ and water and the phases were separated. The organic portion was washed with 5% Na$_2$CO$_3$ solution, water and brine, dried over Na$_2$SO$_4$, filtered and concentrated under reduced pressure to yield a sticky orange foam. Chromatography (SiO$_2$, 97:3 CHCl$_3$:MeOH) gave an off white foam. The foam was triturated with diethyl ether and hexanes and filtered to give 2-ethoxymethyl-N$^1$-(3-methylbutyl)-1H-imidazo[4,5-c]quinoline-1,4-diamine (0.435 g) as a cream colored solid. mp 129–132° C.; $^1$H NMR (300 MHz, CDCl$_3$) δ 8.48 (dd, J=8.1, 1.1 Hz, 1H), 7.78 (d, J=8.3 Hz, 1H), 7.56–7.50 (m, 1H), 7.36–7.30 (m, 1H), 5.59 (t, J=6.7 Hz, 1H), 5.42 (s, 2H), 4.87 (s, 2H), 3.64 (q, J=7.0 Hz, 2H), 3.29 (q, J=7.0 Hz, 2H), 1.76 (s, J=6.7 Hz, 1H), 1.60 (q, J=6.9 Hz, 2H), 1.27 (t, J=7.0 Hz, 3H), 0.97 (d, J=6.6 Hz, 6H); $^{13}$C NMR (75 MHz, CDCl$_3$) δ 151.2, 147.8, 144.9, 133.1, 127.8, 126.6, 124.0, 122.3, 120.7, 115.2, 66.8, 65.3, 51.1, 36.7, 26.0, 22.6, 15.1; MS (APCI) m/z 328 (M+H)$^+$; Anal. Calcd for C$_{18}$H$_{25}$N$_5$O.0.06H$_2$O: C, 65.81; H, 7.71; N, 21.32; Found: C, 65.42; H, 7.75; N, 21.11. Karl Fischer analysis 0.32% water.

Example 13

2-Ethoxymethyl-1-(morpholin-4-yl)-1H-imidazo[4,5-c]quinolin-4-amine

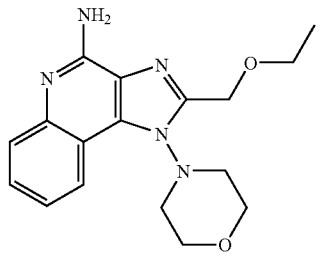

Part A

A solution of 4-chloro-3-nitroquinoline (5.00 g, 24.0 mmol) in 100 mL of CH$_2$Cl$_2$ was treated with triethylamine (6.37 mL, 48.0 mmol) and 4-aminomorpholine (3.47 mL, 36.0 mL) under an atmosphere of nitrogen. After 15 h, the reaction mixture was diluted with 5% Na$_2$CO$_3$ solution and CHCl$_3$, and the phases were separated. The organic portion was washed with another portion of 5% Na$_2$CO$_3$ solution, water and brine, dried over Na$_2$SO$_4$, filtered and concentrated under reduced pressure to yield a bright yellow solid. Recrystallization from acetonitrile gave N-(morpholin4-yl)(3-nitroquinolin-4-yl)amine (4.54 g) as bright yellow needle-like crystals.

Part B

A solution of N-(morpholin-4-yl)(3-nitroquinolin4-yl)amine (4.54 g, 16.6 mmol) in 150 mL of toluene was treated with 5% platinum on carbon (0.65 g, 0.17 mmol) and the mixture was shaken under an atmosphere of hydrogen (3.8×10$^5$ Pa). After 15 h, the reaction mixture was filtered through a pad of CELITE filter agent and rinsed with 4:1 toluene:MeOH. The filtrate was concentrated under reduced pressure to yield N4-(morpholin-4-yl)quinoline-3,4-diamine (4.06 g) as a red foam.

Part C

A solution of N4-(morpholin-4-yl)quinoline-3,4-diamine (4.06 g, 16.6 mmol) in 50 mL of $CH_2Cl_2$ was treated with triethylamine (4.40 mL, 33.2 mmol) and cooled to 0° C. The solution was treated dropwise with ethoxyacetyl chloride (2.40 g, 17.4 mmol) and stirred under an atmosphere of nitrogen. The reaction mixture was allowed to slowly come to room temperature. After 2 d, the reaction mixture was concentrated under reduced pressure to yield a red semi-solid. The material was dissolved in $CHCl_3$ and washed with water, 5% $Na_2CO_3$ solution and brine, dried over $Na_2SO_4$, filtered and dried to yield 2-ethoxy—N-{4-[(morpholin-4-yl)amino]quinolin-3-yl}acetamide (5.35 g) as a red/orange foam.

Part D

A suspension of 2-ethoxy-N-{4-[(morpholin-4-yl)amino]quinolin-3-yl}acetamide (5.35 g, 16.2 mmol) in 65 mL of toluene was treated with pyridine hydrochloride (0.94 g g, 0.081 mmol). The reaction flask was equipped with a Dean-Stark trap and the reaction mixture was heated to reflux under an atmosphere of nitrogen. After 2.5 d, the reaction mixture was concentrated under reduced pressure to yield a brown oil. The oil was dissolved in $CHCl_3$ and was washed with 5% $Na_2CO_3$ solution, water and brine, dried over $Na_2SO_4$, filtered and concentrated under reduced pressure to yield a brown foam. Chromatography ($SiO_2$, 95:5 $CHCl_3$:MeOH) gave 2-ethoxymethyl-1-(morpholin-4-yl)-1H-imidazo[4,5-c]quinoline (1.61 g) as a light brown solid.

Part E

A solution of 2-ethoxymethyl-1-(morpholin-4-yl)-1H-imidazo[4,5-c]quinoline (1.61 g, 5.51 mmol) in 40 mL of $CH_2Cl_2$ was treated with MCPBA (1.78 g, 6.70 mmol, 77% max). After 30 min, the reaction mixture was treated with 20 mL of concentrated $NH_4OH$ solution and p-toluenesulfonyl chloride (1.03 g, 5.41 mmol). After 15 min, the reaction mixture was diluted with $CH_2Cl_2$ and water and the phases were separated. The organic portion was washed with 5% $Na_2CO_3$ solution, water and brine, dried over $Na_2SO_4$, filtered and concentrated under reduced pressure to yield a tan foam. Chromatography ($SiO_2$, 97:3 $CHCl_3$:MeOH) gave a light yellow foam. The foam was triturated with diethyl ether and filtered to give 2-ethoxymethyl-1-(morpholin-4-yl)-1H-imidazo[4,5-c]quinolin-4-amine (0.794 g) as a light cream colored solid. mp 223–224° C.;

$^1$H NMR (300 MHz, $CDCl_3$) δ 8.77 (d, J=8.1 Hz, 1H), 7.79 (d, J=8.4 Hz, 1H), 7.54 (t, J=8.2 Hz, 1H), 7.34 (t, J=8.1 Hz, 1H), 5.48 (s, 2H), 4.85 (s, 2H), 4.06–4.03 (m, 4H), 3.74–3.66 (m, 4H), 3.42–3.38 (m, 2H), 1.29 (t, J=7.0 Hz, 3H); $^{13}$C NMR (75 MHz, $CDCl_3$) δ 151.2, 149.0, 145.3, 133.5, 127.9, 126.9, 123.7, 122.2, 121.3, 115.3, 67.5, 66.5, 65.9, 53.5, 15.1; MS (APCI) m/z 328 (M+H)$^+$; Anal. Calcd for $C_{17}H_{21}N_5O_2$: C, 62.37; H, 6.47; N, 21.39; Found: C, 62.14; H, 6.19; N, 21.34.

Example 14

N-{3-[(4-Amino-2-ethoxymethyl-1H-imidazo[4,5-c]quinolin-1-yl)amino]propyl}methanesulfonamide

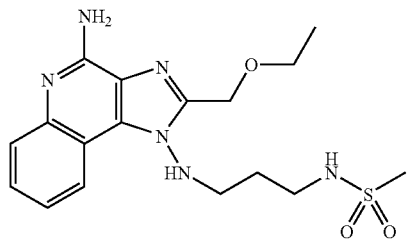

Part A

A solution of 1-amino-3,3-diethoxypropane (5.00 mL, 30.9 mmol) in 5 mL of tetrahydrofuran (THF) was treated with triethylamine (4.51 mL, 34.0 mmol) under an atmosphere of nitrogen and cooled to 0° C. The reaction mixture was then treated dropwise with a solution of di-tert-butyl dicarbonate (7.42 g, 34.0 mmol) in 25 mL of THF. The reaction mixture was stirred for 2 h at 0° C. and then allowed to come to room temperature. After 15 h, the reaction mixture was concentrated under reduced pressure, dissolved in ethyl acetate, washed with water (2×) and brine, dried over $Na_2SO_4$, filtered and concentrated under reduced pressure to yield tert-butyl (3,3-diethoxypropyl)carbamate (8.40 g) as a clear, faintly yellow oil.

Part B

A solution of 2-ethoxymethyl-1H-imidazo[4,5-c]quinolin-1-amine (1.00 g, 4.13 mmol) in 20 mL of acetonitrile and 5 mL of glacial acetic acid was treated with tert-butyl (3,3-diethoxypropyl)carbamate (2.55 g, 10.3 mmol) and heated to reflux under an atmosphere of nitrogen. After 15 h, the reaction mixture was concentrated under reduced pressure to yield a brown oil. The oil was partitioned between $CHCl_3$ and saturated $NaHCO_3$ solution and the phases were separated. The organic portion was washed with water (2×) and brine, dried over $Na_2SO_4$, filtered and concentrated under reduced pressure to yield tert-butyl {3-[(2-ethoxymethyl-1H-imidazo[4,5-c]quinolin-1-yl)imino]propyl}carbamate (1.64 g) as a dark red/orange oil.

Part C

A solution of tert-butyl {3-[(2-ethoxymethyl-1H-imidazo[4,5-c]quinolin-1-yl)imino]propyl}carbamate (1.64 g, 4.13 mmol) in 20 mL of methanol was treated with $NaBH_4$ (0.78 g, 20.6 mmol) under an atmosphere of nitrogen. After 1.5 h, the reaction mixture was quenched with saturated $NH_4Cl$ solution and concentrated under reduced pressure. The residue was partitioned between saturated $NaHCO_3$ solution and $CHCl_3$ and the phases were separated. The organic portion was washed with water and brine, dried over $Na_2SO_4$, filtered and concentrated under reduced pressure to yield a light brown solid. Chromatography [$SiO_2$, 95:5 $CHCl_3$:(80:18:2 $CHCl_3$:MeOH:$NH_4OH$)] yielded tert-butyl {3-[(2-ethoxymethyl-1H-imidazo[4,5-c]quinolin-1-yl)amino]propyl}carbamate (1.34 g) as a tan foam.

Part D

A solution of tert-butyl {3-[(2-ethoxymethyl-1H-imidazo[4,5-c]quinolin-1-yl)amino]propyl}carbamate (1.34 g, 3.35 mmol) in 30 mL of $CHCl_3$ was treated with MCPBA (1.45 g, 5.03 mmol, 77% max). After 3 h, the reaction mixture was diluted with 10% $Na_2CO_3$ solution and $CHCl_3$ and the phases were separated. The organic portion was washed with water and brine, dried over $Na_2SO_4$, filtered and concentrated under reduced pressure to yield tert-butyl {3-[(2-ethoxymethyl-5-oxido-1H-imidazo[4,5-c]quinolin-1-yl)amino]propyl}carbamate (1.39 g) as an orange foam.

Part E

A solution of tert-butyl {3-[(2-ethoxymethyl-5-oxido-1H-imidazo[4,5-c]quinolin-1-yl)amino]propyl}carbamate (1.39 g, 3.35 mmol) in 35 mL of $CHCl_3$ was treated with 15 mL of concentrated $NH_4OH$ solution and p-toluenesulfonyl chloride (0.67 g, 3.51 mmol). After 15 min, the reaction mixture was diluted with water and $CHCl_3$ and the phases were separated. The organic portion was washed with 10% $Na_2CO_3$ solution and water. The combined aqueous washes were back-extracted with $CHCl_3$. The combined organic extracts were washed with brine, dried over $Na_2SO_4$, filtered and concentrated under reduced pressure to yield tert-butyl {3-[(4-amino-2-ethoxymethyl-1H-imidazo[4,5-c]quinolin-1-yl)amino]propyl}carbamate (1.30 g) as an orange foam.

Part F

A solution of tert-butyl {3-[(4-amino-2-ethoxymethyl-1H-imidazo[4,5-c]quinolin-1-yl)amino]propyl}carbamate (1.30 g, 3.14 mmol) in 10 mL of ethanol was treated with a solution of 3 M hydrogen chloride in ethanol (5.0 mL, 15 mmol) and heated to 100° C. After 30 min, the solvent was concentrated under reduced pressure to yield a brown sludge. The material was triturated with diethyl ether and filtered to give a tan solid. The solid was dissolved in water and treated with 10% NaOH solution until pH 13 was reached. The aqueous solution was extracted with $CH_2Cl_2$ (4×). The combined organic extracts were washed with brine, dried over $Na_2SO_4$, filtered and concentrated under reduced pressure to yield $N^1$-(3-aminopropyl)-2-ethoxymethyl-1H-imidazo[4,5-c]quinoline-1,4-diamine (0.77 g) as a gold colored foam.

Part G

A solution of $N^1$-(3-aminopropyl)-2-ethoxymethyl-1H-imidazo[4,5-c]quinoline-1,4-diamine (0.250 g, 0.795 mmol) in 10 mL of $CH_2Cl_2$ was treated with triethylamine (0.221 mL, 1.67 mmol) under an atmosphere of nitrogen and cooled to 0° C. The reaction mixture was treated dropwise with methanesulfonyl chloride (0.065 mL, 0.835 mmol). After 16 h, the reaction mixture was quenched by 10% $Na_2CO_3$ solution, diluted with $CHCl_3$ and the phases were separated. The organic portion was washed with water and brine, dried over $Na_2SO_4$, filtered and concentrated under reduced pressure to yield a light yellow solid. Chromatography ($SiO_2$, 95:5 $CHCl_3$:MeOH) gave an off-white foam. The foam was triturated with diethyl ether and filtered to give N-{3-[(4-amino-2-ethoxymethyl-1H-imidazo[4,5-c]quinolin-1-yl)amino]propyl}methanesulfonamide (0.164 g) as an off white solid. mp 148–150° C.; $^1$H NMR (300 MHz, DMSO-$d_6$) δ 8.46 (d, J=7.8 Hz, 1H), 7.58 (d, J=8.2 Hz, 1H), 7.44 (t, J=7.1 Hz, 1H), 7.25 (t, J=7.4 Hz, 1H), 7.05–6.95 (m, 2H), 6.61 (s, 2H), 4.76 (s, 2H), 3.62 (q, J=7.0 Hz, 2H), 3.22 (q, J=6.8 Hz, 2H), 3.07 (q, J=6.2 Hz, 2H), 2.88 (s, 3H), 1.78 (p, J=6.3 Hz, 2H), 1.18 (t, J=7.0 Hz, 3H); $^{13}$C NMR (125 MHz, DMSO-$d_6$) δ 152.3, 149.5, 145.3, 132.5, 127.4, 126.1, 124.2, 121.3, 121.3, 114.7, 65.9, 63.1, 49.9, 39.6, 28.1, 15.4; MS (APCI) m/z 393 (M+H)$^+$; Anal. Calcd for $C_{17}H_{24}N_6O_3$: C, 52.03; H, 6.16; N, 21.41; Found: C, 51.84; H, 6.28; N, 21.18.

Example 15

1-{3-[(4-Amino-2-ethoxymethyl-1H-imidazo[4,5-c]quinolin-1-yl)amino]propyl}-3-phenylurea

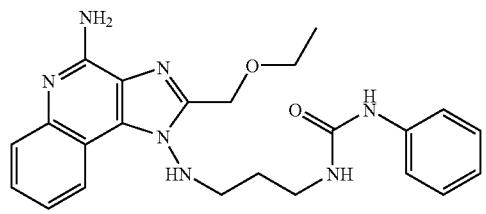

Part A

A solution of $N^1$-(3-aminopropyl)-2-ethoxymethyl-1H-imidazo[4,5-c]quinoline-1,4-diamine (0.250 g, 0.795 mmol) in 10 mL of $CH_2Cl_2$ was cooled to 0° C. under an atmosphere of nitrogen. The reaction mixture was treated dropwise with phenyl isocyanate (0.091 mL, 0.835 mmol). After 16 h, the reaction mixture was quenched by 10% $Na_2CO_3$ solution, diluted with $CHCl_3$ and the phases were separated. The organic portion was washed with brine, dried over $Na_2SO_4$, filtered and concentrated under reduced pressure to yield an off-white solid. Chromatography ($SiO_2$, 95:5 $CHCl_3$:MeOH) gave an off-white foam. The foam was triturated with diethyl ether and filtered to give 1-{3-[(4-amino-2-ethoxymethyl-1H-imidazo[4,5-c]quinolin-1-yl)amino]propyl}-3-phenylurea (0.115 g) as an off-white solid. mp 177–179° C.; $^1$H NMR (300 MHz, DMSO-$d_6$) δ 8.46 (dd, J=8.1, 1.0 Hz, 1H), 8.39 (s, 1H), 7.58 (dd, J=8.4, 0.9 Hz, 1H), 7.44–7.35 (m, 3H), 7.25–7.18 (m, 3H), 6.99 (t, J=5.6 Hz, 1H), 6.90–6.85 (m, 1H), 6.60 (s, 2H), 6.16 (t, J=5.6 Hz, 1H), 4.76 (s, 2H), 3.60 (q, J=7.0 Hz, 2H), 3.26–3.18 (m, 4H), 1.76 (t, J=7.0 Hz, 2H), 1.15 (t, J=7.0 Hz, 3H); $^{13}$C NMR (125 MHz, DMSO-$d_6$) δ 155.2, 151.8, 149.0, 144.8, 140.4, 132.0, 128.5, 126.9, 125.7, 123.7, 120.9, 120.8, 120.8, 117.6, 114.3, 65.4, 62.7, 49.7, 37.0, 28.1, 14.9; MS (APCI) m/z 434 (M+H)$^+$; Anal. Calcd for $C_{23}H_{27}N_7O_2$: C, 63.72; H, 6.28; N, 22.62; Found: C, 63.45; H, 6.04; N, 22.28.

Example 16

$N^1$-Isopropyl-2-propyl-1H-imidazo[4,5-c]quinoline-1,4-diamine

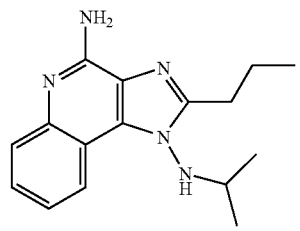

Part A

A suspension of tert-butyl $N^1$-(3-aminoquinolin-4-yl)hydrazinecarboxylate (6.50 g, 23.7 mmol) in 100 mL of toluene was treated with trimethyl orthobutyrate (4.18 mL, 26.1 mmol) and pyridine hydrochloride (0.14 g, 1.2 mmol) and heated to 130° C. under an atmosphere of nitrogen. After 18 h, the reaction mixture was concentrated under reduced pressure to yield a brown oil. The oil was dissolved in 150 mL $CHCl_3$, washed with water (2×50 mL), brine (50 mL), dried over $Na_2SO_4$, filtered and concentrated under reduced pressure to give 7.23 g of tert-butyl (2-propyl-1H-imidazo[4,5-c]quinolin-1-yl)carbamate as an orange foam.

Part B

A solution of tert-butyl (2-propyl-1H-imidazo[4,5-c]quinolin-1-yl)carbamate (7.23 g, 22.2 mmol) in 40 mL of ethanol was treated with HCl (37 mL, 111 mmol, 3 M in ethanol) and heated to reflux. After 1 h, the reaction mixture was cooled to ambient temperature, diluted with 80 mL of diethyl ether, and cooled in an ice water bath. The HCl salt of the product was collected by vacuum filtration and rinsed with diethyl ether until the filtrate ran clear. The dried HCl salt was dissolved in 75 mL of water and treated with 50% NaOH solution until the pH of the water was 12–13. The free base of the product precipitated out and was triturated in the basic water for 30 min while being cooled in an ice water bath. The solid was collected by vacuum filtration and dried under vacuum to give 4.64 g of 2-propyl-1H-imidazo[4,5-c]quinolin-1-amine as a tan granular solid.

Part C

A solution of 2-propyl-1H-imidazo[4,5-c]quinolin-1-amine (4.64 g, 20.5 mmol) in 60 mL of acetonitrile and 15 mL of glacial acetic acid was treated with 2,2-dimethoxypropane (12.6 mL, 103 mmol) and heated to 100° C. under an atmosphere of nitrogen. After 6 d, the reaction mixture was concentrated under reduced pressure to yield a brown oil. The oil was dissolved in 100 mL of CHCl$_3$ and washed with 10% Na$_2$CO$_3$ (2×25 mL), water (25 mL), brine (25 mL), dried over Na$_2$SO$_4$, filtered and concentrated under reduced pressure to give 4.30 g of N-isopropylidene-(2-propyl-1H-imidazo[4,5-c]quinolin-1-yl)amine as a brown oil.

Part D

A solution of N-isopropylidene-(2-propyl-1H-imidazo[4,5-c]quinolin-1-yl)amine (4.30 g, 16.1 mmol) in 100 mL of methanol was cooled in an ice water bath. The solution was treated with sodium borohydride (3.05 g, 80.7 mmol) over 5 min. The reaction mixture was allowed to warm to ambient temperature. After 2.5, the reaction was quenched by addition of 15 mL of saturated NH$_4$Cl solution. The mixture was concentrated under reduced pressure to yield a light brown solid. The solid was partitioned between 100 mL CHCl$_3$ and 25 mL of saturated NaHCO$_3$ solution and then separated. The organic portion was washed with water (25 mL), brine (25 mL), dried over Na$_2$SO$_4$, filtered and concentrated under reduced pressure to yield a light brown solid. The solid was purified by chromatography (SiO$_2$, 97:2.5:0.5 CHCl$_3$:MeOH:NH$_4$OH) to give 2.48 g of N-isopropyl-(2-propyl-1H-imidazo[4,5-c]quinolin-1-yl)amine as a tan solid.

Part E

A solution of N-isopropyl-(2-propyl-1H-imidazo[4,5-c]quinolin-1-yl)amine (2.48 g, 9.24 mmol) in 75 mL of chloroform was cooled in a cold water bath. The solution was treated with MCPBA (3.32 g, 11.6 mmol) over 6 min. The reaction was allowed to come to ambient temperature. After 1.5 h, TLC showed complete conversion to the 5-N-oxide intermediate. The reaction mixture was again cooled in a cold water bath and then treated with concentrated ammonium hydroxide solution (30 mL, 30%) and stirred rapidly. The reaction mixture was treated with p-toluenesulfonyl chloride (1.85 g, 9.70 mmol) over 5 min. The reaction was allowed to come to ambient temperature. After 30 min, the reaction mixture was diluted with 50 mL of chloroform and 30 mL of water and the phases were separated. The organic portion was washed with 5% Na$_2$CO$_3$ solution (30 mL), water (30 mL) and brine (30 mL). The organic portion was dried over Na$_2$SO$_4$, filtered and concentrated under reduced pressure to yield a light brown foam. The material was purified by chromatography (SiO$_2$, 97:3 CHCl$_3$:MeOH) and recrystallized from EtOAc to yield 1.39 g of N$^1$-isopropyl-2-propyl-1H-imidazo[4,5-c]quinoline-1,4-diamine as amber crystals.

mp 181–184° C.; $^1$H NMR (300 MHz, DMSO-d$_6$) δ 8.44 (d, J=8.1 Hz, 1H), 7.57 (d, J=8.3 Hz, 1H), 7.41–7.35 (m, 1H), 7.23–7.18 (m, 1H), 6.95 (d, J=1.6 Hz, 1H), 6.48 (s, 2H), 3.52–3.45 (m, 1H), 2.98–2.85 (m, 2H), 1.91–1.79 (m, 2H), 1.03–0.98 (m, 9H); $^{13}$C NMR (75 MHz, DMSO-d$_6$) δ 154.5, 152.0, 144.9, 132.6, 126.8, 126.1, 124.2, 121.2, 120.9, 115.0, 51.2, 28.2, 21.1, 20.6, 14.3; MS (APCI) m/z 284 (M+H)$^+$; Anal. Calcd for C$_{16}$H$_{21}$N$_5$: C, 67.82; H, 7.47; N, 24.71; Found: C, 67.66; H, 7.39; N, 24.66.

Example 17

N$^1$-Isopropyl-2-propyl-6,7,8,9-tetrahydro-1H-imidazo[4,5-c]quinoline-1,4-diamine

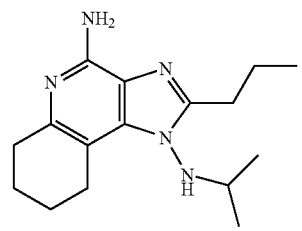

Part A

A solution of N$^1$-isopropyl-2-propyl-1H-imidazo[4,5-c]quinoline-1,4-diamine (0.59 g, 2.1 mmol) in 15 mL of trifluoroacetic acid was treated with platinum(IV) oxide (0.55 g, 2.4 mmol) and shaken under an atmosphere of hydrogen (3.8×10$^5$ Pa). After 6 days, the reaction mixture was filtered through a pad of CELITE filter agent and rinsed with a mixture of 85:15:0.1 CHCl$_3$:MeOH:TFA until the filtrate ran clear. The filtrate was concentrated under reduced pressure to yield a white foam. The material was suspended in water and treated with 50% NaOH solution until the pH reached 13. A white solid precipitated and was triturated in the basic mixture for 1 h. The white solid was collected by vacuum filtration. The solid was purified by chromatography (SiO$_2$, 95:5:0.1 CHCl$_3$:MeOH:NH$_4$OH) to yield 0.23 g of N$^1$-isopropyl-2-propyl-6,7,8,9-tetrahydro-1H-imidazo[4,5-c]quinoline-1,4-diamine as a white solid.

mp 162–164° C.; $^1$H NMR (300 MHz, DMSO-d$_6$) δ 6.34 (s, 1H), 5.64 (s, 2H), 3.38–3.23 (m, 2H), 2.85–2.79 (m, 3H), 2.78–2.71 (m, 2H), 1.84–1.71 (m, 6H), 0.99–0.86 (m, 9H); $^{13}$C NMR (75 MHz, DMSO-d$_6$) δ 154.4, 149.3, 146.1, 137.9, 122.8, 105.7, 52.4, 32.5, 28.4, 23.3, 23.1, 22.9, 21.0, 20.7, 14.3; MS (APCI) m/z 288 (M+H)$^+$; Anal. Calcd for C$_{16}$H$_{25}$N$_5$: C, 66.87; H, 8.77; N, 24.37; Found: C, 66.65; H, 8.90; N, 24.08.

Example 18

N$^1$-Isopropyl-1H-imidazo[4,5-c]quinoline-1,4-diamine

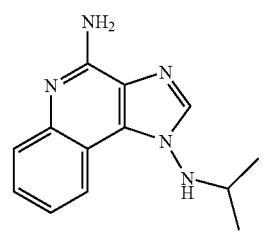

Part A

A suspension of tert-butyl N'-(3-aminoquinolin-4-yl)hydrazinecarboxylate (6.50 g, 23.7 mmol) in 100 mL of toluene was treated with triethyl orthoformate (8.68 mL, 52.2 mmol) and pyridine hydrochloride (0.14 g, 1.2 mmol) and heated to 130° C. under an atmosphere of nitrogen. After 23 h, the reaction mixture was concentrated under reduced pressure to yield a red/brown oil. The oil was dissolved in CHCl$_3$ (150 mL) and washed with water (2×50 mL), brine (50 mL), dried over Na$_2$SO$_4$, filtered and concentrated under reduced pressure to yield 6.74 of tert-butyl N-(1H-imidazo[4,5-c]quinolin-1-yl)carbamate as a red/orange oil.

Part B

A solution of tert-butyl N-(1H-imidazo[4,5-c]quinolin-1-yl)carbamate (6.74 g, 23.7 mmol) in 40 mL of ethanol was treated with 40 mL of HCl (40 mL, 119 mmol, 3 M in ethanol) and heated to reflux. After 1 h, the reaction mixture was cooled to ambient temperature, diluted with 80 mL of diethyl ether, and cooled in an ice water bath which precipitated a tan solid. The HCl salt of the product was collected by vacuum filtration and rinsed with diethyl ether until the filtrate ran clear. The dried HCl salt was dissolved in 75 mL of water and made basic by addition of 50% NaOH solution until the pH of the water was 12–13. The free base of the product precipitated out and was triturated in the basic water for 30 min while being cooled in an ice water bath. The solid was collected by vacuum filtration and dried under vacuum to give 2.86 g of 1H-imidazo[4,5-c]quinolin-1-amine as a tan granular solid.

Part C

A solution of 1H-imidazo[4,5-c]quinolin-1-amine (2.86 g, 15.5 mmol) in 60 mL of acetonitrile and 15 mL of glacial acetic acid was treated with 2,2-dimethoxypropane (9.53 mL, 77.5 mmol) and heated to 100° C. under an atmosphere of nitrogen. After 18 h, the reaction mixture was concentrated under reduced pressure to give a brown oil. The oil was dissolved in 100 mL of CHCl$_3$ and washed with 5% Na$_2$CO$_3$ solution (2×30 mL), water (30 mL) and brine (30 mL). The organic portion was dried over Na$_2$SO$_4$, filtered and concentrated under reduced pressure to yield 3.48 g of N-(1H-imidazo[4,5-c]quinolin-1-yl)isopropylideneamine as a brown oil.

Part D

A solution of N-(1H-imidazo[4,5-c]quinolin-1-yl)isopropylideneamine (3.48 g, 15.5 mmol) in 75 mL of methanol was cooled in an ice water bath. The solution was treated over 5 min with sodium borohydride (2.94 g, 77.6 mmol). After 1 h, the reaction mixture was quenched with 20 mL of saturated NH$_4$Cl solution and then concentrated under reduced pressure to yield a brown soild. The solid was partitioned between 80 mL CHCl$_3$ and 20 mL saturated NaHCO$_3$ solution and the phases were separated. The organic portion was washed with water (20 mL), brine (20 mL), dried over Na$_2$SO$_4$, filtered and concentrated under reduced pressure to give a brown solid. The solid was purified by chromatography (SiO$_2$, 95:5:0.5 CHCl$_3$:MeOH:NH$_4$OH) to give 1.28 g of N-(1H-imidazo[4,5-c]quinolin-1-yl)isopropylamine as a tan foam.

Part E

A solution of N-(1H-imidazo[4,5-c]quinolin-1-yl)isopropylamine (1.36 g, 5.66 mmol) in 50 mL of chloroform was cooled in a cold water bath. The solution was treated with MCPBA (2.03 g, 7.07 mmol) over 5 min and then allowed to warm to ambient temperature. After 1 h, TLC showed complete conversion to the intermediate 5-N-oxide. The reaction mixture was again cooled with a cold water bath. The solution was treated with concentrated ammonium hydroxide solution (25 mL, 30%) and stirred rapidly to homogenize. The reaction mixture was treated with p-toluenesulfonyl chloride (1.13 g, 5.94 g) over 5 min and allowed to warm to ambient temperature. After 30 min, the reaction mixture was diluted with 50 mL of CHCl$_3$ and 25 mL of water. An undissolved solid between the phases was filtered off, saved, and the phases were separated. The organic portion was washed with saturated NaHCO$_3$ solution (30 mL), water (30 mL) and brine (30 mL). The organic portion was then dried over Na$_2$SO$_4$, filtered and concentrated under reduced pressure to yield a tan/orange solid. A high-performance liquid chromatography (HPLC) analysis of the filtered solid matched that of the solid from the concentrated organic extracts. The combined solid was recrystallized twice from MeOH to give 1.18 g of $N^1$-isopropyl-1H-imidazo[4,5-c]quinoline-1,4-diamine as an off-white solid.

mp dec. >250° C.; $^1$H NMR (300 MHz, DMSO-d$_6$) δ 8.61 (dd, J=8.1, 1.1 Hz, 1H), 8.23 (s, 1H), 7.56 (d, J=7.6 Hz, 1H), 7.43–7.37 (m, 1H), 7.23–7.18 (m, 1H), 7.04 (d, J=3.4 Hz, 1H), 6.58 (s, 2H), 3.57–3.47 (m, 1H), 1.03 (d, J=6.2 Hz, 6H); $^{13}$C NMR (75 MHz, DMSO-d$_6$) δ 152.4, 145.3, 132.3, 127.3, 126.0, 125.1, 121.5, 121.0, 115.1, 52.6, 20.6; MS (APCI) m/z 242 (M+H)$^+$; Anal. Calcd for C$_{13}$H$_{15}$N$_5$: C, 64.71; H, 6.27; N, 29.02; Found: C, 63.1 1; H, 6.30; N, 27.96.

Example 19

$N^1$-Isopropyl-2-propyl-7-(pyridin-3-yl)-1H-imidazo[4,5-c]quinoline-1,4-diamine

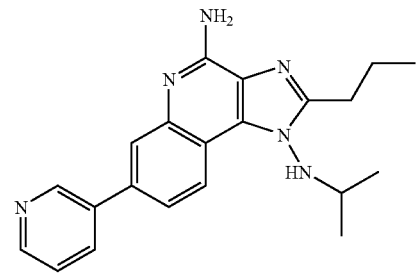

Part A

A suspension of 7-bromo-4-chloro-3-nitroquinoline (75.00 g, 260.9 mmol) in 350 mL of dichloromethane was cooled to 0° C. under an atmosphere of nitrogen. The suspension was treated with triethylamine (43.25 mL, 326.1 mmol), which dissolved most of the material. A solution of tert-butyl carbazate (37.93 g, 287.0 mmol) in 250 mL of dichloromethane was added to the reaction mixture over 20 min. The reaction was allowed to slowly come to ambient temperature. After 15 h, the reaction mixture was washed with 5% Na$_2$CO$_3$ solution (2×100 mL) and water (100 mL). The combined aqueous washes were back-extracted with CHCl$_3$ (50 mL). The combined organic portions were washed with brine (100 mL), dried over Na$_2$SO$_4$, filtered and concentrated under reduced pressure to yield 99.98 g of tert-butyl N'-(7-bromo-3-nitroquinolin-4-yl)hydrazinecarboxylate as a dark red solid.

Part B

A suspension of tert-butyl N'-(7-bromo-3-nitroquinolin-4-yl)hydrazinecarboxylate (50.0 g, 131 mmol) in 320 mL of acetonitrile (MeCN) and 80 mL of methanol was treated with platinum on carbon (5.0 g, 1.3 mmol, 5% w/w) and shaken under an atmosphere of hydrogen (3.8×10$^5$ Pa). After 4 h, the reaction mixture was filtered through a pad of CELITE filter agent and rinsed with portions of MeCN:

MeOH (1:1) until the filtrate ran clear. The filtrate was concentrated under reduced pressure to yield 37.1 g of tert-butyl N'-(3-amino-7-bromoquinolin-4-yl)hydrazinecarboxylate as a tan solid.

Part C

A solution of tert-butyl N'-(3-amino-7-bromoquinolin-4-yl)hydrazinecarboxylate (37.1 g, $10^5$ mmol) in 315 mL of toluene was treated with trimethyl orthobutyrate (16.7 mL, 105 mmol) and pyridine hydrochloride (0.12 g, 1.05 mmol). The reaction mixture was heated to reflux under an atmosphere of nitrogen. After 4 h, the reaction mixture was cooled to ambient temperature and concentrated under reduced pressure to give a brown oil. The oil was dissolved in 300 mL of $CHCl_3$. The solution was washed with 5% $Na_2CO_3$ (100 mL), water (100 mL) and brine (100 mL). The organic portion was dried over $Na_2SO_4$, filtered and concentrated under reduced pressure to yield a brown foam. The foam was purified by chromatography ($SiO_2$, 100:0 gradient to 95:5 $CHCl_3$:MeOH) to yield 30.1 g of tert-butyl (7-bromo-2-propyl-1H-imidazo[4,5-c]quinolin-1-yl)carbamate as a light brown solid.

Part D

A suspension of tert-butyl (7-bromo-2-propyl-1H-imidazo[4,5-c]quinolin-1-yl)carbamate (30.1 g, 74.3 mmol) in 25 mL of ethanol was treated with HCl in ethanol (86.4 mL, 37.1 mmol, 4.3 M) and heated to 100° C. After 30 min, the reaction mixture was cooled to ambient temperature and concentrated under reduced pressure to yield a brown solid. The solid was suspended in 100 mL of water, stirred vigorously and treated with 50% NaOH solution until the pH of the liquid rose to 12–13. A brown solid collected around the stir bar. The water was diluted with 200 mL of dichloromethane and the solid was broken apart. The material was triturated in the biphasic mixture overnight. After triturating for 15 h, the mixture was filtered to give the crude free base as a light brown solid. The solid was dried under vacuum to give 17.6 g of 7-bromo-2-propyl-1H-imidazo[4,5-c]quinolin-1-amine as a light brown solid.

Part E

A suspension of 7-bromo-2-propyl-1H-imidazo[4,5-c]quinolin-1-amine (17.6 g, 57.7 mmol) in 160 mL of acetonitrile and 40 mL of glacial acetic acid was treated with 2,2-dimethoxypropane (35.5 mL, 288 mmol). The reaction mixture was heated to 100° C. under an atmosphere of nitrogen. After 16 h, the reaction was cooled to ambient temperature and concentrated under reduced pressure to yield a brown oil. The oil was dissolved in $CHCl_3$ (200 mL). The $CHCl_3$ solution was washed with saturated $NaHCO_3$ solution (2×50 mL), water (50 mL) and brine (50 mL). The organic portion was then dried over $Na_2SO_4$, filtered and concentrated under reduced pressure to yield 18.4 g of N-(7-bromo-2-propyl-1H-imidazo[4,5-c]quinolin-1-yl)isopropylideneamine as a red/brown foam.

Part F

A solution of N-(7-bromo-2-propyl-1H-imidazo[4,5-c]quinolin-1-yl)isopropylideneamine (18.4 g, 53.3 mmol) in 100 mL of methanol was placed under an atmosphere of nitrogen and cooled in an ice water bath. The solution was treated with sodium borohydride (2.32 g, 61.3 mmol) over 30 min. The reaction mixture was allowed to slowly come to ambient temperature. After 1.5 h, the reaction was quenched by the addition of 25 mL of saturated $NH_4Cl$ solution. The reaction mixture was concentrated under reduced pressure to remove the methanol. The residue was partitioned between chloroform (150 mL) and 10% $Na_2CO_3$ solution (35 mL), and the phases were separated. The organic portion was washed with another portion of 10% $Na_2CO_3$ solution (35 mL), water (35 mL) and brine (35 mL). The organic portion was dried over $Na_2SO_4$, filtered and concentrated under reduced pressure to yield a brown foam. The foam was purified by chromatography ($SiO_2$, 97:3 $CHCl_3$:MeOH gradient to 9:1) to give 16.3 g of N-(7-bromo-2-propyl-1H-imidazo[4,5-c]quinolin-1-yl)isopropylamine as a dark tan solid.

Part G

A solution of N-(7-bromo-2-propyl-1H-imidazo[4,5-c]quinolin-1-yl)isopropylamine (9.10 g, 26.2 mmol) in 200 mL of chloroform was placed under an atmosphere of nitrogen and cooled in an ice water bath. The solution was treated with MCPBA (8.28 g, 28.8 mmol, 77% max) and allowed to slowly come to ambient temperature. After 2 h, LC/MS and HPLC indicated complete conversion to the 5-N-oxide intermediate. The reaction mixture was again cooled in an ice water bath. The reaction mixture was treated with ammonium hydroxide solution (50 mL, 30%) and stirred vigorously. The mixture was treated with p-toluenesulfonyl chloride (5.24 g, 27.5 mmol) and allowed to come to ambient temperature. After 30 min, the reaction was diluted with 50 mL of water, and the phases were separated. The organic portion was washed with water (75 mL), brine (75 mL), dried over $Na_2SO_4$, filtered and concentrated under reduced pressure to yield a light brown solid. The solid was purified by chromatography ($SiO_2$, 95:5 $CHCl_3$:MeOH) and then recrystallized from acetonitrile to give 4.52 g of 7-bromo-$N^1$-isopropyl-2-propyl-1H-imidazo[4,5-c]quinoline-1,4-diamine as off white crystals. mp 226–228° C.; $^1$H NMR (300 MHz, DMSO-$d_6$) δ 8.44 (d, J=8.7 Hz, 1H), 7.71 (d, J=2.1 Hz, 1H), 7.36 (dd, J=8.7, 2.1 Hz, 1H), 6.99 (d, J=1.7 Hz, 1H), 6.73 (s, 2H), 3.53–3.40 (m, 1H), 2.90 (s, 2H), 1.93–1.80 (m, 2H), 1.05–1.00 (m, 9H); $^{13}$C NMR (125 MHz, DMSO-$d_6$) δ 154.9, 152.9, 146.3, 132.5, 127.8, 124.2, 123.5, 123.1, 119.7, 114.0, 79.5, 51.4, 28.2, 21.1, 20.6, 14.3; MS (APCI) m/z 362, 364 (M+H)$^+$; Anal. Calcd for $C_{16}H_{20}BrN_5$·$0.25H_2O$: C, 52.40; H, 5.63; N, 19.09; Found: C, 52.03; H, 5.42; N, 19.14.

Part H

A suspension of 7-bromo-$N^1$-isopropyl-2-propyl-1H-imidazo[4,5-c]quinoline-1,4-diamine (1.00 g, 2.76 mmol) in 20 mL of 1-propanol was treated with pyridine-3-boronic acid 1,3-propane diol cyclic ester (0.540 g, 3.31 mmol). The head-space of the reaction flask was purged and back-filled with nitrogen (3×). The reaction mixture was then treated with triphenylphosphine (11 mg, 0.041 mmol), sodium carbonate (1.66 mL, 3.31 mmol, 2 M solution in water), water (2 mL) and palladium(II) acetate (3.1 mg, 0.014 mmol). Again the head-space of the reaction flask was purged and back-filled with nitrogen (3×). The reaction was heated to 100° C. After 17 h, the reaction was cooled to ambient temperature and concentrated under reduced pressure to yield a brown solid. The solid was dissolved and partitioned between 15 mL of water and 15 mL of chloroform and then separated. The aqueous portion was extracted with chloroform (2×15 mL). The combined organic extracts were washed with brine (15 mL), dried over $Na_2SO_4$, filtered and concentrated under reduced pressure to yield a tan solid. The solid was purified by chromatography ($SiO_2$, 95:5 $CHCl_3$:MeOH) and recrystallized from acetonitrile to give 0.515 g of $N^1$-isopropyl-2-propyl-7-(pyridin-3-yl)-1H-imidazo[4,5-c]quinoline-1,4-diamine as white crystals.

mp 218–219° C.; $^1$H NMR (300 MHz, DMSO-$d_6$) δ 8.99 (d, J=1.7 Hz, 1H), 8.60–8.57 (m, 2H), 8.19–8.16 (m, 1H), 7.88 (d, J=1.9 Hz, 1H), 7.61 (dd, J=8.5, 1.9 Hz, 1H), 7.53–7.49 (m, 1H), 7.04 (s, 1H), 6.59 (s, 2H), 3.57–3.49 (m, 1H), 2.92–2.87 (m, 2H), 1.94–1.82 (m, 2H), 1.06–1.01 (m, 9H); $^{13}$C NMR (75 MHz, DMSO-d$_6$) δ 154.8, 152.5, 148.6, 148.1, 145.4, 136.2, 135.4, 134.5, 132.5, 124.5, 124.3, 123.9, 122.2, 119.6, 114.7, 51.3, 28.2, 21.1, 20.6; MS (APCI) m/z 361 (M+H)$^+$; Anal. Calcd for C$_{21}$H$_{24}$N$_6$: C, 69.97; H, 6.71; N, 23.31; Found: C, 69.78; H, 6.55; N, 23.51.

Example 20

7-Benzyloxy-2-ethoxymethyl-N$^1$-isopropyl-1H-imidazo[4,5-c]quinoline-1,4-diamine

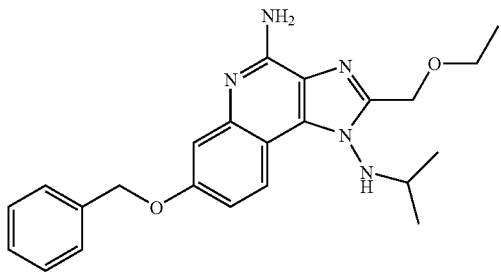

Part A

A mixture of triethyl orthoformate (92 mL, 0.55 mol) and 2,2-dimethyl-1,3-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-1,3-dioxane-4,6-dione (170.65 g) was isolated as a tan, powdery solid.

$^1$H NMR (300 MHz, DMSO-d$_6$) δ 11.21 (d, J=14.2 Hz, 1H), 8.61 (d, J=14.2 Hz, 1H), 7.49–7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-1,3-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

$^1$H NMR (300 MHz, DMSO-d$_6$) δ 11.53 (s, 1H), 7.99 (dd, J=7.4, 2.4 Hz, 1H), 7.79 (d, J=7.4 Hz, 1H), 7.50–7.32 (m, 5H), 7.00 (s, 11H), 6.98 (dd, J=7.4, 2.5 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

$^1$H NMR (300 MHz, DMSO-d$_6$) δ 12.77 (s, 1H), 9.12 (s, 1H), 8.17 (dd, J=6.3, 3.3 Hz, 1H), 7.51–7.33 (m, 5H), 7.21–7.17 (m, 2H), 5.25 (s, 2H).

Part D

A suspension of 7-benzyloxy-3-nitroquinolin-4-ol (75.0 g, 253 mmol), which was made in a separate run, in 500 mL of N,N-dimethylformamide was placed under an atmosphere of nitrogen. The suspension was treated with phosphorous oxychloride (27.8 mL, 304 mmol) dropwise over 1.5 h. After 18 h, the reaction mixture was cooled to 0° C. and then poured into 1 L of ice water. The mixture was stirred until the ice had melted. A tan/yellow precipitate was collected by vacuum filtration. The solid was dissolved in dichloromethane (500 mL), dried over Na$_2$SO$_4$, filtered and concentrated under reduced pressure to yield 71.7 g of 7-benzyloxy-4-chloro-3-nitro-quinoline as an orange solid.

Part E

A solution of tert-butyl carbazate (33.1 g, 251 mmol) in 150 mL of dichloromethane was treated with triethylamine (66.5 mL, 502 mmol). The solution was placed under an atmosphere of nitrogen and cooled in a cold-water bath. The solution was treated with a solution of 7-benzyloxy-4-chloro-3-nitroquinoline (71.7 g, 228 mmol) in 350 mL of dichloromethane over 1 h. The reaction was stirred and allowed to warm to ambient temperature. After 15 h, the reaction was diluted with 200 mL of water and 250 mL of CHCl$_3$ and the phases were separated. The organic portion was washed with water (200 mL), brine (200 mL), dried over Na$_2$SO$_4$, filtered and concentrated under reduced pressure to yield an orange solid. The solid was recrystallized from dichloromethane to yield 53.5 g of tert-butyl N'-(7-benzyloxy-3-nitroquinolin-4-yl)hydrazinecarboxylate as yellow crystals.

Part F

A solution of tert-butyl N'-(7-benzyloxy-3-nitroquinolin-4-yl)hydrazinecarboxylate (20.00 g, 48.73 mmol) in 200 mL of methanol and 200 mL of acetonitrile was treated with platinum on carbon (2.00 g, 0.51 mmol) and shaken under an atmosphere of hydrogen (3.8×10$^5$ Pa). After 17 h, the mixture was filtered through a pad of CELITE filter agent and rinsed with MeOH:MeCN (1:1) until the filtrate ran clear. The filtrate was concentrated under reduced pressure to yield 18.21 g of tert-butyl N'-(3-amino-7-benzyloxyquinolin-4-yl)hydrazinecarboxylate as a red/orange solid.

Part G

A suspension of tert-butyl N'-(3-amino-7-benzyloxyquinolin-4-yl)hydrazinecarboxylate (29.6 g, 77.8 mmol) in 250 mL of 1,2-dichloroethane was placed under an atmosphere of nitrogen. The mixture was treated with triethylamine (30.9 mL, 233 mmol). The mixture was then treated dropwise with ethoxyacetyl chloride (10.5 g, 85.6 mmol). After 2 h, the reaction was concentrated under reduced pressure to give a brown oil. The oil was dissolved in 200 mL of 1-butanol and treated with pyridinium p-toluenesulfonate (0.25 g, 1.0 mmol). The mixture was heated to 135° C. under an atmosphere of nitrogen. After 20 h, the reaction mixture was cooled to ambient temperature and concentrated under reduced pressure to give a brown oil. The oil was dissolved in 250 mL of CHCl$_3$ and washed with saturated NaHCO$_3$ solution (75 mL), water (75 mL) and brine (75 mL). The organic portion was then dried over Na$_2$SO$_4$, filtered and concentrated under reduced pressure to give an orange/brown oil. The oil was purified by chromatography (SiO$_2$, 9:1 CHCl$_3$:MeOH) to yield 14.4 g of tert-butyl (7-benzyloxy-2-ethoxymethyl-1H-imidazo[4,5-c]quinolin-1-yl)carbamate as an orange/brown foam.

Part H

A suspension of tert-butyl (7-benzyloxy-2-ethoxymethyl-1H-imidazo[4,5-c]quinolin-1-yl)carbamate (14.4 g, 32.1 mmol) in 100 mL of ethanol was treated with HCl in ethanol (38 mL, 160 mmol, 4.3 M). The mixture was heated to 100° C. under an atmosphere of nitrogen. After 2 h, the reaction mixture was cooled to ambient temperature at which point a solid precipitated from solution. The mixture was diluted with 100 mL of diethyl ether and the solid was triturated for 15 min. The solid was collected by vacuum filtration and washed with several portions of diethyl ether. The solid was dried under vacuum for 2 h. The dry solid was suspended in 150 mL of water and treated with 50% NaOH solution until the pH of the liquid was 12. A brown solid precipitated. The mixture was diluted with 200 mL of CH$_2$Cl$_2$ and stirred until the solid dissolved. The layers were then separated. The aqueous portion was extracted with CH$_2$Cl$_2$ (2×100 mL). The combined organic extracts were washed with brine (100 mL), dried over Na$_2$SO$_4$, filtered and concentrated under reduced pressure to yield 6.91 g of 7-benzyloxy-2-ethoxymethyl-1H-imidazo[4,5-c]quinolin-1-amine as a dark tan solid.

Part I

A suspension of 7-benzyloxy-2-ethoxymethyl-1H-imidazo[4,5-c]quinolin-1-amine (6.91 g, 19.8 mmol) in 55 mL of acetonitrile was treated with 2,2-dimethoxypropane (12.2 mL, 99.2 mmol) and 14 mL of glacial acetic acid. The reaction mixture was heated to 100° C. under an atmosphere of nitrogen. After 22 h, the reaction was cooled to ambient temperature and concentrated under reduced pressure to yield a brown oil. The oil was dissolved in 125 mL of CHCl$_3$ and washed with saturated NaHCO$_3$ solution (2×30 mL) and water (30 mL). The combined aqueous washes were back-extracted with CHCl$_3$ (25 mL). The combined organic extracts were washed with brine (50 mL), dried over Na$_2$SO$_4$, filtered and concentrated under reduced pressure to yield 7.69 g of N-(7-benzyloxy-2-ethoxymethyl-1H-imidazo[4,5-c]quinolin-1-yl)isopropylideneamine as a brown solid.

Part J

A solution of N-(7-benzyloxy-2-ethoxymethyl-1H-imidazo[4,5-c]quinolin-1-yl)isopropylideneamine (7.69 g, 19.8 mmol) in 50 mL of methanol was cooled to 0° C. The solution was treated with sodium borohydride (1.12 g, 29.7 mmol) over 10 min. The reaction was allowed to slowly come to ambient temperature. After 2 h, the reaction was quenched with 15 mL of saturated NH$_4$Cl solution and concentrated under reduced pressure to yield a tan solid residue. The solid was dissolved in 100 mL of CHCl$_3$ and 25 mL of saturated K$_2$CO$_3$ solution then separated. The organic portion was washed with water (25 mL), brine (25 mL), dried over Na$_2$SO$_4$, filtered and concentrated to yield a brown oil. The oil was purified by chromatography (SiO$_2$, 98:2 CHCl$_3$:MeOH) to yield 6.63 g of N-(7-benzyloxy-2-ethoxymethyl-1H-imidazo[4,5-c]quinolin-1-yl)isopropylamine as a tan foam.

Part K

A solution of N-(7-benzyloxy-2-ethoxymethyl-1H-imidazo[4,5-c]quinolin-1-yl)isopropylamine (6.63 g, 17.0 mmol) in 90 mL of CHCl$_3$ was treated with MPCBA (6.29 g, 25.5 mmol, 70%). After 3 h, HPLC and LC/MS indicated complete conversion to the intermediate 5-N-oxide. The reaction mixture was then treated with concentrated ammonium hydroxide solution (30 mL, 30%). The biphasic reaction mixture was stirred vigorously while p-toluenesulfonyl chloride (3.40 g, 17.9 mmol) was added. After 45 min, LC/MS indicated complete conversion to the 4-amine. The reaction mixture was diluted with 30 mL of water and 45 mL of CHCl$_3$ and separated. The organic portion was washed with 10% Na$_2$CO$_3$ solution (50 mL) and water (50 mL). The combined aqueous portions were then back-extracted with CHCl$_3$ (25 mL). The combined organic portions were washed with brine (50 mL), dried over Na$_2$SO$_4$, filtered and concentrated to yield a tan solid. The solid was purified by chromatography (SiO$_2$, 96:4 CHCl$_3$:MeOH) to give 5.90 g of 7-benzyloxy-2-ethoxymethyl-N$^1$-isopropyl-1H-imidazo[4,5-c]quinoline-1,4-diamine as a light tan solid.

mp 194–196° C.; $^1$H NMR (300 MHz, DMSO-d$_6$) δ 8.47 (d, J=8.9 Hz, 1H), 7.50–7.48 (m, 2H), 7.43–7.38 (m, 2H), 7.35–7.30 (m, 1H), 7.09 (d, J=2.6 Hz, 1H), 6.96 (dd, J=9.0, 2.5 Hz, 1H), 6.91 (d, J=1.5 Hz, 1H), 6.57 (s, 2H), 5.20 (s, 2H), 4.72 (s, 2H), 3.64–3.57 (m, 3H), 1.15 (t, J=7.0 Hz, 3H), 1.01 (d, J=6.1 Hz, 6H); $^{13}$C NMR (75 MHz, DMSO-d$_6$) δ 157.9, 152.6, 149.4, 147.1, 137.7, 133.7, 128.8, 128.1, 128.0, 122.7, 111.8, 109.2, 108.4, 69.5, 65.8, 63.0, 51.6, 20.6, 15.3; MS (APCI) m/z 406 (M+H)$^+$; Anal. Calcd for C$_{23}$H$_{27}$N$_5$O$_2$: C, 68.13; H, 6.71; N, 17.27; Found: C, 68.15; H, 6.91; N, 17.24.

Example 21

4-Amino-2-ethoxymethyl-1-isopropylamino-1H-imidazo[4,5-c]quinolin-7-ol

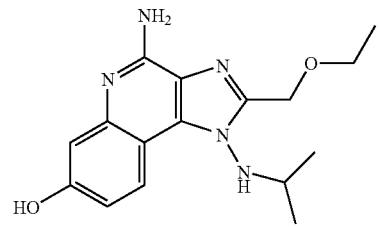

Part A

A solution of 7-benzyloxy-2-ethoxymethyl-N$^1$-isopropyl-1H-imidazo[4,5-c]quinoline-1,4-diamine (1.67 g, 4.12 mmol) in 25 mL of toluene and 25 mL of methanol was treated with palladium on carbon (0.44 g, 0.42 mmol, 10% w/w). The mixture was shaken under an atmosphere of hydrogen (3.8×10$^5$ Pa). After 16 h, the reaction was filtered through a pad of CELITE filter agent and rinsed with solvent until the filtrate ran clear. The filtrate was concentrated under reduced pressure to provide a white solid. Purification by chromatography (SiO$_2$, 3:1 CHCl$_3$:(80:18:2 CHCl$_3$:MeOH: NH$_4$OH) gradient to 1:1) gave 0.50 g of 4-amino-2-ethoxymethyl-1-isopropylamino-1H-imidazo[4,5-c]quinolin-7-ol as a white solid. MS (APCI) m/z 316 (M+H)$^+$.

Example 22

[3-(4-Amino-2-ethoxymethyl-1-isopropylamino-1H-imidazo[4,5-c]quinolin-7-yloxy)propyl]tert-butyl carbamate

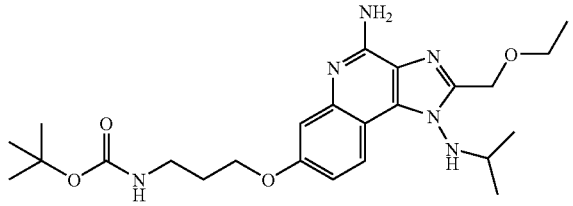

Part A

A solution of di-tert-butyl dicarbonate (19.05 g, 87.29 mmol) in tetrahydrofuran (20 mL) was added dropwise to a mixture of 3-amino-1-propanol (6.55 g, 87.2 mmol), tetrahydrofuran (50 mL), and 10% aqueous sodium hydroxide (35 mL). The reaction was stirred for 16 hours. The tetrahydrofuran was removed under reduced pressure, and the residue was adjusted to pH 3 with the slow addition of 15% aqueous potassium hydrogen sulfate. The mixture was extracted with ethyl acetate (3×), and the combined organic fractions were washed sequentially with water and brine, dried over anhydrous magnesium sulfate, filtered, and concentrated under reduced pressure to provide 16.6 g of tert-butyl 3-hydroxypropylcarbamate as a colorless oil containing some residual ethyl acetate.

Part B

Iodine (21.1 g, 83.1 mmol) was added in three portions to a solution of triphenylphosphine (19.83 g, 75.6 mmol) and imidazole (5.15 g, 75.6 mmol) in dichloromethane (300 mL). The resulting reddish-brown solution with a white precipitate was stirred until all of the iodine had dissolved. A solution of tert-butyl 3-hydroxypropylcarbamate (13.25 g, 75.61 mmol) in dichloromethane (150 mL) was added over a period of 45 minutes, and the reaction was stirred for 16 hours at ambient temperature. The reaction mixture was poured into saturated aqueous sodium thiosulfate and stirred until solution became colorless. The organic layer was separated and washed sequentially with saturated aqueous sodium thiosulfate, water, and brine; dried over anhydrous magnesium sulfate; filtered; and concentrated under reduced pressure to a pale yellow oil. The oil was purified by flash column chromatography (eluting with 80:20 hexanes:ethyl acetate) to a pale yellow oil which slowly crystallizes upon standing to afford 16.2 g of tert-butyl 3-iodopropylcarbamate as a yellow solid.

Part C

A solution of 4-amino-2-ethoxymethyl-1-isopropylamino-1H-imidazo[4,5-c]quinolin-7-ol (0.11 g, 0.35 mmol) in 10 mL of N,N-dimethylformamide was placed under an atmosphere of nitrogen and was treated with cesium carbonate (0.23 g, 0.70 mmol). After 5 min of stirring the mixture was treated with tert-butyl 3-iodopropylcarbamate (0.12 g, 0.35 mmol) and heated to 65° C. After 60 h, the reaction mixture was cooled to ambient temperature and then poured into 100 mL of ice water which resulted in a cloudy suspension. The mixture was extracted with CHCl$_3$ (5×25 mL). The combined organic extracts were then washed with brine (50 mL), dried over Na$_2$SO$_4$, filtered and concentrated under reduced pressure to yield a tan oil. Chromatography (95:5 CHCl$_3$:(80:18:2 CHCl$_3$:MeOH:NH$_4$OH) gradient to 1:1 gave 0.040 g of [3-(4-amino-2-ethoxymethyl-1-isopropylamino-1H-imidazo[4,5-c]quinolin-7-yloxy)propyl]tert-butyl carbamate as a light tan solid. LC/MS (APCI) m/z 473 (M+H)$^+$.

Example 23

[3-(4-Amino-2-ethoxymethyl-1H-imidazo[4,5-c]quinolin-1-ylamino)propyl]morpholine-4-carboxamide

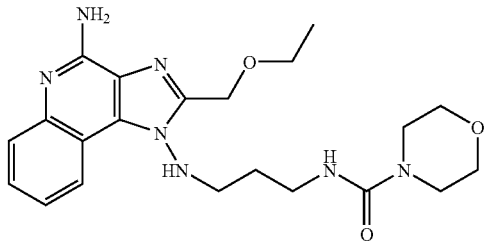

A solution of N$^1$-(3-aminopropyl)-2-ethoxymethyl-1H-imidazo[4,5-c]quinoline-1,4-diamine (0.500 g, 1.59 mmol) in 10 mL of CH$_2$Cl$_2$ was treated with triethylamine (0.443 mL, 3.34 mmol) under an atmosphere of nitrogen and cooled to 0° C. The reaction mixture was treated dropwise with 4-morpholinecarbonyl chloride (0.065 mL, 0.835 mmol) and allowed to slowly come to ambient temperature. After 60 h, the reaction mixture was quenched with 10% Na$_2$CO$_3$ solution, diluted with CHCl$_3$ and the phases were separated. The organic portion was washed with water and brine, dried over Na$_2$SO$_4$, filtered and concentrated under reduced pressure to yield a light yellow solid. Chromatography (SiO$_2$, 9:1 CHCl$_3$:(80:18:2 CHCl$_3$:MeOH:NH$_4$OH) gradient to 1:1) gave a glassy solid. The solid was triturated with diethyl ether and filtered to give 0.046 g of [3-(4-amino-2-ethoxymethyl-1H-imidazo[4,5-c]quinolin-1-ylamino)propyl]morpholine-4-carboxamide as a white solid.

mp 158–160° C.; $^1$H NMR (300 MHz, DMSO-d$_6$) δ 8.44 (d, J=7.9 Hz, 1H), 7.58 (d, J=8.1 Hz, 1H), 7.46–7.41 (m, 1H), 7.26–7.21 (m, 1H), 6.96 (t, J=5.5 Hz, 1H), 6.60 (s, 2H), 6.53 (t, J=5.1 Hz, 1H), 4.75 (s, 2H), 3.61 (q, J=7.0 Hz, 2H), 3.50 (t, J=4.7 Hz, 4H), 3.22–3.15 (m, 8H), 1.72 (p, J=6.9 Hz, 2H), 1.17 (t, J=7.0 Hz, 3H); $^{13}$C NMR (75 MHz, DMSO-d$_6$) δ 158.0, 152.3, 149.5, 145.3, 132.4, 127.4, 126.1, 124.2, 121.2, 114.7, 66.3, 65.8, 63.1, 50.2, 44.1, 38.3, 28.5, 15.4; MS (APCI) m/z 428 (M+H)$^+$; Anal. Calcd for C$_{21}$H$_{29}$N$_7$O$_3$: C, 59.00; H, 6.84; N, 22.93; Found: C, 58.76; H, 7.04; N, 22.82.

Example 24

N-(3-{[4-Amino-2-(ethoxymethyl)-1H-imidazo[4,5-c]quinolin-1-yl]amino}propyl)cyclopentanecarboxamide

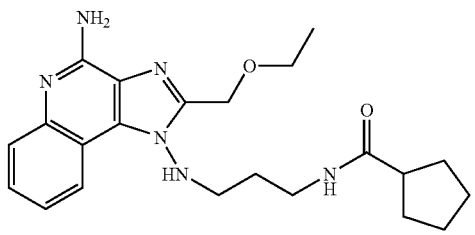

A solution of N$^1$-(3-aminopropyl)-2-ethoxymethyl-1H-imidazo[4,5-c]quinoline-1,4-diamine (0.500 g, 1.59 mmol) in 20 mL of CH$_2$Cl$_2$ was placed under an atmosphere of nitrogen, treated with triethylamine (0.443 mL, 3.34 mmol) and then cooled to 0° C. with an ice water bath. The reaction mixture was treated with cyclopentanecarbonyl chloride (0.203 mL, 1.67 mmol) over 2 min. The reaction was stirred and allowed to come to ambient temperature over 2 h. After 18 h, the reaction was quenched with 15 mL of 10% $Na_2CO_3$ solution. The mixture was diluted with 25 mL $CHCl_3$, mixed and then separated. The organic portion was washed with $H_2O$ (15 mL) and brine (15 mL), dried over $Na_2SO_4$, filtered and concentrated under reduced pressure to yield a tan foam. The foam was purified by chromatography ($SiO_2$, 96:4 $CHCl_3$: methanol (MeOH)) to yield a light tan solid. The solid was dissolved in boiling 2-propanol (IPA), cooled to ambient temperature and then water was added until an off-white solid precipitated from solution. The precipitate was triturated in the IPA/$H_2O$ mixture for 2 h and then collected by vacuum filtration to give N-(3-{[4-amino-2-(ethoxymethyl)-1H-imidazo[4,5-c]quinolin-1-yl]amino}propyl)cyclopentanecarboxamide (0.106 g) as an off-white solid. mp 75–77° C.;

$^1$H NMR (300 MHz, DMSO-$d_6$) δ 8.42 (d, J=7.9 Hz, 1H), 7.74 (t, J=5.2 Hz, 1H), 7.58 (d, J=7.9 Hz, 1H), 7.46–7.41 (m, 1H), 7.26–7.21 (m, 1H), 6.97 (t, J=5.4 Hz, 1H), 6.60 (s, 2H), 4.75 (s, 2H), 3.61 (q, J=7.0 Hz, 2H), 3.19–3.13 (m, 4H), 2.48–2.44 (m, 1H), 1.75–1.38 (m, 10H), 1.17 (t, J=7.0 Hz, 3H); $^{13}$C NMR (75 MHz, DMSO-$d_6$) δ 175.5, 152.3, 149.5, 145.3, 132.4, 127.3, 126.1, 124.2, 121.2, 114.7, 65.8, 63.1, 50.2, 44.7, 36.8, 30.3, 28.0, 25.9, 15.4; MS (APCI) m/z 411 (M+H)$^+$; Anal. Calcd for $C_{22}H_{30}N_6O_2$•0.25$H_2O$: C, 63.67; H, 7.41; N, 20.25; Found: C, 36.37; H, 7.64; N, 20.32.

Example 25

1-(3-{[4-Amino-2-(ethoxymethyl)-1H-imidazo[4,5-c]quinolin-1-yl]amino}propyl)-3-isopropylurea

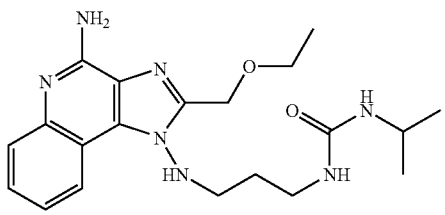

A solution of $N^1$-(3-aminopropyl)-2-ethoxymethyl-1H-imidazo[4,5-c]quinoline-1,4-diamine (1.04 g, 3.31 mmol) in 30 mL of $CH_2Cl_2$ and 5 mL of N,N-dimethylformamide was placed under an atmosphere of nitrogen and slowly treated with isopropyl isocyanate (0.320 mL, 3.31 mmol). After 15 h, the reaction mixture was concentrated under reduced pressure to yield a yellow/orange foam. The foam was purified by chromatography ($SiO_2$, 30% (80:18:2 $CHCl_3$: MeOH: conc. ammonium hydroxide ($NH_4OH$)) in $CHCl_3$) to give an off-white solid. The solid was triturated with diethyl ether ($Et_2O$) and collected by vacuum filtration to yield 1-(3-{[4-amino-2-(ethoxymethyl)-1H-imidazo[4,5-c]quinolin-1-yl]amino}propyl)-3-isopropylurea (0.603 g) as an off-white solid. mp 174–177° C.; $^1$H NMR (300 MHz, DMSO-$d_6$) δ 8.45 (d, J=8.1 Hz, 1H), 7.58 (d, J=8.2 Hz, 1H), 7.46–7.41 (m, 1H), 7.26–7.22 (m, 1H), 6.96 (t, J=5.5 Hz, 1H), 6.60 (s, 2H), 5.72 (t, J=5.5 Hz, 1H), 5.59 (d, J=7.7 Hz, 1H), 4.75 (s, 2H), 3.70–3.58 (m, 3H), 3.19–3.08 (m, 4H), 1.72–1.63 (m, 2H), 1.17 (t, J=7.0 Hz, 3H), 0.99 (d, J=6.5 Hz, 6H); $^{13}$C NMR (75 MHz, DMSO-$d_6$) δ 157.8, 152.3, 149.5, 145.3, 132.4, 127.4, 126.1, 124.2, 121.2, 114.7, 65.9, 63.1, 50.2, 41.2, 37.4, 28.9, 23.6, 15.4; MS (APCI) m/z 400 (M+H)$^+$; Anal. Calcd for $C_{20}H_{29}N_7O_2$: C, 60.13; H, 7.32; N, 24.54; Found: C, 59.94; H, 7.58; N, 24.45.

Example 26

1-(3-{[4-Amino-2-(ethoxymethyl)-6,7,8,9-tetrahydro-1H-imidazo[4,5-c]quinolin-1-yl]amino}propyl)-3-isopropylurea

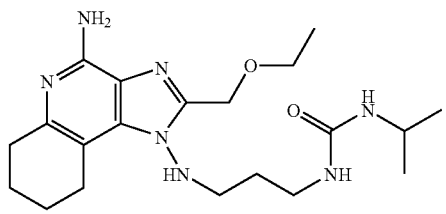

A solution of 1-(3-{[4-amino-2-(ethoxymethyl)-1H-imidazo[4,5-c]quinolin-1-yl]amino}propyl)-3-isopropylurea (0.450 g, 1.13 mmol) in 25 mL of trifluoroacetic acid (TFA) was treated with platinum (IV) oxide (0.256 g, 1.13 mmol) and shaken under an atmosphere of hydrogen (3.8×10$^5$ Pa) at ambient temperature. After 72 h, the reaction mixture was diluted with 4:1 $CHCl_3$:MeOH (25 mL) and filtered through a pad of CELITE filter agent. The filter pad was washed with additional 4:1 $CHCl_3$:MeOH (1% TFA). The clear colorless filtrate was concentrated under reduced pressure to yield a white semi-solid. The material was suspended in 15 mL of $H_2O$ and treated with 50% NaOH solution until the pH of the liquid reached 13. The material was triturated with the basic $H_2O$ for 2 h. An off white solid was collected by vacuum filtration and dried. The material was purified by chromatography ($SiO_2$, 30–50% (80:18:2 $CHCl_3$:MeOH:$NH_4OH$) in $CHCl_3$) to yield the product as a white foam. The foam was triturated with $Et_2O$, filtered and dried to yield 1-(3-{[4-amino-2-(ethoxymethyl)-6,7,8,9-tetrahydro-1H-imidazo[4,5-c]quinolin-1-yl]amino}propyl)-3-isopropylurea (0.223 g) as a white powdery solid. mp 185–187° C.;

$^1$H NMR (300 MHz, DMSO-$d_6$) δ 6.31 (t, J=6.0 Hz, 1H), 5.83 (s, 2H), 5.71 (t, J=5.7 Hz, 1H), 5.60 (d, J=7.8 Hz, 1H), 4.61 (s, 2H), 3.70–3.58 (m, 1H), 3.55 (q, J=7.0 Hz, 2H), 3.11–2.98 (m, 6H), 2.66 (t, J=5.8 Hz, 2H), 1.81–1.67 (m, 4H), 1.59 (p, J=7.1 Hz, 2H), 1.14 (t, J=7.0 Hz, 3H), 1.00 (d, J=6.5 Hz, 6H); $^{13}$C NMR (75 MHz, DMSO-$d_6$) δ 157.8, 149.9, 149.3, 146.9, 137.6, 122.7, 105.5, 65.7, 63.3, 51.7, 41.2, 37.4, 32.4, 28.9, 23.6, 23.2, 23.0, 22.4, 15.3; MS (APCI) m/z 404 (M+H)$^+$; Anal. Calcd for $C_{20}H_{33}N_7O_2$: C, 59.53; H, 8.24; N, 24.30; Found: C, 59.28; H, 8.46; N, 24.04.

Example 27

N-{3-[4-Amino-1-(isopropylamino)-2-propyl-1H-imidazo[4,5-c]quinolin-7-yl]phenyl}methanesulfonamide

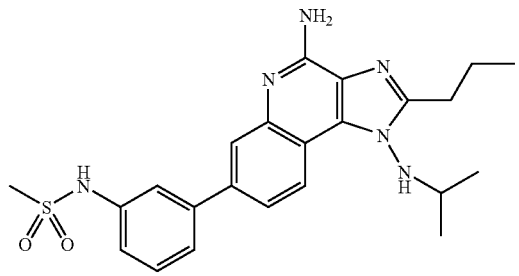

A suspension of 7-bromo-N¹-isopropyl-2-propyl-1H-imidazo[4,5-c]quinoline-1,4-diamine (1.00 g, 2.76 mmol) in 20 mL of 1-propanol was treated with 3-(methanesulfonylamino)phenylboronic acid (0.653 g, 3.04 mmol). The headspace of the reaction flask was purged and back-filled with nitrogen (3×). The reaction mixture was then treated with triphenylphosphine (11 mg, 0.041 mmol), sodium carbonate (1.66 mL, 3.31 mmol, 2 M solution in H₂O), H₂O (2 mL) and palladium (II) acetate (3.1 mg, 0.014 mmol). Again the headspace of the reaction flask was purged and back-filled with nitrogen (3×). The reaction was heated to 100° C. After 17 h, the reaction was cooled to ambient temperature and concentrated under reduced pressure to yield a brown solid. The solid was partitioned between 15 mL of H₂O and 15 mL of CHCl₃ and then separated. The aqueous portion was extracted with CHCl₃ (2×15 mL). The combined organic extracts were washed with brine (15 mL), dried over Na₂SO₄, filtered and concentrated under reduced pressure to yield a tan foam. The material was purified by chromatography (SiO₂, 50% (80:18:2 CHCl₃:MeOH:NH₄OH) in CHCl₃) and then dissolved in boiling CHCl₃ and slowly cooled to yield N-{3-[4-amino-1-(isopropylamino)-2-propyl-1H-imidazo[4,5-c]quinolin-7-yl]phenyl}methanesulfonamide (0.700 g) as a white solid. mp 217–227° C.; ¹H NMR (300 MHz, DMSO-d₆) δ 9.85 (s, 1H), 8.54 (d, J=8.5 Hz, 1H), 7.79 (d, J=1.4 Hz, 1H), 7.60 (s, 1H), 7.52–7.42 (m, 3H), 7.22 (d, J=7.8 Hz, 1H), 7.01 (s, 1H), 6.55 (s, 2H), 3.55–3.51 (m, 1H), 3.06 (s, 3H), 2.92 (bs, 2H), 1.91–1.84 (m, 2H), 1.05–1.01 (m, 9H); ¹³C NMR (125 MHz, DMSO-d₆) δ 155.4, 152.9, 145.8, 142.4, 139.9, 138.6, 133.1, 130.8, 124.9, 124.2, 123.1, 122.5, 120.2, 119.5, 118.7, 114.9, 51.8, 28.7, 21.6, 21.1, 14.8; MS (APCI) m/z 453 (M+H)⁺; Anal. Calcd for C₂₃H₂₈N₆O₂S: C, 61.04; H, 6.24; N, 18.57; Found: C, 60.66; H, 60.40; N, 18.47.

Example 28

N-(3-{[4-Amino-2-(ethoxymethyl)-6,7,8,9-tetrahydro-1H-imidazo[4,5-c]quinolin-1-yl]amino}propyl)morpholine-4-carboxamide

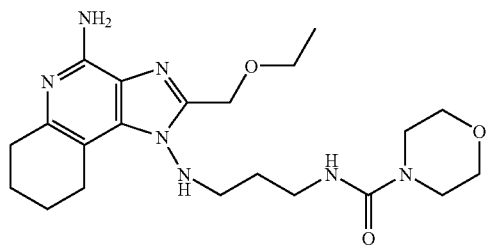

A solution of N-(3-{[4-amino-2-(ethoxymethyl)-1H-imidazo[4,5-c]quinolin-1-yl]amino}propyl)morpholine-4-carboxamide (0.120 g, 0.281 mmol) in 12 mL of TFA was treated with platinum (IV) oxide (0.064 g, 0.28 mmol). The mixture was placed under an atmosphere of hydrogen (3.8× 10⁵ Pa) and shaken at ambient temperature. After 17 h, the reaction mixture was diluted with 15 mL of 4:1 CHCl₃:MeOH and then filtered through a pad of CELITE filter agent and rinsed through with portions of 4:1 CHCl₃:MeOH (1% TFA). The clear colorless filtrate was concentrated under reduced pressure to yield a white solid. The material was suspended in 15 mL of H₂O and treated with 10% NaOH solution until the pH of the liquid was 13. A white solid was collected by vacuum filtration. The solid was purified by chromatography (SiO₂, 25–30% (80:18:2 CHCl₃:MeOH:NH₄OH) in CHCl₃) to yield a white foam. The foam was triturated with Et₂O and filtered to yield N-(3-{[4-amino-2-(ethoxymethyl)-6,7,8,9-tetrahydro-1H-imidazo[4,5-c]quinolin-1-yl]amino}propyl)morpholine-4-carboxamide (0.050 g) as a white solid. mp 152–154° C.; ¹H NMR (300 MHz, DMSO-d₆) δ 6.52 (t, J=5.4 Hz, 1H), 6.31 (t, J=5.9 Hz, 1H), 5.83 (s, 2H), 4.61 (s, 2H), 3.58–3.50 (m, 6H), 3.24–3.21 (m, 4H), 3.12 (q, J=6.7 Hz, 2H), 3.06–3.00 (m, 4H), 2.67–2.64 (m, 2H), 1.78–1.72 (m, 4H), 1.66–1.61 (m, 2H), 1.14 (t, J=7.0 Hz, 3H); ¹³C NMR (75 MHz, DMSO-d₆) δ 157.6, 149.4, 148.9, 146.5, 137.1, 105.0, 65.8, 65.2, 62.9, 51.3, 43.7, 37.8, 32.0, 28.1, 22.8, 22.5, 22.0, 14.9; MS (APCI) m/z 432 (M+H)⁺; Anal. Calcd for C₂₁H₃₃N₇O₃•5H₂O: C, 57.25; H, 7.78; N, 22.26; Found: C, 57.30; H, 7.82; N, 22.29.

Example 29

N¹-Isopropyl-7-[3-(morpholin-4-ylcarbonyl)phenyl]-2-propyl-1H-imidazo[4,5-c]quinoline-1,4-diamine

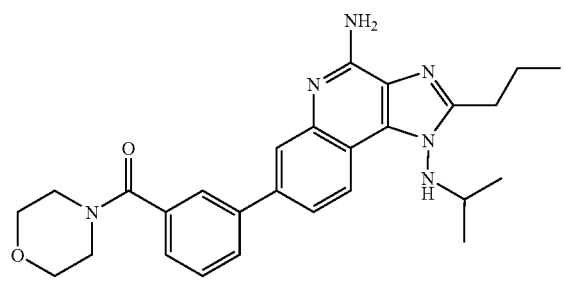

A suspension of 7-bromo-N¹-isopropyl-2-propyl-1H-imidazo[4,5-c]quinoline-1,4-diamine (1.00 g, 2.76 mmol) in 20 mL of 1-propanol was treated with the 3-(morpholine-4-carbonyl)phenylboronic acid (0.715 g, 3.04 mmol). The headspace of the flask was purged and back-filled with nitrogen (3×). The reaction mixture was then treated with triphenylphosphine (11 mg, 0.041 mmol), sodium carbonate (1.66 mL, 3.31 mmol, 2 M solution in H₂O), H₂O (2 mL), and palladium (II) acetate (3.1 mg, 0.014 mmol). Again the headspace of the flask was purged and back filled with nitrogen (3×). The reaction mixture was heated to 100° C. After 16 h, the reaction mixture was concentrated under reduced pressure to yield a brown solid. The solid was partitioned between CHCl₃ (45 mL) and H₂O (15 mL) and separated. The organic portion was washed again with H₂O (15 mL) and brine (15 mL), dried over Na₂SO₄, filtered and concentrated under reduced pressure to yield a tan solid. The solid was purified by chromatography (SiO₂, 95:5 CHCl₃:MeOH) to yield a light yellow foam. The foam was crystallized from 1:1 acetonitrile (MeCN):MeOH to give N¹-isopropyl-7-[3-(morpholin-4-ylcarbonyl)phenyl]-2-propyl-1H-imidazo[4,5-c]quinoline-1,4-diamine (0.683 g) as light yellow crystals. mp 274–276° C.; ¹H NMR (300 MHz, DMSO-d₆, 350 K) δ 8.56 (d, J=8.5 Hz, 1H), 7.86–7.81 (m, 2H), 7.74 (s, 1H), 7.57–7.52 (m, 2H), 7.38 (d, J=7.6 Hz, 1H), 6.81 (s, 1H), 6.21 (s, 2H), 3.65–3.62 (m, 4H), 3.58–3.54 (m, 5H), 2.93 (t, J=7.5 Hz, 2H), 1.96–1.83 (m, 2H), 1.07–1.02 (m, 9H); ¹³C NMR (75 MHz, DMSO-d₆, 350 K) δ 169.5, 154.9, 152.3, 145.4, 141.1, 137.8, 136.9, 132.8, 129.4, 128.1, 126.1, 125.5, 124.6, 124.1, 122.0, 119.9, 114.7, 66.5, 51.4, 45.4, 28.3, 20.9, 20.6, 14.1; MS (APCI) m/z 473 (M+H)+; Anal. Calcd for $C_{27}H_{32}N_6O_2$: C, 68.62; H, 6.83; N, 17.78; Found: C, 68.73; H, 6.71; N, 17.85.

Example 30

N-(3-{[4-Amino-2-(ethoxymethyl)-1-(isopropylamino)-1H-imidazo[4,5-c]quinolin-7-yl]oxy}propyl)methanesulfonamide

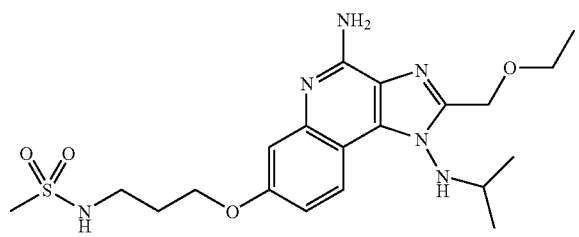

Part A

A solution of tert-butyl [3-(4-amino-2-ethoxymethyl-1-isopropylamino-1H-imidazo[4,5-c]quinolin-7-yloxy)propyl]carbamate (1.24 g, 2.62 mmol) in 5 mL of ethanol (EtOH) was treated with 5 mL of 4.3 M HCl in EtOH. The reaction was heated to 100° C. After 1 h, the reaction was cooled to ambient temperature and concentrated under reduced pressure to yield a brown solid. The solid was dissolved in a minimum amount of $H_2O$ and treated with 10% NaOH solution until the pH of the liquid was 13. The basic aqueous mixture was extracted with $CH_2Cl_2$ (3×25 mL). The combined organic extracts were washed with brine (25 mL), dried over $Na_2SO_4$, filtered and concentrated under reduced pressure to yield 7-(3-aminopropoxy)-2-ethoxymethyl-$N^1$-isopropyl-1H-imidazo[4,5-c]quinoline-1,4-diamine (0.84 g) as a tan solid.

Part B

A solution of 7-(3-aminopropoxy)-2-ethoxymethyl-$N^1$-isopropyl-1H-imidazo[4,5-c]quinoline-1,4-diamine (0.84 g, 2.26 mmol) in 25 mL of $CH_2Cl_2$ was placed under an atmosphere of nitrogen. The solution was treated with triethylamine (0.63 mL, 4.75 mmol) and cooled in an ice water bath. The solution was slowly treated with methanesulfonyl chloride (0.184 mL, 2.37). The reaction was stirred and allowed to slowly come to ambient temperature. After 16 h, the reaction mixture was diluted with $CHCl_3$ (20 mL) and transferred to a separatory funnel. The organic solution was washed with 10% $Na_2CO_3$ solution (15 mL), $H_2O$ (15 mL) and brine (15 mL), dried over $Na_2SO_4$, filtered and concentrated under reduced pressure to yield a tan foam. The foam was purified by chromatography ($SiO_2$, 10–50% (80:18:2 $CHCl_3$:MeOH:$NH_4OH$) in $CHCl_3$) to give a light yellow solid. The solid was crystallized from MeCN to yield N-(3-{[4-amino-2-(ethoxymethyl)-1-(isopropylamino)-1H-imidazo[4,5-c]quinolin-7-yl]oxy}propyl)methanesulfonamide (0.295 g) as white crystals. mp 181–183° C.; $^1$H NMR (300 MHz, DMSO-$d_6$) δ 8.46 (d, J=9.0 Hz, 1H), 7.09 (t, J=6.8 Hz, 1H), 7.02 (d, J=2.6 Hz, 1H), 6.90 (d, J=2.1 Hz, 1H), 6.87 (d, J=2.5 Hz, 1H), 6.54 (s, 2H), 4.71 (s, 2H), 4.11 (t, J=6.1 Hz, 2H), 3.64–3.58 (m, 3H), 3.14 (q, J=6.1 Hz, 2H), 2.91 (s, 3H), 1.96 (p, J=6.6 Hz, 2H), 1.15 (t, J=7.0 Hz, 3H), 1.01 (d, J=6.1 Hz, 6H); $^{13}$C NMR (75 MHz, DMSO-$d_6$) δ 158.1, 152.6, 149.4, 147.2, 133.7, 122.6, 111.5, 109.1, 107.9, 65.8, 65.0, 63.0, 51.6, 29.7, 20.6, 15.3; MS (APCI) m/z 451 (M+H)+; Anal. Calcd for $C_{20}H_{30}N_6O_4S$: C, 53.32; H, 6.71; N, 18.65; S, 7.12; Found: C, 53.44; H, 6.68; N, 18.83; S, 7.09.

Example 31

$N^1$-Isopropyl-7-phenyl-2-propyl-1H-imidazo[4,5-c]quinoline-1,4-diamine

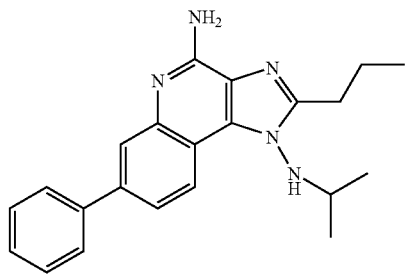

A solution of 7-bromo-$N^1$-isopropyl-2-propyl-1H-imidazo[4,5-c]quinoline-1,4-diamine (1.00 g, 2.76 mmol) in 20 mL 1-propanol was treated with phenylboronic acid (0.371 g, 3.04 mmol) giving a suspension. The headspace of the flask was purged and back-filled with nitrogen (3×). The reaction mixture was then treated with triphenylphosphine (11 mg, 0.041 mmol), sodium carbonate (1.66 mL, 3.31 mmol, 2 M solution in $H_2O$), $H_2O$ (2 mL), and palladium (II) acetate (3.1 mg, 0.014 mmol). Again the headspace of the flask was purged and back-filled with nitrogen (3×). The reaction mixture was heated to 100° C. After 16 h, the reaction mixture was concentrated under reduced pressure to yield a brown solid. The solid was partitioned between $CHCl_3$ (45 mL) and $H_2O$ (15 mL) and separated. The organic portion was washed again with $H_2O$ (15 mL) and brine (15 mL), dried over $Na_2SO_4$, filtered and concentrated under reduced pressure to yield a tan solid. The solid was recrystallized from MeCN to yield $N^1$-isopropyl-7-phenyl-2-propyl-1H-imidazo[4,5-c]quinoline-1,4-diamine (0.401 g) as light yellow crystals. mp 217–220° C.; $^1$H NMR (300 MHz, DMSO-$d_6$) δ 8.53 (d, J=8.5 Hz, 1H), 7.83 (d, J=1.8 Hz, 1H), 7.78–7.76 (m, 2H), 7.55 (dd, J=7.5, 1.9 Hz, 1H), 7.52–7.47 (m, 2H), 7.40–7.35 (m, 1H), 7.01 (s, 1H), 6.53 (s, 2H), 3.57–3.49 (m, 1H), 2.92 (bs, 2H), 1.94–1.81 (m, 2H), 1.06–1.01 (m, 9H); $^{13}$C NMR (75 MHz, DMSO-$d_6$) δ 154.2, 151.9, 144.9, 140.3, 138.1, 132.1, 128.9, 127.2, 126.7, 123.9, 123.2, 121.4, 119.4, 113.8, 50.8, 27.8, 20.7, 20.2, 13.9; MS (ESI) m/z 360 (M+H)+; Anal. Calcd for $C_{22}H_{25}N_5$: C, 73.51; H, 7.01; N, 19.48; Found: C, 73.39; H, 7.20; N, 19.36.

Example 32

N-(3-{[4-Amino-2-(ethoxymethyl)-1H-imidazo[4,5-c]quinolin-1-yl]amino}propyl)-2-methylpropanamide

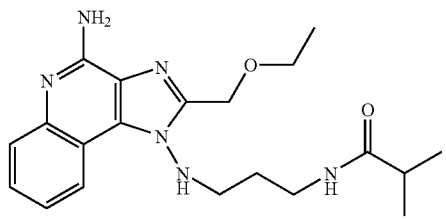

A solution of $N^1$-(3-aminopropyl)-2-ethoxymethyl-1H-imidazo[4,5-c]quinoline-1,4-diamine (1.00 g, 3.18 mmol) in 25 mL of $CH_2Cl_2$ was placed under an atmosphere of nitrogen and then chilled in an ice water bath. The solution was treated with triethylamine (0.89 mL, 6.7 mmol) and then slowly with isobutyryl chloride (0.35 mL, 3.3 mmol). The reaction was stirred and allowed to slowly come to ambient temperature. After 16 h, the reaction was diluted with 15 mL of $CHCl_3$ and 15 mL of 10% $Na_2CO_3$ solution and the layers were separated. The organic portion was washed with $H_2O$ (15 mL). The combined aqueous washes were back-extracted with $CHCl_3$ (10 mL). The combined organic extracts were washed with brine (15 mL), dried over $Na_2SO_4$, filtered and concentrated under reduced pressure to yield a light yellow foam. The foam was purified by chromatography ($SiO_2$, 10–50% (80:18:2 $CHCl_3$:MeOH:$NH_4OH$) in $CHCl_3$) to yield a white foam. The foam was triturated with hexanes and filtered to yield N-(3-{[4-amino-2-(ethoxymethyl)-1H-imidazo[4,5-c]quinolin-1-yl]amino}propyl)-2-methylpropanamide (0.821 g) as a white solid. mp 108–110° C.; $^1H$ NMR (300 MHz, DMSO-$d_6$) δ 8.43 (d, J=7.5 Hz, 1H), 7.72 (t, J=5.4 Hz, 1H), 7.58 (d, J=7.9 Hz, 1H), 7.46–7.41 (m, 1H), 7.26–7.21 (m, 1H), 6.97 (t, J=5.5 Hz, 1H), 6.62 (s, 2H), 4.75 (s, 2H), 3.61 (q, J=7.0 Hz, 2H), 3.17–3.13 (m, 4H), 2.29 (h, J=6.9 Hz, 1H), 1.71 (p, J=7.1 Hz, 2H), 1.17 (t, J=7.0 Hz, 3H), 0.95 (d, J=6.8 Hz, 3H); $^{13}C$ NMR (75 MHz, DMSO-$d_6$) δ 176.4, 152.3, 149.5, 145.3, 132.4, 127.4, 126.1, 124.2, 121.2, 114.7, 65.8, 63.1, 50.2, 36.6, 34.4, 28.0, 19.9, 15.3; MS (APCI) m/z 385 (M+H)$^+$; Anal. Calcd for $C_{20}H_{28}N_6O_2$·0.25$H_2O$: C, 61.76; H, 7.38; N, 21.61; Found: C, 61.67; H, 7.55; N, 21.72.

Example 33

N-(3-{[4-Amino-2-(ethoxymethyl)-6,7,8,9-tetrahydro-1H-imidazo[4,5-c]quinolin-1-yl]amino}propyl)-2-methylpropanamide

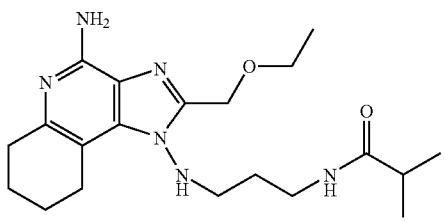

A solution of N-(3-{[4-amino-2-(ethoxymethyl)-1H-imidazo[4,5-c]quinolin-1-yl]amino}propyl)-2-methylpropanamide (0.450 g, 1.17 mmol) in 25 mL of TFA was treated with platinum (IV) oxide (0.266 g, 1.17 mmol). The reaction mixture was shaken under an atmosphere of hydrogen ($3.8\times10^5$ Pa) at ambient temperature. After 17 h, the reaction mixture was filtered through a pad of CELITE filter agent and rinsed with portions of 4:1 $CHCl_3$:MeOH (1% TFA). The filtrate was concentrated under reduced pressure to yield a white oil. The oil was suspended in a minimum amount of $H_2O$ and treated with 50% NaOH solution until the pH was 13. A white solid precipitated and was triturated in the basic $H_2O$ for 1 h and then filtered to yield a sticky white solid. The solid was then triturated with $Et_2O$ for 2 h, filtered and dried to yield N-(3-{[4-amino-2-(ethoxymethyl)-6,7,8,9-tetrahydro-1H-imidazo[4,5-c]quinolin-1-yl]amino}propyl)-2-methylpropanamide (0.237 g) as a white solid. mp 163–165° C.; $^1H$ NMR (500 MHz, DMSO-$d_6$) δ 7.69 (t, J=5.5 Hz, 1H), 6.31 (t, J=5.9 Hz, 1H), 5.80 (s, 2H), 4.61 (s, 2H), 3.55 (q, J=7.0 Hz, 2H), 3.15–3.11 (m, 2H), 3.04–3.00 (m, 4H), 2.66 (t, J=5.7 Hz, 2H), 2.31 (h, J=6.8 Hz, 1H), 1.81–1.69 (m, 4H), 1.62 (p, J=7.1 Hz, 2H), 1.14 (t, J=7.0 Hz, 3H), 0.98 (d, J=6.9 Hz, 6H); $^{13}C$ NMR (75 MHz, DMSO-$d_6$) δ 176.3, 149.9, 149.3, 147.0, 137.6, 122.7, 105.4, 65.7, 63.3, 51.7, 36.6, 34.4, 32.5, 28.0, 23.3, 23.0, 22.4, 19.9, 15.3; MS (ESI) m/z 389 (M+H)$^+$; Anal. Calcd for $C_{20}H_{32}N_6O_2$: C, 61.83; H, 8.30; N, 21.63; Found: C, 61.63; H, 8.23; N, 21.55.

Example 34

N-(3-{[4-Amino-2-(ethoxymethyl)-1H-imidazo[4,5-c]quinolin-1-yl]amino}propyl)acetamide

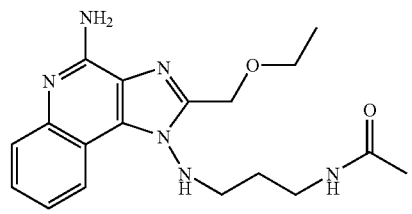

A solution of $N^1$-(3-aminopropyl)-2-ethoxymethyl-1H-imidazo[4,5-c]quinoline-1,4-diamine (1.00 g, 3.18 mmol) in 15 mL of $CH_2Cl_2$ was placed under an atmosphere of nitrogen. The solution was chilled in an ice water bath and treated first with triethylamine (0.89 mL, 6.7 mmol) and then slowly with acetyl chloride (0.89 mL, 3.3 mmol). After 2 h, the reaction was warmed to ambient temperature, quenched with 15 mL of saturated $NaHCO_3$ solution and diluted with 30 mL of $CHCl_3$. The phases were separated and the organic portion was washed with $H_2O$ (15 mL) and brine (15 mL). The organic portion was dried over $Na_2SO_4$, filtered and concentrated under reduced pressure to yield a light yellow foam. The foam was crystallized from MeCN to give light yellow crystals. The crystals were pulverized and then triturated with $Et_2O$ for 18 h and filtered off to yield N-(3-{[4-amino-2-(ethoxymethyl)-1H-imidazo[4,5-c]quinolin-1-yl]amino}propyl)acetamide (0.728 g) as a white solid. mp 178–181° C.; $^1H$ NMR (500 MHz, DMSO-$d_6$) δ 8.44 (d, J=8.1 Hz, 1H), 7.82 (t, J=5.1 Hz, 1H), 7.59 (d, J=8.2 Hz, 1H), 7.45–7.42 (m, 1H), 7.26–7.22 (m, 1H), 6.96 (t, J=5.6 Hz, 1H), 6.59 (s, 2H), 4.75 (s, 2H), 3.61 (q, J=7.0 Hz, 2H), 3.20–3.14 (m, 4H), 1.77 (s, 3H), 1.71 (p, J=7.0 Hz, 2H), 1.17 (t, J=7.0Hz, 3H);
$^{13}C$ NMR (75 MHz, DMSO-$d_6$) δ 169.4, 152.3, 149.5, 145.3, 132.4, 127.4, 126.1, 124.2, 121.2, 114.7, 65.8, 36.1, 50.2, 36.8, 27.9, 22.9, 15.3; MS (ESI) m/z 357 (M+H)$^+$; Anal. Calcd for $C_{18}H_{24}N_6O_2$: C, 60.66; H, 6.79; N, 23.58; Found: C, 60.55; H, 6.84; N, 23.44.

Example 35

$N^1$-Isopropyl-2-propyl-7-(2-pyridin-3-ylethyl)-1H-imidazo[4,5-c]quinoline-1,4-diamine

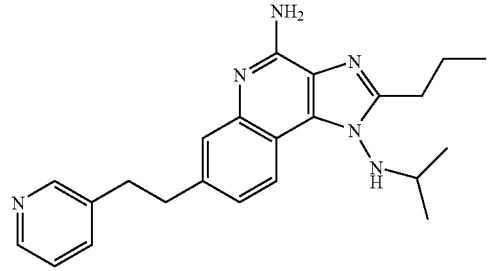

Part A

A suspension of 7-bromo-N$^1$-isopropyl-2-propyl-1H-imidazo[4,5-c]quinoline-1,4-diamine (1.71 g, 4.72 mmol) in 34 mL of 1-propanol was placed under an atmosphere of nitrogen. The mixture was treated with triethylamine (1.25 mL, 9.44 mmol) and then the headspace of the flask was evacuated and back-filled with nitrogen (3×). The reaction mixture was treated with potassium vinylfluoroborate (0.695 g, 5.19 mmol) and dichloro[1,1'-bis(diphenylphosphino)ferrocene]palladium (II) dichloromethane adduct (0.069 g, 0.094 mmol) and the head-space purged and backfilled as before. The reaction was heated to 100° C. After 16 h, the reaction mixture was cooled to ambient temperature and concentrated under reduced pressure. The residue was dissolved in 50 mL of CHCl$_3$ and washed with 5% Na$_2$CO$_3$ solution (15 mL). There was a thick emulsion that did not fully separate. The organic portion was washed with H$_2$O (15 mL) resulting in another slowly separating emulsion. The combined aqueous washes were back extracted with CHCl$_3$ (15 mL). The combined organic extracts were washed with brine (15 mL), dried over Na$_2$SO$_4$, filtered and concentrated under reduced pressure to yield an orange solid. The solid was purified by chromatography (SiO$_2$, 20% (80:18:2 CHCl$_3$:MeOH:NH$_4$OH) in CHCl$_3$) to yield N$^1$-isopropyl-2-propyl-7-vinyl-1H-imidazo[4,5-c]quinoline-1,4-diamine (0.92 g) as a tan solid.

Part B

A suspension of palladium (II) acetate (0.067 g, 0.30 mmol) and tri-o-tolylphosphine (0.271 g, 0.891 mmol) in 10 mL of MeCN was placed in a 50 mL heavy wall glass pressure flask and placed under an atmosphere of nitrogen. The mixture was stirred until homogeneous. The mixture was treated with triethylamine (1.58 mL, 11.9 mmol), 3-bromopyridine (0.430 mL, 4.46 mmol) and N-isopropyl-2-propyl-7-vinyl-1H-imidazo[4,5-c]quinoline-1,4-diamine (0.92 g, 3.0 mmol). Nitrogen was bubbled through the mixture for 1 min and then the flask was sealed. The reaction was heated to 120° C. After 15 h, the homogenous orange solution was cooled to ambient temperature and concentrated under reduced pressure. The residue was partitioned between 75 mL of CHCl$_3$ and 25 mL of 10% Na$_2$CO$_3$ solution. The phases were separated and the organic portion was washed with H$_2$O (25 mL). The combined aqueous portions were back-extracted with CHCl$_3$ (25 mL). The combined organic extracts were washed with brine (30 mL), dried over Na$_2$SO$_4$, filtered and concentrated under reduced pressure to yield an orange solid. The solid was purified by chromatography (SiO$_2$, 20–50% (80:18:2 CHCl$_3$:MeOH:NH$_4$OH) in CHCl$_3$) to yield N$^1$-isopropyl-2-propyl-7-(2-pyridin-3-yl-vinyl)-1H-imidazo[4,5-c]quinoline-1,4-diamine (0.97 g) as a light yellow solid.

Part C

A solution of N$^1$-isopropyl-2-propyl-7-(2-pyridin-3-yl-vinyl)-1H-imidazo[4,5-c]quinoline-1,4-diamine (0.97 g, 2.5 mmol) in 15 mL of EtOH and 15 mL of MeOH was treated with palladium on carbon (0.10 g, 0.050 mmol, 5% w/w). The mixture was placed under an atmosphere of hydrogen (3.8×10$^5$ Pa) and shaken at ambient temperature. After 3 d, the reaction mixture was filtered through a pad of CELITE filter agent and rinsed with a 1:1 MeOH:EtOH until the filtrate ran clear. The filtrate was concentrated under reduced pressure to yield a light green solid. The solid was purified by chromatography (SiO$_2$, 10–50% (80:18:2 CHCl$_3$:MeOH:NH$_4$OH) in CHCl$_3$) to yield a clear oil. The oil was twice crystallized from MeCN to give N$^1$-isopropyl-2-propyl-7-(2-pyridin-3-ylethyl)-1H-imidazo[4,5-c]quinoline-1,4-diamine (0.224 g) as white crystals. mp 100–103° C.; $^1$H NMR (300 MHz, DMSO-d$_6$) δ 8.43 (d, J=1.6 Hz, 1H), 8.37 (dd, J=3.8, 1.6 Hz, 1H), 8.32 (d, J=8.4 Hz, 1H), 7.68–7.64 (m, 1H), 7.37 (d, J=1.5 Hz, 1H), 7.31–7.26 (m, 1H), 7.12 (dd, J=8.4, 1.7 Hz, 1H), 6.93 (d, J=1.4 Hz, 1H), 6.39 (s, 2H), 3.52–3.44 (m, 1H), 3.00 (s, 4H), 2.89 (bs, 2H), 1.91–1.79 (m, 2H), 1.04–1.00 (m, 9H); $^{13}$C NMR (125 MHz, DMSO-d$_6$) δ 154.2, 152.0, 150.1, 147.5, 145.0, 139.6, 137.2, 136.3, 132.8, 125.4, 123.9, 123.7, 122.0, 121.1, 113.1, 51.2, 37.0, 34.1, 28.2, 21.1, 20.6, 14.3; MS (APCI) m/z 389 (M+H)$^+$; Anal. Calcd for C$_{23}$H$_{28}$N$_6$: C, 71.10; H, 7.26; N, 21.63; Found: C, 70.87; H, 7.54; N, 21.58.

Example 36

2-Ethyl-N$^1$-isopropyl-1H-imidazo[4,5-c]quinoline-1,4-diamine

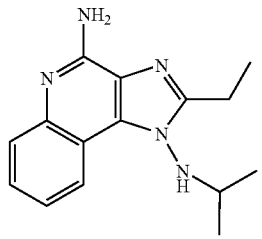

2-Ethyl-N$^1$-isopropyl-1H-imidazo[4,5-c]quinoline-1,4-diamine was prepared in 5 steps from N'-(3-aminoquinolin-4-yl)hydrazine tert-butyl carboxylate in analogous fashion to the preparation of N$^1$-Isopropyl-2-propyl-1H-imidazo[4,5-c]quinoline-1,4-diamine (Example 16). Triethyl orthopropionate was used in lieu of trimethyl orthobutyrate. The material was purified by chromatography (SiO$_2$, 20% (80:18:2 CHCl$_3$:MeOH:NH$_4$OH) in CHCl$_3$) to yield an off white solid. The solid was crystallized from MeCN to yield 2-ethyl-N$^1$-isopropyl-1H-imidazo[4,5-c]quinoline-1,4-diamine (0.358 g) as light pink crystals. mp 245–247° C.; $^1$H NMR (500 MHz, DMSO-d$_6$) δ 8.47 (d, J=8.1 Hz, 1H), 7.57 (d, J=8.0 Hz, 1H), 7.39 (t, J=7.5 Hz, 1H), 7.22 (t, J=7.5 Hz, 1H), 6.95 (s, 1H), 6.44 (s, 2H), 3.54–3.46 (m, 1H), 3.04–2.88 (m, 2H), 1.37 (t, J=7.1 Hz, 3H), 1.01 (d, J=5.8 Hz, 6H); $^{13}$C NMR (125 MHz, DMSO-d$_6$) δ 155.6, 152.0, 145.0, 132.8, 126.8, 126.1, 124.1, 121.3, 120.9, 115.0, 51.2, 20.6, 19.7, 12.4; MS (APCI) m/z 270 (M+H)$^+$; Anal. Calcd for C$_{15}$H$_{19}$N$_5$: C, 66.89; H, 7.11; N, 26.00; Found: C, 66.81; H, 7.22; N, 25.95.

Example 37

N-(3-{[4-Amino-2-(ethoxymethyl)-6,7,8,9-tetrahydro-1H-imidazo[4,5-c]quinolin-1-yl]amino}propyl)acetamide

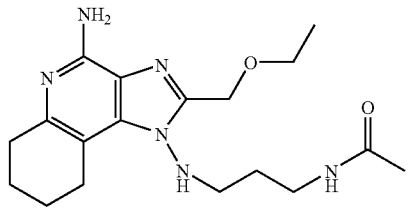

A solution of N-(3-{[4-amino-2-(ethoxymethyl)-1H-imidazo[4,5-c]quinolin-1-yl]amino}propyl)acetamide (0.220 g, 0.617 mmol) in 15 mL of TFA was treated with platinum (IV) oxide (0.140 g, 0.617 mmol). The mixture was placed under an atmosphere of hydrogen (3.8×10$^5$ Pa) and shaken at ambient temperature. After 18 h, the reaction mixture was diluted with CHCl$_3$ (15 mL) and filtered through a pad of CELITE filter agent and rinsed with several portions of CHCl$_3$ (1% TFA). The filtrate was concentrated under reduced pressure to yield an off-white oil. The oil was suspended in a minimum amount of H$_2$O and treated with 50% NaOH solution until the pH of the liquid was 12–13. The mixture was extracted with CH$_2$Cl$_2$ (3×15 mL). The combined organic extracts were washed with brine (15 mL), dried over Na$_2$SO$_4$, filtered and concentrated under reduced pressure to yield an off-white solid. The solid was purified by chromatography (SiO$_2$, 15–20% (80:18:2 CHCl$_3$:MeOH:NH$_4$OH) in CHCl$_3$) to yield a white solid. The solid was recrystallized from MeCN to yield N-(3-{[4-amino-2-(ethoxymethyl)-6,7,8,9-tetrahydro-1H-imidazo[4,5-c]quinolin-1-yl]amino}propyl)acetamide (0.0633 g) as white crystals. mp 198–200° C.; $^1$H NMR (500 MHz, DMSO-d$_6$) δ 7.80 (t, J=5.0 Hz, 1H), 6.30 (t, J=6.0 Hz, 1H), 5.78 (s, 2H), 4.61 s, 2H), 3.55 (q, J=7.0 Hz, 2H), 3.12 (q, J=6.7 Hz, 2H), 3.05–3.01 (m, 4H), 2.66 (t, J=5.9 Hz, 2H), 1.78–1.73 (m, 7H), 1.62 (p, J=7.1 Hz, 2H), 1.14 (t, J=7.0 Hz, 3H); $^{13}$C NMR (125 MHz DMSO-d$_6$) δ 169.4, 149.9, 149.3, 147.1, 137.6, 122.7, 105.5, 65.7, 63.4, 51.6, 36.8, 32.5, 27.9, 23.9, 23.0, 23.0, 22.5, 15.3; MS (APCI) m/z 361 (M+H)$^+$; Anal. Calcd for C$_{18}$H$_{28}$N$_6$O$_2$: C, 59.98; H, 7.83; N, 23.31; Found: C, 59.96; H, 8.04; N, 23.37.

Example 38

1-(3-{[4-Amino-2-(ethoxymethyl)-1H-imidazo[4,5-c]quinolin-1-yl]amino}propyl)-3-ethylurea

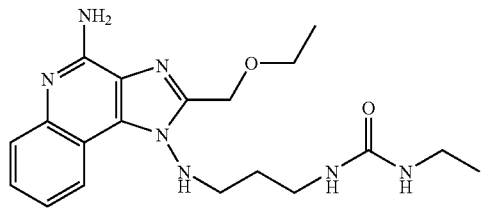

A solution of N$^1$-(3-aminopropyl)-2-ethoxymethyl-1H-imidazo[4,5-c]quinoline-1,4-diamine (1.42 g, 4.52 mmol) in 25 mL of CH$_2$Cl$_2$ was placed under an atmosphere of nitrogen and chilled in an ice water bath. The solution was slowly treated with ethyl isocyanate (0.375 mL, 4.74 mmol). Upon addition the reaction mixture became thick and additional CH$_2$Cl$_2$ had to be added to keep the mixture stirring. The reaction was allowed to slowly warm to ambient temperature. After 17 h, the reaction was concentrated under reduced pressure to yield an off-white solid. The solid was purified by chromatography (SiO$_2$, 15–50% (80:18:2 CHCl$_3$:MeOH:NH$_4$OH) in CHCl$_3$) to yield an off-white solid. The solid was recrystallized from MeCN to give 1-(3-{[4-amino-2-(ethoxymethyl)-1H-imidazo[4,5-c]quinolin-1-yl]amino}propyl)-3-ethylurea (1.16 g) as a white solid. mp 138–141° C.; $^1$H NMR (300 MHz, DMSO-d$_6$) δ 8.45 (dd, J=8.1, 1.0 Hz, 1H), 7.58 (dd, J=8.3, 0.9 Hz, 1H), 7.46–7.41 (m, 1H), 7.27–7.21 (m, 1H), 6.96 (t, J=5.6 Hz, 1H), 6.60 (s, 2H), 5.83 (t, J=5.7 Hz, 1H), 5.73 (t, J=5.5 Hz, 1H), 4.75 (s, 2H), 3.61 (q, J=7.0 Hz, 2H), 3.20–3.08 (m, 4H), 3.03–2.94 (m, 2H), 1.68 (p, J=6.9 Hz, 2H), 1.17 (t, J=7.0 Hz, 3H), 0.96 (t, J=7.1 Hz, 3H); $^{13}$C NMR (125 MHz, DMSO-d$_6$) δ 158.4, 152.3, 149.5, 145.3, 132.4, 127.4, 126.1, 124.2, 121.3, 121.2, 114.8, 65.9, 63.1, 50.2, 37.6, 34.4, 28.9, 16.0, 15.4; MS (ESI) m/z 386 (M+H)$^+$; Anal. Calcd for C$_{19}$H$_{27}$N$_7$O$_2$•0.5H$_2$O: C, 57.85; H, 7.15; N, 24.85; Found: C, 57.84; H, 7.31; N, 25.04.

Example 39

1-(3-{[4-Amino-2-(ethoxymethyl)-6,7,8,9-tetrahydro-1H-imidazo[4,5-c]quinolin-1-yl]amino}propyl)-3-ethylurea

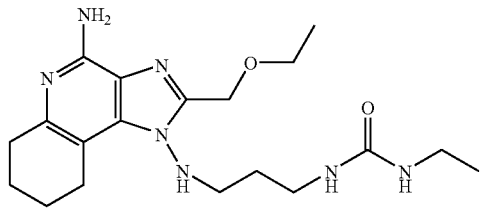

A solution of 1-(3-{[4-amino-2-(ethoxymethyl)-1H-imidazo[4,5-c]quinolin-1-yl]amino}propyl)-3-ethylurea (0.700 g, 1.82 mmol) in 20 mL of TFA was treated with platinum (IV) oxide (0.413 g, 1.82 mmol). The mixture was placed under an atmosphere of nitrogen (3.8×10$^5$ Pa) and shaken at ambient temperature. After 22 h, the reaction mixture was diluted with 50 mL of CHCl$_3$ and 10 mL of MeOH and filtered through a pad of CELITE filter agent. The pad was rinsed with 20% MeOH in CHCl$_3$ until the filtrate ran clear. The filtrate was concentrated under reduced pressure to yield a clear, colorless oil. The oil was suspended in 25 mL of H$_2$O and treated with 50% NaOH until the pH of the liquid reached 13. A white solid precipitated. The solid was triturated in the basic solution for 15 min and then filtered to give a white solid. The solid was recrystallized from MeCN to yield 1-(3-{[4-amino-2-(ethoxymethyl)-6,7,8,9-tetrahydro-1H-imidazo[4,5-c]quinolin-1-yl]amino}propyl)-3-ethylurea (0.400 g) as white crystals. mp 189–191° C.; $^1$H NMR (300 MHz, DMSO-d$_6$) δ 6.31 (t, J=5.9 Hz, 1H), 5.83–5.79 (m, 3H), 5.74 (t, J=5.6 Hz, 1H), 4.61 (s, 2H), 3.55 (q, J=7.0 Hz, 2H), 3.11–2.94 (m, 8H), 2.66 (t, J=5.8 Hz, 2H), 1.83–1.67 (m, 4H), 1.59 (p, J=6.9 Hz, 2H), 1.14 (t, J=7.0 Hz, 3H), 0.97 (t, J=7.1 Hz, 3H); $^{13}$C NMR (75 MHz, DMSO-d$_6$) δ 158.4, 149.9, 149.3, 147.0, 137.6, 122.7, 105.5, 65.7, 63.3, 51.7, 37.5, 34.4, 32.5, 28.9, 23.2, 23.0, 22.4, 16.0, 15.3; MS (APCI) m/z 390 (M+H)$^+$; Anal. Calcd for C$_{19}$H$_{31}$N$_7$O$_2$: C, 58.59; H, 8.02; N, 25.17; Found: C, 58.35; H, 8.30; N, 25.31.

Example 40

N-{3-[(4-Amino-2-ethyl-1H-imidazo[4,5-c]quinolin-1-yl)amino]propyl}acetamide

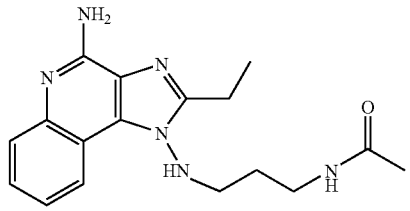

A solution of N$^1$-(3-Aminopropyl)-2-ethyl-1H-imidazo[4,5-c]quinoline-1,4-diamine (0.89 g, 3.1 mmol) in 30 mL of CH$_2$Cl$_2$ was placed under an atmosphere of nitrogen. The solution was treated first with triethylamine (0.92 mL, 6.6 mmol) and then slowly with acetyl chloride (0.234 mL, 3.29 mmol). After 16 h, another equivalent of acetyl chloride was added. After 3 h, the reaction was concentrated under reduced pressure to yield an orange oil. The oil was then treated with 20 mL of 1 M HCl in MeOH and stirred at ambient temperature to hydrolyze any bis-amide. After 16 h, the reaction was quenched with 25 mL of 10% Na$_2$CO$_3$ solution. The mixture was concentrated under reduced pressure to remove MeOH. The aqueous oily suspension was treated with 75 mL of 95:5 CHCl$_3$:MeOH, transferred to a separatory funnel and separated. The organic portion was washed with brine (25 mL), dried over Na$_2$SO$_4$, filtered and concentrated under reduced pressure to yield a yellow foam. The foam was purified by chromatography (40 g SiO$_2$, 25% (80:18:2 CHCl$_3$:MeOH:NH$_4$OH) in CHCl$_3$) to yield a light yellow solid. The solid was recrystallized from MeCN to give N-{3-[(4-amino-2-ethyl-1H-imidazo[4,5-c]quinolin-1-yl)amino]propyl}acetamide (0.67 g) as yellow crystals. mp 167–169° C.; $^1$H NMR (300 MHz, DMSO-d$_6$) δ 8.42 (d, J=8.1 Hz, 1H), 7.85 (t, J=5.2 Hz, 1H), 7.59 (d, J=8.3 Hz, 1H), 7.44–7.38 (m, 1H), 7.25–7.20 (m, 1H), 6.96 (t, J=5.3 Hz, 1H), 6.51 (s, 2H), 3.19–3.08 (m, 4H), 2.97 (q, J=7.4 Hz, 2H), 1.78 (s, 3H), 1.69 (p, J=7.0 Hz, 2H), 1.38 (t, J=7.5 Hz, 3H); $^{13}$C NMR (125 MHz, DMSO-d$_6$) δ 169.5, 154.9, 152.0, 144.9, 132.1, 126.9, 126.1, 124.2, 121.1, 121.0, 114.9, 49.7, 36.8, 28.0, 23.0, 19.5, 12.4; MS (ESI) m/z 327 (M+H)$^+$; Anal. Calcd for C$_{17}$H$_{22}$N$_6$O: C, 62.56; H, 6.79; N, 25.75; Found: C, 62.40; H, 7.06; N, 25.82.

Example 41

N-{3-[(4-Amino-2-ethyl-6,7,8,9-tetrahydro-1H-imidazo[4,5-c]quinolin-1-yl)amino]propyl}acetamide

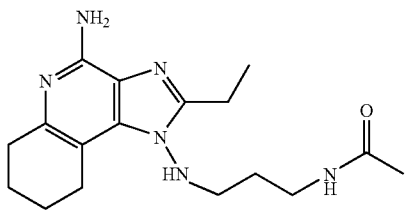

A solution of N-{3-[(4-amino-2-ethyl-1H-imidazo[4,5-c]quinolin-1-yl)amino]propyl}acetamide (0.22 g, 0.67 mmol) in 10 mL of TFA was treated with platinum(IV) oxide (0.15 g, 0.67 mmol). The mixture was placed under an atmosphere of hydrogen (3.8×10$^5$ Pa) and shaken at ambient temperature. After 44 h, the reaction mixture was diluted with 25 mL of 4:1 CHCl$_3$:MeOH and filtered through a pad of CELITE filter agent. The filtrate was concentrated under reduced pressure to yield a clear oil. The oil was suspended in 15 mL of H$_2$O and treated with 50% NaOH solution until the pH of the liquid reached 13. The mixture was extracted with CH$_2$Cl$_2$ (3×15 mL). The combined organic extracts were dried over Na$_2$SO$_4$, filtered and concentrated under reduced pressure to yield a white foam. The foam was purified by chromatography (SiO$_2$, 30% (80:18:2 CHCl$_3$:MeOH:NH$_4$OH) in CHCl$_3$) to yield a clear colorless oil. The oil was crystallized from MeCN to give N-{3-[(4-amino-2-ethyl-6,7,8,9-1H-imidazo[4,5-c]quinolin-1-yl)amino]propyl}acetamide (0.0601 g) as off-white crystals. mp 175–176° C.; $^1$H NMR (500 MHz, DMSO-d$_6$) δ 7.81 (t, J=5.2 Hz, 1H), 6.28 (t, J=5.7 Hz, 1H), 5.60 (s, 2H), 3.12 (q, J=6.8 Hz, 2H), 3.01 (s, 2H), 2.94 (q, J=6.1 Hz, 2H), 2.81 (q, J=7.5 Hz, 2H), 2.65 (t, J=5.8 Hz, 2H), 1.78 (s, 3H), 1.77–1.72 (m, 4H), 1.60 (p, J=7.1 Hz, 2H), 1.29 (t, J=7.5 Hz, 3H); $^{13}$C NMR (125 MHz, DMSO-d$_6$) δ 168.9, 154.1, 148.8, 145.6, 137.0, 122.2, 105.0, 50.7, 36.3, 32.0, 27.5, 22.9, 22.6, 22.5, 22.1, 19.1, 11.8; MS (APCI) m/z 331 (M+H)$^+$; Anal. Calcd for C$_{17}$H$_{26}$N$_6$O: C, 61.79; H, 7.93; N, 25.43; Found: C, 61.80; H, 7.80; N, 25.67.

Example 42

[4-Amino-1-(isopropylamino)-1H-imidazo[4,5-c]quinolin-2-yl]methanol

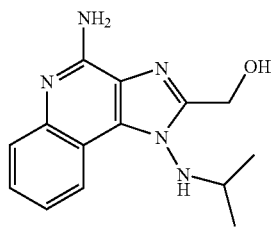

A solution of 2-(ethoxymethyl)-N$^1$-isopropyl-1H-imidazo[4,5-c]quinoline-1,4-diamine (prepared as described in Example 5, 0.502 g, 1.68 mmol) in dichloromethane (15 mL) under a nitrogen atmosphere was cooled in an ice bath. A solution of boron tribromide in dichloromethane (1 M, 4.19 mL, 4.19 mmol) was added dropwise. The mixture was allowed to warm slowly to room temperature, then was stirred for 16 hours. The reaction was quenched with methanol (10 mL) and concentrated under reduced pressure to yield a white solid. The solid was treated with 6 M aqueous hydrochloric acid (20 mL) to form a white suspension that was stirred at 50° C. for 2 hours. The mixture was allowed to cool to room temperature and was adjusted to pH 7 with 50% aqueous sodium hydroxide solution. A white solid was isolated by filtration, washed with water, and dried under vacuum. The crude product was purified by chromatography (silica gel, eluted with 1:1 CHCl$_3$:(80:18:2 CHCl$_3$:MeOH:NH$_4$OH)) then was recrystallized from acetonitrile to afford 0.0577 g of [4-amino-1-(isopropylamino)-1H-imidazo[4,5-c]quinolin-2-yl]methanol as white crystals, mp 228–229° C.;

$^1$H NMR (300 MHz, DMSO-d$_6$) δ 8.61 (dd, J=8.2, 1.2 Hz, 1H), 7.57 (dd, J=8.4, 0.9 Hz, 1H), 7.44–7.38 (m, 1H), 7.25–7.20 (m, 1H), 6.87 (d, J=2.2 Hz, 1H), 6.56 (s, 2H), 5.58 (t, J=5.8 Hz, 1H), 4.77 (d, J=5.7 Hz, 2H), 3.71–3.62 (m, 1H), 1.03 (d, J=6.1 Hz, 6H);

MS (APCI) m/z 272 (M+H)$^+$;

Anal. Calcd for C$_{14}$H$_{17}$N$_5$O: C, 61.98; H, 6.32; N, 25.81; Found: C, 62.17; H, 6.25; N, 25.93.

Example 43

[4-Amino-1-(isopropylamino)-6,7,8,9-tetrahydro-1H-imidazo[4,5-c]quinolin-2-yl]methanol

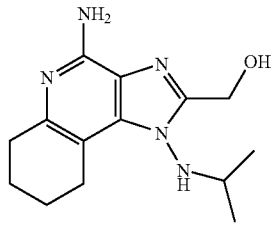

A mixture of [4-amino-1-(isopropylamino)-1H-imidazo[4,5-c]quinolin-2-yl]methanol (0.120 g, 0.442 mmol) and platinum (IV) oxide (0.100 g, 0.422 mmol) in trifloroacetic acid (10 mL) was hydrogenated on a Parr apparatus at 50 psi (3.4×10$^5$ Pa) at room temperature for 18 hours. The mixture was diluted with chloroform (20 mL) and filtered through a pad of CELITE filter agent. The filter agent was rinsed with a 4:1 chloroform/methanol solution. The filtrate was concentrated under reduced pressure to yield an oil that was suspended in water (10 mL) and treated with 10% aqueous sodium hydroxide until pH 7 was reached. A white precipitate was isolated by filtration, rinsed with water, and dried overnight under vacuum to provide [4-amino-1-(isopropylamino)-6,7,8,9-tetrahydro-1H-imidazo[4,5-c]quinolin-2-yl]methanol.

MS (APCI) m/z 276 (M+H)$^+$.

Exemplary Compounds

Certain exemplary compounds, including some of those described above in the Examples, have the following Formula (I-1d) and the following $R_1$, $R_2$, and $R_3$ substituents, wherein each line of the table represents a specific compound.

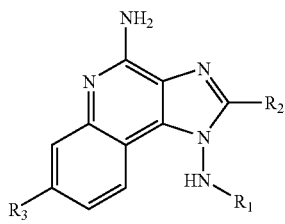

I-1d

| $R_1$ | $R_2$ | $R_3$ |
|---|---|---|
| isopropyl | hydrogen | pyridin-3-yl |
| isopropyl | hydrogen | benzyloxy |
| isopropyl | hydrogen | 2-methanesulfonylaminoethoxy |
| isopropyl | hydrogen | 3-methanesulfonylaminopropoxy |
| isopropyl | hydrogen | 2-(pyridin-3-yl)ethyl |
| isopropyl | hydrogen | 2-(hydroxymethyl)phenyl |
| isopropyl | hydrogen | 5-(hydroxymethyl)pyridin-3-yl |
| isopropyl | methyl | pyridin-3-yl |
| isopropyl | methyl | benzyloxy |
| isopropyl | methyl | 2-methanesulfonylaminoethoxy |
| isopropyl | methyl | 3-methanesulfonylaminopropoxy |
| isopropyl | methyl | 2-(pyridin-3-yl)ethyl |
| isopropyl | methyl | 2-(hydroxymethyl)phenyl |
| isopropyl | methyl | 5-(hydroxymethyl)pyridin-3-yl |
| isopropyl | ethyl | pyridin-3-yl |
| isopropyl | ethyl | benzyloxy |
| isopropyl | ethyl | 2-methanesulfonylaminoethoxy |
| isopropyl | ethyl | 3-methanesulfonylaminopropoxy |
| isopropyl | ethyl | 2-(pyridin-3-yl)ethyl |
| isopropyl | ethyl | 2-(hydroxymethyl)phenyl |
| isopropyl | ethyl | 5-(hydroxymethyl)pyridin-3-yl |
| isopropyl | propyl | pyridin-3-yl |
| isopropyl | propyl | benzyloxy |
| isopropyl | propyl | 2-methanesulfonylaminoethoxy |
| isopropyl | propyl | 3-methanesulfonylaminopropoxy |
| isopropyl | propyl | 2-(pyridin-3-yl)ethyl |
| isopropyl | propyl | 2-(hydroxymethyl)phenyl |
| isopropyl | propyl | 5-(hydroxymethyl)pyridin-3-yl |
| isopropyl | butyl | pyridin-3-yl |
| isopropyl | butyl | benzyloxy |
| isopropyl | butyl | 2-methanesulfonylaminoethoxy |
| isopropyl | butyl | 3-methanesulfonylaminopropoxy |
| isopropyl | butyl | 2-(pyridin-3-yl)ethyl |
| isopropyl | butyl | 2-(hydroxymethyl)phenyl |
| isopropyl | butyl | 5-(hydroxymethyl)pyridin-3-yl |
| isopropyl | methoxymethyl | pyridin-3-yl |
| isopropyl | methoxymethyl | benzyloxy |
| isopropyl | methoxymethyl | 2-methanesulfonylaminoethoxy |
| isopropyl | methoxymethyl | 3-methanesulfonylaminopropoxy |

-continued

I-1d

| $R_1$ | $R_2$ | $R_3$ |
|---|---|---|
| isopropyl | methoxymethyl | 2-(pyridin-3-yl)ethyl |
| isopropyl | methoxymethyl | 2-(hydroxymethyl)phenyl |
| isopropyl | methoxymethyl | 5-(hydroxymethyl)pyridin-3-yl |
| isopropyl | hydroxymethyl | pyridin-3-yl |
| isopropyl | hydroxymethyl | benzyloxy |
| isopropyl | hydroxymethyl | 2-methanesulfonylaminoethoxy |
| isopropyl | hydroxymethyl | 3-methanesulfonylaminopropoxy |
| isopropyl | hydroxymethyl | 2-(pyridin-3-yl)ethyl |
| isopropyl | hydroxymethyl | 2-(hydroxymethyl)phenyl |
| isopropyl | hydroxymethyl | 5-(hydroxymethyl)pyridin-3-yl |
| isopropyl | 2-methoxyethyl | pyridin-3-yl |
| isopropyl | 2-methoxyethyl | benzyloxy |
| isopropyl | 2-methoxyethyl | 2-methanesulfonylaminoethoxy |
| isopropyl | 2-methoxyethyl | 3-methanesulfonylaminopropoxy |
| isopropyl | 2-methoxyethyl | 2-(pyridin-3-yl)ethyl |
| isopropyl | 2-methoxyethyl | 2-(hydroxymethyl)phenyl |
| isopropyl | 2-methoxyethyl | 5-(hydroxymethyl)pyridin-3-yl |
| isopropyl | 2-hydroxyethyl | pyridin-3-yl |
| isopropyl | 2-hydroxyethyl | benzyloxy |
| isopropyl | 2-hydroxyethyl | 2-methanesulfonylaminoethoxy |
| isopropyl | 2-hydroxyethyl | 3-methanesulfonylaminopropoxy |
| isopropyl | 2-hydroxyethyl | 2-(pyridin-3-yl)ethyl |
| isopropyl | 2-hydroxyethyl | 2-(hydroxymethyl)phenyl |
| isopropyl | 2-hydroxyethyl | 5-(hydroxymethyl)pyridin-3-yl |
| isopropyl | ethoxymethyl | pyridin-3-yl |
| isopropyl | ethoxymethyl | benzyloxy |
| isopropyl | ethoxymethyl | 2-methanesulfonylaminoethoxy |
| isopropyl | ethoxymethyl | 3-methanesulfonylaminopropoxy |
| isopropyl | ethoxymethyl | 2-(pyridin-3-yl)ethyl |
| isopropyl | ethoxymethyl | 2-(hydroxymethyl)phenyl |
| isopropyl | ethoxymethyl | 5-(hydroxymethyl)pyridin-3-yl |
| benzyl | hydrogen | pyridin-3-yl |
| benzyl | hydrogen | benzyloxy |
| benzyl | hydrogen | 2-methanesulfonylaminoethoxy |
| benzyl | hydrogen | 3-methanesulfonylaminopropoxy |
| benzyl | hydrogen | 2-(pyridin-3-yl)ethyl |
| benzyl | hydrogen | 2-(hydroxymethyl)phenyl |
| benzyl | hydrogen | 5-(hydroxymethyl)pyridin-3-yl |
| benzyl | methyl | pyridin-3-yl |
| benzyl | methyl | benzyloxy |
| benzyl | methyl | 2-methanesulfonylaminoethoxy |
| benzyl | methyl | 3-methanesulfonylaminopropoxy |
| benzyl | methyl | 2-(pyridin-3-yl)ethyl |
| benzyl | methyl | 2-(hydroxymethyl)phenyl |
| benzyl | methyl | 5-(hydroxymethyl)pyridin-3-yl |
| benzyl | ethyl | pyridin-3-yl |
| benzyl | ethyl | benzyloxy |
| benzyl | ethyl | 2-methanesulfonylaminoethoxy |
| benzyl | ethyl | 3-methanesulfonylaminopropoxy |
| benzyl | ethyl | 2-(pyridin-3-yl)ethyl |
| benzyl | ethyl | 2-(hydroxymethyl)phenyl |
| benzyl | ethyl | 5-(hydroxymethyl)pyridin-3-yl |
| benzyl | propyl | pyridin-3-yl |
| benzyl | propyl | benzyloxy |
| benzyl | propyl | 2-methanesulfonylaminoethoxy |
| benzyl | propyl | 3-methanesulfonylaminopropoxy |
| benzyl | propyl | 2-(pyridin-3-yl)ethyl |
| benzyl | propyl | 2-(hydroxymethyl)phenyl |
| benzyl | propyl | 5-(hydroxymethyl)pyridin-3-yl |
| benzyl | butyl | pyridin-3-yl |
| benzyl | butyl | benzyloxy |
| benzyl | butyl | 2-methanesulfonylaminoethoxy |
| benzyl | butyl | 3-methanesulfonylaminopropoxy |
| benzyl | butyl | 2-(pyridin-3-yl)ethyl |

-continued

I-1d

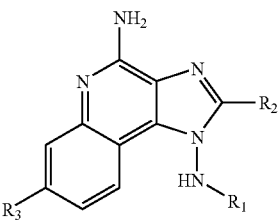

| R₁ | R₂ | R₃ |
|---|---|---|
| benzyl | butyl | 2-(hydroxymethyl)phenyl |
| benzyl | butyl | 5-(hydroxymethyl)pyridin-3-yl |
| benzyl | methoxymethyl | pyridin-3-yl |
| benzyl | methoxymethyl | benzyloxy |
| benzyl | methoxymethyl | 2-methanesulfonylaminoethoxy |
| benzyl | methoxymethyl | 3-methanesulfonylaminopropoxy |
| benzyl | methoxymethyl | 2-(pyridin-3-yl)ethyl |
| benzyl | methoxymethyl | 2-(hydroxymethyl)phenyl |
| benzyl | methoxymethyl | 5-(hydroxymethyl)pyridin-3-yl |
| benzyl | hydroxymethyl | pyridin-3-yl |
| benzyl | hydroxymethyl | benzyloxy |
| benzyl | hydroxymethyl | 2-methanesulfonylaminoethoxy |
| benzyl | hydroxymethyl | 3-methanesulfonylaminopropoxy |
| benzyl | hydroxymethyl | 2-(pyridin-3-yl)ethyl |
| benzyl | hydroxymethyl | 2-(hydroxymethyl)phenyl |
| benzyl | hydroxymethyl | 5-(hydroxymethyl)pyridin-3-yl |
| benzyl | 2-methoxyethyl | pyridin-3-yl |
| benzyl | 2-methoxyethyl | benzyloxy |
| benzyl | 2-methoxyethyl | 2-methanesulfonylaminoethoxy |
| benzyl | 2-methoxyethyl | 3-methanesulfonylaminopropoxy |
| benzyl | 2-methoxyethyl | 2-(pyridin-3-yl)ethyl |
| benzyl | 2-methoxyethyl | 2-(hydroxymethyl)phenyl |
| benzyl | 2-methoxyethyl | 5-(hydroxymethyl)pyridin-3-yl |
| benzyl | 2-hydroxyethyl | pyridin-3-yl |
| benzyl | 2-hydroxyethyl | benzyloxy |
| benzyl | 2-hydroxyethyl | 2-methanesulfonylaminoethoxy |
| benzyl | 2-hydroxyethyl | 3-methanesulfonylaminopropoxy |
| benzyl | 2-hydroxyethyl | 2-(pyridin-3-yl)ethyl |
| benzyl | 2-hydroxyethyl | 2-(hydroxymethyl)phenyl |
| benzyl | 2-hydroxyethyl | 5-(hydroxymethyl)pyridin-3-yl |
| benzyl | ethoxymethyl | pyridin-3-yl |
| benzyl | ethoxymethyl | benzyloxy |
| benzyl | ethoxymethyl | 2-methanesulfonylaminoethoxy |
| benzyl | ethoxymethyl | 3-methanesulfonylaminopropoxy |
| benzyl | ethoxymethyl | 2-(pyridin-3-yl)ethyl |
| benzyl | ethoxymethyl | 2-(hydroxymethyl)phenyl |
| benzyl | ethoxymethyl | 5-(hydroxymethyl)pyridin-3-yl |
| 3-phenylpropyl | hydrogen | pyridin-3-yl |
| 3-phenylpropyl | hydrogen | benzyloxy |
| 3-phenylpropyl | hydrogen | 2-methanesulfonylaminoethoxy |
| 3-phenylpropyl | hydrogen | 3-methanesulfonylaminopropoxy |
| 3-phenylpropyl | hydrogen | 2-(pyridin-3-yl)ethyl |
| 3-phenylpropyl | hydrogen | 2-(hydroxymethyl)phenyl |
| 3-phenylpropyl | hydrogen | 5-(hydroxymethyl)pyridin-3-yl |
| 3-phenylpropyl | methyl | pyridin-3-yl |
| 3-phenylpropyl | methyl | benzyloxy |
| 3-phenylpropyl | methyl | 2-methanesulfonylaminoethoxy |
| 3-phenylpropyl | methyl | 3-methanesulfonylaminopropoxy |
| 3-phenylpropyl | methyl | 2-(pyridin-3-yl)ethyl |
| 3-phenylpropyl | methyl | 2-(hydroxyethyl)phenyl |
| 3-phenylpropyl | methyl | 5-(hydroxymethyl)pyridin-3-yl |
| 3-phenylpropyl | ethyl | pyridin-3-yl |
| 3-phenylpropyl | ethyl | benzyloxy |
| 3-phenylpropyl | ethyl | 2-methanesulfonylaminoethoxy |
| 3-phenylpropyl | ethyl | 3-methanesulfonylaminopropoxy |
| 3-phenylpropyl | ethyl | 2-(pyridin-3-yl)ethyl |
| 3-phenylpropyl | ethyl | 2-(hydroxymethyl)phenyl |
| 3-phenylpropyl | ethyl | 5-(hydroxymethyl)pyridin-3-yl |
| 3-phenylpropyl | propyl | pyridin-3-yl |
| 3-phenylpropyl | propyl | benzyloxy |
| 3-phenylpropyl | propyl | 2-methanesulfonylaminoethoxy |
| 3-phenylpropyl | propyl | 3-methanesulfonylaminopropoxy |
| 3-phenylpropyl | propyl | 2-(pyridin-3-yl)ethyl |
| 3-phenylpropyl | propyl | 2-(hydroxymethyl)phenyl |

-continued

I-1d

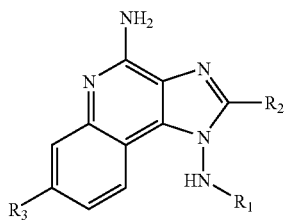

| R₁ | R₂ | R₃ |
|---|---|---|
| 3-phenylpropyl | propyl | 5-(hydroxymethyl)pyridin-3-yl |
| 3-phenylpropyl | butyl | pyridin-3-yl |
| 3-phenylpropyl | butyl | benzyloxy |
| 3-phenylpropyl | butyl | 2-methanesulfonylaminoethoxy |
| 3-phenylpropyl | butyl | 3-methanesulfonylaminopropoxy |
| 3-phenylpropyl | butyl | 2-(pyridin-3-yl)ethyl |
| 3-phenylpropyl | butyl | 2-(hydroxymethyl)phenyl |
| 3-phenylpropyl | butyl | 5-(hydroxymethyl)pyridin-3-yl |
| 3-phenylpropyl | methoxymethyl | pyridin-3-yl |
| 3-phenylpropyl | methoxymethyl | benzyloxy |
| 3-phenylpropyl | methoxymethyl | 2-methanesulfonylaminoethoxy |
| 3-phenylpropyl | methoxymethyl | 3-methanesulfonylaminopropoxy |
| 3-phenylpropyl | methoxymethyl | 2-(pyridin-3-yl)ethyl |
| 3-phenylpropyl | methoxymethyl | 2-(hydroxymethyl)phenyl |
| 3-phenylpropyl | methoxymethyl | 5-(hydroxymethyl)pyridin-3-yl |
| 3-phenylpropyl | hydroxymethyl | pyridin-3-yl |
| 3-phenylpropyl | hydroxymethyl | benzyloxy |
| 3-phenylpropyl | hydroxymethyl | 2-methanesulfonylaminoethoxy |
| 3-phenylpropyl | hydroxymethyl | 3-methanesulfonylaminopropoxy |
| 3-phenylpropyl | hydroxymethyl | 2-(pyridin-3-yl)ethyl |
| 3-phenylpropyl | hydroxymethyl | 2-(hydroxymethyl)phenyl |
| 3-phenylpropyl | hydroxymethyl | 5-(hydroxymethyl)pyridin-3-yl |
| 3-phenylpropyl | 2-methoxyethyl | pyridin-3-yl |
| 3-phenylpropyl | 2-methoxyethyl | benzyloxy |
| 3-phenylpropyl | 2-methoxyethyl | 2-methanesulfonylaminoethoxy |
| 3-phenylpropyl | 2-methoxyethyl | 3-methanesulfonylaminopropoxy |
| 3-phenylpropyl | 2-methoxyethyl | 2-(pyridin-3-yl)ethyl |
| 3-phenylpropyl | 2-methoxyethyl | 2-droxyethyl)phenyl |
| 3-phenylpropyl | 2-methoxyethyl | 5-(hydroxymethyl)pyridin-3-yl |
| 3-phenylpropyl | 2-hydroxyethyl | pyridin-3-yl |
| 3-phenylpropyl | 2-hydroxyethyl | benzyloxy |
| 3-phenylpropyl | 2-hydroxyethyl | 2-methanesulfonylaminoethoxy |
| 3-phenylpropyl | 2-hydroxyethyl | 3-methanesulfonylaminopropoxy |
| 3-phenylpropyl | 2-hydroxyethyl | 2-(pyridin-3-yl)ethyl |
| 3-phenylpropyl | 2-hydroxyethyl | 2-(hydroxyethyl)phenyl |
| 3-phenylpropyl | 2-hydroxyethyl | 5-(hydroxymethyl)pyridin-3-yl |
| 3-phenylpropyl | ethoxymethyl | pyridin-3-yl |
| 3-phenylpropyl | ethoxymethyl | benzyloxy |
| 3-phenylpropyl | ethoxymethyl | 2-methanesulfonylaminoethoxy |
| 3-phenylpropyl | ethoxymethyl | 3-methanesulfonylaminopropoxy |
| 3-phenylpropyl | ethoxymethyl | 2-(pyridin-3-yl)ethyl |
| 3-phenylpropyl | ethoxymethyl | 2-(hydroxymethyl)phenyl |
| 3-phenylpropyl | ethoxymethyl | 5-(hydroxymethyl)pyridin-3-yl |
| 3-[3-(isopropyl)-ureido]propyl | hydrogen | pyridin-3-yl |
| 3-[3-(isopropyl)-ureido]propyl | hydrogen | benzyloxy |
| 3-[3-(isopropyl)-ureido]propyl | hydrogen | 2-methanesulfonylaminoethoxy |
| 3-[3-(isopropyl)-ureido]propyl | hydrogen | 3-methanesulfonylaminopropoxy |
| 3-[3-(isopropyl)-ureido]propyl | hydrogen | 2-(pyridin-3-yl)ethyl |
| 3-[3-(isopropyl)-ureido]propyl | hydrogen | 2-(hydroxymethyl)phenyl |
| 3-[3-(isopropyl)-ureido]propyl | hydrogen | 5-(hydroxymethyl)pyridin-3-yl |
| 3-[3-(isopropyl)-ureido]propyl | methyl | pyridin-3-yl |
| 3-[3-(isopropyl)-ureido]propyl | methyl | benzyloxy |
| 3-[3-(isopropyl)-ureido]propyl | methyl | 2-methanesulfonylaminoethoxy |

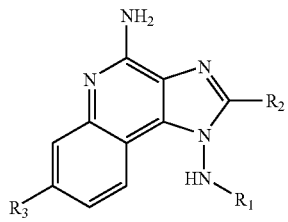

I-1d

| R₁ | R₂ | R₃ |
|---|---|---|
| 3-[3-(isopropyl)ureido]propyl | methyl | 3-methanesulfonylaminopropoxy |
| 3-[3-(isopropyl)ureido]propyl | methyl | 2-(pyridin-3-yl)ethyl |
| 3-[3-(isopropyl)ureido]propyl | methyl | 2-(hydroxymethyl)phenyl |
| 3-[3-(isopropyl)ureido]propyl | methyl | 5-(hydroxymethyl)pyridin-3-yl |
| 3-[3-(isopropyl)ureido]propyl | ethyl | pyridin-3-yl |
| 3-[3-(isopropyl)ureido]propyl | ethyl | benzyloxy |
| 3-[3-(isopropyl)ureido]propyl | ethyl | 2-methanesulfonylaminoethoxy |
| 3-[3-(isopropyl)ureido]propyl | ethyl | 3-methanesulfonylaminopropoxy |
| 3-[3-(isopropyl)ureido]propyl | ethyl | 2-(pyridin-3-yl)ethyl |
| 3-[3-(isopropyl)ureido]propyl | ethyl | 2-(hydroxymethyl)phenyl |
| 3-[3-(isopropyl)ureido]propyl | ethyl | 5-(hydroxymethyl)pyridin-3-yl |
| 3-[3-(isopropyl)ureido]propyl | propyl | pyridin-3-yl |
| 3-[3-(isopropyl)ureido]propyl | propyl | benzyloxy |
| 3-[3-(isopropyl)ureido]propyl | propyl | 2-methanesulfonylaminoethoxy |
| 3-[3-(isopropyl)ureido]propyl | propyl | 3-methanesulfonylaminopropoxy |
| 3-[3-(isopropyl)ureido]propyl | propyl | 2-(pyridin-3-yl)ethyl |
| 3-[3-(isopropyl)ureido]propyl | propyl | 2-(hydroxymethyl)phenyl |
| 3-[3-(isopropyl)ureido]propyl | propyl | 5-(hydroxymethyl)pyridin-3-yl |
| 3-[3-(isopropyl)ureido]propyl | butyl | pyridin-3-yl |
| 3-[3-(isopropyl)ureido]propyl | butyl | benzyloxy |
| 3-[3-(isopropyl)ureido]propyl | butyl | 2-methanesulfonylaminoethoxy |
| 3-[3-(isopropyl)ureido]propyl | butyl | 3-methanesulfonylaminopropoxy |
| 3-[3-(isopropyl)ureido]propyl | butyl | 2-(pyridin-3-yl)ethyl |
| 3-[3-(isopropyl)ureido]propyl | butyl | 2-(hydroxymethyl)phenyl |
| 3-[3-(isopropyl)ureido]propyl | butyl | 5-(hydroxymethyl)pyridin-3-yl |
| 3-[3-(isopropyl)ureido]propyl | methoxymethyl | pyridin-3-yl |
| 3-[3-(isopropyl)ureido]propyl | methoxymethyl | benzyloxy |
| 3-[3-(isopropyl)ureido]propyl | methoxymethyl | 2-methanesulfonylaminoethoxy |
| 3-[3-(isopropyl)ureido]propyl | methoxymethyl | 3-methanesulfonylaminopropoxy |
| 3-[3-(isopropyl)ureido]propyl | methoxymethyl | 2-(pyridin-3-yl)ethyl |
| 3-[3-(isopropyl)ureido]propyl | methoxymethyl | 2-(hydroxyethyl)phenyl |
| 3-[3-(isopropyl)ureido]propyl | methoxymethyl | 5-(hydroxymethyl)pyridin-3-yl |

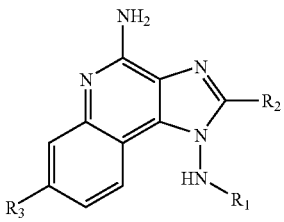

I-1d

| R₁ | R₂ | R₃ |
|---|---|---|
| 3-[3-(isopropyl)ureido]propyl | hydroxymethyl | pyridin-3-yl |
| 3-[3-(isopropyl)ureido]propyl | hydroxymethyl | benzyloxy |
| 3-[3-(isopropyl)ureido]propyl | hydroxymethyl | 2-methanesulfonylaminoethoxy |
| 3-[3-(isopropyl)ureido]propyl | hydroxymethyl | 3-methanesulfonylaminopropoxy |
| 3-[3-(isopropyl)ureido]propyl | hydroxymethyl | 2-(pyridin-3-yl)ethyl |
| 3-[3-(isopropyl)ureido]propyl | hydroxymethyl | 2-(hydroxymethyl)phenyl |
| 3-[3-(isopropyl)ureido]propyl | hydroxymethyl | 5-(hydroxymethyl)pyridin-3-yl |
| 3-[3-(isopropyl)ureido]propyl | 2-methoxyethyl | pyridin-3-yl |
| 3-[3-(isopropyl)ureido]propyl | 2-methoxyethyl | benzyloxy |
| 3-[3-(isopropyl)ureido]propyl | 2-methoxyethyl | 2-methanesulfonylaminoethoxy |
| 3-[3-(isopropyl)ureido]propyl | 2-methoxyethyl | 3-methanesulfonylaminopropoxy |
| 3-[3-(isopropyl)ureido]propyl | 2-methoxyethyl | 2-(pyridin-3-yl)ethyl |
| 3-[3-(isopropyl)ureido]propyl | 2-methoxyethyl | 2-(hydroxymethyl)phenyl |
| 3-[3-(isopropyl)ureido]propyl | 2-methoxyethyl | 5-(hydroxymethyl)pyridin-3-yl |
| 3-[3-(isopropyl)ureido]propyl | 2-hydroxyethyl | pyridin-3-yl |
| 3-[3-(isopropyl)ureido]propyl | 2-hydroxyethyl | benzyloxy |
| 3-[3-(isopropyl)ureido]propyl | 2-hydroxyethyl | 2-methanesulfonylaminoethoxy |
| 3-[3-(isopropyl)ureido]propyl | 2-hydroxyethyl | 3-methanesulfonylaminopropoxy |
| 3-[3-(isopropyl)ureido]propyl | 2-hydroxyethyl | 2-(pyridin-3-yl)ethyl |
| 3-[3-(isopropyl)ureido]propyl | 2-hydroxyethyl | 2-(hydroxymethyl)phenyl |
| 3-[3-(isopropyl)ureido]propyl | 2-hydroxyethyl | 5-(hydroxymethyl)pyridin-3-yl |
| 3-[3-(isopropyl)ureido]propyl | ethoxymethyl | pyridin-3-yl |
| 3-[3-(isopropyl)ureido]propyl | ethoxymethyl | benzyloxy |
| 3-[3-(isopropyl)ureido]propyl | ethoxymethyl | 2-methanesulfonylaminoethoxy |
| 3-[3-(isopropyl)ureido]propyl | ethoxymethyl | 3-methanesulfonylaminopropoxy |
| 3-[3-(isopropyl)ureido]propyl | ethoxymethyl | 2-(pyridin-3-yl)ethyl |
| 3-[3-(isopropyl)ureido]propyl | ethoxymethyl | 2-(hydroxymethyl)phenyl |
| 3-[3-(isopropyl)ureido]propyl | ethoxymethyl | 5-(hydroxymethyl)pyridin-3-yl |
| 3-methanesulfonylaminopropyl | hydrogen | pyridin-3-yl |
| 3-methanesulfonylaminopropyl | hydrogen | benzyloxy |
| 3-methanesulfonylaminopropyl | hydrogen | 2-methanesulfonylaminoethoxy |
| 3-methanesulfonylaminopropyl | hydrogen | 3-methanesulfonylaminopropoxy |

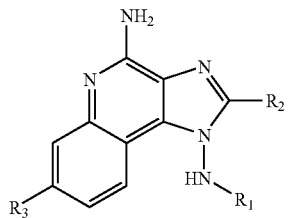

I-1d

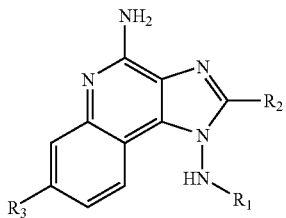

I-1d

| R₁ | R₂ | R₃ |
|---|---|---|
| 3-methanesulfonylaminopropyl | hydrogen | 2-(pyridin-3-yl)ethyl |
| 3-methanesulfonylaminopropyl | hydrogen | 2-(hydroxymethyl)phenyl |
| 3-methanesulfonylaminopropyl | hydrogen | 5-(hydroxymethyl)pyridin-3-yl |
| 3-methanesulfonylaminopropyl | methyl | pyridin-3-yl |
| 3-methanesulfonylaminopropyl | methyl | benzyloxy |
| 3-methanesulfonylaminopropyl | methyl | 2-methanesulfonylaminoethoxy |
| 3-methanesulfonylaminopropyl | methyl | 3-methanesulfonylaminopropoxy |
| 3-methanesulfonylaminopropyl | methyl | 2-(pyridin-3-yl)ethyl |
| 3-methanesulfonylaminopropyl | methyl | 2-(hydroxymethyl)phenyl |
| 3-methanesulfonylaminopropyl | methyl | 5-(hydroxymethyl)pyridin-3-yl |
| 3-methanesulfonylaminopropyl | ethyl | pyridin-3-yl |
| 3-methanesulfonylaminopropyl | ethyl | benzyloxy |
| 3-methanesulfonylaminopropyl | ethyl | 2-methanesulfonylaminoethoxy |
| 3-methanesulfonylaminopropyl | ethyl | 3-methanesulfonylaminopropoxy |
| 3-methanesulfonylaminopropyl | ethyl | 2-(pyridin-3-yl)ethyl |
| 3-methanesulfonylaminopropyl | ethyl | 2-(hydroxymethyl)phenyl |
| 3-methanesulfonylaminopropyl | ethyl | 5-(hydroxymethyl)pyridin-3-yl |
| 3-methanesulfonylaminopropyl | propyl | pyridin-3-yl |
| 3-methanesulfonylaminopropyl | propyl | benzyloxy |
| 3-methanesulfonylaminopropyl | propyl | 2-methanesulfonylaminoethoxy |
| 3-methanesulfonylaminopropyl | propyl | 3-methanesulfonylaminopropoxy |
| 3-methanesulfonylaminopropyl | propyl | 2-(pyridin-3-yl)ethyl |
| 3-methanesulfonylaminopropyl | propyl | 2-(hydroxymethyl)phenyl |
| 3-methanesulfonylaminopropyl | propyl | 5-(hydroxymethyl)pyridin-3-yl |
| 3-methanesulfonylaminopropyl | butyl | pyridin-3-yl |
| 3-methanesulfonylaminopropyl | butyl | benzyloxy |
| 3-methanesulfonylaminopropyl | butyl | 2-methanesulfonylaminoethoxy |
| 3-methanesulfonylaminopropyl | butyl | 3-methanesulfonylaminopropoxy |
| 3-methanesulfonylaminopropyl | butyl | 2-(pyridin-3-yl)ethyl |
| 3-methanesulfonylaminopropyl | butyl | 2-(hydroxymethyl)phenyl |
| 3-methanesulfonylaminopropyl | butyl | 5-(hydroxymethyl)pyridin-3-yl |
| 3-methanesulfonylaminopropyl | methoxymethyl | pyridin-3-yl |
| 3-methanesulfonylaminopropyl | methoxymethyl | benzyloxy |
| 3-methanesulfonylaminopropyl | methoxymethyl | 2-methanesulfonylaminoethoxy |
| 3-methanesulfonylaminopropyl | methoxymethyl | 3-methanesulfonylaminopropoxy |
| 3-methanesulfonylaminopropyl | methoxymethyl | 2-(pyridin-3-yl)ethyl |
| 3-methanesulfonylaminopropyl | methoxymethyl | 2-(hydroxymethyl)phenyl |
| 3-methanesulfonylaminopropyl | methoxymethyl | 5-(hydroxymethyl)pyridin-3-yl |
| 3-methanesulfonylaminopropyl | hydroxymethyl | pyridin-3-yl |
| 3-methanesulfonylaminopropyl | hydroxymethyl | benzyloxy |
| 3-methanesulfonylaminopropyl | hydroxymethyl | 2-methanesulfonylaminoethoxy |
| 3-methanesulfonylaminopropyl | hydroxymethyl | 3-methanesulfonylaminopropoxy |
| 3-methanesulfonylaminopropyl | hydroxymethyl | 2-(pyridin-3-yl)ethyl |
| 3-methanesulfonylaminopropyl | hydroxymethyl | 2-(hydroxymethyl)phenyl |
| 3-methanesulfonylaminopropyl | hydroxymethyl | 5-(hydroxymethyl)pyridin-3-yl |
| 3-methanesulfonylaminopropyl | 2-methoxyethyl | pyridin-3-yl |
| 3-methanesulfonylaminopropyl | 2-methoxyethyl | benzyloxy |
| 3-methanesulfonylaminopropyl | 2-methoxyethyl | 2-methanesulfonylaminoethoxy |
| 3-methanesulfonylaminopropyl | 2-methoxyethyl | 3-methanesulfonylaminopropoxy |
| 3-methanesulfonylaminopropyl | 2-methoxyethyl | 2-(pyridin-3-yl)ethyl |
| 3-methanesulfonylaminopropyl | 2-methoxyethyl | 2-(hydroxymethyl)phenyl |
| 3-methanesulfonylaminopropyl | 2-methoxyethyl | 5-(hydroxymethyl)pyridin-3-yl |
| 3-methanesulfonylaminopropyl | 2-hydroxyethyl | pyridin-3-yl |
| 3-methanesulfonylaminopropyl | 2-hydroxyethyl | benzyloxy |
| 3-methanesulfonylaminopropyl | 2-hydroxyethyl | 2-methanesulfonylaminoethoxy |
| 3-methanesulfonylaminopropyl | 2-hydroxyethyl | 3-methanesulfonylaminopropoxy |
| 3-methanesulfonylaminopropyl | 2-hydroxyethyl | 2-(pyridin-3-yl)ethyl |
| 3-methanesulfonylaminopropyl | 2-hydroxyethyl | 2-(hydroxymethyl)phenyl |
| 3-methanesulfonylaminopropyl | 2-hydroxyethyl | 5-(hydroxymethyl)pyridin-3-yl |
| 3-methanesulfonylaminopropyl | ethoxymethyl | pyridin-3-yl |
| 3-methanesulfonylaminopropyl | ethoxymethyl | benzyloxy |
| 3-methanesulfonylaminopropyl | ethoxymethyl | 2-methanesulfonylaminoethoxy |
| 3-methanesulfonylaminopropyl | ethoxymethyl | 3-methanesulfonylaminopropoxy |
| 3-methanesulfonylaminopropyl | ethoxymethyl | 2-(pyridin-3-yl)ethyl |

-continued

I-1d

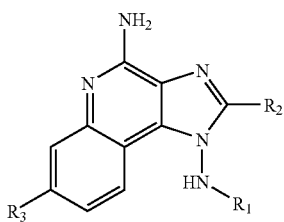

| R₁ | R₂ | R₃ |
|---|---|---|
| 3-methanesulfonyl-aminopropyl | ethoxymethyl | 2-(hydroxymethyl)phenyl |
| 3-methanesulfonyl-aminopropyl | ethoxymethyl | 5-(hydroxymethyl)pyridin-3-yl |
| 3-(morpholine-4-carbonylamino)propyl | hydrogen | pyridin-3-yl |
| 3-(morpholine-4-carbonylamino)propyl | hydrogen | benzyloxy |
| 3-(morpholine-4-carbonylamino)propyl | hydrogen | 2-methanesulfonylaminoethoxy |
| 3-(morpholine-4-carbonylamino)propyl | hydrogen | 3-methanesulfonylaminopropoxy |
| 3-(morpholine-4-carbonylamino)propyl | hydrogen | 2-(pyridin-3-yl)ethyl |
| 3-(morpholine-4-carbonylamino)propyl | hydrogen | 2-(hydroxymethyl)phenyl |
| 3-(morpholine-4-carbonylamino)propyl | hydrogen | 5-(hydroxymethyl)pyridin-3-yl |
| 3-(morpholine-4-carbonylamino)propyl | methyl | pyridin-3-yl |
| 3-(morpholine-4-carbonylamino)propyl | methyl | benzyloxy |
| 3-(morpholine-4-carbonylamino)propyl | methyl | 2-methanesulfonylaminoethoxy |
| 3-(morpholine-4-carbonylamino)propyl | methyl | 3-methanesulfonylaminopropoxy |
| 3-(morpholine-4-carbonylamino)propyl | methyl | 2-(pyridin-3-yl)ethyl |
| 3-(morpholine-4-carbonylamino)propyl | methyl | 2-(hydroxymethyl)phenyl |
| 3-(morpholine-4-carbonylamino)propyl | methyl | 5-(hydroxymethyl)pyridin-3-yl |
| 3-(morpholine-4-carbonylamino)propyl | ethyl | pyridin-3-yl |
| 3-(morpholine-4-carbonylamino)propyl | ethyl | benzyloxy |
| 3-(morpholine-4-carbonylamino)propyl | ethyl | 2-methanesulfonylaminoethoxy |
| 3-(morpholine-4-carbonylamino)propyl | ethyl | 3-methanesulfonylaminopropoxy |
| 3-(morpholine-4-carbonylamino)propyl | ethyl | 2-(pyridin-3-yl)ethyl |
| 3-(morpholine-4-carbonylamino)propyl | ethyl | 2-(hydroxymethyl)phenyl |
| 3-(morpholine-4-carbonylamino)propyl | ethyl | 5-(hydroxymethyl)pyridin-3-yl |
| 3-(morpholine-4-carbonylamino)propyl | propyl | pyridin-3-yl |
| 3-(morpholine-4-carbonylamino)propyl | propyl | benzyloxy |
| 3-(morpholine-4-carbonylamino)propyl | propyl | 2-methanesulfonylaminoethoxy |
| 3-(morpholine-4-carbonylamino)propyl | propyl | 3-methanesulfonylaminopropoxy |
| 3-(morpholine-4-carbonylamino)propyl | propyl | 2-(pyridin-3-yl)ethyl |
| 3-(morpholine-4-carbonylamino)propyl | propyl | 2-(hydroxymethyl)phenyl |
| 3-(morpholine-4-carbonylamino)propyl | propyl | 5-(hydroxymethyl)pyridin-3-yl |

-continued

I-1d

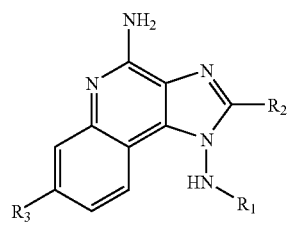

| R₁ | R₂ | R₃ |
|---|---|---|
| 3-(morpholine-4-carbonylamino)propyl | butyl | pyridin-3-yl |
| 3-(morpholine-4-carbonylamino)propyl | butyl | benzyloxy |
| 3-(morpholine-4-carbonylamino)propyl | butyl | 2-methanesulfonylaminoethoxy |
| 3-(morpholine-4-carbonylamino)propyl | butyl | 3-methanesulfonylaminopropoxy |
| 3-(morpholine-4-carbonylamino)propyl | butyl | 2-(pyridin-3-yl)ethyl |
| 3-(morpholine-4-carbonylamino)propyl | butyl | 2-(hydroxymethyl)phenyl |
| 3-(morpholine-4-carbonylamino)propyl | butyl | 5-(hydroxymethyl)pyridin-3-yl |
| 3-(morpholine-4-carbonylamino)propyl | methoxymethyl | pyridin-3-yl |
| 3-(morpholine-4-carbonylamino)propyl | methoxymethyl | benzyloxy |
| 3-(morpholine-4-carbonylamino)propyl | methoxymethyl | 2-methanesulfonylaminoethoxy |
| 3-(morpholine-4-carbonylamino)propyl | methoxymethyl | 3-methanesulfonylaminopropoxy |
| 3-(morpholine-4-carbonylamino)propyl | methoxymethyl | 2-(pyridin-3-yl)ethyl |
| 3-(morpholine-4-carbonylamino)propyl | methoxymethyl | 2-(hydroxymethyl)phenyl |
| 3-(morpholine-4-carbonylamino)propyl | methoxymethyl | 5-(hydroxymethyl)pyridin-3-yl |
| 3-(morpholine-4-carbonylamino)propyl | hydroxymethyl | pyridin-3-yl |
| 3-(morpholine-4-carbonylamino)propyl | hydroxymethyl | benzyloxy |
| 3-(morpholine-4-carbonylamino)propyl | hydroxymethyl | 2-methanesulfonylaminoethoxy |
| 3-(morpholine-4-carbonylamino)propyl | hydroxymethyl | 3-methanesulfonylaminopropoxy |
| 3-(morpholine-4-carbonylamino)propyl | hydroxymethyl | 2-(pyridin-3-yl)ethyl |
| 3-(morpholine-4-carbonylamino)propyl | hydroxymethyl | 2-(hydroxymethyl)phenyl |
| 3-(morpholine-4-carbonylamino)propyl | hydroxymethyl | 5-(hydroxymethyl)pyridin-3-yl |
| 3-(morpholine-4-carbonylamino)propyl | 2-methoxyethyl | pyridin-3-yl |
| 3-(morpholine-4-carbonylamino)propyl | 2-methoxyethyl | benzyloxy |
| 3-(morpholine-4-carbonylamino)propyl | 2-methoxyethyl | 2-methanesulfonylaminoethoxy |
| 3-(morpholine-4-carbonylamino)propyl | 2-methoxyethyl | 3-methanesulfonylaminopropoxy |
| 3-(morpholine-4-carbonylamino)propyl | 2-methoxyethyl | 2-(pyridin-3-yl)ethyl |
| 3-(morpholine-4-carbonylamino)propyl | 2-methoxyethyl | 2-(hydroxymethyl)phenyl |
| 3-(morpholine-4-carbonylamino)propyl | 2-methoxyethyl | 5-(hydroxymethyl)pyridin-3-yl |
| 3-(morpholine-4-carbonylamino)propyl | 2-hydroxyethyl | pyridin-3-yl |
| 3-(morpholine-4-carbonylamino)propyl | 2-hydroxyethyl | benzyloxy |

-continued

I-1d

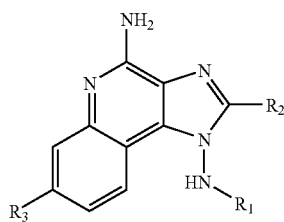

| R₁ | R₂ | R₃ |
|---|---|---|
| 3-(morpholine-4-carbonylamino)propyl | 2-hydroxyethyl | 2-methanesulfonylaminoethoxy |
| 3-(morpholine-4-carbonylamino)propyl | 2-hydroxyethyl | 3-methanesulfonylaminopropoxy |
| 3-(morpholine-4-carbonylamino)propyl | 2-hydroxyethyl | 2-(pyridin-3-yl)ethyl |
| 3-(morpholine-4-carbonylamino)propyl | 2-hydroxyethyl | 2-(hydroxymethyl)phenyl |
| 3-(morpholine-4-carbonylamino)propyl | 2-hydroxyethyl | 5-(hydroxymethyl)pyridin-3-yl |
| 3-(morpholine-4-carbonylamino)propyl | ethoxymethyl | pyridin-3-yl |
| 3-(morpholine-4-carbonylamino)propyl | ethoxymethyl | benzyloxy |
| 3-(morpholine-4-carbonylamino)propyl | ethoxymethyl | 2-methanesulfonylaminoethoxy |
| 3-(morpholine-4-carbonylamino)propyl | ethoxymethyl | 3-methanesulfonylaminopropoxy |
| 3-(morpholine-4-carbonylamino)propyl | ethoxymethyl | 2-(pyridin-3-yl)ethyl |
| 3-(morpholine-4-carbonylamino)propyl | ethoxymethyl | 2-(hydroxymethyl)phenyl |
| 3-(morpholine-4-carbonylamino)propyl | ethoxymethyl | 5-(hydroxymethyl)pyridin-3-yl |
| 3-(isopropyl-carbonylamino)propyl | hydrogen | pyridin-3-yl |
| 3-(isopropylcarbonyl-amino)propyl | hydrogen | benzyloxy |
| 3-(isopropylcarbonyl-amino)propyl | hydrogen | 2-methanesulfonylaminoethoxy |
| 3-(isopropylcarbonyl-amino)propyl | hydrogen | 3-methanesulfonylaminopropoxy |
| 3-(isopropylcarbonyl-amino)propyl | hydrogen | 2-(pyridin-3-yl)ethyl |
| 3-(isopropylcarbonyl-amino)propyl | hydrogen | 2-(hydroxymethyl)phenyl |
| 3-(isopropylcarbonyl-amino)propyl | hydrogen | 5-(hydroxymethyl)pyridin-3-yl |
| 3-(isopropylcarbonyl-amino)propyl | methyl | pyridin-3-yl |
| 3-(isopropylcarbonyl-amino)propyl | methyl | benzyloxy |
| 3-(isopropylcarbonyl-amino)propyl | methyl | 2-methanesulfonylaminoethoxy |
| 3-(isopropylcarbonyl-amino)propyl | methyl | 3-methanesulfonylaminopropoxy |
| 3-(isopropylcarbonyl-amino)propyl | methyl | 2-(pyridin-3-yl)ethyl |
| 3-(isopropylcarbonyl-amino)propyl | methyl | 2-(hydroxymethyl)phenyl |
| 3-(isopropylcarbonyl-amino)propyl | methyl | 5-(hydroxymethyl)pyridin-3-yl |
| 3-(isopropylcarbonyl-amino)propyl | ethyl | pyridin-3-yl |
| 3-(isopropylcarbonyl-amino)propyl | ethyl | benzyloxy |
| 3-(isopropylcarbonyl-amino)propyl | ethyl | 2-methanesulfonylaminoethoxy |
| 3-(isopropylcarbonyl-amino)propyl | ethyl | 3-methanesulfonylaminopropoxy |

-continued

I-1d

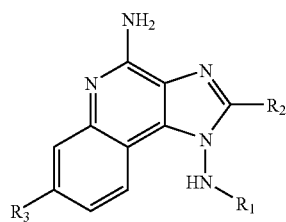

| R₁ | R₂ | R₃ |
|---|---|---|
| 3-(isopropylcarbonyl-amino)propyl | ethyl | 2-(pyridin-3-yl)ethyl |
| 3-(isopropylcarbonyl-amino)propyl | ethyl | 2-(hydroxymethyl)phenyl |
| 3-(isopropylcarbonyl-amino)propyl | ethyl | 5-(hydroxymethyl)pyridin-3-yl |
| 3-(isopropylcarbonyl-amino)propyl | propyl | pyridin-3-yl |
| 3-(isopropylcarbonyl-amino)propyl | propyl | benzyloxy |
| 3-(isopropylcarbonyl-amino)propyl | propyl | 2-methanesulfonylaminoethoxy |
| 3-(isopropylcarbonyl-amino)propyl | propyl | 3-methanesulfonylaminopropoxy |
| 3-(isopropylcarbonyl-amino)propyl | propyl | 2-(pyridin-3-yl)ethyl |
| 3-(isopropylcarbonyl-amino)propyl | propyl | 2-(hydroxymethyl)phenyl |
| 3-(isopropylcarbonyl-amino)propyl | propyl | 5-(hydroxymethyl)pyridin-3-yl |
| 3-(isopropylcarbonyl-amino)propyl | butyl | pyridin-3-yl |
| 3-(isopropylcarbonyl-amino)propyl | butyl | benzyloxy |
| 3-(isopropylcarbonyl-amino)propyl | butyl | 2-methanesulfonylaminoethoxy |
| 3-(isopropylcarbonyl-amino)propyl | butyl | 3-methanesulfonylaminopropoxy |
| 3-(isopropylcarbonyl-amino)propyl | butyl | 2-(pyridin-3-yl)ethyl |
| 3-(isopropylcarbonyl-amino)propyl | butyl | 2-(hydroxymethyl)phenyl |
| 3-(isopropylcarbonyl-amino)propyl | butyl | 5-(hydroxymethyl)pyridin-3-yl |
| 3-(isopropylcarbonyl-amino)propyl | methoxymethyl | pyridin-3-yl |
| 3-(isopropylcarbonyl-amino)propyl | methoxymethyl | benzyloxy |
| 3-(isopropylcarbonyl-amino)propyl | methoxymethyl | 2-methanesulfonylaminoethoxy |
| 3-(isopropylcarbonyl-amino)propyl | methoxymethyl | 3-methanesulfonylaminopropoxy |
| 3-(isopropylcarbonyl-amino)propyl | methoxymethyl | 2-(pyridin-3-yl)ethyl |
| 3-(isopropylcarbonyl-amino)propyl | methoxymethyl | 2-(hydroxymethyl)phenyl |
| 3-(isopropylcarbonyl-amino)propyl | methoxymethyl | 5-(hydroxymethyl)pyridin-3-yl |
| 3-(isopropylcarbonyl-amino)propyl | hydroxymethyl | pyridin-3-yl |
| 3-(isopropylcarbonyl-amino)propyl | hydroxymethyl | benzyloxy |
| 3-(isopropylcarbonyl-amino)propyl | hydroxymethyl | 2-methanesulfonylaminoethoxy |
| 3-(isopropylcarbonyl-amino)propyl | hydroxymethyl | 3-methanesulfonylaminopropoxy |
| 3-(isopropylcarbonyl-amino)propyl | hydroxymethyl | 2-(pyridin-3-yl)ethyl |
| 3-(isopropylcarbonyl-amino)propyl | hydroxymethyl | 2-(hydroxymethyl)phenyl |

-continued

I-1d

[Structure: 4-amino imidazoquinoline with R₂ at 2-position, R₁ on N, R₃ on benzo ring]

| R₁ | R₂ | R₃ |
|---|---|---|
| 3-(isopropylcarbonyl-amino)propyl | hydroxymethyl | 5-(hydroxymethyl)pyridin-3-yl |
| 3-(isopropylcarbonyl-amino)propyl | 2-methoxyethyl | pyridin-3-yl |
| 3-(isopropylcarbonyl-amino)propyl | 2-methoxyethyl | benzyloxy |
| 3-(isopropylcarbonyl-amino)propyl | 2-methoxyethyl | 2-methanesulfonylaminoethoxy |
| 3-(isopropylcarbonyl-amino)propyl | 2-methoxyethyl | 3-methanesulfonylaminopropoxy |
| 3-(isopropylcarbonyl-amino)propyl | 2-methoxyethyl | 2-(pyridin-3-yl)ethyl |
| 3-(isopropylcarbonyl-amino)propyl | 2-methoxyethyl | 2-(hydroxymethyl)phenyl |
| 3-(isopropylcarbonyl-amino)propyl | 2-methoxyethyl | 5-(hydroxymethyl)pyridin-3-yl |
| 3-(isopropylcarbonyl-amino)propyl | 2-hydroxyethyl | pyridin-3-yl |
| 3-(isopropylcarbonyl-amino)propyl | 2-hydroxyethyl | benzyloxy |
| 3-(isopropylcarbonyl-amino)propyl | 2-hydroxyethyl | 2-methanesulfonylaminoethoxy |
| 3-(isopropylcarbonyl-amino)propyl | 2-hydroxyethyl | 3-methanesulfonylaminopropoxy |
| 3-(isopropylcarbonyl-amino)propyl | 2-hydroxyethyl | 2-(pyridin-3-yl)ethyl |
| 3-(isopropylcarbonyl-amino)propyl | 2-hydroxyethyl | 2-(hydroxymethyl)phenyl |
| 3-(isopropylcarbonyl-amino)propyl | 2-hydroxyethyl | 5-(hydroxymethyl)pyridin-3-yl |
| 3-(isopropylcarbonyl-amino)propyl | ethoxymethyl | pyridin-3-yl |
| 3-(isopropylcarbonyl-amino)propyl | ethoxymethyl | benzyloxy |
| 3-(isopropylcarbonyl-amino)propyl | ethoxymethyl | 2-methanesulfonylaminoethoxy |
| 3-(isopropylcarbonyl-amino)propyl | ethoxymethyl | 3-methanesulfonylaminopropoxy |
| 3-(isopropylcarbonyl-amino)propyl | ethoxymethyl | 2-(pyridin-3-yl)ethyl |
| 3-(isopropylcarbonyl-amino)propyl | ethoxymethyl | 2-(hydroxymethyl)phenyl |
| 3-(isopropylcarbonyl-amino)propyl | ethoxymethyl | 5-(hydroxymethyl)pyridin-3-yl |

Certain exemplary compounds, including some of those described above in the Examples, have the following Formulas (Ii, IIb, Ij, or Ik) and the following R₁ and R₂ substituents, wherein each line of the table is matched with Formula Ii, IIb, Ij, or Ik to represent a specific compound.

[Structures: Ii, IIb, Ij, Ik — 4-amino imidazoquinoline variants with R₁ and R₂ substituents]

| R₁ | R₂ |
|---|---|
| isopropyl | hydrogen |
| isopropyl | methyl |
| isopropyl | ethyl |
| isopropyl | propyl |
| isopropyl | butyl |
| isopropyl | methoxymethyl |
| isopropyl | hydroxymethyl |
| isopropyl | 2-methoxyethyl |
| isopropyl | 2-hydroxyethyl |
| isopropyl | ethoxyethyl |
| benzyl | hydrogen |
| benzyl | methyl |
| benzyl | ethyl |
| benzyl | propyl |
| benzyl | butyl |
| benzyl | methoxymethyl |
| benzyl | hydroxymethyl |
| benzyl | 2-methoxyethyl |
| benzyl | 2-hydroxyethyl |
| benzyl | ethoxymethyl |
| 3-phenylpropyl | hydrogen |
| 3-phenylpropyl | methyl |
| 3-phenylpropyl | ethyl |
| 3-phenylpropyl | propyl |
| 3-phenylpropyl | butyl |
| 3-phenylpropyl | methoxymethyl |
| 3-phenylpropyl | hydroxymethyl |
| 3-phenylpropyl | 2-methoxyethyl |
| 3-phenylpropyl | 2-hydroxyethyl |
| 3-phenylpropyl | ethoxymethyl |
| 3-[3-(isopropyl)ureido]propyl | hydrogen |
| 3-[3-(isopropyl)ureido]propyl | methyl |
| 3-[3-(isopropyl)ureido]propyl | ethyl |
| 3-[3-(isopropyl)ureido]propyl | propyl |
| 3-[3-(isopropyl)ureido]propyl | butyl |
| 3-[3-(isopropyl)ureido]propyl | methoxymethyl |
| 3-[3-(isopropyl)ureido]propyl | hydroxymethyl |
| 3-[3-(isopropyl)ureido]propyl | 2-methoxyethyl |
| 3-[3-(isopropyl)ureido]propyl | 2-hydroxyethyl |
| 3-[3-(isopropyl)ureido]propyl | ethoxymethyl |
| 3-methanesulfonylaminopropyl | hydrogen |
| 3-methanesulfonylaminopropyl | methyl |
| 3-methanesulfonylaminopropyl | ethyl |
| 3-methanesulfonylaminopropyl | propyl |
| 3-methanesulfonylaminopropyl | butyl |
| 3-methanesulfonylaminopropyl | methoxymethyl |
| 3-methanesulfonylaminopropyl | hydroxymethyl |
| 3-methanesulfonylaminopropyl | 2-methoxyethyl |
| 3-methanesulfonylaminopropyl | 2-hydroxyethyl |
| 3-methanesulfonylaminopropyl | ethoxymethyl |

-continued

| | |
|---|---|
| 3-(methylcarbonylamino)propyl | hydrogen |
| 3-(methylcarbonylamino)propyl | methyl |
| 3-(methylcarbonylamino)propyl | ethyl |
| 3-(methylcarbonylamino)propyl | propyl |
| 3-(methylcarbonylamino)propyl | butyl |
| 3-(methylcarbonylamino)propyl | methoxymethyl |
| 3-(methylcarbonylamino)propyl | hydroxymethyl |
| 3-(methylcarbonylamino)propyl | 2-methoxyethyl |
| 3-(methylcarbonylamino)propyl | 2-hydroxyethyl |
| 3-(methylcarbonylamino)propyl | ethoxymethyl |
| 3-(isopropylcarbonylamino)propyl | hydrogen |
| 3-(isopropylcarbonylamino)propyl | methyl |
| 3-(isopropylcarbonylamino)propyl | ethyl |
| 3-(isopropylcarbonylamino)propyl | propyl |
| 3-(isopropylcarbonylamino)propyl | butyl |
| 3-(isopropylcarbonylamino)propyl | methoxymethyl |
| 3-(isopropylcarbonylamino)propyl | hydroxymethyl |
| 3-(isopropylcarbonylamino)propyl | 2-methoxyethyl |
| 3-(isopropylcarbonylamino)propyl | 2-hydroxyethyl |
| 3-(isopropylcarbonylamino)propyl | ethoxymethyl |
| 3-[(morpholin-4-carbonyl)amino]propyl | hydrogen |
| 3-[(morpholin-4-carbonyl)amino]propyl | methyl |
| 3-[(morpholin-4-carbonyl)amino]propyl | ethyl |
| 3-[(morpholin-4-carbonyl)amino]propyl | propyl |
| 3-[(morpholin-4-carbonyl)amino]propyl | butyl |
| 3-[(morpholin-4-carbonyl)amino]propyl | methoxymethyl |
| 3-[(morpholin-4-carbonyl)amino]propyl | hydroxymethyl |
| 3-[(morpholin-4-carbonyl)amino]propyl | 2-methoxyethyl |
| 3-[(morpholin-4-carbonyl)amino]propyl | 2-hydroxyethyl |
| 3-[(morpholin-4-carbonyl)amino]propyl | ethoxymethyl |

In the above tables, the term "ureido" has the same meaning as "aminocarbonylamino".

Compounds of the invention have been found to modulate cytokine biosynthesis by inducing the production of interferon α and/or tumor necrosis factor α in human cells when tested using the method described below.

CYTOKINE INDUCTION IN HUMAN CELLS

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Imiquimod and S-27609", Journal of Leukocyte Biology, 58, 365–372 (September, 1995).

Blood Cell Preparation for Culture:

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation:

The compounds are solubilized in dimethyl sulfoxide (DMSO). The DMSO concentration should not exceed a final concentration of 1% for addition to the culture wells. The compounds are generally tested at concentrations ranging from 30–0.014 μM.

Incubation:

The solution of test compound is added at 60 μM to the first well containing RPMI complete and serial 3 fold dilutions are made in the wells. The PBMC suspension is then added to the wells in an equal volume, bringing the test compound concentrations to the desired range (30–0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation:

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA:

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN., M-8 analyzer from IGEN International, Gaithersburg, Md. The immunoassay uses a human TNF capture and detection antibody pair from Biosource International, Camarillo, Calif. Results are expressed in pg/mL.

Certain compounds of the invention may modulate cytokine biosynthesis by inhibiting production of tumor necrosis factor α (TNF-α) when tested using the method described below.

TNF-α INHIBITION IN MOUSE CELLS

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccaride from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 µL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula (I-1):

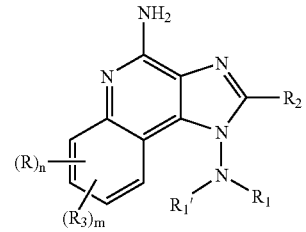

I-1 wherein:
$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;
$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—S(O)$_2$—N($R_6$)—$R_4$, and
—X—O—$R_4$;
$R_2$ is selected from the group consisting of:
  hydrogen,
  alkyl,
  alkenyl,
  aryl,
  heteroaryl,
  heterocyclyl,
  -alkylene-Z-alkyl,
  -alkylene-Z-aryl,
  -alkylene-Z-alkenyl, and
  alkyl or alkenyl substituted by one or more substituents selected from the group consisting of:
    —OH,
    halogen,
    —N($R_6$)$_2$,
    —C($R_7$)—N($R_6$)$_2$,
    —S(O)$_2$—N($R_6$)$_2$,
    —N($R_6$)—C($R_7$)—$C_{1-10}$ alkyl,
    —N($R_6$)—C($R_7$)-aryl,
    —N($R_6$)—S(O)$_2$—$C_{1-10}$ alkyl,
    —N($R_6$)—S(O)$_2$-aryl,
    —C(O)—$C_{1-10}$ alkyl,
    —O—C($R_7$)—$C_{1-10}$ alkyl,
    —O—C($R_7$)-aryl,
    —O—C($R_7$)—N($R_6$)—$C_{1-10}$ alkyl,
    —O—C($R_7$)—N($R_6$)-aryl;
    —C(O)—O—$C_{1-10}$ alkyl,
    —$N_3$,
    aryl,
    heteroaryl,
    heterocyclyl,
    —C(O)-aryl, and
    —C(O)-heteroaryl;

R₃ is selected from the group consisting of:
 -Z'-R₄',
 -Z'-X'—R₄',
 -Z'-X'—Y'—R₄, and
 -Z'-X'—R₅',
each R is independently selected from the group consisting of alkyl, alkenyl, alkoxy, halogen, fluoroalkyl, hydroxy, amino, alkylamino, and dialkylamino;
n is an integer from 0 to 4;
m is 0 or 1; with the proviso that when m is 1, then n is 0, 1, or 2;
R₄ is selected from the group consisting of hydrogen, alkyl, alkenyl, alkynyl, aryl, heteroaryl, and heterocyclyl wherein the alkyl, alkenyl, alkynyl, aryl, heteroaxyl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclyalkylenyl, amino, alkylamino, (arylalkylenyl)amino, dialkylamino, and in the case of alkyl, alkenyl, alkynyl, and heterocyclyl, oxo, with the proviso that when R₄ is a substituted alkyl group and the substituent contains a hetero atom which bonds directly to the alkyl group then the alkyl group contains at least two carbons between the substituent and the nitrogen atom to which R₁ is bonded;
R₅ is selected from the group consisting of:

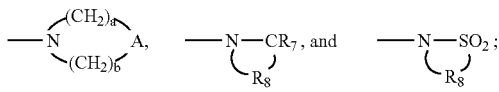

X is C₂₋₂₀ alkylene;
Y is selected from the group consisting of —C(R₇)—, —C(R₇)—O—, —S(O)₂—, —S(O)₂—N(R₆)—, and —C(R₇)—N(R₉)—; wherein R₉ is selected from the group consisting of hydrogen, alkyl, and arylalkylenyl; or R₉ and R₄ together with the nitrogen atom to which R₉ is bonded can join to form the group

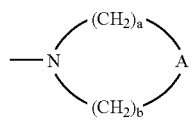

Z is selected from the group consisting of —O— and —S(O)₀₋₂—;
A is selected from the group consisting of —CH(R₆)—, —O—, —N(R₆)—, —N(Y—R₄)—, and —N(X—N(R₆)—Y—R₄)—;
a and b are independently integers from 1 to 4 with the proviso that when A is —O—, —N(R₆)—, —N(Y—R₄)—, or —N(X—N(R₆)—Y—R₄)— then a and b are independently integers from 2 to 4;
R₄' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R₅' is selected from the group consisting of:

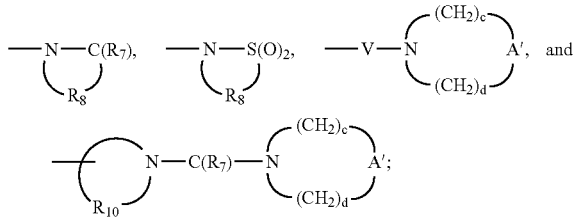

X' is selected from the group consisting of alkylene, alkenylene, alkynylene, arylene, heteroarylene, and heterocyclylene wherein the alkylene, alkenylene, and alkynylene groups can be optionally interrupted or terminated by azylene, heteroarylene, or heterocyclylene and optionally interrupted by one or more —O— groups;
Y' is selected from the group consisting of:

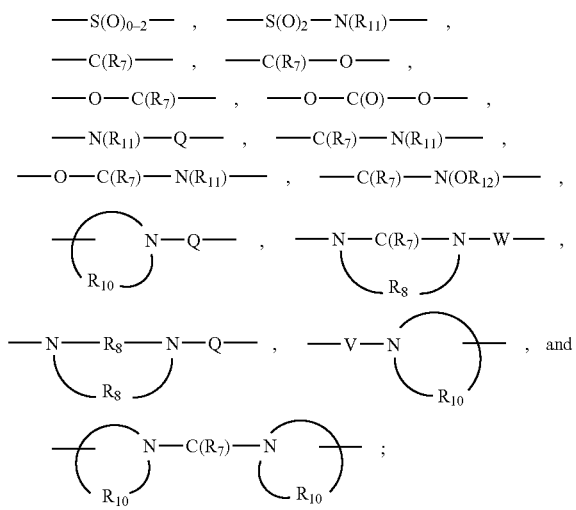

Z' is a bond or —O—;
A' is selected from the group consisting of CH₂—, —O—, —C(O)—, —S(O)₀₋₂—, and —N(R₄')—;
Q is selected from the group consisting of a bond, —C(R₇)—, —C(R₇)—C(R₇)—, —S(O)₂—, —C(R₇—N(R₁₁)—W—, —S(O)₂—N(R₁₁)—, —C(R₇)—O—, and —C(R₇)—N(OR₁₂)—;
V is selected from the group consisting of —C(R₇)—, —O—C(R₇)—, —N(R₁₁)—C(R₇)—, and —S(O)₂;
W is selected from the group consisting of a bond, —C(O)—, and S(O)₂—;

c and d are independently integers from 1 to 6 with the proviso that c+d is ≦7, and when A' is —O— or —N(R$_4$')— then c and d are independently integers from 2 to 4;

each R$_6$ is independently selected from the group consisting of hydrogen, alkyl, and arylalkylenyl;

each R$_7$ is independently selected from the group consisting of =O and =S;

each R$_8$ is independently C$_{2-7}$ alkylene;

R$_{10}$ is C$_{3-8}$ alkylene;

each R$_{11}$ is independently selected from the group consisting of hydrogen, C$_{1-10}$ alkyl, C$_{2-10}$ alkenyl, C$_{1-10}$ alkoxy C$_{2-10}$ alkylenyl, and arylC$_{1-10}$ alkylenyl; and R$_{12}$ is selected from the group consisting of hydrogen and alkyl;

or a pharmaceutically acceptable salt thereof.

2. The compound or salt of claim 1 wherein R$_1$ is selected from the group consisting of —R$_4$, —Y—R$_4$, —X—R$_5$, —X—N(R$_6$)—Y—R$_4$, —X—C(R$_7$)—N(R$_6$)—R$_4$, and —X—O—R$_4$; R$_1$' is selected from the group consisting of hydrogen and alkyl; and R$_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of:
—OH,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—S(O)$_2$—C$_{1-10}$ alkyl,
—C(O)—C$_{1-10}$ alkyl,
—C(O)—O—C$_{1-10}$ alkyl,
—N$_3$,
aryl,
heteroaryl,
heterocyclyl,
—C(O)-aryl, and
—C(O)-heteroaryl.

3. The compound or salt of claim 1 wherein R$_1$ is selected from the group consisting of —R$_4$, —Y—R$_4$, and —X—N(R$_6$)—Y—R$_4$ wherein Y is —C(R$_7$)—, —S(O)$_2$—, or —C(R$_7$)—N(R$_9$)—.

4. The compound or salt of claim 3 wherein R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylcarbonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, arylaminocarbonylaminoalkylenyl, heteroarylcarbonylaminoalkylenyl, and heteroarylaminocarbonylaminoalkylenyl.

5. The compound or salt of claim 4 wherein R$_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein R$_{13}$ is selected from the group consisting of methylcarbonyl, isopropylcarbonyl, cyclopentylcarbonyl, tetrahydropyran-4-ylcarbonyl, methanesulfonyl, phenylsulfonyl, benzyl, ethylaminocarbonyl, isopropylaminocarbonyl, morpholine-4-carbonyl, phenylaminocarbonyl, pyridin-3-ylcarbonyl, and pyridin-3-ylaminocarbonyl.

6. The compound or salt of claim 1 wherein R$_1$' is hydrogen.

7. The compound or salt of claim 1 wherein R$_1$ and R$_1$' are each independently alkyl.

8. The compound or salt of claim 1 wherein R$_2$ is selected from the group consisting of hydrogen, alkyl, alkoxyalkylenyl, and hydroxyalkylenyl.

9. The compound or salt of claim 8 wherein R$_2$ is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

10. The compound or salt of claim 1 wherein n is 0.

11. The compound or salt of claim 1 wherein n is 0, and R$_3$ is selected from the group consisting of -Z'-R$_4$', -Z'-X—R$_4$', and -Z'-X—Y'—R$_4$'.

12. The compound or salt of claim 11 wherein R$_3$ is selected from the group consisting of 2-(pyridin-3-yl)ethyl, pyridinyl, (hydroxymethyl)pyridinyl, phenyl, (hydroxymethyl)phenyl, ethoxyphenyl, (morpholine-4-carbonyl)phenyl, 3-(methanesulfonylamino)phenyl, 2-(methanesulfonylamino)ethoxy, 3-(methanesulfonylamino)propoxy, and benzyloxy.

13. The compound or salt of claim 1 wherein m is 0 and n is 1.

14. The compound or salt of claim 13 wherein R is halogen or hydroxy.

15. The compound or salt of claim 1 wherein m and n are each 0.

16. A compound of the Formula (I-2):

wherein:

R$_B$ is selected from the group consisting of alkyl, alkoxy, halogen, hydroxy, and trifluoromethyl;

n is an integer from 0 to 4;

R$_1$' is selected from the group consisting of hydrogen and alkyl;

R$_1$ is selected from the group consisting of:
—R$_4$,
—Y—R$_4$,
—X—R$_5$,
—X—N(R$_6$)—Y—R$_4$,
—X—C(R$_7$)—N(R$_6$)—R$_4$, and
—X—O—R$_4$;

or R$_1$' and R$_1$ together with the nitrogen atom to which they are bonded can join to form a group selected from the group consisting of:

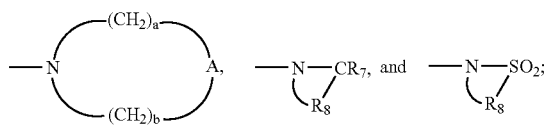

$R_2$ is selected from the group consisting of:
- hydrogen,
- alkyl,
- alkenyl,
- aryl,
- heteroaryl,
- heterocyclyl,
- alkylene-Z-alkyl,
- alkylene-Z-aryl,
- alkylene-Z-alkenyl, and
- alkyl or alkenyl substituted by one or more substituents selected from the group consisting of:
  - —OH,
  - halogen,
  - —N($R_6$)$_2$,
  - —C($R_7$)—N($R_6$)$_2$,
  - —S(O)$_2$—N($R_6$)$_2$,
  - —N($R_6$)—C($R_7$)—$C_{1-10}$ alkyl,
  - —N($R_6$)—S(O)$_2$—$C_{1-10}$ alkyl,
  - —C(O)—$C_{1-10}$ alkyl,
  - —C(O)—O—$C_{1-10}$ alkyl,
  - —$N_3$,
  - aryl,
  - heteroaryl,
  - heterocyclyl,
  - —C(O)-aryl, and
  - —C(O)-heteroaryl;

$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of:

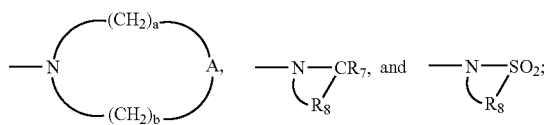

each $R_6$ is independently selected from the group consisting of hydrogen, alkyl, and arylalkylenyl;
each $R_7$ is independently selected from the group consisting of =O and =S;

$R_8$ is $C_{2-7}$ alkylene;
A is selected from the group consisting of —CH($R_6$)—, —O—, —N($R_6$)—, —N(Y—$R_4$)—, and —N(X—N($R_6$)—Y—$R_4$)—;
X is $C_{2-20}$ alkylene;
Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

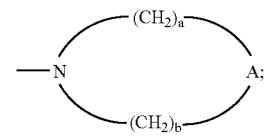

Z is selected from the group consisting of —O— and —S(O)$_{0-2}$—; and
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;
or a pharmaceutically acceptable salt thereof.

17. The compound or salt according to claim 16 wherein $R_1$ is selected from the group consisting of —$R_4$, —Y—$R_4$, and —X—N($R_6$)—Y—$R_4$ wherein Y is —C($R_7$)—, —S(O)$_2$—, or —C($R_7$)—N($R_9$)—.

18. The compound or salt according to claim 17 wherein $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl)aminoalkylenyl, and arylaminocarbonylaminoalkylenyl.

19. The compound or salt according to claim 18 wherein $R_1$ is selected from the group consisting of hydrogen, methyl, isopropyl, butyl, 2-methylpropyl, 1-ethylpropyl, 3-methylbutyl, cyclohexyl, benzyl, cinnamyl, furan-2-ylmethyl, and —CH$_2$CH$_2$CH$_2$—NHR$_{13}$, wherein $R_{13}$ is selected from the group consisting of methanesulfonyl, phenylsulfonyl, benzyl, and phenylaminocarbonyl.

20. The compound or salt according to claim 16 wherein $R_1'$ is hydrogen.

21. The compound or salt of claim 16 wherein $R_1$ and $R_1'$ are each independently alkyl.

22. The compound or salt of claim 16 wherein $R_1$ and $R_1'$ join to form the group:

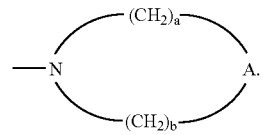

23. The compound or salt according to claim 16 wherein $R_2$ is selected from the group consisting of hydrogen, alkyl, and alkoxyalkylenyl.

24. The compound or salt according to claim 23 wherein $R_2$ is selected from the group consisting of hydrogen, butyl, 2-methoxyethyl, and ethoxymethyl.

25. The compound or salt according to claim 16 wherein n is 0.

26. The compound or salt according to claim 16 wherein n is 1, and $R_B$ is halogen or hydroxy.

27. A compound of the Formula (I-3):

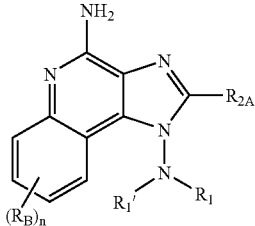

I-3 wherein:
$R_B$ is selected from alkyl, alkoxy, halogen, hydroxy, and trifluoromethyl;
n is an integer from 0 to 4;
$R_1'$ is selected from hydrogen and alkyl;
$R_1$ is selected from:
—$R_4$,
—Y—$R_4$,
—X—$R_5$,
—X—N($R_6$)—Y—$R_4$,
—X—$CR_7$—N($R_6$)—$R_4$, and
—X—O—$R_4$;
or $R_1'$ and $R_1$ together with the nitrogen atom to which they are bonded can join to form a group selected from:

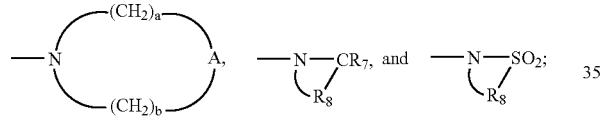

$R_{2A}$ is selected from:
-hydrogen,
-alkyl,
-alkenyl,
-aryl,
-heteroaryl,
-alkylene-Z-alkyl,
-alkylene-Z-aryl,
-alkylene-Z-alkenyl, and
-alkyl or alkenyl substituted by one or more substituents selected from:
—OH,
-halogen,
—N($R_6$)$_2$,
—$CR_7$—N($R_6$)$_2$,
—$SO_2$—N($R_2$)$_2$,
—N($R_6$)—$CR_7$—$C_{1-10}$ alkyl,
—N($R_6$)—$SO_2$—$C_{1-10}$ alkyl,
—C(O)—$C_{1-10}$ alkyl,
—C(O)—O—$C_{1-10}$ alkyl,
—$N_3$,
-aryl,
-heteroaryl,
-heterocyclyl,
—C(O)-aryl, and
—C(O)-heteroaryl;
$R_4$ is selected from hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;
$R_5$ is selected from:

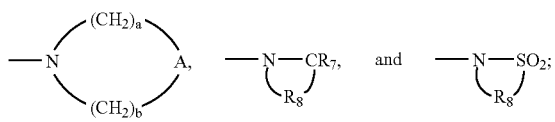

$R_6$ is selected from hydrogen, alkyl, and arylalkylenyl;
$R_7$ is selected from =O and =S;
$R_8$ is $C_{2-7}$ alkylene;
$R_9$ is selected from hydrogen, alkyl, and arylalkylenyl, or $R_9$ and $R_4$ together with the nitrogen atom to which $R_9$ is bonded can join to form the group

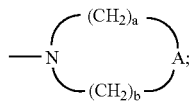

A is selected from —$CHR_6$—, —O—, —N($R_6$)—, —N(Y—$R_4$)—, and —N(X—N($R_6$)—Y—$R_4$)—;
X is $C_{2-20}$ alkylene;
Y is selected from —$CR_7$—, —$SO_2$—, —$SO_2$—N($R_6$)—, and —$CR_7$—N($R_9$)—;
Z is selected from —O— and —S(O)$_{0-2}$—;
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;
and pharmaceutically acceptable salts thereof.

28. The compound or salt according to claim 27 wherein $R_1$ is selected from —$R_4$, —Y—$R_4$, and —X—N($R_6$)—Y—$R_4$ wherein Y is —$CR_7$—, —$SO_2$—, or —$CR_7$—N($R_9$)—.

29. The compound or salt according to claim 28 wherein $R_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl)aminoalkylenyl, and arylaminocarbonylaminoalkylenyl.

30. The compound or salt according to claim 29 wherein $R_1$ is selected from hydrogen, isopropyl, butyl, cyclohexyl, benzyl, cinnamyl, and —$CH_2CH_2CH_2$—$NHR_{13}$, wherein $R_{13}$ is selected from methanesulfonyl, phenylsulfonyl, benzyl, and phenylaminocarbonyl.

31. The compound or salt according to claim 27 wherein $R_1'$ is hydrogen.

32. The compound or salt according to claim 27 wherein $R_{2A}$ is selected from hydrogen, alkyl, and alkoxyalkylenyl.

33. The compound or salt according to claim 32 wherein $R_{2A}$ is selected from hydrogen, butyl, methoxyethyl, and ethoxymethyl.

34. The compound or salt according to claim 27 wherein n is 0.

35. A compound of the Formula (II-1):

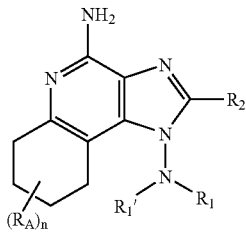

II-1 wherein:
each $R_A$ is independently selected from the group consisting of:
halogen,
hydroxy,
alkyl,
alkenyl,
haloalkyl,
alkoxy,
alkylthio,
—$NH_2$,
—NH(alkyl), and
—N(alkyl)$_2$;
n is an integer from 0 to 4;
$R_1$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;
$R_1$ is selected from the group consisting of:
  —$R_4$,
  —Y—$R_4$,
  —X—$R_5$,
  —X—N($R_6$)—Y—$R_4$,
  —X—C($R_7$)—N($R_6$)—$R_4$,
  —X—S(O)$_2$—N($R_6$)—$R_4$, and
  —X—O—$R_4$;
$R_2$ is selected from the group consisting of:
  hydrogen,
  alkyl,
  alkenyl,
  aryl,
  heteroaryl,
  heterocyclyl,
  -alkylene-Z-alkyl,
  -alkylene-Z-aryl,
  -alkylene-Z-alkenyl, and
  alkyl or alkenyl substituted by one or more substituents selected from the group consisting of:
    —OH,
    halogen,
    —N($R_6$)$_2$,
    —C($R_7$)—N($R_6$)$_2$,
    —S(O)$_2$—N($R_6$)$_2$,
    —N($R_6$)—C($R_7$)—$C_{1-10}$ alkyl,
    —N($R_6$)—C($R_7$)-aryl,
    —N($R_6$)—S(O)$_2$—$C_{1-10}$ alkyl,
    —N($R_6$)—S(O)$_2$-aryl,
    —C(O)—$C_{1-10}$ alkyl,
    —O—C($R_7$)—$C_{1-10}$ alkyl,
    —O—C($R_7$)-aryl,
    —O—C($R_7$)—N($R_6$)—$C_{1-10}$ alkyl,
    —O—C($R_7$)—N($R_6$)-aryl;
    —C(O)—O—$C_{1-10}$ alkyl,
    —$N_3$,
    aryl,
    heteroaryl,
    heterocyclyl,
    —C(O)-aryl, and
    —C(O)-heteroaryl;
$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaxyl, heteroaryloxy, heteroarylalkoxy, heterocyclyl, heterocyclylalkylenyl, amino, alkykmino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;
$R_5$ is selected from the group consisting of:

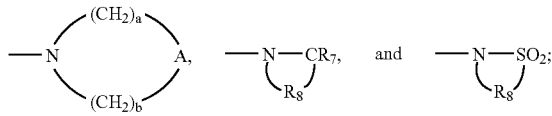

each $R_6$ is independently selected from the group consisting of hydrogen, alkyl, and arylalkylenyl;
each $R_7$ is independently selected from the group consisting of =O and =S;
$R_8$ is $C_{2-7}$ alkylene;
A is selected from the group consisting of —CH($R_6$)—, —O—, —N($R_6$)—, —N(Y—$R_4$)—, and —N(X—N($R_6$)—Y—$R_4$)—;
X is $C_{2-20}$ alkylene;
Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

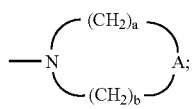

Z is selected from the group consisting of —O— and —S(O)$_{0-2}$—; and
a and b are independently integers from 1 to 4 with the proviso that when A is —O—, —N($R_6$)—, —N(Y—

R$_4$)—, or —N(X—N(R$_6$)—Y—R$_4$— then a and b are independently integers from 2 to 4;
or a pharmaceutically acceptable salt thereof.

36. The compound or salt of claim 35 wherein R$_1$ is selected from the group consisting of —R$_4$, —Y—R$_4$, —X—R$_5$, —X—N(R$_6$)—Y—R$_4$, —X—C(R$_7$)—N(R$_6$)—R$_4$, and —X—O—R$_4$; R$_1$' is selected from the group consisting of hydrogen and alkyl; and R$_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of:
—OH,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—S(O)$_2$—C$_{1-10}$ alkyl,
—C(O)—C$_{1-10}$ alkyl,
—C(O)—O—C$_{1-10}$ alkyl,
—N$_3$,
aryl,
heteroaryl,
heterocyclyl,
—C(O)-aryl, and
—C(O)-heteroaryl.

37. The compound or salt according to claim 36 wherein R$_1$ is selected from the group consisting of —R$_4$, —Y—R$_4$, and —X—N(R$_6$)—Y—R$_4$ wherein Y is —C(R$_7$)—, —S(O)$_2$—, or —C(R$_7$)—N(R$_9$)—.

38. The compound or salt according to claim 37 wherein R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, arylaminocarbonyl, (arylalkylenyl)aminoalkylenyl, and arylaminocarbonylaminoalkylenyl.

39. The compound or salt according to claim 38 wherein R$_1$ is selected from the group consisting of hydrogen, methyl, isopropyl, butyl, 2-methylpropyl, 1-ethylpropyl, 3-methylbutyl, cyclohexyl, benzyl, cinnamyl, furan-2-ylmethyl, and —CH$_2$CH$_2$CH$_2$—NHR$_{13}$, wherein R$_{13}$ is selected from the group consisting of methanesulfonyl, phenylsulfonyl, benzyl, and phenylaminocarbonyl.

40. The compound or salt according to claim 37 wherein R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, and arylaminocarbonylaminoalkylenyl.

41. The compound or salt according to claim 40 wherein R$_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein R$_{13}$ is selected from the group consisting of methanesulfonyl, phenylsulfonyl, benzyl, isopropylaminocarbonyl, morpholine-4-carbonyl, and phenylaminocarbonyl.

42. The compound or salt of claim 37 wherein R$_1$ is selected from the group consisting of hydrogen, alkyl, alkenyl, arylalkylenyl, arylalkenylenyl, heteroarylalkylenyl, heteroarylalkenylenyl, aminoalkylenyl, alkoxyalkylenyl, acyl, alkylsulfonylaminoalkylenyl, arylsulfonylaminoalkylenyl, alkylcarbonylaminoalkylenyl, alkylaminocarbonyl, alkylaminocarbonylaminoalkylenyl, arylaminocarbonyl, (arylalkylenyl)aminoalkylenyl, heterocyclylcarbonylaminoalkylenyl, arylaminocarbonylaminoalkylenyl, heteroarylcarbonylaminoalkylenyl, and heteroarylaminocarbonylaminoalkylenyl.

43. The compound or salt of claim 42 wherein R$_1$ is selected from the group consisting of hydrogen, methyl, isopropyl, butyl, 2-methylpropyl, 1-ethylpropyl, 3-methylbutyl, cyclohexyl, benzyl, 3-phenylpropyl, cinnamyl, furan-2-ylmethyl, and —CH$_2$CH$_2$CH$_2$—NHR$_{13}$, wherein R$_{13}$ is selected from the group consisting of methylcarbonyl, isopropylcarbonyl, cyclopentylcarbonyl, tetrahydropyran-4-ylcarbonyl, methanesulfonyl, phenylsulfonyl, benzyl, ethylaminocarbonyl, isopropylaminocarbonyl, morpholine-4-carbonyl, phenylaminocarbonyl, pyridin-3-ylcarbonyl, and pyridin-3-ylaminocarbonyl.

44. The compound or salt according to claim 36 wherein R$_1$' is hydrogen.

45. The compound or salt of claim 36 wherein R$_1$ and R$_1$' are each independently alkyl.

46. The compound or salt according to claim 36 wherein R$_2$ is selected from the group consisting of hydrogen, alkyl, and alkoxyalkylenyl.

47. The compound or salt according to claim 46 wherein R$_2$ is selected from the group consisting of hydrogen, butyl, 2-methoxyethyl, and ethoxymethyl.

48. The compound or salt according to claim 46 wherein R$_2$ is selected from the group consisting of hydrogen, methyl, propyl, butyl, 2-methoxyethyl, and ethoxymethyl.

49. The compound or salt of claim 35 wherein R$_2$ is selected from the group consisting of hydrogen, alkyl, alkoxyalkylenyl, and hydroxyalkylenyl.

50. The compound or salt of claim 49 wherein R$_2$ is selected from the group consisting of hydrogen, methyl, ethyl, n-propyl, n-butyl, methoxymethyl, 2-methoxyethyl, ethoxymethyl, hydroxymethyl, 2-hydroxyethyl, and 3-hydroxypropyl.

51. The compound or salt according to claim 36 wherein n is 0.

52. A pharmaceutical composition comprising a therapeutically effective amount of a compound or salt of claim 1 and a pharmaceutically acceptable carrier.

53. A pharmaceutical composition comprising a therapeutically effective amount of a compound or salt of claim 16 and a pharmaceutically acceptable carrier.

54. A pharmaceutical composition comprising a therapeutically effective amount of a compound or salt of claim 27 and a pharmaceutically acceptable carrier.

55. A pharmaceutical composition comprising a therapeutically effective amount of a compound or salt of claim 35 and a pharmaceutically acceptable carrier.

56. A compound of the Formula (X):

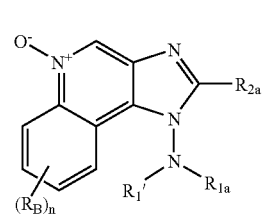

wherein:
each $R_B$ is independently selected from the group consisting of alkyl, alkoxy, halogen, hydroxy, and trifluoromethyl;
n is an integer from 0 to 4;
$R_1'$ is hydrogen or alkyl;
$R_{1a}$ is selected from the group consisting of:
 $R_{4a}$,
 —Y—$R_{4a}$,
 —X—$R_5$,
 —X—N($R_6$)—Y—$R_{4a}$,
 —X—C($R_7$)—N($R_6$)—$R_{4a}$, and
 —X—O—$R_{4a}$;
or $R_1'$ and $R_{1a}$ together with the nitrogen atom to which they are bonded can join to form a group selected from the group consisting of:

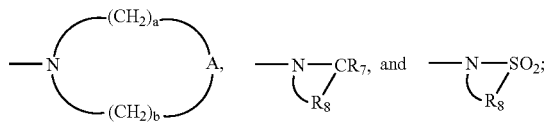

$R_{2a}$ is selected from the group consisting of:
 -hydrogen,
 -alkyl,
 -alkenyl,
 -aryl,
 -alkylene-Z"-alkyl,
 -alkylene-Z"-aryl,
 -alkylene-Z"-alkenyl, and
 -alkyl or alkenyl substituted by one or more substituents selected from the group consisting of:
  —OH,
  -halogen,
  —N($R_6$)$_2$,
  —C($R_7$)—N($R_6$)$_2$,
  —S(O)$_2$—N($R_6$)$_2$,
  —N($R_6$)—C($R_7$)—$C_{1-10}$ alkyl,
  —N($R_6$)—S(O)$_2$—$C_{1-10}$ alkyl,
  —C(O)—$C_{1-10}$ alkyl,
  —C(O)—O—$C_{1-10}$ alkyl,
  —N$_3$,
  -aryl,
  -heterocyclyl, and
  —C(O)-aryl;
$R_{4a}$ is selected from the group consisting of hydrogen, alkyl, alkenyl, alkynyl, aryl, and heterocyclyl wherein the alkyl, alkenyl, alkynyl, aryl, and heterocyclyl groups can be unsubstituted or substituted by one or more substituents independently selected from the group consisting of alkyl, alkoxy, haloalkyl, haloalkoxy, halogen, nitro, hydroxy, cyano, carboxy, formyl, aryl, aryloxy, arylalkoxy, heterocyclyl, heterocyclylalkylenyl, amino, alkylamino, (arylalkylenyl) amino, dialkylamino, and in the case of alkyl, alkenyl, alkynyl, and heterocyclyl, oxo, with the proviso that when $R_{4a}$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of

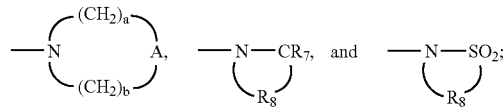

each $R_6$ is independently selected from the group consisting of hydrogen, alkyl, and arylalkylenyl;
each $R_7$ is independently selected from the group consisting of =O and =S;
$R_8$ is $C_{2-7}$ alkylene;
A is selected from the group consisting of —CH($R_6$)—, —O—, —N($R_6$)—, —N(Y—$R_4$)—, and —N(X—N($R_6$)—Y—$R_4$)—;
X is $C_{2-20}$ alkylene;
Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl and arylalkylenyl, or $R_9$ and $R_4$ together with the nitrogen atom to which $R_9$ is bonded can join to form the group

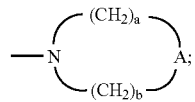

Z" is selected from the group consisting of —O— and —S(O)$_2$—; and
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;
or a pharmaceutically acceptable salt thereof.

57. A compound of the Formula XLII:

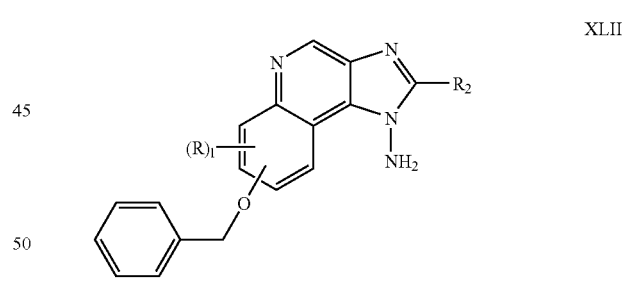

wherein:
R is selected from the group consisting of alkyl, alkenyl, alkoxy, halogen, fluoroalkyl, hydroxy, amino, alkylamino, and dialkylamino;
l is 0, 1, or 2;
$R_2$ is selected from the group consisting of:
 hydrogen,
 alkyl,
 alkenyl,
 aryl,
 heteroaryl,
 heterocyclyl,
 -alkylene-Z-alkyl,
 -alkylene-Z-aryl, -alkylene-Z-alkenyl, and
alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—C($R_7$)-aryl,
—N($R_6$)—S(O)$_2$—$C_{1-10}$ alkyl,
—N($R_6$)—S(O)$_2$-aryl,
—C(O)—$C_{1-10}$ alkyl,
—O—C($R_7$)—$C_{1-10}$ alkyl,
—O—C($R_7$)-aryl,
—O—C($R_7$)—N($R_6$)—$C_{1-10}$ alkyl,
—O—C($R_7$)—N($R_6$)-aryl;
—C(O)—O—$C_{1-10}$ alkyl,
—$N_3$,
aryl,
heteroaryl,
heterocyclyl,
—C(O)-aryl, and
—C(O)-heteroaryl;
each $R_6$ is independently selected from the group consisting of hydrogen, alkyl, and arylalkylenyl;
$R_7$ is selected from the group consisting of =O and =S; and
Z is selected from the group consisting of —O— and —S(O)$_{0-2}$—;
or a pharmaceutically acceptable salt thereof.

58. The compound or salt of claim 57 wherein $R_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—$N_3$,
aryl,
heteroaryl,
heterocyclyl,
—C(O)-aryl, and
—C(O)-heteroaryl.

59. A compound of the Formula XLIII:

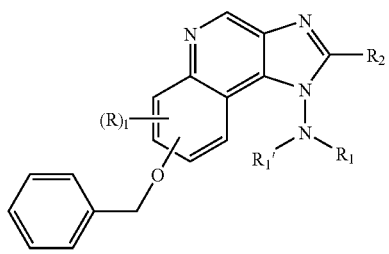

XLIII wherein:
R is selected from the group consisting of alkyl, alkenyl, alkoxy, halogen, fluoroalkyl, hydroxy, amino, alkylamino, and dialkylamino;
l is 0, 1, or 2;
$R_1'$ is selected from the group consisting of hydrogen, alkyl, alkoxyalkylenyl, and hydroxyalkylenyl wherein the alkylenyl group contains at least two carbon atoms between the hydroxy or alkoxy substituent and the nitrogen atom to which $R_1'$ is bonded;
$R_1$ is selected from the group consisting of:
—$R_4$,
—Y—$R_4$,
—X—$R_5$,
—X—N($R_6$)—Y—$R_4$,
—X—C($R_7$)—N($R_6$)—$R_4$,
—X—O—C($R_7$)—N($R_6$)—$R_4$,
—X—S(O)$_2$—N($R_6$)—$R_4$, and
—X—O—$R_4$;
or $R_1'$ and $R_1$ together with the nitrogen atom to which they are bonded can join to form a group selected from the group consisting of:

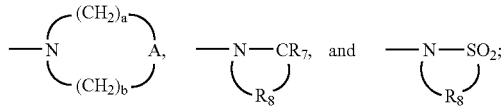

$R_2$ is selected from the group consisting of:
hydrogen,
alkyl,
alkenyl,
aryl,
heteroaryl,
heterocyclyl,
-alkylene-Z-alkyl,
-alkylene-Z-aryl,
-alkylene-Z-alkenyl, and
alkyl or alkenyl substituted by one or more substituents selected from the group consisting of:
—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—C($R_7$)-aryl,
—N($R_6$)—S(O)$_2$—$C_{1-10}$ alkyl,
—N($R_6$)—S(O)$_2$-aryl,
—C(O)—$C_{1-10}$ alkyl,
—O—C($R_7$)—$C_{1-10}$ alkyl,
—O—C($R_7$)-aryl,
—O—C($R_7$)—N($R_6$)—$C_{1-10}$ alkyl,
—O—C($R_7$)—N($R_6$)-aryl;
—C(O)—O—$C_{1-10}$ alkyl,
—$N_3$,
aryl,
heteroaryl,
heterocyclyl,
—C(O)-aryl, and
—C(O)-heteroaryl;
$R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the nitrogen atom to which $R_1$ is bonded;

$R_5$ is selected from the group consisting of

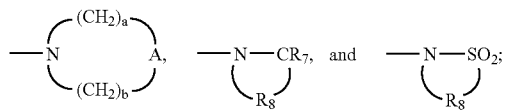

each $R_6$ is independently selected from the group consisting of hydrogen, alkyl, and arylalkylenyl;

each $R_7$ is independently selected from the group consisting of =O and =S;

$R_8$ is $C_{2-7}$ alkylene;

A is selected from the group consisting of —CH($R_6$)—, —O—, —N($R_6$)—, —N(Y—$R_4$)—, and —N(X—N($R_6$)—Y—$R_4$)—;

X is $C_{2-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—; wherein $R_9$ is selected from the group consisting of hydrogen, alkyl, and arylalkylenyl; or $R_9$ and $R_4$ together with the nitrogen atom to which $R_9$ is bonded can join to form the group

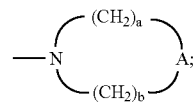

Z is selected from the group consisting of —O— and —S(O)$_{0-2}$—; and a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

or a pharmaceutically acceptable salt thereof.

60. The compound or salt of claim 59 wherein $R_1$ is selected from the group consisting of —$R_4$, —Y—$R_4$, —X—$R_5$, —X—N($R_6$)—Y—$R_4$, —X—C($R_7$)—N($R_6$)—$R_4$, and —X—O—$R_4$; $R_1'$ is selected from the group consisting of hydrogen and alkyl; and $R_2$ is selected from the group consisting of hydrogen, alkyl, alkenyl, aryl, heteroaryl, heterocyclyl, -alkylene-Z-alkyl, -alkylene-Z-aryl, -alkylene-Z-alkenyl, and alkyl or alkenyl substituted by one or more substituents selected from the group consisting of:

—OH,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—N$_3$,
aryl,
heteroaryl,
heterocyclyl,
—C(O)-aryl, and
—C(O)-heteroaryl.

* * * * *